(12) United States Patent
Angsana et al.

(10) Patent No.: US 11,548,941 B2
(45) Date of Patent: Jan. 10, 2023

(54) SAFE AND EFFECTIVE METHOD OF TREATING PSORIASIS WITH ANTI-IL-23 SPECIFIC ANTIBODY

(71) Applicant: Janssen Biotech, Inc., Horsham, PA (US)

(72) Inventors: Julianty Angsana, San Diego, CA (US); Patrick Branigan, Lansdowne, PA (US); Samuel DePrimo, Carlsbad, CA (US); Susan Flavin, Spring City, PA (US); Shu Li, Dresher, PA (US); Xuejun Liu, San Diego, CA (US); Ernesto Munoz, Santa Fe, CA (US); Bruce Randazzo, Rydal, PA (US)

(73) Assignee: JANSSEN BIOTECH, INC., Horsham, PA (US)

( * ) Notice: Subject to any disclaimer, the term of this patent is extended or adjusted under 35 U.S.C. 154(b) by 0 days.

(21) Appl. No.: 16/688,178

(22) Filed: Nov. 19, 2019

(65) Prior Publication Data

US 2020/0157209 A1    May 21, 2020

Related U.S. Application Data

(60) Provisional application No. 62/769,889, filed on Nov. 20, 2018, provisional application No. 62/796,673, filed on Jan. 25, 2019, provisional application No. 62/810,617, filed on Feb. 26, 2019, provisional application No. 62/817,711, filed on Mar. 13, 2019, provisional application No. 62/915,115, filed on Oct. 15, 2019.

(51) Int. Cl.
| | |
|---|---|
| *C07K 16/24* | (2006.01) |
| *A61K 39/395* | (2006.01) |
| *A61P 17/06* | (2006.01) |
| *A61K 45/06* | (2006.01) |

(52) U.S. Cl.
CPC .......... *C07K 16/244* (2013.01); *A61K 39/395* (2013.01); *A61P 17/06* (2018.01); *C07K 16/241* (2013.01); *A61K 45/06* (2013.01); *C07K 2317/21* (2013.01); *C07K 2317/565* (2013.01)

(58) Field of Classification Search
None
See application file for complete search history.

(56) References Cited

U.S. PATENT DOCUMENTS

| | | |
|---|---|---|
| 4,309,989 A | 1/1982 | Fahim |
| 4,399,216 A | 8/1983 | Axel |
| 4,634,665 A | 1/1987 | Axel |
| 4,656,134 A | 4/1987 | Ringold |
| 4,676,980 A | 6/1987 | Segal |
| 4,683,195 A | 7/1987 | Mullis |
| 4,683,202 A | 7/1987 | Mullis |
| 4,704,692 A | 11/1987 | Ladner |
| 4,766,067 A | 8/1988 | Biswas |
| 4,767,402 A | 8/1988 | Kost |
| 4,795,699 A | 1/1989 | Tabor |
| 4,800,159 A | 1/1989 | Mullis |
| 4,816,567 A | 3/1989 | Cabilly |
| 4,873,316 A | 10/1989 | Meade |
| 4,889,818 A | 12/1989 | Gelfand |
| 4,921,794 A | 5/1990 | Tabor |
| 4,939,666 A | 7/1990 | Hardman |
| 4,946,778 A | 8/1990 | Ladner |
| 4,956,288 A | 9/1990 | Barsoum |
| 4,965,188 A | 10/1990 | Mullis |
| 4,994,370 A | 2/1991 | Silver |
| 5,066,584 A | 11/1991 | Gyllensten |
| 5,091,310 A | 2/1992 | Innis |
| 5,122,464 A | 6/1992 | Wilson |
| 5,130,238 A | 7/1992 | Malek |
| 5,142,033 A | 8/1992 | Innis |
| 5,149,636 A | 9/1992 | Axel |
| 5,168,062 A | 12/1992 | Stinski |
| 5,179,017 A | 1/1993 | Axel |
| 5,223,409 A | 6/1993 | Ladner |
| 5,225,539 A | 7/1993 | Winter |
| 5,260,203 A | 11/1993 | Ladner |
| 5,266,491 A | 11/1993 | Nagata |
| 5,304,489 A | 4/1994 | Rosen |
| 5,385,839 A | 1/1995 | Stinski |
| 5,403,484 A | 4/1995 | Ladner |
| 5,427,908 A | 6/1995 | Dower |
| 5,455,030 A | 10/1995 | Ladner |

(Continued)

FOREIGN PATENT DOCUMENTS

| | | |
|---|---|---|
| EP | 229246 | 10/1986 |
| EP | 368684 | 5/1990 |

(Continued)

OTHER PUBLICATIONS

US 5,733,746 A, 03/1998, Treco (withdrawn)
Clinical trials. gov, NCT03090100, (Mar. 22, 2017).*
Yiu et al; Immunotherapy; 2015; vol. 7, No. ; pp. 119-133.*
Guselkumab prescribing information, (Jul. 2017).*
Ritchlin et al, Current Opinion Rheumatology; 2016; vol. 28; No. 3, pp. 204-210.*
Li et al, Journal of Immunology Research; vol. 2019, Article ID 2546161, published Sep. 2019.*
Reich et al, The Lancet, 2019; vol. 394, pp. 831-839.*
Aggarwal, et al., "Interleukin-23 Promotes a Distinct CD4 T Cell Activation State characterized by the Production of Interleukin-17," The Journal of Biological Chemistry, 278(3): 1910-1914 (2003).

(Continued)

*Primary Examiner* — Bridget E Bunner
*Assistant Examiner* — Fozia M Hamud
(74) *Attorney, Agent, or Firm* — Riverside Law LLP

(57) ABSTRACT

A method of treating psoriasis in a patient by administering an IL-23 specific antibody, e.g., guselkumab, in a clinically proven safe and clinically proven effective amount and the patient achieves PASI90, PASI100 or IGA 0 or 1 score as measured 16, 24, 32, 40 and 48 weeks after initial treatment and the patient achieves higher efficacy than a patient treated with the secukinumab antibody.

31 Claims, 9 Drawing Sheets

Specification includes a Sequence Listing.

(56) References Cited

U.S. PATENT DOCUMENTS

| | | |
|---|---|---|
| 5,496,549 A | 3/1996 | Yamazaki |
| 5,518,889 A | 5/1996 | Ladner |
| 5,530,101 A | 6/1996 | Queen |
| 5,534,621 A | 7/1996 | Ladner |
| 5,545,806 A | 8/1996 | Lonberg |
| 5,545,807 A | 8/1996 | Surani |
| 5,565,362 A | 10/1996 | Rosen |
| 5,569,825 A | 10/1996 | Lonberg |
| 5,571,698 A | 11/1996 | Ladner |
| 5,576,195 A | 11/1996 | Robinson |
| 5,580,717 A | 12/1996 | Dower |
| 5,580,734 A | 12/1996 | Treco |
| 5,582,996 A | 12/1996 | Curtis |
| 5,585,089 A | 12/1996 | Queen |
| 5,595,898 A | 1/1997 | Robinson |
| 5,601,819 A | 2/1997 | Wong |
| 5,618,920 A | 4/1997 | Robinson |
| 5,625,126 A | 4/1997 | Lonberg |
| 5,625,825 A | 4/1997 | Rostoker |
| 5,627,052 A | 5/1997 | Schrader |
| 5,633,425 A | 5/1997 | Lonberg |
| 5,641,670 A | 6/1997 | Treco |
| 5,643,759 A | 7/1997 | Pfreundschuh |
| 5,643,768 A | 7/1997 | Kawasaki |
| 5,656,730 A | 8/1997 | Lee |
| 5,658,754 A | 8/1997 | Kawasaki |
| 5,661,016 A | 8/1997 | Lonberg |
| 5,693,493 A | 12/1997 | Robinson |
| 5,693,762 A | 12/1997 | Queen |
| 5,698,417 A | 12/1997 | Robinson |
| 5,698,435 A | 12/1997 | Robinson |
| 5,714,352 A | 2/1998 | Aya |
| 5,723,323 A | 3/1998 | Kauffman |
| 5,733,761 A | 3/1998 | Treco |
| 5,750,373 A | 5/1998 | Garrard |
| 5,763,192 A | 6/1998 | Kauffman |
| 5,763,733 A | 6/1998 | Whitlow |
| 5,766,886 A | 6/1998 | Studnicka |
| 5,767,260 A | 6/1998 | Whitlow |
| 5,770,359 A | 6/1998 | Wilson |
| 5,770,428 A | 6/1998 | Boris-Lawrie |
| 5,789,650 A | 8/1998 | Lonberg |
| 5,807,706 A | 9/1998 | Carter |
| 5,814,476 A | 9/1998 | Kauffman |
| 5,817,483 A | 10/1998 | Kauffman |
| 5,821,333 A | 10/1998 | Carter |
| 5,824,514 A | 10/1998 | Kauffman |
| 5,827,690 A | 10/1998 | Meade |
| 5,827,739 A | 10/1998 | Wilson |
| 5,833,985 A | 11/1998 | Ball |
| 5,837,500 A | 11/1998 | Ladner |
| 5,839,446 A | 11/1998 | Waner |
| 5,849,992 A | 12/1998 | Meade |
| 5,851,198 A | 12/1998 | Castellano |
| 5,856,456 A | 1/1999 | Whitlow |
| 5,859,205 A | 1/1999 | Adair |
| 5,885,793 A | 3/1999 | Griffiths |
| 5,932,448 A | 8/1999 | Tso |
| 5,959,083 A | 9/1999 | Bosslet |
| 5,959,084 A | 9/1999 | Ring |
| 5,962,255 A | 10/1999 | Griffiths |
| 5,976,862 A | 11/1999 | Kauffman |
| 5,989,530 A | 11/1999 | Lorenz |
| 5,994,616 A | 11/1999 | Rosen |
| 6,010,902 A | 1/2000 | Ledbetter |
| 6,037,453 A | 3/2000 | Jardieu |
| 6,060,284 A | 5/2000 | Bazan |
| 6,060,285 A | 5/2000 | Lenz |
| 6,106,833 A | 8/2000 | Ring |
| 6,132,992 A | 10/2000 | Ledbetter |
| 6,180,370 B1 | 1/2001 | Queen |
| 6,193,967 B1 | 2/2001 | Morganelli |
| 6,204,023 B1 | 3/2001 | Robinson |
| 6,210,668 B1 | 4/2001 | Lindhofer |
| 6,479,634 B1 | 11/2002 | Bazan |
| 6,495,667 B1 | 12/2002 | Bazan |
| 6,610,285 B1 | 8/2003 | Hirata |
| 6,756,481 B2 | 6/2004 | Chirica |
| 6,800,460 B1 | 10/2004 | Oppmann |
| 6,835,825 B1 | 12/2004 | Bazan |
| RE39,015 E | 3/2006 | Bazan |
| 7,090,847 B1 | 8/2006 | Oppmann |
| 7,183,382 B2 | 2/2007 | Oppmann |
| 7,247,711 B2 | 7/2007 | Benson |
| 7,252,971 B2 | 8/2007 | Benson |
| 7,282,204 B2 | 10/2007 | Oft |
| 7,491,391 B2 | 2/2009 | Benson |
| 7,807,414 B2 | 10/2010 | Benson |
| 7,935,344 B2 | 5/2011 | Benson |
| 7,993,645 B2 | 8/2011 | Benson |
| 8,106,177 B2 | 1/2012 | Benson |
| 8,221,760 B2 | 7/2012 | Benson |
| 9,353,181 B2 | 5/2016 | Benson |
| 9,353,645 B1 | 5/2016 | Kennedy |
| 9,783,607 B2 | 10/2017 | Benson |
| 10,030,070 B2 | 7/2018 | Benson |
| 2002/0042386 A1 | 4/2002 | Rosen |
| 2003/0003097 A1 | 1/2003 | Reff |
| 2003/0124617 A1 | 7/2003 | Gram |
| 2003/0162261 A1 | 8/2003 | Oppmann |
| 2004/0185506 A1 | 9/2004 | Heavner |
| 2004/0258686 A1 | 12/2004 | Chirica |
| 2005/0049402 A1 | 3/2005 | Babcook |
| 2005/0053598 A1 | 3/2005 | Burke |
| 2005/0175611 A1 | 8/2005 | Mahler |
| 2005/0208052 A1 | 9/2005 | Katsikis |
| 2005/0244874 A1 | 11/2005 | Kastelein |
| 2007/0048315 A1 | 3/2007 | Presta |
| 2009/0181027 A1 | 7/2009 | Dal Monte |
| 2010/0322863 A1 | 12/2010 | Benson |
| 2011/0040249 A1 | 2/2011 | Benson |
| 2011/0287028 A1 | 11/2011 | Benson |
| 2011/0319292 A1 | 12/2011 | Benson |
| 2014/0178295 A1 | 6/2014 | Giles-Komar |
| 2015/0147337 A1 | 5/2015 | Reichert |
| 2016/0222102 A1 | 8/2016 | Arndt |
| 2016/0237151 A1 | 8/2016 | Benson |
| 2018/0094052 A1 | 4/2018 | Randazzo |
| 2018/0134784 A1 | 5/2018 | Fitzgerald |
| 2020/0385454 A1 | 12/2020 | Randazzo |
| 2021/0179703 A1 | 6/2021 | Fitzgerald |

FOREIGN PATENT DOCUMENTS

| | | |
|---|---|---|
| EP | 371998 | 6/1990 |
| EP | 0438474 | 7/1991 |
| EP | 0463151 | 1/1992 |
| EP | 550400 | 7/1993 |
| EP | 0229246 B1 | 8/1993 |
| EP | 0368684 B1 | 3/1994 |
| EP | 0371998 B1 | 3/1994 |
| EP | 590689 | 4/1994 |
| EP | 0438474 B1 | 5/1996 |
| EP | 0710719 | 5/1996 |
| EP | 0463151 B1 | 6/1996 |
| EP | 0550400 B1 | 7/1996 |
| EP | 0814259 | 12/1997 |
| EP | 0590689 B1 | 5/2002 |
| EP | 0710719 B1 | 3/2007 |
| GB | 2272400 A | 5/1994 |
| GB | 2272440 | 5/1994 |
| WO | 8605803 | 10/1986 |
| WO | 8605803 A1 | 10/1986 |
| WO | 8806630 | 9/1988 |
| WO | 8806630 A1 | 9/1988 |
| WO | 8906283 | 7/1989 |
| WO | 8906283 A1 | 7/1989 |
| WO | 9004036 | 4/1990 |
| WO | 9004036 A1 | 4/1990 |
| WO | 1990005370 | 5/1990 |
| WO | 9014424 | 11/1990 |
| WO | 9014424 A1 | 11/1990 |
| WO | 9014430 | 11/1990 |
| WO | 9014430 A1 | 11/1990 |

(56) References Cited

FOREIGN PATENT DOCUMENTS

| | | |
|---|---|---|
| WO | 9014443 | 11/1990 |
| WO | 9014443 A1 | 11/1990 |
| WO | 9100360 | 1/1991 |
| WO | 9100360 A1 | 1/1991 |
| WO | 9117271 | 11/1991 |
| WO | 9117271 A1 | 11/1991 |
| WO | 1991017271 | 11/1991 |
| WO | 9118980 | 12/1991 |
| WO | 9118980 A1 | 12/1991 |
| WO | 9119818 | 12/1991 |
| WO | 9119818 A1 | 12/1991 |
| WO | 9200373 | 1/1992 |
| WO | 9200373 A1 | 1/1992 |
| WO | 9201047 A1 | 1/1992 |
| WO | 1992001047 | 1/1992 |
| WO | 9203461 A1 | 3/1992 |
| WO | 1992003461 | 3/1992 |
| WO | 9205258 | 4/1992 |
| WO | 9205258 A1 | 4/1992 |
| WO | 9206204 A1 | 4/1992 |
| WO | 1992006204 | 4/1992 |
| WO | 9211272 A1 | 7/1992 |
| WO | 1992011272 | 7/1992 |
| WO | 9214843 | 9/1992 |
| WO | 9214843 A1 | 9/1992 |
| WO | 9216221 | 10/1992 |
| WO | 9216221 A1 | 10/1992 |
| WO | 9218619 | 10/1992 |
| WO | 9218619 A1 | 10/1992 |
| WO | 9220791 A1 | 11/1992 |
| WO | 1992020791 | 11/1992 |
| WO | 9308278 | 4/1993 |
| WO | 9308278 A1 | 4/1993 |
| WO | 1993006213 | 4/1993 |
| WO | 1993006213 A1 | 4/1993 |
| WO | 9308829 | 5/1993 |
| WO | 9308829 A1 | 5/1993 |
| WO | 1993011236 | 6/1993 |
| WO | 1993011236 A1 | 6/1993 |
| WO | 1993019172 | 9/1993 |
| WO | 1993019172 A1 | 9/1993 |
| WO | 9418219 A1 | 8/1994 |
| WO | 1994018219 | 8/1994 |
| WO | 9425585 | 11/1994 |
| WO | 9425585 A1 | 11/1994 |
| WO | 9501438 A1 | 1/1995 |
| WO | 1995001438 | 1/1995 |
| WO | 9515388 A1 | 6/1995 |
| WO | 9516027 | 6/1995 |
| WO | 9516027 A1 | 6/1995 |
| WO | 1995015388 | 6/1995 |
| WO | 9607754 | 3/1996 |
| WO | 9607754 A1 | 3/1996 |
| WO | 9613583 | 5/1996 |
| WO | 9613583 A2 | 5/1996 |
| WO | 9619256 | 6/1996 |
| WO | 9619256 A1 | 6/1996 |
| WO | 9634096 | 10/1996 |
| WO | 9634096 A1 | 10/1996 |
| WO | 9708320 | 3/1997 |
| WO | 9708320 A1 | 3/1997 |
| WO | 9713852 | 4/1997 |
| WO | 9713852 A1 | 4/1997 |
| WO | 9720032 A1 | 6/1997 |
| WO | 1997020032 | 6/1997 |
| WO | 9801757 A1 | 1/1998 |
| WO | 1998001757 | 1/1998 |
| WO | 9824884 | 6/1998 |
| WO | 9824884 A1 | 6/1998 |
| WO | 9824893 | 6/1998 |
| WO | 9824893 A1 | 6/1998 |
| WO | 9850433 | 11/1998 |
| WO | 9850433 A2 | 11/1998 |
| WO | 9853847 | 12/1998 |
| WO | 9853847 A1 | 12/1998 |
| WO | 9905280 | 2/1999 |
| WO | 9906834 A2 | 2/1999 |
| WO | 1999006834 | 2/1999 |
| WO | 9940195 | 8/1999 |
| WO | 9954342 | 10/1999 |
| WO | 9954342 A1 | 10/1999 |
| WO | 0009552 | 2/2000 |
| WO | 0053631 | 9/2000 |
| WO | 0070049 | 11/2000 |
| WO | 0118051 | 3/2001 |
| WO | 0185790 | 11/2001 |
| WO | 03011878 | 2/2003 |
| WO | 03011878 A2 | 2/2003 |
| WO | 2004042009 | 5/2004 |
| WO | 2004058178 | 7/2004 |
| WO | 2004071517 | 8/2004 |
| WO | 2004081190 | 9/2004 |
| WO | 2004101750 | 11/2004 |
| WO | 2005103083 | 11/2005 |
| WO | 2005108425 | 11/2005 |
| WO | 2007024846 | 3/2007 |
| WO | 2014004436 | 1/2014 |
| WO | 2015119841 A1 | 8/2015 |
| WO | 2016031250 | 3/2016 |
| WO | 2018093841 | 5/2018 |

OTHER PUBLICATIONS

Alex Hoffman, "Prefilled syringes point to the future," Beremans Limited, 1-4 (2004).
Barrie, et al., "The interleukin-12 family of cytokines: Therapeutic targets for inflammatory disease mediation," Clinical and Applied Immunology Reviews, 5: 225-240 (1995).
Belladonna, et al., "IL-23 and IL-12 Have Overlapping, but Distinct, Effects on Murine Dendritic Cells," The Journal of Immunology, 168: 5448-5454 (2002).
Blauvelt, et al. "Efficacy and safety of guselkumab, an anti-interleukin-23 monoclonal antibody, compared with adalimumab for the continuous treatment of patients with moderate to severe psoriasis: Results from the phase III, double-blinded, placebo- and active comparator-controlled VOYAGE 1 trial." Journal of the American Academy of Dermatology, Mosby, Inc. US., vol. 76, No. 3 (Jan. 2, 2017).
Cunningham and Wells, "High-Resolution Epitope Mapping of hGH-Receptor Interations by Alanine-Scanning Mutagenesis", Science Ausubel, supra, Chapters 8, 15; 244:1081-1085 (1989)).
David M. Frucht, "IL-23: A Cytokine That Acts on Memory T Cells," Science STKE, 114: 1-3 (2002).
Eduardo Padlan, "Anatomy of the Antibody Molecule," Molecular Immunology, 31(3): 169-217 (1994).
Elliott, M.J. et al., "A Repeated Therapy with Monoclonal Antibody to Tumour Necrosis Factor a (cA2) in Patients with Rheumatoid Arthritis", The Lancet, 344:1125-1127, 1994.
GenBank Accession No. AA418747, Hillier, et al., May 12, 1997.
GenBank Accession No. AA418955, Hillier, et al., May 12, 1997.
GenBank Accession No. AF301620, Oppmann, et al., Dec. 4, 2000.
GenBank Accession No. C06368, J. Takeda, Aug. 9, 1996.
Harlow, et al., Antibodies A Laboratory Manual, Cold Spring Harbor Laboratory, pp. 567-569 (1988).
Knappik, et al., "Fully Synthetic Human Combinatorial Antibody Libraries (HuCAL) Based on Modular Consensus Frameworks and CDRs Randomized with Trinucleotides," Journal of Molecular Biology, 296(1): 57-86 (2000).
Kretzschmar, et al., "Antibody discovery: phage display," Current Opinion in Biotechnology, 13: 598-602 (2002).
Krnjevic-Pezic, et al., "Our experience using ustekinumab in patients with plaque psoriasis," British Journal of Dermatology, Abstract p. 24 (2011). Abstract only.
Lee, et al., "Increased Expression of Interleukin 23 p19 and p40 in Lesional Skin of Patients with Psoriasis Vulgaris," Journal of Experimental Medicine, 199(1): 125-130 (2004).
Maguire van Seventer, et al., "Interferon-D differentially regulates expression of the IL-12 family members p35, p40, p19 and EB13 in activated human dendritic cells," Journal of Neuroimmunology, 133:60-71 (2002).

(56) References Cited

OTHER PUBLICATIONS

Nakamura et al., "Guselkumab for the Treatment of Psoriasis: A Review of Phase III Trials." Dermatology and Therapy, vol. 7, No. 3 (Jun. 21, 2017).
NCT02203032 A Study of Guselkumab in Participants With Moderate to Severe Plaque-type Psoriasis and an Inadequate Response to Ustekinumab (NAVIGAIE)☐Clinical Trials.gov archive☐Jul. 12, 2016☐ https://www.clinicaltrials.gov/ct2/history/NCT02203032.
Notice of Allowance dated Sep. 2, 2021 for U.S. Appl. No. 15/813,767 (pp. 1-9).
Peter J. Barnes, "Cytokine-directed therapies for the treatment of chronic airway diseases," Cytokine & Growth Factor Reviews 14 (2003): 511-522 (2003).
Portolano, et al., "Lack of Promiscuity in Autoantigen-Specific H and L Chain Combinations as Revealed by Human H and L Chain 'Roulette'," Journal of Immunology, 150(3): 880-887 (1993).
Powell et al., "Gel Microdroplets and Flow Cytometry: Rapid Determination of Antibody Secretion by Individual Cells Within a Cell Population", Biotechnol. 8:333-337 (1990.
Reich et al., "Effect and safety of guselkumab, an anti-interleukin-23 monoclonal antibody, compared with adalimumab for the treatment of patients with moderate to severe psoriasis with randomized withdrawal and retreatment: Results from the phase III, double-blind, placebo- and active comprator-controlled VOYAGE 2 trial." Journal of the American Academy of Dermatology, Mosby Inc. US., vol. 76, No. 3 (Jan. 2, 2017).
Schmidt, et al., Expression of Interleukin-12-Related Cytokine Transcripts in Inflammatory Bowel Disease: Elevated Interleukin-23p19 and Interneukin-27p28 in Crohn's Disease But Not in Ulcerative Colitis, 11: 16-23 (2005).
Sofen, et al., "Guselkumab (an IL-23-specific mAb) demonstrates clinical and molecular response in patients with moderate-to-severe psoriasis," Journal of Allergy and Clinical Immunology, 133(4): 1032-1040 (2014).
Sofen, et al., "Results of a single ascending dose study to assess the safety and tolerability of CNTO1959 following intravenous or subcutaneous administration in healthy subjects and in subjects with moderate to severe psoriasis," British Journal of Dermatology, Abstract FC-21 (2011). Abstract only.
Vajdos, et al., "Comprehensive Functional Maps of the Antigen-Binding Site of an Anti-ErbB2 Antibody Obtained with Shotgun Scanning Mutagenesis," Journal of Molecular Biology, 320(2): 415-428 (2002).
Wiekowski, et al., "Ubiquitous Transgenic Expression of the IL-23 Subunit p19 Induces Multiorgan Inflammation, Runting, Infertility, and Premature Death," Journal of Immunology, 166: 7563-7570 (2001).
Wiendl, et al., "Therapeutic Approaches in Multiple Sclerosis: Lessons from Failed and Interrupted Treatment Trials," BioDrugs, 16(3): 183-200 (2002).
Yadav, et al., "Cytokines and autoimmunity: redundancy defines their complex nature," Current Opinion in Immunology, 15: 697-703 (2003).
Blauvelt Andrew et al: "Efficacy of guselkumab versus secukinumab in subpopulations of patients with moderate-to-severe plaque psoriasis: results from the ECLIPSE study.", The Journal of Dermatological Treatment Aug. 4, 2021, Aug. 4, 2021 (Aug. 4, 2021), pp. 1-8.
Gordon K B et al: "Efficacy of guselkumab in subpopulations of patients with moderate-to-severe plaque psoriasis: a pooled analysis of the phase III Voyage 1 and Voyage 2 studies", British Journal of Dermatology, John Wiley, Hoboken, USA, vol. 178, No. 1, Dec. 14, 2017 (Dec. 14, 2017), pp. 132-139.
Langley R G et al: "Efficacy and safety of guselkumab in patients with psoriasis who have an inadequate response to ustekinumab: results of the randomized, double-blind, phase III Navigate trial", British Journal of Dermatology, John Wiley, Hoboken, USA, vol. 178, No. 1, Oct. 10, 2017 (Oct. 10, 2017), pp. 114-123.
Mamitaro Ohtsuki et al.: "Guselkumab, an anti-interleukin-23 monoclonal antibody, for the treatment of moderate to severe plaque-type psoriasis in Japanese patients: Efficacy and safety results from a phase 3, randomized, double-blind, placebo-controlled study", Journal of Dermatology., vol. 45, No. 9, Jun. 15, 2018 (Jun. 15, 2018), pp. 1053-1062.
Reich K et al: "Safety of guselkumab in patients with moderate-to-severe psoriasis treated through 100 weeks: a pooled analysis from the randomized Voyage 1 and Voyage 2 studies", British Journal of Dermatology, John Wiley, Hoboken, USA, vol. 180, No. 5, Apr. 26, 2019 (Apr. 26, 2019), pp. 1039-1049.
Sano Shigetoshi et al: "Guselkumab, a human interleukin-23 monoclonal antibody in Japanese patients with generalized pustular psoriasis and erythrodermic psoriasis: Efficacy and safety analyses of a 52-week, phase 3, multicenter, open-label study", Journal of Dermatology., vol. 45, No. 5, May 1, 2018 (May 1, 2018), pp. 529-539.
Teeple and Muser, "Cost-per-responder analysis of guselkumab versus secukinumab with the use of efficacy results from pivotal clinical trials in patients with moderate to severe plaque psoriasis ED—Lim Henry W", Journal of the American Academy of Dermatology, Mosby, Inc, US, vol. 79, No. 3, Aug. 2, 2018 (Aug. 2, 2018).
Supplemental Notice of Allowability dated Nov. 9, 2021 for U.S. Appl. No. 15/813,767 (pp. 1-3).
Aggarwal, et al., "Signalling pathways of the TNF superfamily: a double-edged sword," National Review of Immunology, 3: 745-756 (2003).
Altschul, et al., "Basic Local Alignment Search Tool," Journal of Molecular Biology, 215: 403-410 (1990).
Anonymous, "Guselkumab for moderate to severe Psoriasis," NIHR HSRIC ID: 7526, Nov. 1, 2015.
Babcook et al., "A novel strategy for generating monoclonal antibodies from single, isolated lymphocytes producing antibodies of defined specificities", Proc. Natl. Acad. Sci. USA 93:7843-7848(1996));.
Benson, et al., "Therapeutic targeting of the IL-12/23 pathways: generation and characterization of ustekinumab", Nature Biotechnology, vol. 29, No. 7, pp. 615-624, (2011).
Bruggemann, et al., "Strategies forexpressing human antibody repertoires in transgenic mice," Immunology Today, 17(8): 391-397 (1996).
Capellas, et al., "Enzymatic Condensation of Cholecystokinin CCK-8 (4-6) and CCK-8 (7-8) Peptide Fragments in Organic Media," Biotechnology and Bioengineering, 56(4): 456-463 (1997).
Carillo, et al., The Multiple Sequence Alignment Problem in Biology, Siam Journal of Applied Math, 48: 1073-1082 (1988).
Carter, et al., "Humanization of an anfi-plSS™12 antibody for human Cancer therapy," Proceedings of the National Academy of Science USA, 89: 4285-4289 (1992).
Chothia, et al., "Canonical Structures for the Hypervariable Regions of Immunoglobulins," Journal of Molecular Biology, 196: 901-917 (1987).
Conrad et al., "Compartment-specific accumulation of recombinant immunoglobulins in plant cells: an essential tool for antibody production and immunomodulation of physiological functions and pathogen activity", Plant Mol. Biol. 38:101-109 (1998).
Cramer et al., "Transgenic Plants for Therapeutic Proteins: Linking Upstream and Downstream Strategies", Curr. Top. Microbol. Immunol. 240:95-118 (1999).
Cua, et al., "Interleukin-23 ratherthan interleukin-12 is the critical cytokine for autoimmune inflammation of the brain," Nature, 421: 744-748 (2003).
Davidson, et al., "IL-12, But Not IFN-y, Plays a Major Role in Sustaining the Chronic Phase of Colitis inIL-10-DeficientMice," The Journal of Immunology, 161: 3143-3149 (1998).
De Vos, et al., "Human Growth Hormone and Extracellular Domain of Its Receptor: Crystal Structure of the Complex", Science 255:306-312 (1992)).
Devereaux, et al., "A comprehensive set of sequence analysis programs for the VAX," Nucleic Acids Research, 12(1): 387-395 (1984).
Eren et al. "Human monoclonal antibodies specific to hepatitis B virus generated in a human/mouse radiation chimera: the Trimera system", Immunol. 93: 154-161 (1998).

(56) References Cited

OTHER PUBLICATIONS

Fisch et al., "Site-Specific Modification of a Fragment of a Chimeric Monoclonal Antibody Using Reverse Proteolysis", Bioconjugate Chem., 3:147-153 (1992);.

Fischer et al., "Towards molecular farming in the future: moving from diagnostic protein and antibody production in microbes to plants", Biotechnol. Appl. Biochem. 30:101-108 (Oct. 1999),.

Fishwald et al., "High-avidity human IgGk monoclonal antibodies from a novel strain of minilocus transgenic mice", Nat Biotechnol 14(7):845-851 (1996).

Golmia et al. When anti-TNF fails, anti-IL12-23 is an alternate Option in Psoriasis and psoriatic arthritis. Rev Bras Reumatol. May 2014-Jun.; 54(3):247-9.

Gordon, et al., "A Phase 2 Trial of Guselkumab versus Adalimumab for Plaque Psoriasis", New England Journal of Medicine, vol. 373, No. 2, pp. 136-144, (2015).

Gray et al., "Secretion capture and report web: use of affinity derivatized agarose microdroplets for the selection of hybridoma cells", J. Imm. Meth. 182:155-163 (1995);.

Green et al., "Antigen-specific human monoclonal antibodies from mice engineered with human Ig heavy and light chain YACs", Nature Genetics 7:13-21 (1994).

Hanes et al. "Ribosome display efficiently selects and evolves high-affinity antibodies in vitro from immune libraries", Proc Natl. Aca. Sci USA 95 14130-14135 (Nov. 1998).

Hanes et al., "In vitro selection and evolution of functional proteins by using ribosome display", Proc. Natl. Acad. Sci. USA 94:4937-4942 (May 1997).

Henikoff, et al., "Amino acid Substitution matrices from protein blocks," Proceedings of the National Academy of Sciences USA, 89: 10915-10919 (1992).

Hong, et al., IL-12, independently of IFN-gamma, plays a crucial role in the pathogenesis of a murine psoriasis-like skindisorder,' Journal of Immunology, 162(12): 7480-7491 (1999).

Hood et al., "Molecular Farming of Industrial Proteins from Transgenic Maize", Adv. Exp. Med. Biol. 464:127-147(1999).

Hu, et al., "Information contributed by meta-analysis in exposure-response modeling: application to phase 2 dose selection of guselkumab in patients with moderate-to-severe Psoriasis", Journal of Pharmacokinetics and Pharmacodynamics, vol. 41, No. 3, pp. 239-250, (2014).

Itoh et al., "Application of Inverse Substrates to Trypsin-Catalyzed Peptide Synthesis", Bioorg. Chem., 24(1): 59-68 (1996).

Janssen Research & Development, LLC) A Study to Evaluate the Comparative Efficacy of CNTO 1959 (Guselkumab) and Secukinumab for the Treatment of Moderate to Plaque-type Psoriasis (ECLIPSE). Oct. 9, 2018; retrieved from the Internet <https://clinicaltrials.gov/ct2lshow/NCT03090100.

Jones, et al., "Replacing the complementarity-determining regions in a human antibody with those from a mouse," Nature, 321: 522-525 (1986).

Katsube, Y., et al., "Analysis of k light chain contribution to anti-DNA antibody activity of a human VH4-21-encoded monoclonal antibody (NE-1) by antibody-phage display technique", Int J Mol. Med, 1(5):863-868 (1998)).

Kavanaugh, et al., "Ustekinumab, an anti-IL-12/23 p40 monoclonal antibody, inhibits radiographic progression in patients with active psoriatic arthritis: results of an integrated analysis of radiographic data from the phase 3, mulficenter, randomized, double-blind, placebo-controlled PSUMMIT-1 and PSUMMIT-2 trials," Annais of Rheumatology Disease, 73: 1000-1006 (2014).

Kenny et al., "Production of Monoclonal Antiboodies Using a Secretion Capture Report Web", Bio/Technol. 13:787-790 (1995).

Kumaran et al., "Conformationally driven protease-catalyzed splicing of peptide segments: V8 protease-mediated synthesis of fragments derived from thermolysin and ribonuclease A", Protein Sci. 6(10):2233-2241 (1997);.

Langrish, et al., "IL-23 drives a pathogenic T cell population that induces autoimmune inflammation," Journal of Experimental Medicine, 201 (20: 233-240 (2005).

Leonard, et al., "Prevention of experimental autoimmune encephalomyelitis by antibodies against interleukin 12," Journal of Experimental Medicine, 181(1): 381-386 (1995).

Levin, et al., "Specific targeting of interleukin-23pl9 as effective treatment for psoriasis," Journal of the American Academy of Dermatology, 70(3): 551-561 (2014).

Lonberg et al. "Antigen-specific human antibodies from mice comprising four distinct genetic modifications", Nature 368:856-859 (1994).

Lonberg et al., "Human Antibodies from Transgenic Mice", Int Rev Immunol 13(1):65-93 (1995).

Mendez, et al., "Functional transplant of megabase human immunoglobulin loci recapitulates human antibody response in mice," Nature Genetics, 15(2): 146-156 (1997).

Ma et al., "Immunotherapeutic potential of antibodies produced in plants", Trends Biotechnol. 13:522-7(1995).

Ma et al., "Plant Antibodies for Immunotherapy", Plant Physiol. 109:341-6 (1995).

Malfait, et al., "Blockade of IL-12 during the induction of collagen-induced arthritis (CIA) markedly attenuates the severity of the arthritis," Clinical and Experimental Immunology, 111:327-383 (1998).

Milstein, et al., "Hybrid hybridomas and their Use in Immunohistochemistry," Nature, 305: 537-540 (1983).

Murphy, et al., "Divergent pro- and anti-inflammatory roles for IL-23 and IL-12 in Joint autoimmune inflammation," Journal of Experimental Medicine, 198(12): 1951-1957 (2003).

Needleman, et al., "A General Method Applicable to the Search for Similarities in the Amino Acid Sequence of Two Proteins," Journal of Molecular Biology, 48: 443-453 (1970).

Nguyen et al., "Production of Human Monoclonal Antibodies in SCID Mouse", Microbiol. Immunol. 41:901-907(1997).

Oppmann, et al., "Novel p19 Protein Engages IL-12p40 to Form a Cytokine, IL-23, with Biological Activities Similar as Well as Distinct from IL-12," Immunity, 13: 715-725 (2000).

Parham, et al., "A Receptor for the Heterodimeric Cytokine IL-23 is Composed of IL-12R• and a Novel Cytokine Receptor Subunit, IL-23R," The Journal of Immunology, 168: 5699-5708 (2002).

Presky et al., "Afunctional interleukin 12 receptor complex is composed of two beta-type cytokine receptor subunits," Proceedings of the National Academy of Science USA, 93(24): 14002-14007 (1996).

Presta, et al., "Humanization of an antibody y directed against IgE," Journal of Immunology, 151: 2623-2632 (1993).

Reichert, et al., "Antibodies to watch in 2015," MABS, 7(1): 1-8 (2014).

Reichmann, et al., "Reshaping human antibodies for therapy," Nature, 332: 323-327 (1988).

Sandhu, et al., "The use of SCID in mice inbiotechnology and as a model for human disease," Critical Reviews in Biotechnology, 16: 95-118 (1996).

Shields, et al., "High Resolution Mapping of the Binding Site onHuman IgFI for FOyRI, FCyRII, FCyRIII, and RcRn and Design of IgGI Variants with Improved Binding to the RCyR," The Journal of Biological Chemistry, 276(9): 6591-6604 (2001).

Sims, et al., "A humanized CD18 antibody canblock function without cell destruction," The Journal of Immunology, 151(4): 2296-2308 (1993).

Smith, et al., "Human Interleukin 4: The Solution Structure of a Four-helix Bundle Protein", J. Mol. Biol. 224:899-904 (1992).

Sprague, et al., "Expression of a Recombinant DNA Gene Coding for the Vesiclar Stomatitis Virus Nucleocapsid Protein", J. Virol. 45:773-781 (1983)).

Steenbakkers et al., "Efficient generation of monoclonal antibodies from preselected antigenspecific B", Molec. Biol. Reports 19:125-134 (1994).

Suresh et al., "Bispecific Monoclonal Antibodies from Hybrid Hybridomas", Methods in Enzymology 121:210 (1986).

Taylor et al., "A transgenic mouse that expresses a diversity of human sequence heavy and light chain immunoglobulins", Nucleic Acids Research 20(23):6287-6295 (1992),.

(56) References Cited

OTHER PUBLICATIONS

Taylor, et al., "Human immunoglobulin transgenes undergo rearrangement, somatic mutation and class switching in mice that lack endogenous IgM," International Immunology, 6(4): 579-591 (1994).

Teng, et al., "IL-12 and IL-23 cytokines: from discovery to targeted therapies for immune-mediated inflammatory diseases," Nature Medicine, 21(7): 719-729 (2015).

Traunecker, et al., "Bispecific Single chain molecules (Janusins) target cytotoxic lymphocytes on HIV infected cells," EMBO Journal, 10(12): 3655-3659 (1991).

Trinchieri, et al., "The IL-12 Family of Heterodimeric Cytokines: New Players in the Regulation of T Cell Responses," Immunity, 19: 641-644 (2003).

Tuaillon et al., "Human immunoglobulin heavy-chain minilocus recombination in transgenic mice: Gene-segment use in u and y transcripts", Proc Natl Acad Sci USA 90(8)3720-3724 (1993).

Umana, et al., "Engineered glycoforms of an anfineuro-blastoma IgGI with optimized antibodydependent cellular cytotoxic activity," Nature Biotechnology, 17: 176-190 (1999).

Verhoeyen et al., "Reshaping Human Antibodies:Grafting an Antilysozyme Activity", Science 239:1534(1988).

Wen et al., "Limiting diluation assay for human B cells based on their activation by mutant EL4 thymoma cells:total and antimalaria responder B cell frequencies" J. Immunol. 17:887-892 (1987).

Werlen et al., "Site-Specific Conjugation of an Enzyme and an Antibody Fragment", Bioconjugate Chem., 5:411-417 (1994).

Whitelam, et al., "Antibody production in transgenic plants," Biochemical Society Transactions, Transgenic Plants and Plan Biochemistry, 22: 940-944 (1994).

Zhuang, et al., "First-in-human study to assess guselkumab (anti-IL-23 mAb) pharmacokinetics/safety in healthy subjects and patients with moderate-to-severe Psoriasis," European Journal of Clinical Pharmacology, 72(11): 1303-1310 (2016).

\* cited by examiner

SEQUENCE LISTING

```
<160> NUMBER OF SEQ ID NOS: 148

<210> SEQ ID NO 1
<211> LENGTH: 5
<212> TYPE: PRT
<213> ORGANISM: Homo sapiens

<400> SEQUENCE: 1

Asn Tyr Ala Ile Ser
1               5

<210> SEQ ID NO 2
<211> LENGTH: 5
<212> TYPE: PRT
<213> ORGANISM: Homo sapiens

<400> SEQUENCE: 2

Ser Asn Tyr Ile Ser
1               5

<210> SEQ ID NO 3
<211> LENGTH: 5
<212> TYPE: PRT
<213> ORGANISM: Homo sapiens

<400> SEQUENCE: 3

Asn Tyr Trp Ile Ser
1               5

<210> SEQ ID NO 4
<211> LENGTH: 5
<212> TYPE: PRT
<213> ORGANISM: Homo sapiens

<400> SEQUENCE: 4

Ser Tyr Trp Ile Thr
1               5
```

```
<210> SEQ ID NO 5
<211> LENGTH: 5
<212> TYPE: PRT
<213> ORGANISM: Homo sapiens

<400> SEQUENCE: 5

Asn Tyr Trp Ile Gly
1               5

<210> SEQ ID NO 6
<211> LENGTH: 5
<212> TYPE: PRT
<213> ORGANISM: Homo sapiens

<400> SEQUENCE: 6

Ser Phe Gly Met Ser
1               5

<210> SEQ ID NO 7
<211> LENGTH: 17
<212> TYPE: PRT
<213> ORGANISM: Homo sapiens

<400> SEQUENCE: 7

Gly Ile Ile Pro Met Phe Gly Tyr Ala Asn Tyr Ala Gln Lys Phe Gln
1               5                   10                  15

Gly

<210> SEQ ID NO 8
<211> LENGTH: 17
<212> TYPE: PRT
<213> ORGANISM: Homo sapiens

<400> SEQUENCE: 8

Gly Ile Ile Pro Val Phe Gly Phe Thr His Tyr Ala Gln Lys Phe Gln
1               5                   10                  15

Gly

<210> SEQ ID NO 9
<211> LENGTH: 17
<212> TYPE: PRT
<213> ORGANISM: Homo sapiens

<400> SEQUENCE: 9

Gly Ile Ile Pro Ile Phe Gly His Ala Asn Tyr Ala Gln Lys Phe Gln
1               5                   10                  15

Gly

<210> SEQ ID NO 10
<211> LENGTH: 17
<212> TYPE: PRT
<213> ORGANISM: Homo sapiens

<400> SEQUENCE: 10

Ile Ile Ile Pro Pro Ile Gly Asn Ala Trp Tyr Ala Gln Lys Phe Gln
1               5                   10                  15

Gly

<210> SEQ ID NO 11
<211> LENGTH: 17
<212> TYPE: PRT
```

-continued

<213> ORGANISM: Homo sapiens

<400> SEQUENCE: 11

Leu Ile Asp Pro Asn Phe Gly Gly Ala Tyr Tyr Ala Gln Lys Phe Gln
1               5                   10                  15

Gly

<210> SEQ ID NO 12
<211> LENGTH: 17
<212> TYPE: PRT
<213> ORGANISM: Homo sapiens

<400> SEQUENCE: 12

Leu Ile Asp Pro Val Phe Gly Gly Ala Tyr Tyr Ala Gln Lys Phe Gln
1               5                   10                  15

Gly

<210> SEQ ID NO 13
<211> LENGTH: 17
<212> TYPE: PRT
<213> ORGANISM: Homo sapiens

<400> SEQUENCE: 13

Leu Ile Asp Pro Met Phe Gly Gly Ala Tyr Tyr Ala Gln Lys Phe Gln
1               5                   10                  15

Gly

<210> SEQ ID NO 14
<211> LENGTH: 16
<212> TYPE: PRT
<213> ORGANISM: Homo sapiens

<400> SEQUENCE: 14

Ile Asn Ala His Leu Gly Gly Thr Trp Tyr Ala Gln Lys Phe Gln Gly
1               5                   10                  15

<210> SEQ ID NO 15
<211> LENGTH: 17
<212> TYPE: PRT
<213> ORGANISM: Homo sapiens

<400> SEQUENCE: 15

Ile Ser Pro Gly Thr Gly Ile Asn Ala Tyr Tyr Ala Gln Lys Phe Gln
1               5                   10                  15

Gly

<210> SEQ ID NO 16
<211> LENGTH: 17
<212> TYPE: PRT
<213> ORGANISM: Artificial Sequence
<220> FEATURE:
<223> OTHER INFORMATION: Synthesized human sequence
<220> FEATURE:
<221> NAME/KEY: unsure
<222> LOCATION: (1)
<223> OTHER INFORMATION: Where Xaa can be G, I, or L
<220> FEATURE:
<221> NAME/KEY: unsure
<222> LOCATION: (2)
<223> OTHER INFORMATION: Where Xaa can be I or S
<220> FEATURE:
<221> NAME/KEY: unsure
<222> LOCATION: (3)
<223> OTHER INFORMATION: Where Xaa can be I, P, N, or D
<220> FEATURE:

```
<221> NAME/KEY: unsure
<222> LOCATION: (4)
<223> OTHER INFORMATION: Where Xaa can be P, G, or A
<220> FEATURE:
<221> NAME/KEY: unsure
<222> LOCATION: (5)
<223> OTHER INFORMATION: Where Xaa can be I, M, P,
<223> OTHER INFORMATION: T, H, N, or V
<220> FEATURE:
<221> NAME/KEY: unsure
<222> LOCATION: (6)
<223> OTHER INFORMATION: Where Xaa can be F, I, G, or L
<220> FEATURE:
<221> NAME/KEY: unsure
<222> LOCATION: (7)
<223> OTHER INFORMATION: Where Xaa can G or I
<220> FEATURE:
<221> NAME/KEY: unsure
<222> LOCATION: (8)
<223> OTHER INFORMATION: Where Xaa can be H, Y, N, or G
<220> FEATURE:
<221> NAME/KEY: unsure
<222> LOCATION: (9)
<223> OTHER INFORMATION: Where Xaa can be A or T
<220> FEATURE:
<221> NAME/KEY: unsure
<222> LOCATION: (10)
<223> OTHER INFORMATION: Where Xaa can be N, W, or Y

<400> SEQUENCE: 16

Xaa Xaa Xaa Xaa Xaa Xaa Xaa Xaa Xaa Xaa Tyr Ala Gln Lys Phe Gln
1               5                   10                  15

Gly

<210> SEQ ID NO 17
<211> LENGTH: 17
<212> TYPE: PRT
<213> ORGANISM: Homo sapiens

<400> SEQUENCE: 17

Trp Ile Arg Pro Gly Asp Ser Asp Thr Arg Tyr Ser Pro Ser Phe Glu
1               5                   10                  15

Gly

<210> SEQ ID NO 18
<211> LENGTH: 19
<212> TYPE: PRT
<213> ORGANISM: Homo sapiens

<400> SEQUENCE: 18

Val Ser Tyr Ile Ser Ser Ser Gly Ser Ser Thr Tyr Tyr Ala Asp Ser
1               5                   10                  15

Val Lys Gly

<210> SEQ ID NO 19
<211> LENGTH: 17
<212> TYPE: PRT
<213> ORGANISM: Homo sapiens

<400> SEQUENCE: 19

Ile Ile Asp Pro Ser Asn Ser Tyr Thr Asn Tyr Ser Pro Ser Phe Gln
1               5                   10                  15

Gly

<210> SEQ ID NO 20
<211> LENGTH: 17
<212> TYPE: PRT
```

```
<213> ORGANISM: Homo sapiens

<400> SEQUENCE: 20

Ile Ile Asp Pro Ser Asn Ser Tyr Thr Arg Tyr Ser Pro Ser Phe Gln
1               5                   10                  15
Gly

<210> SEQ ID NO 21
<211> LENGTH: 17
<212> TYPE: PRT
<213> ORGANISM: Homo sapiens

<400> SEQUENCE: 21

Ile Ile Asp Pro Ser Asn Ser Tyr Thr Asp Tyr Ser Pro Ser Phe Gln
1               5                   10                  15
Gly

<210> SEQ ID NO 22
<211> LENGTH: 17
<212> TYPE: PRT
<213> ORGANISM: Homo sapiens

<400> SEQUENCE: 22

Ile Ile Ser Pro Thr Gly Ser Val Thr Trp Tyr Ser Pro Ser Phe Gln
1               5                   10                  15
Gly

<210> SEQ ID NO 23
<211> LENGTH: 17
<212> TYPE: PRT
<213> ORGANISM: Homo sapiens

<400> SEQUENCE: 23

Ile Ile Ser Pro Thr Gly Ser Ser Thr Trp Tyr Ser Pro Ser Phe Gln
1               5                   10                  15
Gly

<210> SEQ ID NO 24
<211> LENGTH: 17
<212> TYPE: PRT
<213> ORGANISM: Homo sapiens

<400> SEQUENCE: 24

Phe Ile Ser Pro Asp Gly Ser His Thr Trp Tyr Ser Pro Ser Phe Gln
1               5                   10                  15
Gly

<210> SEQ ID NO 25
<211> LENGTH: 17
<212> TYPE: PRT
<213> ORGANISM: Homo sapiens

<400> SEQUENCE: 25

Ile Ile Ser Pro Ser Gly Ser Thr Thr Trp Tyr Ser Pro Ser Phe Gln
1               5                   10                  15
Gly

<210> SEQ ID NO 26
<211> LENGTH: 17
<212> TYPE: PRT
<213> ORGANISM: Homo sapiens
```

```
<400> SEQUENCE: 26

Ile Ile Ser Pro Thr Gly Ser Ala Thr Trp Tyr Ser Pro Ser Phe Gln
1               5                   10                  15

Gly

<210> SEQ ID NO 27
<211> LENGTH: 17
<212> TYPE: PRT
<213> ORGANISM: Homo sapiens

<400> SEQUENCE: 27

Ile Ile Asp Pro Val Ser Ser Trp Thr Lys Tyr Ser Pro Ser Phe Gln
1               5                   10                  15

Gly

<210> SEQ ID NO 28
<211> LENGTH: 17
<212> TYPE: PRT
<213> ORGANISM: Artificial Sequence
<220> FEATURE:
<223> OTHER INFORMATION: Synthesized human sequence
<220> FEATURE:
<221> NAME/KEY: unsure
<222> LOCATION: (3)
<223> OTHER INFORMATION: Where Xaa can be D or S
<220> FEATURE:
<221> NAME/KEY: unsure
<222> LOCATION: (5)
<223> OTHER INFORMATION: Where Xaa can be S, V, D, or T
<220> FEATURE:
<221> NAME/KEY: unsure
<222> LOCATION: (6)
<223> OTHER INFORMATION: Where Xaa can be N, S, or G
<220> FEATURE:
<221> NAME/KEY: unsure
<222> LOCATION: (8)
<223> OTHER INFORMATION: Where Xaa can be Y, W, T, H, V, S, or A
<220> FEATURE:
<221> NAME/KEY: unsure
<222> LOCATION: (10)
<223> OTHER INFORMATION: Where Xaa can be N, D, R, K, or W

<400> SEQUENCE: 28

Ile Ile Xaa Pro Xaa Xaa Ser Xaa Thr Xaa Tyr Ser Pro Ser Phe Gln
1               5                   10                  15

Gly

<210> SEQ ID NO 29
<211> LENGTH: 17
<212> TYPE: PRT
<213> ORGANISM: Homo sapiens

<400> SEQUENCE: 29

Asn Ile Ser Ser Ser Gly Ser Ser Thr Tyr Tyr Ala Asp Ser Val Lys
1               5                   10                  15

Gly

<210> SEQ ID NO 30
<211> LENGTH: 19
<212> TYPE: PRT
<213> ORGANISM: Homo sapiens
```

```
<400> SEQUENCE: 30

Asn Ile Glu His Lys Tyr Leu Asn Tyr Ala Thr Tyr Tyr Ala Ala Ser
1               5                   10                  15

Val Lys Gly

<210> SEQ ID NO 31
<211> LENGTH: 19
<212> TYPE: PRT
<213> ORGANISM: Homo sapiens

<400> SEQUENCE: 31

Asn Ile Glu His Lys Phe Met Gly Tyr Thr Thr Tyr Tyr Ala Ala Gly
1               5                   10                  15

Val Lys Gly

<210> SEQ ID NO 32
<211> LENGTH: 19
<212> TYPE: PRT
<213> ORGANISM: Homo sapiens

<400> SEQUENCE: 32

Gly Ile Glu His Lys Tyr Leu Ser Tyr Thr Thr His Tyr Ala Ala Ser
1               5                   10                  15

Val Lys Gly

<210> SEQ ID NO 33
<211> LENGTH: 19
<212> TYPE: PRT
<213> ORGANISM: Homo sapiens

<400> SEQUENCE: 33

Ser Ile Glu His Lys Tyr Thr Gly Tyr Thr Thr Tyr Tyr Ala Ala Pro
1               5                   10                  15

Val Lys Gly

<210> SEQ ID NO 34
<211> LENGTH: 19
<212> TYPE: PRT
<213> ORGANISM: Homo sapiens

<400> SEQUENCE: 34

Gln Ile Glu His Lys Tyr Leu Ser Tyr Thr Thr Leu Tyr Ala Ala Ser
1               5                   10                  15

Val Lys Gly

<210> SEQ ID NO 35
<211> LENGTH: 19
<212> TYPE: PRT
<213> ORGANISM: Homo sapiens

<400> SEQUENCE: 35

Ser Ile Glu His Lys Tyr Leu Ser Tyr Thr Thr Phe Tyr Ala Ala Ser
1               5                   10                  15

Val Lys Gly

<210> SEQ ID NO 36
<211> LENGTH: 19
<212> TYPE: PRT
<213> ORGANISM: Homo sapiens
```

```
<400> SEQUENCE: 36

Asn Ile Glu Gly Lys Tyr Thr Ser Tyr Thr Thr Tyr Tyr Ala Ala Ser
1               5                   10                  15

Val Lys Gly

<210> SEQ ID NO 37
<211> LENGTH: 19
<212> TYPE: PRT
<213> ORGANISM: Homo sapiens

<400> SEQUENCE: 37

Gly Ile Glu His Lys Tyr Leu Ser Tyr Ala Thr Leu Tyr Ala Ala Ser
1               5                   10                  15

Val Lys Gly

<210> SEQ ID NO 38
<211> LENGTH: 19
<212> TYPE: PRT
<213> ORGANISM: Homo sapiens

<400> SEQUENCE: 38

Asn Ile Glu His Lys Tyr Leu Gly Tyr Ala Thr Val Tyr Ala Ala Ser
1               5                   10                  15

Val Lys Gly

<210> SEQ ID NO 39
<211> LENGTH: 19
<212> TYPE: PRT
<213> ORGANISM: Homo sapiens

<400> SEQUENCE: 39

Ser Ile Glu His Lys Tyr Leu Ser Tyr Ala Thr Tyr Tyr Ala Ala Gly
1               5                   10                  15

Val Lys Gly

<210> SEQ ID NO 40
<211> LENGTH: 8
<212> TYPE: PRT
<213> ORGANISM: Homo sapiens

<400> SEQUENCE: 40

Asp Ile Tyr Ala Gly Met Asp Val
1               5

<210> SEQ ID NO 41
<211> LENGTH: 18
<212> TYPE: PRT
<213> ORGANISM: Homo sapiens

<400> SEQUENCE: 41

Ser Lys Lys Gly Met Tyr Gly Gly Trp Thr Tyr Pro Leu Met Met Phe
1               5                   10                  15

Asp Leu

<210> SEQ ID NO 42
<211> LENGTH: 7
<212> TYPE: PRT
<213> ORGANISM: Homo sapiens
```

<400> SEQUENCE: 42

His Tyr Tyr Gly Met Asp Tyr
1               5

<210> SEQ ID NO 43
<211> LENGTH: 12
<212> TYPE: PRT
<213> ORGANISM: Homo sapiens

<400> SEQUENCE: 43

Gly Thr Phe Trp Ser Phe Gly Asn Tyr Phe Ala Asn
1               5                   10

<210> SEQ ID NO 44
<211> LENGTH: 8
<212> TYPE: PRT
<213> ORGANISM: Homo sapiens

<400> SEQUENCE: 44

Trp Tyr Tyr Lys Pro Phe Asp Val
1               5

<210> SEQ ID NO 45
<211> LENGTH: 12
<212> TYPE: PRT
<213> ORGANISM: Homo sapiens

<400> SEQUENCE: 45

Tyr Trp Gly Thr Pro Tyr Leu Met Gln Phe Asp Asn
1               5                   10

<210> SEQ ID NO 46
<211> LENGTH: 12
<212> TYPE: PRT
<213> ORGANISM: Homo sapiens

<400> SEQUENCE: 46

Arg Ala Ser Gln Ser Val Leu Gly Asn Tyr Leu Ala
1               5                   10

<210> SEQ ID NO 47
<211> LENGTH: 12
<212> TYPE: PRT
<213> ORGANISM: Homo sapiens

<400> SEQUENCE: 47

Arg Ala Ser Gln Ser Val Ser Ser Asn Tyr Leu Ala
1               5                   10

<210> SEQ ID NO 48
<211> LENGTH: 13
<212> TYPE: PRT
<213> ORGANISM: Homo sapiens

<400> SEQUENCE: 48

Ser Gly Ser Ser Ser Asn Ile Gly Ser Tyr Tyr Val Asn
1               5                   10

<210> SEQ ID NO 49
<211> LENGTH: 11
<212> TYPE: PRT
<213> ORGANISM: Homo sapiens

```
<400> SEQUENCE: 49

Arg Ala Ser Gln Ser Ile Phe Tyr Asn Leu Ala
1               5                   10

<210> SEQ ID NO 50
<211> LENGTH: 14
<212> TYPE: PRT
<213> ORGANISM: Homo sapiens

<400> SEQUENCE: 50

Thr Gly Ser Ser Ser Asn Ile Gly Ser Gly Tyr Asp Val His
1               5                   10

<210> SEQ ID NO 51
<211> LENGTH: 14
<212> TYPE: PRT
<213> ORGANISM: Homo sapiens

<400> SEQUENCE: 51

Thr Gly Thr Ser Ser Asp Val Gly Gly Tyr Asn Ser Val Ser
1               5                   10

<210> SEQ ID NO 52
<211> LENGTH: 7
<212> TYPE: PRT
<213> ORGANISM: Homo sapiens

<400> SEQUENCE: 52

Gly Ala Ser Ser Arg Ala Thr
1               5

<210> SEQ ID NO 53
<211> LENGTH: 7
<212> TYPE: PRT
<213> ORGANISM: Homo sapiens

<400> SEQUENCE: 53

Tyr Ala Ser Arg Arg Ala Thr
1               5

<210> SEQ ID NO 54
<211> LENGTH: 7
<212> TYPE: PRT
<213> ORGANISM: Homo sapiens

<400> SEQUENCE: 54

Gly Asn Thr His Arg Pro Ser
1               5

<210> SEQ ID NO 55
<211> LENGTH: 7
<212> TYPE: PRT
<213> ORGANISM: Homo sapiens

<400> SEQUENCE: 55

Gly Ala Ser Asn Arg Ala Thr
1               5

<210> SEQ ID NO 56
<211> LENGTH: 7
<212> TYPE: PRT
<213> ORGANISM: Homo sapiens
```

```
<400> SEQUENCE: 56

Gly Asn Ser Lys Arg Pro Ser
1               5

<210> SEQ ID NO 57
<211> LENGTH: 7
<212> TYPE: PRT
<213> ORGANISM: Homo sapiens

<400> SEQUENCE: 57

Ser Val Ser Ser Arg Pro Ser
1               5

<210> SEQ ID NO 58
<211> LENGTH: 9
<212> TYPE: PRT
<213> ORGANISM: Homo sapiens

<400> SEQUENCE: 58

His Gln Tyr Gly Ser Ile Ser Thr Thr
1               5

<210> SEQ ID NO 59
<211> LENGTH: 9
<212> TYPE: PRT
<213> ORGANISM: Homo sapiens

<400> SEQUENCE: 59

Gln Gln Tyr Ser His Leu Leu Ile Thr
1               5

<210> SEQ ID NO 60
<211> LENGTH: 9
<212> TYPE: PRT
<213> ORGANISM: Homo sapiens

<400> SEQUENCE: 60

Gln Gln Tyr Ser His Ile Ser Leu Thr
1               5

<210> SEQ ID NO 61
<211> LENGTH: 9
<212> TYPE: PRT
<213> ORGANISM: Homo sapiens

<400> SEQUENCE: 61

Gln Gln Phe Ala His Ile Leu Leu Thr
1               5

<210> SEQ ID NO 62
<211> LENGTH: 9
<212> TYPE: PRT
<213> ORGANISM: Homo sapiens

<400> SEQUENCE: 62

Gln Gln Thr Ser Asn Thr Pro Phe Thr
1               5

<210> SEQ ID NO 63
<211> LENGTH: 9
<212> TYPE: PRT
<213> ORGANISM: Homo sapiens
```

<400> SEQUENCE: 63

Gln Gln Phe Ile Thr Tyr Leu Pro Thr
1               5

<210> SEQ ID NO 64
<211> LENGTH: 9
<212> TYPE: PRT
<213> ORGANISM: Homo sapiens

<400> SEQUENCE: 64

Gln Gln Asp Ala Leu Ser Pro Phe Thr
1               5

<210> SEQ ID NO 65
<211> LENGTH: 9
<212> TYPE: PRT
<213> ORGANISM: Homo sapiens

<400> SEQUENCE: 65

Gln Gln Asp Arg Gly Thr Pro Phe Thr
1               5

<210> SEQ ID NO 66
<211> LENGTH: 9
<212> TYPE: PRT
<213> ORGANISM: Homo sapiens

<400> SEQUENCE: 66

Gln Gln Ser Leu Asn Ile Pro Phe Thr
1               5

<210> SEQ ID NO 67
<211> LENGTH: 9
<212> TYPE: PRT
<213> ORGANISM: Homo sapiens

<400> SEQUENCE: 67

Gln Gln Asp Thr Ser Ser Pro Phe Thr
1               5

<210> SEQ ID NO 68
<211> LENGTH: 10
<212> TYPE: PRT
<213> ORGANISM: Artificial Sequence
<220> FEATURE:
<223> OTHER INFORMATION: Synthesized human sequence
<220> FEATURE:
<221> NAME/KEY: unsure
<222> LOCATION: (3)
<223> OTHER INFORMATION: Where Xaa can be T, F, D, or S
<220> FEATURE:
<221> NAME/KEY: unsure
<222> LOCATION: (4)
<223> OTHER INFORMATION: Where Xaa can be S, I, A, T, R, or L
<220> FEATURE:
<221> NAME/KEY: unsure
<222> LOCATION: (5)
<223> OTHER INFORMATION: Where Xaa can be N, T, L, S, or G
<220> FEATURE:
<221> NAME/KEY: unsure
<222> LOCATION: (6)
<223> OTHER INFORMATION: Where Xaa can be T, Y, S, or I
<220> FEATURE:
<221> NAME/KEY: unsure
<222> LOCATION: (7)
<223> OTHER INFORMATION: Where Xaa can be P or L
<220> FEATURE:
<221> NAME/KEY: unsure

```
<222> LOCATION: (8)
<223> OTHER INFORMATION: Where Xaa can be F or P

<400> SEQUENCE: 68

Gln Gln Xaa Xaa Xaa Xaa Xaa Xaa Phe Thr
1               5                   10

<210> SEQ ID NO 69
<211> LENGTH: 11
<212> TYPE: PRT
<213> ORGANISM: Homo sapiens

<400> SEQUENCE: 69

Gln Thr Tyr Ala Ser Leu Gly Pro Gly Glu Val
1               5                   10

<210> SEQ ID NO 70
<211> LENGTH: 9
<212> TYPE: PRT
<213> ORGANISM: Homo sapiens

<400> SEQUENCE: 70

Gln Gln Tyr Ser Ser Glu Pro Val Thr
1               5

<210> SEQ ID NO 71
<211> LENGTH: 9
<212> TYPE: PRT
<213> ORGANISM: Homo sapiens

<400> SEQUENCE: 71

Ser Ser Trp Thr Pro Ser Ser Val Val
1               5

<210> SEQ ID NO 72
<211> LENGTH: 11
<212> TYPE: PRT
<213> ORGANISM: Homo sapiens

<400> SEQUENCE: 72

Ser Ser Trp Thr Asp Thr Pro Asn Met Ile Val
1               5                   10

<210> SEQ ID NO 73
<211> LENGTH: 11
<212> TYPE: PRT
<213> ORGANISM: Homo sapiens

<400> SEQUENCE: 73

Ala Ser Trp Thr Asp Gly Leu Ser Leu Val Val
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Synthesized human sequence
<220> FEATURE:
<221> NAME/KEY: unsure
<222> LOCATION: (1)
<223> OTHER INFORMATION: Where Xaa can be S or A
<220> FEATURE:
<221> NAME/KEY: unsure
<222> LOCATION: (6)
<223> OTHER INFORMATION: Where Xaa can be T or G
<220> FEATURE:
```

```
<221> NAME/KEY: unsure
<222> LOCATION: (7)
<223> OTHER INFORMATION: Where Xaa can be P or L
<220> FEATURE:
<221> NAME/KEY: unsure
<222> LOCATION: (8)
<223> OTHER INFORMATION: Where Xaa can be S or N
<220> FEATURE:
<221> NAME/KEY: unsure
<222> LOCATION: (9)
<223> OTHER INFORMATION: Where Xaa can be S, M, or L
<220> FEATURE:
<221> NAME/KEY: unsure
<222> LOCATION: (10)
<223> OTHER INFORMATION: Where Xaa can be I or V

<400> SEQUENCE: 74

Xaa Ser Trp Thr Asp Xaa Xaa Xaa Xaa Xaa Val
1               5                   10

<210> SEQ ID NO 75
<211> LENGTH: 11
<212> TYPE: PRT
<213> ORGANISM: Homo sapiens

<400> SEQUENCE: 75

Ser Ser Tyr Asp Thr Asn Lys Pro Leu Val Val
1               5                   10

<210> SEQ ID NO 76
<211> LENGTH: 11
<212> TYPE: PRT
<213> ORGANISM: Homo sapiens

<400> SEQUENCE: 76

Gly Ser Tyr Asp Val Tyr Gly Arg Phe Tyr Val
1               5                   10

<210> SEQ ID NO 77
<211> LENGTH: 11
<212> TYPE: PRT
<213> ORGANISM: Homo sapiens

<400> SEQUENCE: 77

Ser Ser Tyr Tyr Phe Tyr Leu Gln Arg Ile Val
1               5                   10

<210> SEQ ID NO 78
<211> LENGTH: 11
<212> TYPE: PRT
<213> ORGANISM: Homo sapiens

<400> SEQUENCE: 78

Gln Thr Tyr Tyr Phe Ser Tyr Ser Gly Pro Val
1               5                   10

<210> SEQ ID NO 79
<211> LENGTH: 11
<212> TYPE: PRT
<213> ORGANISM: Homo sapiens

<400> SEQUENCE: 79

Gly Ser Trp Asp Pro Ile Phe Ser Tyr Glu Val
1               5                   10

<210> SEQ ID NO 80
<211> LENGTH: 117
```

```
<212> TYPE: PRT
<213> ORGANISM: Homo sapiens

<400> SEQUENCE: 80

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Gly Ile Ile Pro Met Phe Gly Tyr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ile Tyr Ala Gly Met Asp Val Trp Gly Gln Gly Thr Leu
            100                 105                 110

Val Thr Val Ser Ser
        115

<210> SEQ ID NO 81
<211> LENGTH: 117
<212> TYPE: PRT
<213> ORGANISM: Homo sapiens

<400> SEQUENCE: 81

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Gly Ile Ile Pro Val Phe Gly Phe Thr His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ile Tyr Ala Gly Met Asp Val Trp Gly Gln Gly Thr Leu
            100                 105                 110

Val Thr Val Ser Ser
        115

<210> SEQ ID NO 82
<211> LENGTH: 108
<212> TYPE: PRT
<213> ORGANISM: Homo sapiens

<400> SEQUENCE: 82

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Leu Gly Asn
            20                  25                  30

Tyr Leu Ala Trp Tyr Gln Gln Lys Pro Gly Gln Ala Pro Arg Leu Leu
        35                  40                  45
```

Ile Tyr Gly Ala Ser Ser Arg Ala Thr Gly Val Pro Ala Arg Phe Ser
            50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys His Gln Tyr Gly Ser Ile Ser
                85                  90                  95

Thr Thr Phe Gly Gln Gly Thr Lys Val Glu Ile Lys
            100                 105

<210> SEQ ID NO 83
<211> LENGTH: 108
<212> TYPE: PRT
<213> ORGANISM: Homo sapiens

<400> SEQUENCE: 83

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Leu Gly Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Ser His Ile Ser
                85                  90                  95

Leu Thr Phe Gly Gln Gly Thr Lys Val Glu Ile Lys
            100                 105

<210> SEQ ID NO 84
<211> LENGTH: 108
<212> TYPE: PRT
<213> ORGANISM: Homo sapiens

<400> SEQUENCE: 84

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Leu Gly Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Ser His Leu Ile
                85                  90                  95

Ile Thr Phe Gly Gln Gly Thr Lys Val Glu Ile Lys
            100                 105

<210> SEQ ID NO 85
<211> LENGTH: 108
<212> TYPE: PRT
<213> ORGANISM: Homo sapiens

<400> SEQUENCE: 85

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Leu Gly Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Phe Ala His Ile Leu
                85                  90                  95

Leu Thr Phe Gly Gln Gly Thr Lys Val Glu Ile Lys
            100                 105

<210> SEQ ID NO 86
<211> LENGTH: 127
<212> TYPE: PRT
<213> ORGANISM: Homo sapiens

<400> SEQUENCE: 86

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Asn
            20                  25                  30

Tyr Ile Ser Trp Val Arg Gln Ala Pro Gly Gln Gly Leu Glu Trp Met
        35                  40                  45

Gly Gly Ile Ile Pro Ile Phe Gly His Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Lys Gly Met Tyr Gly Gly Trp Thr Tyr Pro Leu Met
            100                 105                 110

Met Phe Asp Leu Trp Gly Gln Gly Thr Leu Val Thr Val Ser Ser
        115                 120                 125

<210> SEQ ID NO 87
<211> LENGTH: 127
<212> TYPE: PRT
<213> ORGANISM: Homo sapiens

<400> SEQUENCE: 87

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Asn
            20                  25                  30

Tyr Ile Ser Trp Val Arg Gln Ala Pro Gly Gln Gly Leu Glu Trp Met
        35                  40                  45

Gly Ile Ile Ile Pro Pro Ile Gly Asn Ala Trp Tyr Ala Gln Lys Phe
    50                  55                  60

Gln Gly Arg Val Thr Ile Thr Ala Asp Glu Ser Thr Ser Thr Ala Tyr
65                  70                  75                  80

```
Met Glu Leu Ser Ser Leu Arg Ser Glu Asp Thr Ala Val Tyr Tyr Cys
                85                  90                  95

Ala Arg Ser Lys Lys Gly Met Tyr Gly Gly Trp Thr Tyr Pro Leu Met
            100                 105                 110

Met Phe Asp Leu Trp Gly Gln Gly Thr Leu Val Thr Val Ser Ser
        115                 120                 125
```

<210> SEQ ID NO 88
<211> LENGTH: 127
<212> TYPE: PRT
<213> ORGANISM: Homo sapiens

<400> SEQUENCE: 88

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Asn
            20                  25                  30

Tyr Ile Ser Trp Val Arg Gln Ala Pro Gly Gln Gly Leu Glu Trp Met
        35                  40                  45

Gly Ile Ser Pro Gly Thr Gly Ile Asn Ala Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Lys Gly Met Tyr Gly Gly Trp Thr Tyr Pro Leu Met
            100                 105                 110

Met Phe Asp Leu Trp Gly Gln Gly Thr Leu Val Thr Val Ser Ser
        115                 120                 125
```

<210> SEQ ID NO 89
<211> LENGTH: 126
<212> TYPE: PRT
<213> ORGANISM: Homo sapiens

<400> SEQUENCE: 89

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Asn
            20                  25                  30

Tyr Ile Ser Trp Val Arg Gln Ala Pro Gly Gln Gly Leu Glu Trp Met
        35                  40                  45

Gly Ile Asn Ala His Leu Gly Gly Thr Trp Tyr Ala Gln Lys Phe Gln
    50                  55                  60

Gly Arg Val Thr Ile Thr Ala Asp Glu Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Ser Lys Lys Gly Met Tyr Gly Gly Trp Thr Tyr Pro Leu Met Met
            100                 105                 110

Phe Asp Leu Trp Gly Gln Gly Thr Leu Val Thr Val Ser Ser
        115                 120                 125
```

<210> SEQ ID NO 90
<211> LENGTH: 127
<212> TYPE: PRT
<213> ORGANISM: Homo sapiens

<400> SEQUENCE: 90

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Asn
            20                  25                  30

Tyr Ile Ser Trp Val Arg Gln Ala Pro Gly Gln Gly Leu Glu Trp Met
        35                  40                  45

Gly Leu Ile Asp Pro Asn Phe Gly Gly Ala Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Lys Gly Met Tyr Gly Gly Trp Thr Tyr Pro Leu Met
            100                 105                 110

Met Phe Asp Leu Trp Gly Gln Gly Thr Leu Val Thr Val Ser Ser
        115                 120                 125

<210> SEQ ID NO 91
<211> LENGTH: 127
<212> TYPE: PRT
<213> ORGANISM: Homo sapiens

<400> SEQUENCE: 91

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Asn
            20                  25                  30

Tyr Ile Ser Trp Val Arg Gln Ala Pro Gly Gln Gly Leu Glu Trp Met
        35                  40                  45

Gly Leu Ile Asp Pro Val Phe Gly Gly Ala Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Lys Gly Met Tyr Gly Gly Trp Thr Tyr Pro Leu Met
            100                 105                 110

Met Phe Asp Leu Trp Gly Gln Gly Thr Leu Val Thr Val Ser Ser
        115                 120                 125

<210> SEQ ID NO 92
<211> LENGTH: 127
<212> TYPE: PRT
<213> ORGANISM: Homo sapiens

<400> SEQUENCE: 92

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Asn
            20                  25                  30

Tyr Ile Ser Trp Val Arg Gln Ala Pro Gly Gln Gly Leu Glu Trp Met
        35                  40                  45

Gly Leu Ile Asp Pro Met Phe Gly Gly Ala Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Lys Gly Met Tyr Gly Gly Trp Thr Tyr Pro Leu Met
            100                 105                 110

Met Phe Asp Leu Trp Gly Gln Gly Thr Leu Val Thr Val Ser Ser
        115                 120                 125

<210> SEQ ID NO 93
<211> LENGTH: 108
<212> TYPE: PRT
<213> ORGANISM: Homo sapiens

<400> SEQUENCE: 93

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Tyr Ala Ser Arg Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Gln Gln Thr Ser Asn Thr Pro
                85                  90                  95

Phe Thr Phe Gly Gln Gly Thr Lys Val Glu Ile Lys
            100                 105

<210> SEQ ID NO 94
<211> LENGTH: 108
<212> TYPE: PRT
<213> ORGANISM: Homo sapiens

<400> SEQUENCE: 94

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Tyr Ala Ser Arg Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Thr Ser Asn Thr Pro
                85                  90                  95

Phe Thr Phe Gly Gln Gly Thr Lys Val Glu Ile Lys
            100                 105

<210> SEQ ID NO 95
<211> LENGTH: 108
<212> TYPE: PRT
<213> ORGANISM: Homo sapiens

<400> SEQUENCE: 95

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Tyr Ala Ser Arg Arg Ala Thr Gly Val Pro Ala Arg Phe Ser
50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Phe Ile Thr Tyr Leu
                85                  90                  95

Pro Thr Phe Gly Gln Gly Thr Lys Val Glu Ile Lys
            100                 105

<210> SEQ ID NO 96
<211> LENGTH: 108
<212> TYPE: PRT
<213> ORGANISM: Homo sapiens

<400> SEQUENCE: 96

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Tyr Ala Ser Arg Arg Ala Thr Gly Val Pro Ala Arg Phe Ser
50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Asp Ala Leu Ser Pro
                85                  90                  95

Phe Thr Phe Gly Gln Gly Thr Lys Val Glu Ile Lys
            100                 105

<210> SEQ ID NO 97
<211> LENGTH: 108
<212> TYPE: PRT
<213> ORGANISM: Homo sapiens

<400> SEQUENCE: 97

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Tyr Ala Ser Arg Arg Ala Thr Gly Val Pro Ala Arg Phe Ser
50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Asp Arg Gly Thr Pro
                85                  90                  95

Phe Thr Phe Gly Gln Gly Thr Lys Val Glu Ile Lys
            100                 105

<210> SEQ ID NO 98
<211> LENGTH: 108
<212> TYPE: PRT
<213> ORGANISM: Homo sapiens

<400> SEQUENCE: 98

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Tyr Ala Ser Arg Arg Ala Thr Gly Val Pro Ala Arg Phe Ser
50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Ser Leu Asn Ile Pro
                85                  90                  95

Phe Thr Phe Gly Gln Gly Thr Lys Val Glu Ile Lys
            100                 105

<210> SEQ ID NO 99
<211> LENGTH: 116
<212> TYPE: PRT
<213> ORGANISM: Homo sapiens

<400> SEQUENCE: 99

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Ser Trp Val Arg Gln Ala Pro Gly Lys Gly Leu Glu Trp Met
        35                  40                  45

Gly Trp Ile Arg Pro Gly Asp Ser Asp Thr Arg Tyr Ser Pro Ser Phe
50                  55                  60

Glu Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Tyr Tyr Gly Met Asp Tyr Trp Gly Gln Gly Thr Leu Val
            100                 105                 110

Thr Val Ser Ser
        115

<210> SEQ ID NO 100
<211> LENGTH: 110
<212> TYPE: PRT
<213> ORGANISM: Homo sapiens

<400> SEQUENCE: 100

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Tyr
            20                  25                  30

```
Tyr Val Asn Trp Tyr Gln Gln Leu Pro Gly Thr Ala Pro Lys Leu Leu
            35                  40                  45

Ile Tyr Gly Asn Thr His Arg Pro Ser Gly Val Pro Asp Arg Phe Ser
 50                  55                  60

Gly Ser Lys Ser Gly Thr Ser Ala Ser Leu Ala Ile Thr Gly Leu Gln
 65                  70                  75                  80

Ser Glu Asp Glu Ala Asp Tyr Tyr Cys Gln Thr Tyr Ala Ser Leu Gly
                85                  90                  95

Pro Gly Glu Val Phe Gly Gly Gly Thr Lys Leu Thr Val Leu
               100                 105                 110

<210> SEQ ID NO 101
<211> LENGTH: 121
<212> TYPE: PRT
<213> ORGANISM: Homo sapiens

<400> SEQUENCE: 101

Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                20                  25                  30

Trp Ile Thr Trp Val Arg Gln Ala Pro Gly Lys Gly Leu Glu Trp Val
            35                  40                  45

Ser Tyr Ile Ser Ser Ser Gly Ser Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Thr Phe Trp Ser Phe Gly Asn Tyr Phe Ala Asn Trp Gly
               100                 105                 110

Gln Gly Thr Leu Val Thr Val Ser Ser
           115                 120

<210> SEQ ID NO 102
<211> LENGTH: 107
<212> TYPE: PRT
<213> ORGANISM: Homo sapiens

<400> SEQUENCE: 102

Asp Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Ile Phe Tyr Asn
                20                  25                  30

Leu Ala Trp Tyr Gln Gln Lys Pro Gly Gln Ala Pro Arg Leu Leu Ile
            35                  40                  45

Tyr Gly Ala Ser Asn Arg Ala Thr Gly Val Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Thr Tyr Tyr Cys Gln Gln Tyr Ser Ser Glu Pro Val
                85                  90                  95

Thr Phe Gly Gln Gly Thr Lys Val Glu Ile Lys
               100                 105

<210> SEQ ID NO 103
```

```
<211> LENGTH: 117
<212> TYPE: PRT
<213> ORGANISM: Homo sapiens

<400> SEQUENCE: 103

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
        35                  40                  45

Gly Ile Ile Asp Pro Ser Asn Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Tyr Tyr Lys Pro Phe Asp Val Trp Gly Gln Gly Thr Leu
                100                 105                 110

Val Thr Val Ser Ser
            115

<210> SEQ ID NO 104
<211> LENGTH: 117
<212> TYPE: PRT
<213> ORGANISM: Homo sapiens

<400> SEQUENCE: 104

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
        35                  40                  45

Gly Ile Ile Asp Pro Ser Asn Ser Tyr Thr Asp Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Tyr Tyr Lys Pro Phe Asp Val Trp Gly Gln Gly Thr Leu
                100                 105                 110

Val Thr Val Ser Ser
            115

<210> SEQ ID NO 105
<211> LENGTH: 117
<212> TYPE: PRT
<213> ORGANISM: Homo sapiens

<400> SEQUENCE: 105

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
        35                  40                  45
```

Gly Ile Ile Asp Pro Ser Asn Ser Tyr Thr Arg Tyr Ser Pro Ser Phe
            50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Trp Tyr Tyr Lys Pro Phe Asp Val Trp Gly Gln Gly Thr Leu
                100                 105                 110

Val Thr Val Ser Ser
            115

<210> SEQ ID NO 106
<211> LENGTH: 117
<212> TYPE: PRT
<213> ORGANISM: Homo sapiens

<400> SEQUENCE: 106

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Ser Asn Tyr
                 20                  25                  30

Trp Ile Gly Trp Val Arg Gln Met Pro Gly Lys Gly Leu Glu Trp Met
             35                  40                  45

Gly Ile Ile Asp Pro Ser Asn Ser Tyr Thr Arg Tyr Ser Pro Ser Phe
            50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Trp Tyr Tyr Lys Pro Phe Asp Val Trp Gly Gln Gly Thr Leu
                100                 105                 110

Val Thr Val Ser Ser
            115

<210> SEQ ID NO 107
<211> LENGTH: 117
<212> TYPE: PRT
<213> ORGANISM: Homo sapiens

<400> SEQUENCE: 107

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Ser Asn Tyr
                 20                  25                  30

Trp Ile Gly Trp Val Arg Gln Met Pro Gly Lys Gly Leu Glu Trp Met
             35                  40                  45

Gly Ile Ile Asp Pro Val Ser Ser Trp Thr Lys Tyr Ser Pro Ser Phe
            50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Trp Tyr Tyr Lys Pro Phe Asp Val Trp Gly Gln Gly Thr Leu
                100                 105                 110

Val Thr Val Ser Ser
            115

<210> SEQ ID NO 108
<211> LENGTH: 117
<212> TYPE: PRT
<213> ORGANISM: Homo sapiens

<400> SEQUENCE: 108

Gln Val Gln Leu Val Gln Ser Gly Ala Glu Val Lys Lys Pro Gly Glu
1               5                   10                  15
Ser Leu Lys Ile Ser Cys Lys Gly Ser Gly Tyr Ser Phe Ser Asn Tyr
            20                  25                  30
Trp Ile Gly Trp Val Arg Gln Met Pro Gly Lys Gly Leu Glu Trp Met
        35                  40                  45
Gly Ile Ile Ser Pro Ser Gly Ser Thr Thr Trp Tyr Ser Pro Ser Phe
    50                  55                  60
Gln Gly Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Ala Arg Trp Tyr Tyr Lys Pro Phe Asp Val Trp Gly Gln Gly Thr Leu
            100                 105                 110
Val Thr Val Ser Ser
        115

<210> SEQ ID NO 109
<211> LENGTH: 117
<212> TYPE: PRT
<213> ORGANISM: Homo sapiens

<400> SEQUENCE: 109

Gln Val Gln Leu Val Gln Ser Gly Ala Glu Val Lys Lys Pro Gly Glu
1               5                   10                  15
Ser Leu Lys Ile Ser Cys Lys Gly Ser Gly Tyr Ser Phe Ser Asn Tyr
            20                  25                  30
Trp Ile Gly Trp Val Arg Gln Met Pro Gly Lys Gly Leu Glu Trp Met
        35                  40                  45
Gly Phe Ile Ser Pro Asp Gly Ser His Thr Trp Tyr Ser Pro Ser Phe
    50                  55                  60
Gln Gly Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Ala Arg Trp Tyr Tyr Lys Pro Phe Asp Val Trp Gly Gln Gly Thr Leu
            100                 105                 110
Val Thr Val Ser Ser
        115

<210> SEQ ID NO 110
<211> LENGTH: 117
<212> TYPE: PRT
<213> ORGANISM: Homo sapiens

<400> SEQUENCE: 110

Gln Val Gln Leu Val Gln Ser Gly Ala Glu Val Lys Lys Pro Gly Glu
1               5                   10                  15
Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
            35                  40                  45

Gly Ile Ile Ser Pro Thr Gly Ser Val Thr Trp Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Tyr Tyr Lys Pro Phe Asp Val Trp Gly Gln Gly Thr Leu
            100                 105                 110

Val Thr Val Ser Ser
        115

<210> SEQ ID NO 111
<211> LENGTH: 117
<212> TYPE: PRT
<213> ORGANISM: Homo sapiens

<400> SEQUENCE: 111

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
            35                  40                  45

Gly Ile Ile Ser Pro Thr Gly Ser Ser Thr Trp Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Tyr Tyr Lys Pro Phe Asp Val Trp Gly Gln Gly Thr Leu
            100                 105                 110

Val Thr Val Ser Ser
        115

<210> SEQ ID NO 112
<211> LENGTH: 117
<212> TYPE: PRT
<213> ORGANISM: Homo sapiens

<400> SEQUENCE: 112

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
            35                  40                  45

Gly Ile Ile Ser Pro Thr Gly Ser Ala Thr Trp Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Tyr Tyr Lys Pro Phe Asp Val Trp Gly Gln Gly Thr Leu
            100                 105                 110

Val Thr Val Ser Ser
        115

<210> SEQ ID NO 113
<211> LENGTH: 109
<212> TYPE: PRT
<213> ORGANISM: Homo sapiens

<400> SEQUENCE: 113

Asp Ile Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ser Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Lys Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ser Glu Asp Glu Ala Asp Tyr Tyr Cys Ser Ser Trp Thr Pro Ser
                85                  90                  95

Ser Val Val Phe Gly Gly Gly Thr Lys Leu Thr Val Leu
            100                 105

<210> SEQ ID NO 114
<211> LENGTH: 111
<212> TYPE: PRT
<213> ORGANISM: Homo sapiens

<400> SEQUENCE: 114

Asp Ile Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ser Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Lys Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ser Glu Asp Glu Ala Asp Tyr Tyr Cys Ser Ser Trp Thr Asp Thr
                85                  90                  95

Pro Asn Met Ile Val Phe Gly Gly Thr Lys Leu Thr Val Leu
            100                 105                 110

<210> SEQ ID NO 115
<211> LENGTH: 111
<212> TYPE: PRT
<213> ORGANISM: Homo sapiens

<400> SEQUENCE: 115

Asp Ile Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ser Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Lys Arg Pro Ser Gly Val Pro Asp Arg Phe
            50                  55                  60

Ser Gly Ser Lys Ser Gly Thr Ser Ala Ser Leu Ala Ile Thr Gly Leu
65                  70                  75                  80

Gln Ser Glu Asp Glu Ala Asp Tyr Tyr Cys Ala Ser Trp Thr Asp Gly
                85                  90                  95

Leu Ser Leu Val Val Phe Gly Gly Gly Thr Lys Leu Thr Val Leu
            100                 105                 110

<210> SEQ ID NO 116
<211> LENGTH: 111
<212> TYPE: PRT
<213> ORGANISM: Homo sapiens

<400> SEQUENCE: 116

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ser Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Lys Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ser Glu Asp Glu Ala Asp Tyr Tyr Cys Ala Ser Trp Thr Asp Gly
                85                  90                  95

Leu Ser Leu Val Val Phe Gly Gly Gly Thr Lys Leu Thr Val Leu
            100                 105                 110

<210> SEQ ID NO 117
<211> LENGTH: 121
<212> TYPE: PRT
<213> ORGANISM: Homo sapiens

<400> SEQUENCE: 117

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Asn Ile Ser Ser Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Gly Thr Pro Tyr Leu Met Gln Phe Asp Asn Trp Gly
            100                 105                 110

Gln Gly Thr Leu Val Thr Val Ser Ser
        115                 120

<210> SEQ ID NO 118
<211> LENGTH: 123
<212> TYPE: PRT
<213> ORGANISM: Homo sapiens -continued

<400> SEQUENCE: 118

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Asn Ile Glu His Lys Phe Met Gly Tyr Thr Thr Tyr Tyr Ala Ala
    50                  55                  60

Gly Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Tyr Trp Gly Thr Pro Tyr Leu Met Gln Phe Asp Asn
            100                 105                 110

Trp Gly Gln Gly Thr Leu Val Thr Val Ser Ser
            115                 120

<210> SEQ ID NO 119
<211> LENGTH: 123
<212> TYPE: PRT
<213> ORGANISM: Homo sapiens

<400> SEQUENCE: 119

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Glu His Lys Tyr Thr Gly Tyr Thr Thr Tyr Tyr Ala Ala
    50                  55                  60

Pro Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Tyr Trp Gly Thr Pro Tyr Leu Met Gln Phe Asp Asn
            100                 105                 110

Trp Gly Gln Gly Thr Leu Val Thr Val Ser Ser
            115                 120

<210> SEQ ID NO 120
<211> LENGTH: 123
<212> TYPE: PRT
<213> ORGANISM: Homo sapiens

<400> SEQUENCE: 120

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Asn Ile Glu His Lys Tyr Thr Ser Tyr Thr Thr Tyr Tyr Ala Ala
    50                  55                  60

```
Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg Tyr Trp Gly Thr Pro Tyr Leu Met Gln Phe Asp Asn
            100                 105                 110

Trp Gly Gln Gly Thr Leu Val Thr Val Ser Ser
        115                 120
```

<210> SEQ ID NO 121
<211> LENGTH: 123
<212> TYPE: PRT
<213> ORGANISM: Homo sapiens

<400> SEQUENCE: 121

```
Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Phe
                 20                  25                  30

Gly Met Ser Trp Val Arg Gln Ala Pro Gly Lys Gly Leu Glu Trp Val
             35                  40                  45

Ser Asn Ile Glu His Lys Tyr Leu Asn Tyr Ala Thr Tyr Tyr Ala Ala
         50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg Tyr Trp Gly Thr Pro Tyr Leu Met Gln Phe Asp Asn
            100                 105                 110

Trp Gly Gln Gly Thr Leu Val Thr Val Ser Ser
        115                 120
```

<210> SEQ ID NO 122
<211> LENGTH: 123
<212> TYPE: PRT
<213> ORGANISM: Homo sapiens

<400> SEQUENCE: 122

```
Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Phe
                 20                  25                  30

Gly Met Ser Trp Val Arg Gln Ala Pro Gly Lys Gly Leu Glu Trp Val
             35                  40                  45

Ser Asn Ile Glu His Lys Tyr Leu Gly Tyr Ala Thr Val Tyr Ala Ala
         50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg Tyr Trp Gly Thr Pro Tyr Leu Met Gln Phe Asp Asn
            100                 105                 110

Trp Gly Gln Gly Thr Leu Val Thr Val Ser Ser
        115                 120
```

<210> SEQ ID NO 123

```
<211> LENGTH: 123
<212> TYPE: PRT
<213> ORGANISM: Homo sapiens

<400> SEQUENCE: 123

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Glu His Lys Tyr Leu Ser Tyr Ala Thr Tyr Tyr Ala Ala
    50                  55                  60

Gly Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Tyr Trp Gly Thr Pro Tyr Leu Met Gln Phe Asp Asn
            100                 105                 110

Trp Gly Gln Gly Thr Leu Val Thr Val Ser Ser
        115                 120

<210> SEQ ID NO 124
<211> LENGTH: 123
<212> TYPE: PRT
<213> ORGANISM: Homo sapiens

<400> SEQUENCE: 124

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Glu His Lys Tyr Leu Ser Tyr Thr Thr Phe Tyr Ala Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Tyr Trp Gly Thr Pro Tyr Leu Met Gln Phe Asp Asn
            100                 105                 110

Trp Gly Gln Gly Thr Leu Val Thr Val Ser Ser
        115                 120

<210> SEQ ID NO 125
<211> LENGTH: 123
<212> TYPE: PRT
<213> ORGANISM: Homo sapiens

<400> SEQUENCE: 125

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45
```

Ser Gly Ile Glu His Lys Tyr Leu Ser Tyr Thr Thr His Tyr Ala Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Tyr Trp Gly Thr Pro Tyr Leu Met Gln Phe Asp Asn
                100                 105                 110

Trp Gly Gln Gly Thr Leu Val Thr Val Ser Ser
            115                 120

<210> SEQ ID NO 126
<211> LENGTH: 123
<212> TYPE: PRT
<213> ORGANISM: Homo sapiens

<400> SEQUENCE: 126

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Gln Ile Glu His Lys Tyr Leu Ser Tyr Thr Thr Leu Tyr Ala Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Tyr Trp Gly Thr Pro Tyr Leu Met Gln Phe Asp Asn
                100                 105                 110

Trp Gly Gln Gly Thr Leu Val Thr Val Ser Ser
            115                 120

<210> SEQ ID NO 127
<211> LENGTH: 123
<212> TYPE: PRT
<213> ORGANISM: Homo sapiens

<400> SEQUENCE: 127

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Gly Ile Glu His Lys Tyr Leu Ser Tyr Ala Thr Leu Tyr Ala Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Tyr Trp Gly Thr Pro Tyr Leu Met Gln Phe Asp Asn
                100                 105                 110

Trp Gly Gln Gly Thr Leu Val Thr Val Ser Ser
            115                 120

<210> SEQ ID NO 128
<211> LENGTH: 111
<212> TYPE: PRT
<213> ORGANISM: Homo sapiens

<400> SEQUENCE: 128

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
        35                  40                  45

Met Ile Tyr Ser Val Ser Ser Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Asp Thr Asn
                85                  90                  95

Lys Pro Leu Val Val Phe Gly Gly Gly Thr Lys Leu Thr Val Leu
            100                 105                 110

<210> SEQ ID NO 129
<211> LENGTH: 111
<212> TYPE: PRT
<213> ORGANISM: Homo sapiens

<400> SEQUENCE: 129

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
        35                  40                  45

Met Ile Tyr Ser Val Ser Ser Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Tyr Phe Tyr
                85                  90                  95

Leu Gln Arg Ile Val Phe Gly Gly Gly Thr Lys Leu Thr Val Leu
            100                 105                 110

<210> SEQ ID NO 130
<211> LENGTH: 111
<212> TYPE: PRT
<213> ORGANISM: Homo sapiens

<400> SEQUENCE: 130

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
        35                  40                  45

Met Ile Tyr Ser Val Ser Ser Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Thr Tyr Tyr Phe Ser
                85                  90                  95

Tyr Ser Gly Pro Val Phe Gly Gly Gly Thr Lys Leu Thr Val Leu
            100                 105                 110

<210> SEQ ID NO 131
<211> LENGTH: 111
<212> TYPE: PRT
<213> ORGANISM: Homo sapiens

<400> SEQUENCE: 131

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
        35                  40                  45

Met Ile Tyr Ser Val Ser Ser Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Asp Val Tyr
                85                  90                  95

Gly Arg Phe Tyr Val Phe Gly Gly Gly Thr Lys Leu Thr Val Leu
            100                 105                 110

<210> SEQ ID NO 132
<211> LENGTH: 111
<212> TYPE: PRT
<213> ORGANISM: Homo sapiens

<400> SEQUENCE: 132

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
        35                  40                  45

Met Ile Tyr Ser Val Ser Ser Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Trp Asp Pro Ile
                85                  90                  95

Phe Ser Tyr Glu Val Phe Gly Gly Gly Thr Lys Leu Thr Val Leu
            100                 105                 110

<210> SEQ ID NO 133
<211> LENGTH: 381
<212> TYPE: DNA
<213> ORGANISM: Homo sapiens

<400> SEQUENCE: 133
caggtgcagc tggtgcagtc tggggctgag gtgaagaagc ctgggtcctc ggtgaaggtc    60
tcctgcaagg cttctggagg caccttcagc agcaactaca tcagctgggt gcgacaggcc   120

```
cctggacaag ggcttgagtg gatggggatc agccctggca ccggtatcaa cgcatactac        180
gcacagaagt tccagggcag agtcacgatt accgcggacg aatccacgag cacagcctac        240
atggagctga gcagcctgag atctgaggac acggccgtgt attactgtgc gagaagcaag        300
aagggcatgt acggcggctg gacctacccc ctgatgatgt tcgacctgtg gggccagggc        360
accctggtga ccgtgagcag c                                                  381

<210> SEQ ID NO 134
<211> LENGTH: 381
<212> TYPE: DNA
<213> ORGANISM: Homo sapiens

<400> SEQUENCE: 134
caggtgcagc tggtgcagag cggcgccgag gtgaagaagc ccggcagcag cgtgaaggtg         60
agctgcaagg ccagcggcgg caccttcagc agcaactaca tcagctgggt gcgccaggcc        120
cccggccagg gcctggagtg gatgggcatc agccccggca ccggcatcaa cgcctactac        180
gcccagaagt tccagggccg cgtgaccatc accgccgacg agagcaccag caccgcctac        240
atggagctga gcagcctgcg cagcgaggac accgccgtgt actactgcgc ccgcagcaag        300
aagggcatgt acggcggctg gacctacccc ctgatgatgt tcgacctgtg gggccagggc        360
accctggtga ccgtgagcag c                                                  381

<210> SEQ ID NO 135
<211> LENGTH: 381
<212> TYPE: DNA
<213> ORGANISM: Homo sapiens

<400> SEQUENCE: 135
caggtgcaat tggttcagtc tggcgcggaa gtgaaaaaac cgggcagcag cgtgaaagtg         60
agctgcaaag cctccggagg cactttttct tctaattata tttcttgggt gcgccaagcc        120
cctgggcagg gtctcgagtg gatgggcatt tctcctggta ctggtattaa tgcttattat        180
gctcagaagt ttcagggtcg ggtgaccatt accgcggatg aaagcaccag caccgcgtat        240
atggaactga gcagcctgcg tagcgaagat acggccgtgt attattgcgc gcgttctaag        300
aagggtatgt atggtggttg gacttatcct cttatgatgt ttgatctttg gggccaaggc        360
accctggtga cggttagctc a                                                  381

<210> SEQ ID NO 136
<211> LENGTH: 324
<212> TYPE: DNA
<213> ORGANISM: Homo sapiens

<400> SEQUENCE: 136
gagatcgtgc tgacccagag cccccgccacc ctgagcctga gccccggcga gcgcgccacc        60
ctgagctgcc gcgccagcca gagcgtgagc agcaactacc tggcctggta ccagcagaag        120
cccggccagg cccccccgcct gctgatctac tacgccagcc gccgcgccac cggcgtgccc        180
gcccgcttca gcggcagcgg cagcggcacc gacttcaccc tgaccatcag cagcctggag        240
cccgaggact tcgccgtgta ctactgccag cagaccagca cacccccctt caccttcggc        300
cagggcacca aggtggagat caag                                               324

<210> SEQ ID NO 137
<211> LENGTH: 324
<212> TYPE: DNA
```

<213> ORGANISM: Homo sapiens

<400> SEQUENCE: 137

| | |
|---|---|
| gaaattgtgt tgacacagtc tccagccacc ctgtctttgt ctccagggga aagagccacc | 60 |
| ctctcctgca gggccagtca gagtgttagc agcaactact tagcctgta ccaacagaaa | 120 |
| cctggccagg ctcccaggct cctcatctat tacgcatccc gcagggccac tggcgtgcca | 180 |
| gccaggttca gtggcagtgg gtctgggaca gacttcactc tcaccatcag cagcctagag | 240 |
| cctgaagatt ttgcagttta ttactgtcag cagacttcta atactccttt tacctttggc | 300 |
| cagggtacga agttgaaat taaa | 324 |

<210> SEQ ID NO 138
<211> LENGTH: 324
<212> TYPE: DNA
<213> ORGANISM: Homo sapiens

<400> SEQUENCE: 138

| | |
|---|---|
| gagatcgtgc tgacccagag cccggcgacc ctgagcctgt ctccgggcga acgtgcgacc | 60 |
| ctgagctgca gagcgagcca gtctgttct tctaattatc tggcttggta ccagcagaaa | 120 |
| ccaggtcaag caccgcgtct attaatttat tatgcttctc gtcgtgcaac tggggtcccg | 180 |
| gcgcgttta gcggctctgg atccggcacg gatttacccc tgaccattag cagcctggaa | 240 |
| cctgaagact ttgcggtgta ttattgccag cagacttcta atactccttt tacctttggc | 300 |
| cagggtacga agttgaaat taaa | 324 |

<210> SEQ ID NO 139
<211> LENGTH: 351
<212> TYPE: DNA
<213> ORGANISM: Homo sapiens

<400> SEQUENCE: 139

| | |
|---|---|
| gaggtgcagc tggtgcagtc tggagcagag gtgaaaaagc ccggggagtc tctgaagatc | 60 |
| tcctgtaagg gttctggata cagctttagc aactactgga tcggctgggt gcgccagatg | 120 |
| cccgggaaag gcctggagtg gatggggatc atcgacccta gcaactctta caccagatac | 180 |
| agcccgtcct tccaaggcca ggtcaccatc tcagccgaca gtccatcag caccgcctac | 240 |
| ctgcagtgga gcagcctgaa ggcctcggac accgccatgt attactgtgc gagatggtac | 300 |
| tacaagccct cgacgtgtg gggccagggc accctggtga ccgtgagcag c | 351 |

<210> SEQ ID NO 140
<211> LENGTH: 351
<212> TYPE: DNA
<213> ORGANISM: Homo sapiens

<400> SEQUENCE: 140

| | |
|---|---|
| gaggtgcagc tggtgcagag cggcgccgag gtgaagaagc ccggcgagag cctgaagatc | 60 |
| agctgcaagg gcagcggcta cagcttcagc aactactgga tcggctgggt gcgccagatg | 120 |
| cccggcaagg gcctggagtg gatgggcatc atcgacccca gcaacagcta cacccgctac | 180 |
| agccccagct ccagggcca ggtgaccatc agcgccgaca gagcatcag caccgcctac | 240 |
| ctgcagtgga gcagcctgaa ggccagcgac accgccatgt actactgcgc ccgctggtac | 300 |
| tacaagccct cgacgtgtg gggccagggc accctggtga ccgtgagcag c | 351 |

<210> SEQ ID NO 141
<211> LENGTH: 351

```
<212> TYPE: DNA
<213> ORGANISM: Homo sapiens

<400> SEQUENCE: 141
gaggtgcaat tggttcagag cggcgcggaa gtgaaaaaac cgggcgaaag cctgaaaatt    60
agctgcaaag gttccggata ttccttttct aattattgga ttggttgggt gcgccagatg   120
cctgggaagg gtctcgagtg gatgggcatt atcgatccgt ctaatagcta tacccgctat   180
tctccgagct ttcagggcca ggtgaccatt agcgcggata aaagcattag caccgcgtat   240
cttcaatgga gcagcctgaa agcgagcgat acggccatgt attattgcgc gcgttggtat   300
tataagcctt ttgatgtttg gggccaaggc accctggtga cggttagctc a            351

<210> SEQ ID NO 142
<211> LENGTH: 336
<212> TYPE: DNA
<213> ORGANISM: Homo sapiens

<400> SEQUENCE: 142
cagtctgtgc tgacgcagcc gcccctcagtg tctggggccc cagggcagag ggtcaccatc    60
tcctgcactg ggagcagctc caacatcggg agcggttatg atgtacactg gtaccagcag   120
cttccaggaa cagcccccaa actcctcatc tatggtaaca gcaagcggcc ctcaggggtc   180
cctgaccgat tctctggctc caagtctggc acctcagcct ccctggccat cactgggctc   240
cagagcgagg atgaggctga ttattactgc gccagctgga ccgacggcct gagcctggtg   300
gtgttcggcg gcggcaccaa gctgaccgtg ctgggc                               336

<210> SEQ ID NO 143
<211> LENGTH: 336
<212> TYPE: DNA
<213> ORGANISM: Homo sapiens

<400> SEQUENCE: 143
cagagcgtgc tgacccagcc ccccagcgtg agcggcgccc ccggccagcg cgtgaccatc    60
agctgcaccg gcagcagcag caacatcggc agcggctacg acgtgcactg gtaccagcag   120
ctgcccggca ccgccccccaa gctgctgatc tacggcaaca gcaagcgccc cagcggcgtg   180
cccgaccgct tcagcggcag caagagcggc accagcgcca gcctggccat caccggcctc   240
cagagcgagg acgaggccga ctactactgt gccagctgga ccgacggcct gagcctggtg   300
gtgttcggcg gcggcaccaa gctgaccgtg ctgggc                               336

<210> SEQ ID NO 144
<211> LENGTH: 336
<212> TYPE: DNA
<213> ORGANISM: Homo sapiens

<400> SEQUENCE: 144
cagagcgtgc tgacccagcc gccttcagtg agtggcgcac caggtcagcg tgtgaccatc    60
tcgtgtacgg gcagcagcag caacattggt tctggttatg atgtgcattg gtaccagcag   120
ttgcccggga cggcgccgaa acttctgatt tatggtaatt ctaagcgtcc ctcaggcgtg   180
ccggatcgtt ttagcggatc caaaagcggc accagcgcga gccttgcgat tacgggcctg   240
caaagcgaag acgaagcgga ttattattgc gcttcttgga ctgatggtct ttctcttgtt   300
gtgtttggcg gcggcacgaa gttaaccgtt cttggc                               336

<210> SEQ ID NO 145
```

<211> LENGTH: 189
<212> TYPE: PRT
<213> ORGANISM: Homo sapiens

<400> SEQUENCE: 145

Met Leu Gly Ser Arg Ala Val Met Leu Leu Leu Leu Pro Trp Thr
1               5                   10                  15

Ala Gln Gly Arg Ala Val Pro Gly Gly Ser Ser Pro Ala Trp Thr Gln
            20                  25                  30

Cys Gln Gln Leu Ser Gln Lys Leu Cys Thr Leu Ala Trp Ser Ala His
                35                  40                  45

Pro Leu Val Gly His Met Asp Leu Arg Glu Glu Gly Asp Glu Glu Thr
    50                  55                  60

Thr Asn Asp Val Pro His Ile Gln Cys Gly Asp Gly Cys Asp Pro Gln
65                  70                  75                  80

Gly Leu Arg Asp Asn Ser Gln Phe Cys Leu Gln Arg Ile His Gln Gly
                85                  90                  95

Leu Ile Phe Tyr Glu Lys Leu Leu Gly Ser Asp Ile Phe Thr Gly Glu
            100                 105                 110

Pro Ser Leu Leu Pro Asp Ser Pro Val Ala Gln Leu His Ala Ser Leu
        115                 120                 125

Leu Gly Leu Ser Gln Leu Leu Gln Pro Glu Gly His His Trp Glu Thr
    130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
            180                 185

<210> SEQ ID NO 146
<211> LENGTH: 19
<212> TYPE: PRT
<213> ORGANISM: Homo sapiens

<400> SEQUENCE: 146

Asn Ile Glu His Lys Tyr Leu Gly Tyr Ala Thr Ser Tyr Ala Ala Ser
1               5                   10                  15

Val Lys Gly

<210> SEQ ID NO 147
<211> LENGTH: 123
<212> TYPE: PRT
<213> ORGANISM: Homo sapiens

<400> SEQUENCE: 147

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Asn Ile Glu His Lys Tyr Leu Gly Tyr Ala Thr Ser Tyr Ala Ala
    50                  55                  60

Ser Val Lys Gly Arg Phe Thr Ile Ser Arg Asp Asn Ser Lys Asn Thr
65                  70                  75                  80

```
Leu Tyr Leu Gln Met Asn Ser Leu Arg Ala Glu Asp Thr Ala Val Tyr
                85                  90                  95

Tyr Cys Ala Arg Tyr Trp Gly Thr Pro Tyr Leu Met Gln Phe Asp Asn
            100                 105                 110

Trp Gly Gln Gly Thr Leu Val Thr Val Ser Ser
        115                 120

<210> SEQ ID NO 148
<211> LENGTH: 12
<212> TYPE: PRT
<213> ORGANISM: Homo sapiens

<400> SEQUENCE: 148

His Gln Gly Leu Ile Phe Tyr Glu Lys Leu Leu Gly
1               5                   10
```

SAFE AND EFFECTIVE METHOD OF TREATING PSORIASIS WITH ANTI-IL-23 SPECIFIC ANTIBODY

CROSS-REFERENCE TO RELATED APPLICATIONS

This application claims priority to U.S. Application Provisional Ser. No. 62/769,889, filed 20 Nov. 2018, 62/796,673, filed 25 Jan. 2019, 62/810,617, filed 26 Feb. 2019, 62/817,711, filed 13 Mar. 2019 and 62/915,115, filed 15 Oct. 2019, the entire contents of which are incorporated herein by reference in their entireties.

REFERENCE TO SEQUENCE LISTING SUBMITTED ELECTRONICALLY

This application contains a sequence listing, which is submitted electronically via EFS-Web as an ASCII formatted sequence listing with a file name "JBI6025USNP1Sequence Listing.txt" creation date of 18 Nov. 2018, and having a size of 79,961 bytes.

FIELD OF THE INVENTION

The present invention concerns methods for treating psoriasis with an antibody that binds the human IL-23 protein. In particular, it relates to a method of administering an anti-IL-23 specific antibody and specific pharmaceutical compositions of an antibody, e.g., guselkumab, which is safe and effective for patients suffering from psoriasis.

BACKGROUND OF THE INVENTION

Interleukin (IL)-12 is a secreted heterodimeric cytokine comprised of 2 disulfide-linked glycosylated protein subunits, designated p35 and p40 for their approximate molecular weights. IL-12 is produced primarily by antigen-presenting cells and drives cell-mediated immunity by binding to a two-chain receptor complex that is expressed on the surface of T cells or natural killer (NK) cells. The IL-12 receptor beta-1 (IL-12β1) chain binds to the p40 subunit of IL-12, providing the primary interaction between IL-12 and its receptor. However, it is IL-12p35 ligation of the second receptor chain, IL-12β2, that confers intracellular signaling (e.g. STAT4 phosphorylation) and activation of the receptor-bearing cell (Presky et al, 1996). IL-12 signaling concurrent with antigen presentation is thought to invoke T cell differentiation towards the T helper 1 (Th1) phenotype, characterized by interferon gamma (IFNγ) production (Trinchieri, 2003). Th1 cells are believed to promote immunity to some intracellular pathogens, generate complement-fixing antibody isotypes, and contribute to tumor immunosurveillance. Thus, IL-12 is thought to be a significant component to host defense immune mechanisms.

It was discovered that the p40 protein subunit of IL-12 can also associate with a separate protein subunit, designated p19, to form a novel cytokine, IL-23 (Oppman et al, 2000). IL-23 also signals through a two-chain receptor complex. Since the p40 subunit is shared between IL-12 and IL-23, it follows that the IL-12β1 chain is also shared between IL-12 and IL-23. However, it is the IL-23p19 ligation of the second component of the IL-23 receptor complex, IL-23R, that confers IL-23 specific intracellular signaling (e.g., STAT3 phosphorylation) and subsequent IL-17 production by T cells (Parham et al, 2002; Aggarwal et al. 2003). Recent studies have demonstrated that the biological functions of IL-23 are distinct from those of IL-12, despite the structural similarity between the two cytokines (Langrish et al, 2005).

Abnormal regulation of IL-12 and Th1 cell populations has been associated with many immune-mediated diseases since neutralization of IL-12 by antibodies is effective in treating animal models of psoriasis, multiple sclerosis (MS), rheumatoid arthritis, inflammatory bowel disease, insulin-dependent (type 1) diabetes mellitus, and uveitis (Leonard et al, 1995; Hong et al, 1999; Malfait et al, 1998; Davidson et al, 1998). However, since these studies targeted the shared p40 subunit, both IL-12 and IL-23 were neutralized in vivo. Therefore, it was unclear whether IL-12 or IL-23 was mediating disease, or if both cytokines needed to be inhibited to achieve disease suppression. Recent studies have confirmed through IL-23p19 deficient mice or specific antibody neutralization of IL-23 that IL-23 inhibition can provide equivalent benefit as anti-IL-12p40 strategies (Cua et al, 2003, Murphy et al, 2003, Benson et al 2004). Therefore, there is increasing evidence for the specific role of IL-23 in immune-mediated disease. Neutralization of IL-23 without inhibition of IL-12 pathways could then provide effective therapy of immune-mediated disease with limited impact on important host defense immune mechanism. This would represent a significant improvement over current therapeutic options.

Psoriasis is a common, chronic immune-mediated skin disorder with significant co-morbidities, such as psoriatic arthritis (PsA), depression, cardiovascular disease, hypertension, obesity, diabetes, metabolic syndrome, and Crohn's disease. Plaque psoriasis is the most common form of the disease and manifests in well demarcated erythematous lesions topped with white silver scales. Plaques are pruritic, painful, often disfiguring and disabling, and a significant proportion of psoriatic patients have plaques on hands/nails face, feet and genitalia. As such, psoriasis negatively impacts health-related quality of life (HRQoL) to a significant extent, including imposing physical and psychosocial burdens that extend beyond the physical dermatological symptoms and interfere with everyday activities. For example, psoriasis negatively impacts familial, spousal, social, and work relationships, and is associated with a higher incidence of depression and increased suicidal tendencies.

Histologic characterization of psoriasis lesions reveals a thickened epidermis resulting from aberrant keratinocyte proliferation and differentiation as well as dermal infiltration and co-localization of CD3+T lymphocytes and dendritic cells. While the etiology of psoriasis is not well defined, gene and protein analysis have shown that IL-12, IL-23 and their downstream molecules are over-expressed in psoriatic lesions, and some may correlate with psoriasis disease severity. Some therapies used in the treatment of psoriasis modulate IL-12 and IL-23 levels, which is speculated to contribute to their efficacy. Th1 and Th17 cells can produce effector cytokines that induce the production of vasodilators, chemoattractants and expression of adhesion molecules on endothelial cells which in turn, promote monocyte and neutrophil recruitment, T cell infiltration, neovascularization and keratinocyte activation and hyperplasia. Activated keratinocytes can produce chemoattractant factors that promote neutrophil, monocyte, T cell, and dendritic cell trafficking, thus establishing a cycle of inflammation and keratinocyte hyperproliferation.

Elucidation of the pathogenesis of psoriasis has led to effective biologic treatments targeting tumor necrosis factor-alpha (TNF-α), both interleukin (IL)-12 and IL-23 and, most recently, IL-17 as well as IL-23 alone (including in Phase 1 and 2 clinical trials using guselkumab). Guselkumab (also known as CNTO 1959) is a fully human IgG1 lambda monoclonal antibody that binds to the p19 subunit of IL-23 and inhibits the intracellular and downstream signaling of IL-23, required for terminal differentiation of T helper (Th)17 cells.

SUMMARY OF THE INVENTION

In a first aspect, the invention concerns a method of treating psoriasis in a patient comprising subcutaneously administering an anti-IL-23 specific antibody (also referred to as IL-23p19 antibody), e.g., guselkumab, to the patient, wherein the anti-IL-23 specific antibody is administered at an initial dose, a dose 4 weeks thereafter, and at a dosing interval of once every 8 weeks thereafter, e.g., a dose at 0, 4, 8, 16, 24, 32, 40 and 48 weeks.

In the method of treating psoriasis in a patient, the patient treated with the antibody to IL-23 demonstrates greater efficacy in a psoriasis clinical endpoint than efficacy in the psoriasis clinical endpoint achieved by a patient treated with the antibody secukinumab (marketed as Cosentyx® by Novartis). The psoriasis clinical endpoint may be PASI90, PASI100, IGA 0 and/or IGA 1 and is measured 24, 28, 32, 36, 40, 44 and/or 48 weeks after initial treatment, preferably, 48 weeks after initial treatment.

In the method of the invention, the antibody to IL-23 is administered in an initial dose, 4 weeks after the initial dose and every 8 weeks after the dose at 4 weeks and the secukinumab antibody is administered in an initial dose, 1 week after the initial dose, 2 weeks after the initial dose, 3 weeks after the initial dose, 4 weeks after the initial dose and every 4 weeks after the dose at 4 weeks. In an embodiment of the method, the antibody to IL-23 is administered at a dose of 100 mg and the antibody to IL-23 is safe and effective treating psoriasis at an area of a patient selected from the group consisting of scalp, nails, hands and feet.

In another embodiment of the method, the antibody to IL-23 is effective to reduce a symptom of psoriasis in the patient, induce clinical response, induce or maintain clinical remission, inhibit disease progression, or inhibit a disease complication in the patient and the patient is treated for moderate to severe psoriasis.

In a further embodiment of the invention, the method further comprises the step of discontinuing treatment of a patient previously treated with at least one dose of secukinumab and deciding to treat the patient with guselkumab. In an additional embodiment, the method further comprises the step of measuring the psoriasis clinical endpoint PASI90, PASI100, IGA 0 and/or IGA 1 at 24, 28, 32, 36, 40, 44 and/or 48 weeks after initial treatment and discontinuing treatment of a patient previously treated with at least one dose of secukinumab and treating the patient with guselkumab.

In another aspect, the composition used in the method of the invention comprises a pharmaceutical composition comprising: an anti-IL-23 specific antibody in an amount from about 1.0 µg/ml to about 1000 mg/ml, specifically at 50 mg or 100 mg. In a preferred embodiment the anti-IL-23 specific antibody is guselkumab at 100 mg/mL; 7.9% (w/v) sucrose, 4.0 mM Histidine, 6.9 mM L-Histidine monohydrochloride monohydrate; 0.053% (w/v) Polysorbate 80 of the pharmaceutical composition; wherein the diluent is water at standard state.

In an embodiment, the psoriasis patient achieved the endpoints of achieving an IGA score of cleared or minimal disease (IGA 0/1) and 90% improvement in PASI response (PASI 90) or 100% improvement in PASI response (PASI 100) at week 16.

In another aspect of the invention the pharmaceutical composition comprises an isolated anti-IL23 specific antibody having the guselkumab CDR sequences comprising (i) the heavy chain CDR amino acid sequences of SEQ ID NO: 5, SEQ ID NO: 20, and SEQ ID NO: 44; and (ii) the light chain CDR amino acid sequences of SEQ ID NO: 50, SEQ ID NO: 56, and SEQ ID NO: 73 at 100 mg/mL; 7.9% (w/v) sucrose, 4.0 mM Histidine, 6.9 mM L-Histidine monohydrochloride monohydrate; 0.053% (w/v) Polysorbate 80 of the pharmaceutical composition; wherein the diluent is water at standard state.

Another aspect of the method of the invention comprises administering a pharmaceutical composition comprising an isolated anti-IL-23 specific antibody having the guselkumab heavy chain variable region amino acid sequence of SEQ ID NO: 106 and the guselkumab light chain variable region amino acid sequence of SEQ ID NO: 116 at 100 mg/mL; 7.9% (w/v) sucrose, 4.0 mM Histidine, 6.9 mM L-Histidine monohydrochloride monohydrate; 0.053% (w/v) Polysorbate 80 of the pharmaceutical composition; wherein the diluent is water at standard state.

DETAILED DESCRIPTION OF THE PREFERRED EMBODIMENTS

Figures 1A, 1B, 1C, 1D:
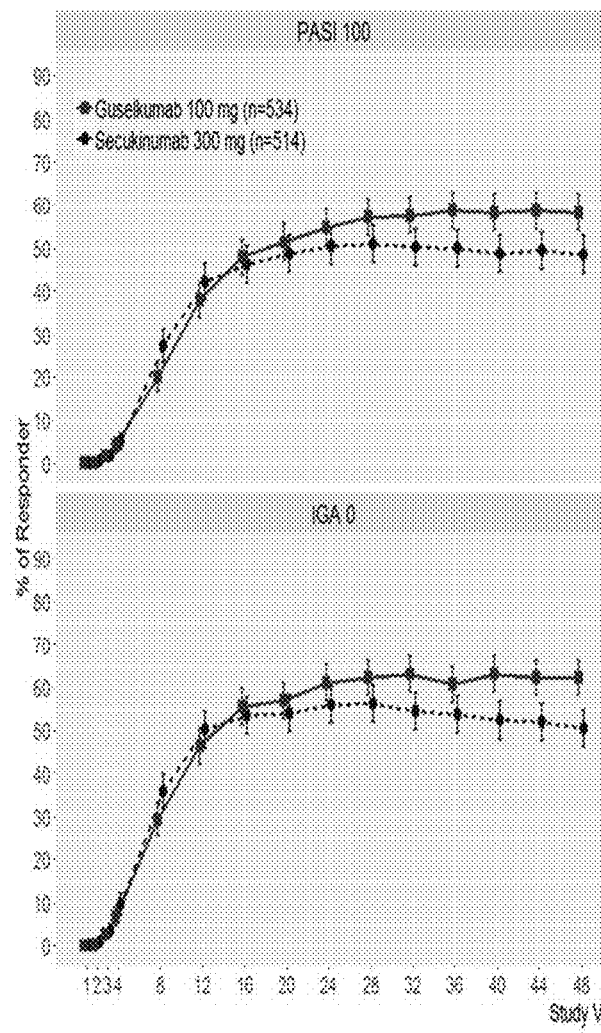
FIG. 1A through FIG. 1D shows the proportions of subjects achieving a PASI 100 response (FIG. 1A), a PASI 90 response (FIG. 1B) an IGA score of cleared (0) (FIG. 1C), and an IGA score of cleared (0) or minimal (1) (FIG. 1D) from Week 1 through Week 48.

As used herein the method of treatment of psoriasis comprises administering isolated, recombinant and/or synthetic anti-IL-23 specific human antibodies and diagnostic and therapeutic compositions, methods and devices.

As used herein, an "anti-IL-23 specific antibody," "anti-IL-23 antibody," "antibody portion," or "antibody fragment" and/or "antibody variant" and the like include any protein or peptide containing molecule that comprises at least a portion of an immunoglobulin molecule, such as but not limited to, at least one complementarity determining region (CDR) of a heavy or light chain or a ligand binding portion thereof, a heavy chain or light chain variable region, a heavy chain or light chain constant region, a framework region, or any portion thereof, or at least one portion of an IL-23 receptor or binding protein, which can be incorporated into an antibody of the present invention. Such antibody optionally further affects a specific ligand, such as but not limited to, where such antibody modulates, decreases, increases, antagonizes, agonizes, mitigates, alleviates, blocks, inhibits, abrogates and/or interferes with at least one IL-23 activity or binding, or with IL-23 receptor activity or binding, in vitro, in situ and/or in vivo. As a non-limiting example, a suitable anti-IL-23 antibody, specified portion or variant of the present invention can bind at least one IL-23 molecule, or specified portions, variants or domains thereof. A suitable anti-IL-23 antibody, specified portion, or variant can also optionally affect at least one of IL-23 activity or function, such as but not limited to, RNA, DNA or protein synthesis, IL-23 release, IL-23 receptor signaling, membrane IL-23 cleavage, IL-23 activity, IL-23 production and/or synthesis.

The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof. Functional fragments include antigen-binding fragments that bind to a mammalian IL-23. For example, antibody fragments capable of binding to IL-23 or portions thereof, including, but not limited to, Fab (e.g., by papain digestion), Fab' (e.g., by pepsin digestion and partial reduction) and F(ab')$_2$ (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention (see, e.g., Colligan, Immunology, supra).

Such fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a F(ab')$_2$ heavy chain portion can be designed to include DNA sequences encoding the $C_H1$ domain and/or hinge region of the heavy chain. The various portions of antibodies can be joined together chemically by conventional techniques, or can be prepared as a contiguous protein using genetic engineering techniques.

As used herein, the term "human antibody" refers to an antibody in which substantially every part of the protein (e.g., CDR, framework, $C_L$, $C_H$ domains (e.g., $C_H1$, $C_H2$, $C_H3$), hinge, ($V_L$, $V_H$)) is substantially non-immunogenic in humans, with only minor sequence changes or variations. A "human antibody" may also be an antibody that is derived from or closely matches human germline immunoglobulin sequences. Human antibodies may include amino acid residues not encoded by germline immunoglobulin sequences (e.g., mutations introduced by random or site-specific mutagenesis in vitro or by somatic mutation in vivo). Often, this means that the human antibody is substantially non-immunogenic in humans. Human antibodies have been classified into groupings based on their amino acid sequence similarities. Accordingly, using a sequence similarity search, an antibody with a similar linear sequence can be chosen as a template to create a human antibody. Similarly, antibodies designated primate (monkey, baboon, chimpanzee, etc.), rodent (mouse, rat, rabbit, guinea pig, hamster, and the like) and other mammals designate such species, sub-genus, genus, sub-family, and family specific antibodies. Further, chimeric antibodies can include any combination of the above. Such changes or variations optionally and preferably retain or reduce the immunogenicity in humans or other species relative to non-modified antibodies. Thus, a human antibody is distinct from a chimeric or humanized antibody.

It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

Bispecific, heterospecific, heteroconjugate or similar antibodies can also be used that are monoclonal, preferably, human or humanized, antibodies that have binding specificities for at least two different antigens. In the present case, one of the binding specificities is for at least one IL-23 protein, the other one is for any other antigen. Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature 305:537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed, e.g., in WO 93/08829, U.S. Pat. Nos. 6,210,668, 6,193,967, 6,132,992, 6,106,833, 6,060,285, 6,037,453, 6,010,902, 5,989,530, 5,959,084, 5,959,083, 5,932,448, 5,833,985, 5,821,333, 5,807,706, 5,643,759, 5,601,819, 5,582,996, 5,496,549, 4,676,980, WO 91/00360, WO 92/00373, EP 03089, Traunecker et al., EMBO J. 10:3655 (1991), Suresh et al., Methods in Enzymology 121:210 (1986), each entirely incorporated herein by reference.

Anti-IL-23 specific (also termed IL-23 specific antibodies) (or antibodies to IL-23) useful in the methods and compositions of the present invention can optionally be characterized by high affinity binding to IL-23 and, optionally and preferably, having low toxicity. In particular, an antibody, specified fragment or variant of the invention, where the individual components, such as the variable region, constant region and framework, individually and/or collectively, optionally and preferably possess low immunogenicity, is useful in the present invention. The antibodies that can be used in the invention are optionally characterized by their ability to treat patients for extended periods with measurable alleviation of symptoms and low and/or acceptable toxicity. Low or acceptable immunogenicity and/or high affinity, as well as other suitable properties, can contribute to the therapeutic results achieved. "Low immunogenicity" is defined herein as raising significant HAHA, HACA or HAMA responses in less than about 75%, or preferably less than about 50% of the patients treated and/or raising low titres in the patient treated (less than about 300, preferably less than about 100 measured with a double antigen enzyme immunoassay) (Elliott et al., Lancet 344:

1125-1127 (1994), entirely incorporated herein by reference). "Low immunogenicity" can also be defined as the incidence of titrable levels of antibodies to the anti-IL-23 antibody in patients treated with anti-IL-23 antibody as occurring in less than 25% of patients treated, preferably, in less than 10% of patients treated with the recommended dose for the recommended course of therapy during the treatment period.

The terms "clinically proven efficacy" and "clinically proven effective" as used herein in the context of a dose, dosage regimen, treatment or method refer to the effectiveness of a particular dose, dosage or treatment regimen. Efficacy can be measured based on change in the course of the disease in response to an agent of the present invention. For example, an anti-IL-23 antibody of the present invention (e.g., the anti-IL-23 antibody guselkumab) is administered to a patient in an amount and for a time sufficient to induce an improvement, preferably a sustained improvement, in at least one indicator that reflects the severity of the disorder that is being treated. Various indicators that reflect the extent of the subject's illness, disease or condition may be assessed for determining whether the amount and time of the treatment is sufficient. Such indicators include, for example, clinically recognized indicators of disease severity, symptoms, or manifestations of the disorder in question. The degree of improvement generally is determined by a physician, who may make this determination based on signs, symptoms, biopsies, or other test results, and who may also employ questionnaires that are administered to the subject, such as quality-of-life questionnaires developed for a given disease. For example, an anti-IL23 antibody of the present invention may be administered to achieve an improvement in a patient's condition related to psoriasis. Improvement may be indicated by an improvement in an index of disease activity, by amelioration of clinical symptoms or by any other measure of disease activity. Examples of such indices of disease are PASI75, PASI90, PASI100, IGA1 and IGA0. The Psoriasis Area and Severity Index (PAST) is a score used by doctors and nurses to record psoriasis severity and PASI75 is shorthand for a 75% reduction of the PASI score from the start to the end of the trial (with PASI90 meaning a 90% reduction and PASI100 meaning a 100% reduction). Investigator's Global Assessment (IGA) tool is a visual assessment that consists of a score ranging from 0 (clear) to 4 (severe). IGA0 signifies cleared and IGA1 signifies almost clear.

The term "clinically proven safe", as it relates to a dose, dosage regimen, treatment or method with an anti-IL-23 antibody of the present invention (e.g., the anti-IL-23 antibody guselkumab), refers to a favorable risk:benefit ratio with an acceptable frequency and/or acceptable severity of treatment-emergent adverse events (referred to as AEs or TEAEs) compared to the standard of care or to another comparator. An adverse event is an untoward medical occurrence in a patient administered a medicinal product. In particular, safe as it relates to a dose, dosage regimen or treatment with an anti-IL-23 antibody of the present invention refers to with an acceptable frequency and/or acceptable severity of adverse events associated with administration of the antibody if attribution is considered to be possible, probable, or very likely due to the use of the anti-IL23 antibody.

As used herein, unless otherwise noted, the term "clinically proven" (used independently or to modify the terms "safe" and/or "effective") shall mean that it has been proven by a clinical trial wherein the clinical trial has met the approval standards of U.S. Food and Drug Administration, EMEA or a corresponding national regulatory agency. For example, the clinical study may be an adequately sized, randomized, double-blinded study used to clinically prove the effects of the drug.

Utility

The isolated nucleic acids of the present invention can be used for production of at least one anti-IL-23 antibody or specified variant thereof, which can be used to measure or effect in an cell, tissue, organ or animal (including mammals and humans), to diagnose, monitor, modulate, treat, alleviate, help prevent the incidence of, or reduce the symptoms of psoriasis.

Such a method can comprise administering an effective amount of a composition or a pharmaceutical composition comprising at least one anti-IL-23 antibody to a cell, tissue, organ, animal or patient in need of such modulation, treatment, alleviation, prevention, or reduction in symptoms, effects or mechanisms. The effective amount can comprise an amount of about 0.001 to 500 mg/kg per single (e.g., bolus), multiple or continuous administration, or to achieve a serum concentration of 0.01-5000 μg/ml serum concentration per single, multiple, or continuous administration, or any effective range or value therein, as done and determined using known methods, as described herein or known in the relevant arts.

Citations

All publications or patents cited herein, whether or not specifically designated, are entirely incorporated herein by reference as they show the state of the art at the time of the present invention and/or to provide description and enablement of the present invention. Publications refer to any scientific or patent publications, or any other information available in any media format, including all recorded, electronic or printed formats. The following references are entirely incorporated herein by reference: Ausubel, et al., ed., Current Protocols in Molecular Biology, John Wiley & Sons, Inc., NY, N.Y. (1987-2001); Sambrook, et al., Molecular Cloning: A Laboratory Manual, $2^{nd}$ Edition, Cold Spring Harbor, N.Y. (1989); Harlow and Lane, antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001).

Antibodies of the Present Invention—Production and Generation

At least one anti-IL-23 antibody used in the method of the present invention can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, N.Y. (1987-2001); Sambrook, et al., Molecular Cloning: A Laboratory Manual, $2^{nd}$ Edition, Cold Spring Harbor, N.Y. (1989); Harlow and Lane, antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001), each entirely incorporated herein by reference.

A preferred anti-IL-23 antibody is guselkumab (also referred to as CNTO1959) having the heavy chain variable region amino acid sequence of SEQ ID NO: 106 and the light chain variable region amino acid sequence of SEQ ID NO: 116 and having the heavy chain CDR amino acid sequences of SEQ ID NO: 5, SEQ ID NO: 20, and SEQ ID NO: 44; and the light chain CDR amino acid sequences of SEQ ID NO: 50, SEQ ID NO: 56, and SEQ ID NO: 73. Other anti-IL-23 antibodies have sequences listed herein and are described in U.S. Pat. No. 7,935,344, the entire contents of which are incorporated herein by reference).

Human antibodies that are specific for human IL-23 proteins or fragments thereof can be raised against an appropriate immunogenic antigen, such as an isolated IL-23 protein and/or a portion thereof (including synthetic molecules, such as synthetic peptides). Other specific or general mammalian antibodies can be similarly raised. Preparation of immunogenic antigens, and monoclonal antibody production can be performed using any suitable technique.

In one approach, a hybridoma is produced by fusing a suitable immortal cell line (e.g., a myeloma cell line, such as, but not limited to, Sp2/0, Sp2/0-AG14, NSO, NS1, NS2, AE-1, L.5, L243, P3X63Ag8.653, Sp2 SA3, Sp2 MAI, Sp2 SS1, Sp2 SA5, U937, MLA 144, ACT IV, MOLT4, DA-1, JURKAT, WEHI, K-562, COS, RAJI, NIH 3T3, HL-60, MLA 144, NAMALWA, NEURO 2A, or the like, or heteromylomas, fusion products thereof, or any cell or fusion cell derived therefrom, or any other suitable cell line as known in the art) (see, e.g., www.atcc.org, www.lifetech.com., and the like), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. See, e.g., Ausubel, supra, and Colligan, Immunology, supra, chapter 2, entirely incorporated herein by reference.

Antibody producing cells can also be obtained from the peripheral blood or, preferably, the spleen or lymph nodes, of humans or other suitable animals that have been immunized with the antigen of interest. Any other suitable host cell can also be used for expressing heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods. Cells which produce antibodies with the desired specificity can be selected by a suitable assay (e.g., ELISA).

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from Cambridge antibody Technologies, Cambridgeshire, UK; MorphoSys, Martinsreid/Planegg, DE; Biovation, Aberdeen, Scotland, UK; Biolnvent, Lund, Sweden; Dyax Corp., Enzon, Affymax/Biosite; Xoma, Berkeley, Calif.; Ixsys. See, e.g., EP 368,684, PCT/GB91/01134; PCT/GB92/01755; PCT/GB92/002240; PCT/GB92/00883; PCT/GB93/00605; U.S. Ser. No. 08/350,260 (May 12, 1994); PCT/GB94/01422; PCT/GB94/02662; PCT/GB97/01835; (CAT/MRC); WO90/14443; WO90/14424; WO90/14430; PCT/US94/1234; WO92/18619; WO96/07754; (Scripps); WO96/13583, WO97/08320 (MorphoSys); WO95/16027 (Biolnvent); WO88/06630; WO90/3809 (Dyax); U.S. Pat. No. 4,704,692 (Enzon); PCT/US91/02989 (Affymax); WO89/06283; EP 371 998; EP 550 400; (Xoma); EP 229 046; PCT/US91/07149 (Ixsys); or stochastically generated peptides or proteins—U.S. Pat. Nos. 5,723,323, 5,763,192, 5,814,476, 5,817,483, 5,824,514, 5,976,862, WO 86/05803, EP 590 689 (Ixsys, predecessor of Applied Molecular Evolution (AME), each entirely incorporated herein by reference)) or that rely upon immunization of transgenic animals (e.g., SCID mice, Nguyen et al., Microbiol. Immunol. 41:901-907 (1997); Sandhu et al., Crit. Rev. Biotechnol. 16:95-118 (1996); Eren et al., Immunol. 93:154-161 (1998), each entirely incorporated by reference as well as related patents and applications) that are capable of producing a repertoire of human antibodies, as known in the art and/or as described herein. Such techniques, include, but are not limited to, ribosome display (Hanes et al., Proc. Natl. Acad. Sci. USA, 94:4937-4942 (May 1997); Hanes et al., Proc. Natl. Acad. Sci. USA, 95:14130-14135 (November 1998)); single cell antibody producing technologies (e.g., selected lymphocyte antibody method ("SLAM") (U.S. Pat. No. 5,627,052, Wen et al., J. Immunol. 17:887-892 (1987); Babcook et al., Proc. Natl. Acad. Sci. USA 93:7843-7848 (1996)); gel microdroplet and flow cytometry (Powell et al., Biotechnol. 8:333-337 (1990); One Cell Systems, Cambridge, Mass.; Gray et al., J. Imm. Meth. 182:155-163 (1995); Kenny et al., Bio/Technol. 13:787-790 (1995)); B-cell selection (Steenbakkers et al., Molec. Biol. Reports 19:125-134 (1994); Jonak et al., Progress Biotech, Vol. 5, In Vitro Immunization in Hybridoma Technology, Borrebaeck, ed., Elsevier Science Publishers B.V., Amsterdam, Netherlands (1988)).

Methods for engineering or humanizing non-human or human antibodies can also be used and are well known in the art. Generally, a humanized or engineered antibody has one or more amino acid residues from a source that is non-human, e.g., but not limited to, mouse, rat, rabbit, non-human primate or other mammal. These non-human amino acid residues are replaced by residues often referred to as "import" residues, which are typically taken from an "import" variable, constant or other domain of a known human sequence.

Known human Ig sequences are disclosed, e.g., www.ncbi.nlm.nih.gov/entrez/query.fcgi; www.ncbi.nih.gov/igblast; www.atcc.org/phage/hdb.html; www.mrc-cpe.cam.ac.uk/ALIGNMENTS.php; www.kabatdatabase.com/top.html; ftp.ncbi.nih.gov/repository/kabat; www.sciquest.com; www.abcam.com; www.antibodyresource.com/online-comp.html; www.public.iastate.edu/~pedro/research_tools.html; www.whfreeman.com/immunology/CH05/kuby05.htm; www.hhmi.org/grants/lectures/1996/vlab; www.path.cam.ac.uk/~mrc7/mikeimages.html; mcb.harvard.edu/BioLinks/Immunology.html; www.immunogylink.com; pathbox.wustl.edu/~hcenter/index.html; www.appliedbiosystems.com; www.nal.usda.gov/awic/pubs/antibody; www.m.ehime-u.ac.jp/~yasuhito/Elisa.html; www.biodesign.com; www.cancerresearchuk.org; www.biotech.ufl.edu; www.isac-net.org; baserv.uci.kun.nl/~jraats/links1.html; www.recab.uni-hd.de/immuno.bme.nwu.edu; www.mrc-cpe.cam.ac.uk; www.ibt.unam.mx/vir/V_mice.html; http://www.bioinforg.uk/abs; antibody.bath.ac.uk; www.unizh.ch; www.cryst.bbk.ac.uk/~ubcg07s; www.nimr.mrc.ac.uk/CC/ccaewg/ccaewg.html; www.path.cam.ac.uk/~mrc7/humanisation/TAHHP.html; www.ibt.unam.mx/vir/structure/stat_aim.html; www.biosci.missouri.edu/smithgp/index.html; www.jerini.de; Kabat et al., Sequences of Proteins of Immunological Interest, U.S. Dept. Health (1983), each entirely incorporated herein by reference.

Such imported sequences can be used to reduce immunogenicity or reduce, enhance or modify binding, affinity, on-rate, off-rate, avidity, specificity, half-life, or any other suitable characteristic, as known in the art. In general, the CDR residues are directly and most substantially involved in influencing antigen binding. Accordingly, part or all of the non-human or human CDR sequences are maintained while the non-human sequences of the variable and constant regions may be replaced with human or other amino acids.

Antibodies can also optionally be humanized or human antibodies engineered with retention of high affinity for the antigen and other favorable biological properties. To achieve this goal, humanized (or human) antibodies can be optionally prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, framework (FR) residues can be selected and combined from the consensus and import sequences so that the desired antibody characteristic, such as increased affinity for the target antigen(s), is achieved.

In addition, the human IL-23 specific antibody used in the method of the present invention may comprise a human germline light chain framework. In particular embodiments, the light chain germline sequence is selected from human VK sequences including, but not limited to, A1, A10, A11, A14, A17, A18, A19, A2, A20, A23, A26, A27, A3, A30, A5, A7, B2, B3, L1, L10, L11, L12, L14, L15, L16, L18, L19, L2, L20, L22, L23, L24, L25, L4/18a, L5, L6, L8, L9, O1, O11, O12, O14, O18, O2, O4, and 08. In certain embodiments, this light chain human germline framework is selected from V1-11, V1-13, V1-16, V1-17, V1-18, V1-19, V1-2, V1-20, V1-22, V1-3, V1-4, V1-5, V1-7, V1-9, V2-1, V2-11, V2-13, V2-14, V2-15, V2-17, V2-19, V2-6, V2-7, V2-8, V3-2, V3-3, V3-4, V4-1, V4-2, V4-3, V4-4, V4-6, V5-1, V5-2, V5-4, and V5-6.

In other embodiments, the human IL-23 specific antibody used in the method of the present invention may comprise a human germline heavy chain framework. In particular embodiments, this heavy chain human germline framework is selected from VH1-18, VH1-2, VH1-24, VH1-3, VH1-45, VH1-46, VH1-58, VH1-69, VH1-8, VH2-26, VH2-5, VH2-70, VH3-11, VH3-13, VH3-15, VH3-16, VH3-20, VH3-21, VH3-23, VH3-30, VH3-33, VH3-35, VH3-38, VH3-43, VH3-48, VH3-49, VH3-53, VH3-64, VH3-66, VH3-7, VH3-72, VH3-73, VH3-74, VH3-9, VH4-28, VH4-31, VH4-34, VH4-39, VH4-4, VH4-59, VH4-61, VH5-51, VH6-1, and VH7-81.

In particular embodiments, the light chain variable region and/or heavy chain variable region comprises a framework region or at least a portion of a framework region (e.g., containing 2 or 3 subregions, such as FR2 and FR3). In certain embodiments, at least FRL1, FRL2, FRL3, or FRL4 is fully human. In other embodiments, at least FRH1, FRH2, FRH3, or FRH4 is fully human. In some embodiments, at least FRL1, FRL2, FRL3, or FRL4 is a germline sequence (e.g., human germline) or comprises human consensus sequences for the particular framework (readily available at the sources of known human Ig sequences described above). In other embodiments, at least FRH1, FRH2, FRH3, or FRH4 is a germline sequence (e.g., human germline) or comprises human consensus sequences for the particular framework. In preferred embodiments, the framework region is a fully human framework region.

Humanization or engineering of antibodies of the present invention can be performed using any known method, such as but not limited to those described in, Winter (Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323, 5,976,862, 5,824,514, 5,817,483, 5,814,476, 5,763,192, 5,723,323, 5,766886, 5714352, 6204023, 6180370, 5693762, 5530101, 5585089, 5225539; 4816567, PCT/US98/16280, US96/18978, US91/09630, US91/05939, US94/01234, GB89/01334, GB91/01134, GB92/01755; WO90/14443, WO90/14424, WO90/14430, EP 229246, each entirely incorporated herein by reference, included references cited therein.

In certain embodiments, the antibody comprises an altered (e.g., mutated) Fc region. For example, in some embodiments, the Fc region has been altered to reduce or enhance the effector functions of the antibody. In some embodiments, the Fc region is an isotype selected from IgM, IgA, IgG, IgE, or other isotype. Alternatively or additionally, it may be useful to combine amino acid modifications with one or more further amino acid modifications that alter C1q binding and/or the complement dependent cytotoxicity function of the Fc region of an IL-23 binding molecule. The starting polypeptide of particular interest may be one that binds to C1q and displays complement dependent cytotoxicity (CDC). Polypeptides with pre-existing C1q binding activity, optionally further having the ability to mediate CDC may be modified such that one or both of these activities are enhanced. Amino acid modifications that alter C1q and/or modify its complement dependent cytotoxicity function are described, for example, in WO0042072, which is hereby incorporated by reference.

As disclosed above, one can design an Fc region of the human IL-23 specific antibody of the present invention with altered effector function, e.g., by modifying C1q binding and/or FcγR binding and thereby changing complement dependent cytotoxicity (CDC) activity and/or antibody-dependent cell-mediated cytotoxicity (ADCC) activity. "Effector functions" are responsible for activating or diminishing a biological activity (e.g., in a subject). Examples of effector functions include, but are not limited to: C1q binding; CDC; Fc receptor binding; ADCC; phagocytosis; down regulation of cell surface receptors (e.g., B cell receptor; BCR), etc. Such effector functions may require the Fc region to be combined with a binding domain (e.g., an antibody variable domain) and can be assessed using various assays (e.g., Fc binding assays, ADCC assays, CDC assays, etc.).

For example, one can generate a variant Fc region of the human IL-23 (or anti-IL-23) antibody with improved C1q binding and improved FcγRIIIbinding (e.g., having both improved ADCC activity and improved CDC activity). Alternatively, if it is desired that effector function be reduced or ablated, a variant Fc region can be engineered with reduced CDC activity and/or reduced ADCC activity. In other embodiments, only one of these activities may be increased, and, optionally, also the other activity reduced (e.g., to generate an Fc region variant with improved ADCC activity, but reduced CDC activity and vice versa).

Fc mutations can also be introduced in engineer to alter their interaction with the neonatal Fc receptor (FcRn) and improve their pharmacokinetic properties. A collection of human Fc variants with improved binding to the FcRn have been described (Shields et al., (2001). High resolution mapping of the binding site on human IgG1 for FcγRI, FcγRII, FcγRIII, and FcRn and design of IgG1 variants with improved binding to the FcγR, J. Biol. Chem. 276:6591-6604).

Another type of amino acid substitution serves to alter the glycosylation pattern of the Fc region of the human IL-23 specific antibody. Glycosylation of an Fc region is typically either N-linked or O-linked. N-linked refers to the attachment of the carbohydrate moiety to the side chain of an asparagine residue. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. The recognition sequences for enzymatic attachment of the carbohydrate moiety to the asparagine side chain peptide sequences are asparagine-X-serine and asparagine-X-threonine, where X is any amino acid except proline. Thus, the presence of either of these peptide sequences in a polypeptide creates a potential glycosylation site.

The glycosylation pattern may be altered, for example, by deleting one or more glycosylation site(s) found in the polypeptide, and/or adding one or more glycosylation sites that are not present in the polypeptide. Addition of glycosylation sites to the Fc region of a human IL-23 specific antibody is conveniently accomplished by altering the amino acid sequence such that it contains one or more of the above-described tripeptide sequences (for N-linked glycosylation sites). An exemplary glycosylation variant has an amino acid substitution of residue Asn 297 of the heavy chain. The alteration may also be made by the addition of, or substitution by, one or more serine or threonine residues to the sequence of the original polypeptide (for O-linked glycosylation sites). Additionally, a change of Asn 297 to Ala can remove one of the glycosylation sites.

In certain embodiments, the human IL-23 specific antibody of the present invention is expressed in cells that express beta (1,4)-N-acetylglucosaminyltransferase III (GnT III), such that GnT III adds GlcNAc to the human IL-23 antibody. Methods for producing antibodies in such a fashion are provided in WO/9954342, WO/03011878, patent publication 20030003097A1, and Umana et al., Nature Biotechnology, 17:176-180, February 1999; all of which are herein specifically incorporated by reference in their entireties.

The anti-IL-23 antibody can also be optionally generated by immunization of a transgenic animal (e.g., mouse, rat, hamster, non-human primate, and the like) capable of producing a repertoire of human antibodies, as described herein and/or as known in the art. Cells that produce a human anti-IL-23 antibody can be isolated from such animals and immortalized using suitable methods, such as the methods described herein.

Transgenic mice that can produce a repertoire of human antibodies that bind to human antigens can be produced by known methods (e.g., but not limited to, U.S. Pat. Nos. 5,770,428, 5,569,825, 5,545,806, 5,625,126, 5,625,825, 5,633,425, 5,661,016 and 5,789,650 issued to Lonberg et al.; Jakobovits et al. WO 98/50433, Jakobovits et al. WO 98/24893, Lonberg et al. WO 98/24884, Lonberg et al. WO 97/13852, Lonberg et al. WO 94/25585, Kucherlapate et al. WO 96/34096, Kucherlapate et al. EP 0463 151 B1, Kucherlapate et al. EP 0710 719 A1, Surani et al. U.S. Pat. No. 5,545,807, Bruggemann et al. WO 90/04036, Bruggemann et al. EP 0438 474 B1, Lonberg et al. EP 0814 259 A2, Lonberg et al. GB 2 272 440 A, Lonberg et al. *Nature* 368:856-859 (1994), Taylor et al., *Int. Immunol.* 6(4)579-591 (1994), Green et al, *Nature Genetics* 7:13-21 (1994), Mendez et al., *Nature Genetics* 15:146-156 (1997), Taylor et al., *Nucleic Acids Research* 20(23):6287-6295 (1992), Tuaillon et al., *Proc Natl Acad Sci USA* 90(8)3720-3724 (1993), Lonberg et al., *Int Rev Immunol* 13(1):65-93 (1995) and Fishwald et al., *Nat Biotechnol* 14(7):845-851 (1996), which are each entirely incorporated herein by reference). Generally, these mice comprise at least one transgene comprising DNA from at least one human immunoglobulin locus that is functionally rearranged, or which can undergo functional rearrangement. The endogenous immunoglobulin loci in such mice can be disrupted or deleted to eliminate the capacity of the animal to produce antibodies encoded by endogenous genes.

Screening antibodies for specific binding to similar proteins or fragments can be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5-100 amino acids long, and often from about 8 to 25 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Publication Nos. 91/17271, 91/18980, 91/19818, and 93/08278.

Other systems for generating libraries of peptides have aspects of both in vitro chemical synthesis and recombinant methods. See, PCT Patent Publication Nos. 92/05258, 92/14843, and 96/19256. See also, U.S. Pat. Nos. 5,658,754; and 5,643,768. Peptide display libraries, vector, and screening kits are commercially available from such suppliers as Invitrogen (Carlsbad, Calif.), and Cambridge antibody Technologies (Cambridgeshire, UK). See, e.g., U.S. Pat. Nos. 4,704,692, 4,939,666, 4,946,778, 5,260,203, 5,455,030, 5,518,889, 5,534,621, 5,656,730, 5,763,733, 5,767,260, 5,856,456, assigned to Enzon; U.S. Pat. Nos. 5,223,409, 5,403,484, 5,571,698, 5,837,500, assigned to Dyax, 5427908, 5580717, assigned to Affymax; 5885793, assigned to Cambridge antibody Technologies; 5750373, assigned to Genentech, 5618920, 5595898, 5576195, 5698435, 5693493, 5698417, assigned to Xoma, Colligan, supra; Ausubel, supra; or Sambrook, supra, each of the above patents and publications entirely incorporated herein by reference.

Antibodies used in the method of the present invention can also be prepared using at least one anti-IL23 antibody encoding nucleic acid to provide transgenic animals or mammals, such as goats, cows, horses, sheep, rabbits, and the like, that produce such antibodies in their milk. Such animals can be provided using known methods. See, e.g., but not limited to, U.S. Pat. Nos. 5,827,690; 5,849,992; 4,873,316; 5,849,992; 5,994,616; 5,565,362; 5,304,489, and the like, each of which is entirely incorporated herein by reference.

Antibodies used in the method of the present invention can additionally be prepared using at least one anti-IL23 antibody encoding nucleic acid to provide transgenic plants and cultured plant cells (e.g., but not limited to, tobacco and maize) that produce such antibodies, specified portions or variants in the plant parts or in cells cultured therefrom. As a non-limiting example, transgenic tobacco leaves expressing recombinant proteins have been successfully used to provide large amounts of recombinant proteins, e.g., using an inducible promoter. See, e.g., Cramer et al., Curr. Top. Microbol. Immunol. 240:95-118 (1999) and references cited therein. Also, transgenic maize have been used to express mammalian proteins at commercial production levels, with biological activities equivalent to those produced in other recombinant systems or purified from natural sources. See, e.g., Hood et al., Adv. Exp. Med. Biol. 464:127-147 (1999) and references cited therein. Antibodies have also been produced in large amounts from transgenic plant seeds including antibody fragments, such as single chain antibodies (scFv's), including tobacco seeds and potato tubers. See, e.g., Conrad et al., Plant Mol. Biol. 38:101-109 (1998) and references cited therein. Thus, antibodies of the present invention can also be produced using transgenic plants, according to known methods. See also, e.g., Fischer et al., Biotechnol. Appl. Biochem. 30:99-108 (October, 1999), Ma et al., Trends Biotechnol. 13:522-7 (1995); Ma et al., Plant Physiol. 109:341-6 (1995); Whitelam et al., Biochem. Soc. Trans. 22:940-944 (1994); and references cited therein. Each of the above references is entirely incorporated herein by reference.

The antibodies used in the method of the invention can bind human IL-23 with a wide range of affinities ($K_D$). In a preferred embodiment, a human mAb can optionally bind human IL-23 with high affinity. For example, a human mAb can bind human IL-23 with a $K_D$ equal to or less than about $10^{-7}$M, such as but not limited to, 0.1-9.9 (or any range or value therein)$\times 10^{-7}$, $10^{-8}$, $10^{-9}$, $10^{-10}$, $10^{-11}$, $10^{-12}$, $10^{-13}$ or any range or value therein.

The affinity or avidity of an antibody for an antigen can be determined experimentally using any suitable method. (See, for example, Berzofsky, et al., "Antibody-Antigen Interactions," In *Fundamental Immunology*, Paul, W. E., Ed., Raven Press: New York, N.Y. (1984); Kuby, Janis Immunology, W. H. Freeman and Company: New York, N.Y. (1992); and methods described herein). The measured affinity of a particular antibody-antigen interaction can vary if measured under different conditions (e.g., salt concentration, pH). Thus, measurements of affinity and other antigen-binding parameters (e.g., $K_D$, $K_a$, $K_d$) are preferably made with standardized solutions of antibody and antigen, and a standardized buffer, such as the buffer described herein.

Nucleic Acid Molecules

Using the information provided herein, for example, the nucleotide sequences encoding at least 70-100% of the contiguous amino acids of at least one of the light or heavy chain variable or CDR regions described herein, among other sequences disclosed herein, specified fragments, variants or consensus sequences thereof, or a deposited vector comprising at least one of these sequences, a nucleic acid molecule of the present invention encoding at least one anti-IL-23 antibody can be obtained using methods described herein or as known in the art.

Nucleic acid molecules of the present invention can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules used in the method of the present invention can include nucleic acid molecules comprising an open reading frame (ORF), optionally, with one or more introns, e.g., but not limited to, at least one specified portion of at least one CDR, such as CDR1, CDR2 and/or CDR3 of at least one heavy chain or light chain; nucleic acid molecules comprising the coding sequence for an anti-IL-23 antibody or variable region; and nucleic acid molecules which comprise a nucleotide sequence substantially different from those described above but which, due to the degeneracy of the genetic code, still encode at least one anti-IL-23 antibody as described herein and/or as known in the art. Of course, the genetic code is well known in the art. Thus, it would be routine for one skilled in the art to generate such degenerate nucleic acid variants that code for specific anti-IL-23 antibodies used in the method of the present invention. See, e.g., Ausubel, et al., supra, and such nucleic acid variants are included in the present invention. Non-limiting examples of isolated nucleic acid molecules include nucleic acids encoding HC CDR1, HC CDR2, HC CDR3, LC CDR1, LC CDR2, and LC CDR3, respectively.

As indicated herein, nucleic acid molecules which comprise a nucleic acid encoding an anti-IL-23 antibody can include, but are not limited to, those encoding the amino acid sequence of an antibody fragment, by itself; the coding sequence for the entire antibody or a portion thereof; the coding sequence for an antibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example, ribosome binding and stability of mRNA); an additional coding sequence that codes for additional amino acids, such as those that provide additional functionalities. Thus, the sequence encoding an antibody can be fused to a marker sequence, such as a sequence encoding a peptide that facilitates purification of the fused antibody comprising an antibody fragment or portion.

Polynucleotides Selectively Hybridizing to a Polynucleotide as Described Herein

The method of the present invention uses isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library.

Preferably, the cDNA library comprises at least 80% full-length sequences, preferably, at least 85% or 90% full-length sequences, and, more preferably, at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

Optionally, polynucleotides will encode at least a portion of an antibody. The polynucleotides embrace nucleic acid sequences that can be employed for selective hybridization to a polynucleotide encoding an antibody of the present invention. See, e.g., Ausubel, supra; Colligan, supra, each entirely incorporated herein by reference.

Construction of Nucleic Acids

The isolated nucleic acids can be made using (a) recombinant methods, (b) synthetic techniques, (c) purification techniques, and/or (d) combinations thereof, as well-known in the art.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention, excluding the coding sequence, is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra)

Recombinant Methods for Constructing Nucleic Acids

The isolated nucleic acid compositions, such as RNA, cDNA, genomic DNA, or any combination thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. The isolation of RNA, and construction of cDNA and genomic libraries, are well known to those of ordinary skill in the art. (See, e.g., Ausubel, supra; or Sambrook, supra)

Nucleic Acid Screening and Isolation Methods

A cDNA or genomic library can be screened using a probe based upon the sequence of a polynucleotide used in the method of the present invention, such as those disclosed herein. Probes can be used to hybridize with genomic DNA or cDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent, such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 70-100%, or any range or value therein. However, it should be understood that minor sequence variations in the probes and primers can be compensated for by reducing the stringency of the hybridization and/or wash medium.

Methods of amplification of RNA or DNA are well known in the art and can be used according to the present invention without undue experimentation, based on the teaching and guidance presented herein.

Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; 4,795,699 and 4,921,794 to Tabor, et al; U.S. Pat. No. 5,142,033 to Innis; U.S. Pat. No. 5,122,464 to Wilson, et al.; U.S. Pat. No. 5,091,310 to Innis; U.S. Pat. No. 5,066,584 to Gyllensten, et al; U.S. Pat. No. 4,889,818 to Gelfand, et al; U.S. Pat. No. 4,994,370 to Silver, et al; U.S. Pat. No. 4,766,067 to Biswas; U.S. Pat. No. 4,656,134 to Ringold) and RNA mediated amplification that uses anti-sense RNA to the target sequence as a template for double-stranded DNA synthesis (U.S. Pat. No. 5,130,238 to Malek, et al, with the tradename NASBA), the entire contents of which references are incorporated herein by reference. (See, e.g., Ausubel, supra; or Sambrook, supra.)

For instance, polymerase chain reaction (PCR) technology can be used to amplify the sequences of polynucleotides used in the method of the present invention and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, supra, Sambrook, supra, and Ausubel, supra, as well as Mullis, et al., U.S. Pat. No. 4,683,202 (1987); and Innis, et al., PCR Protocols A Guide to Methods and Applications, Eds., Academic Press Inc., San Diego, Calif. (1990). Commercially available kits for genomic PCR amplification are known in the art. See, e.g., Advantage-GC Genomic PCR Kit (Clontech). Additionally, e.g., the T4 gene 32 protein (Boehringer Mannheim) can be used to improve yield of long PCR products.

Synthetic Methods for Constructing Nucleic Acids

The isolated nucleic acids used in the method of the present invention can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

Recombinant Expression Cassettes

The present invention uses recombinant expression cassettes comprising a nucleic acid. A nucleic acid sequence, for example, a cDNA or a genomic sequence encoding an antibody used in the method of the present invention, can be used to construct a recombinant expression cassette that can be introduced into at least one desired host cell. A recombinant expression cassette will typically comprise a polynucleotide operably linked to transcriptional initiation regulatory sequences that will direct the transcription of the polynucleotide in the intended host cell. Both heterologous and non-heterologous (i.e., endogenous) promoters can be employed to direct expression of the nucleic acids.

In some embodiments, isolated nucleic acids that serve as promoter, enhancer, or other elements can be introduced in the appropriate position (upstream, downstream or in the intron) of a non-heterologous form of a polynucleotide of the present invention so as to up or down regulate expression of a polynucleotide. For example, endogenous promoters can be altered in vivo or in vitro by mutation, deletion and/or substitution.

Vectors and Host Cells

The present invention also relates to vectors that include isolated nucleic acid molecules, host cells that are genetically engineered with the recombinant vectors, and the production of at least one anti-IL-23 antibody by recombinant techniques, as is well known in the art. See, e.g., Sambrook, et al., supra; Ausubel, et al., supra, each entirely incorporated herein by reference.

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but are not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), mycophenolic acid, or glutamine synthetase (GS, U.S. Pat. Nos. 5,122,464; 5,770,359; 5,827,739) resistance for eukaryotic cell culture, and tetracycline or ampicillin resistance genes for culturing in *E. coli* and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra, Chapters 1-4 and 16-18; Ausubel, supra, Chapters 1, 9, 13, 15, 16.

At least one antibody used in the method of the present invention can be expressed in a modified form, such as a fusion protein, and can include not only secretion signals, but also additional heterologous functional regions. For instance, a region of additional amino acids, particularly charged amino acids, can be added to the N-terminus of an antibody to improve stability and persistence in the host cell, during purification, or during subsequent handling and storage. Also, peptide moieties can be added to an antibody of the present invention to facilitate purification. Such regions can be removed prior to final preparation of an antibody or at least one fragment thereof. Such methods are described in many standard laboratory manuals, such as Sambrook, supra, Chapters 17.29-17.42 and 18.1-18.74; Ausubel, supra, Chapters 16, 17 and 18.

Those of ordinary skill in the art are knowledgeable in the numerous expression systems available for expression of a nucleic acid encoding a protein used in the method of the present invention. Alternatively, nucleic acids can be expressed in a host cell by turning on (by manipulation) in a host cell that contains endogenous DNA encoding an antibody. Such methods are well known in the art, e.g., as described in U.S. Pat. Nos. 5,580,734, 5,641,670, 5,733,746, and 5,733,761, entirely incorporated herein by reference.

Illustrative of cell cultures useful for the production of the antibodies, specified portions or variants thereof, are mammalian cells. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, CHO cells, hep G2 cells, P3X63Ag8.653, SP2/0-Ag14, 293 cells, HeLa cells and the like, which are readily available from, for example, American Type Culture Collection, Manassas, Va. (www.atcc.org). Preferred host cells include cells of lymphoid origin, such as myeloma and lymphoma cells. Particularly preferred host cells are P3X63Ag8.653 cells (ATCC Accession Number CRL-1580) and SP2/0-Ag14 cells (ATCC Accession Number CRL-1851). In a particularly preferred embodiment, the recombinant cell is a P3X63Ab8.653 or a SP2/0-Ag14 cell.

Expression vectors for these cells can include one or more of the following expression control sequences, such as, but not limited to, an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human immunoglobulin promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present invention are known and/or available, for instance, from the American Type Culture Collection Catalogue of Cell Lines and Hybridomas (www.atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., J. Virol. 45:773-781 (1983)). Additionally, gene sequences to control replication in the host cell can be incorporated into the vector, as known in the art.

Purification of an Antibody

An anti-IL-23 antibody can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., Chapters 1, 4, 6, 8, 9, 10, each entirely incorporated herein by reference.

Antibodies used in the method of the present invention include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody can be glycosylated or can be non-glycosylated, with glycosylated preferred. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

Anti-IL-23 Antibodies.

An anti-IL-23 antibody according to the present invention includes any protein or peptide containing molecule that comprises at least a portion of an immunoglobulin molecule, such as but not limited to, at least one ligand binding portion (LBP), such as but not limited to, a complementarity determining region (CDR) of a heavy or light chain or a ligand binding portion thereof, a heavy chain or light chain variable region, a framework region (e.g., FR1, FR2, FR3, FR4 or fragment thereof, further optionally comprising at least one substitution, insertion or deletion), a heavy chain or light chain constant region, (e.g., comprising at least one $C_H1$, hinge1, hinge2, hinge3, hinge4, $C_H2$, or $C_H3$ or fragment thereof, further optionally comprising at least one substitution, insertion or deletion), or any portion thereof, that can be incorporated into an antibody. An antibody can include or be derived from any mammal, such as but not limited to, a human, a mouse, a rabbit, a rat, a rodent, a primate, or any combination thereof, and the like.

The isolated antibodies used in the method of the present invention comprise the antibody amino acid sequences disclosed herein encoded by any suitable polynucleotide, or any isolated or prepared antibody. Preferably, the human antibody or antigen-binding fragment binds human IL-23 and, thereby, partially or substantially neutralizes at least one biological activity of the protein. An antibody, or specified portion or variant thereof, that partially or preferably substantially neutralizes at least one biological activity of at least one IL-23 protein or fragment can bind the protein or fragment and thereby inhibit activities mediated through the binding of IL-23 to the IL-23 receptor or through other IL-23-dependent or mediated mechanisms. As used herein, the term "neutralizing antibody" refers to an antibody that can inhibit an IL-23-dependent activity by about 20-120%, preferably by at least about 10, 20, 30, 40, 50, 55, 60, 65, 70, 75, 80, 85, 90, 91, 92, 93, 94, 95, 96, 97, 98, 99, 100% or more depending on the assay. The capacity of an anti-IL-23 antibody to inhibit an IL-23-dependent activity is preferably assessed by at least one suitable IL-23 protein or receptor assay, as described herein and/or as known in the art. A human antibody can be of any class (IgG, IgA, IgM, IgE, IgD, etc.) or isotype and can comprise a kappa or lambda light chain. In one embodiment, the human antibody comprises an IgG heavy chain or defined fragment, for example, at least one of isotypes, IgG1, IgG2, IgG3 or IgG4 (e.g., γ1, γ2, γ3, γ4). Antibodies of this type can be prepared by employing a transgenic mouse or other trangenic non-human mammal comprising at least one human light chain (e.g., IgG, IgA, and IgM) transgenes as described herein and/or as known in the art. In another embodiment, the anti-IL-23 human antibody comprises an IgG1 heavy chain and an IgG1 light chain.

An antibody binds at least one specified epitope specific to at least one IL-23 protein, subunit, fragment, portion or any combination thereof. The at least one epitope can comprise at least one antibody binding region that comprises at least one portion of the protein, which epitope is preferably comprised of at least one extracellular, soluble, hydrophillic, external or cytoplasmic portion of the protein.

Generally, the human antibody or antigen-binding fragment will comprise an antigen-binding region that comprises at least one human complementarity determining region (CDR1, CDR2 and CDR3) or variant of at least one heavy chain variable region and at least one human complementarity determining region (CDR1, CDR2 and CDR3) or variant of at least one light chain variable region. The CDR sequences may be derived from human germline sequences or closely match the germline sequences. For example, the CDRs from a synthetic library derived from the original non-human CDRs can be used. These CDRs may be formed by incorporation of conservative substitutions from the original non-human sequence. In another particular embodiment, the antibody or antigen-binding portion or variant can have an antigen-binding region that comprises at least a portion of at least one light chain CDR (i.e., CDR1, CDR2 and/or CDR3) having the amino acid sequence of the corresponding CDRs 1, 2 and/or 3.

Such antibodies can be prepared by chemically joining together the various portions (e.g., CDRs, framework) of the antibody using conventional techniques, by preparing and expressing a (i.e., one or more) nucleic acid molecule that encodes the antibody using conventional techniques of recombinant DNA technology or by using any other suitable method.

The anti-IL-23 specific antibody can comprise at least one of a heavy or light chain variable region having a defined amino acid sequence. For example, in a preferred embodiment, the anti-IL-23 antibody comprises at least one of at least one heavy chain variable region, optionally having the amino acid sequence of SEQ ID NO:106 and/or at least one light chain variable region, optionally having the amino acid sequence of SEQ ID NO:116. Antibodies that bind to human IL-23 and that comprise a defined heavy or light chain variable region can be prepared using suitable methods, such as phage display (Katsube, Y., et al., Int J Mol. Med, 1(5):863-868 (1998)) or methods that employ transgenic animals, as known in the art and/or as described herein. For example, a transgenic mouse, comprising a functionally rearranged human immunoglobulin heavy chain transgene and a transgene comprising DNA from a human immunoglobulin light chain locus that can undergo functional rearrangement, can be immunized with human IL-23 or a fragment thereof to elicit the production of antibodies. If desired, the antibody producing cells can be isolated and hybridomas or other immortalized antibody-producing cells can be prepared as described herein and/or as known in the art. Alternatively, the antibody, specified portion or variant can be expressed using the encoding nucleic acid or portion thereof in a suitable host cell.

The invention also relates to antibodies, antigen-binding fragments, immunoglobulin chains and CDRs comprising amino acids in a sequence that is substantially the same as an amino acid sequence described herein. Preferably, such antibodies or antigen-binding fragments and antibodies comprising such chains or CDRs can bind human IL-23 with high affinity (e.g., $K_D$ less than or equal to about $10^{-9}$M). Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g., charge, structure, polarity, hydrophobicity/hydrophilicity) that are similar to those of the first amino acid. Conservative substitutions include, without limitation, replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

Amino Acid Codes

The amino acids that make up anti-IL-23 antibodies of the present invention are often abbreviated. The amino acid designations can be indicated by designating the amino acid by its single letter code, its three letter code, name, or three nucleotide codon(s) as is well understood in the art (see Alberts, B., et al., Molecular Biology of The Cell, Third Ed., Garland Publishing, Inc., New York, 1994):

TABLE 19

| SINGLE LETTER CODE | THREE LETTER CODE | NAME | THREE NUCLEOTIDE CODON(S) |
| --- | --- | --- | --- |
| A | Ala | Alanine | GCA, GCC, GCG, GCU |
| C | Cys | Cysteine | UGC, UGU |
| D | Asp | Aspartic acid | GAC, GAU |
| E | Glu | Glutamic acid | GAA, GAG |
| F | Phe | Phenylalanine | UUC, UUU |
| G | Gly | Glycine | GGA, GGC, GGG, GGU |
| H | His | Histidine | CAC, CAU |
| I | Ile | Isoleucine | AUA, AUC, AUU |
| K | Lys | Lysine | AAA, AAG |
| L | Leu | Leucine | UUA, UUG, CUA, CUC, CUG, CUU |
| M | Met | Methionine | AUG |
| N | Asn | Asparagine | AAC, AAU |
| P | Pro | Proline | CCA, CCC, CCG, CCU |
| Q | Gln | Glutamine | CAA, CAG |
| R | Arg | Arginine | AGA, AGG, CGA, CGC, CGG, CGU |
| S | Ser | Serine | AGC, AGU, UCA, UCC, UCG, UCU |
| T | Thr | Threonine | ACA, ACC, ACG, ACU |
| V | Val | Valine | GUA, GUC, GUG, GUU |
| W | Trp | Tryptophan | UGG |
| Y | Tyr | Tyrosine | UAC, UAU |

An anti-IL-23 antibody used in the method of the present invention can include one or more amino acid substitutions, deletions or additions, either from natural mutations or human manipulation, as specified herein.

The number of amino acid substitutions a skilled artisan would make depends on many factors, including those described above. Generally speaking, the number of amino acid substitutions, insertions or deletions for any given anti-IL-23 antibody, fragment or variant will not be more than 40, 30, 20, 19, 18, 17, 16, 15, 14, 13, 12, 11, 10, 9, 8, 7, 6, 5, 4, 3, 2, 1, such as 1-30 or any range or value therein, as specified herein.

Amino acids in an anti-IL-23 specific antibody that are essential for function can be identified by methods known in the art, such as site-directed mutagenesis or alanine-scanning mutagenesis (e.g., Ausubel, supra, Chapters 8, 15; Cunningham and Wells, Science 244:1081-1085 (1989)). The latter procedure introduces single alanine mutations at every residue in the molecule. The resulting mutant molecules are then tested for biological activity, such as, but not limited to, at least one IL-23 neutralizing activity. Sites that are critical for antibody binding can also be identified by structural analysis, such as crystallization, nuclear magnetic resonance or photoaffinity labeling (Smith, et al., J. Mol. Biol. 224:899-904 (1992) and de Vos, et al., Science 255: 306-312 (1992)).

Anti-IL-23 antibodies can include, but are not limited to, at least one portion, sequence or combination selected from 5 to all of the contiguous amino acids of at least one of SEQ ID NOS: 5, 20, 44, 50, 56, and 73.

IL-23 antibodies or specified portions or variants can include, but are not limited to, at least one portion, sequence or combination selected from at least 3-5 contiguous amino acids of the SEQ ID NOs above; 5-17 contiguous amino acids of the SEQ ID NOs above, 5-10 contiguous amino acids of the SEQ ID NOs above, 5-11 contiguous amino acids of the SEQ ID NOs above, 5-7 contiguous amino acids of the SEQ ID NOs above; 5-9 contiguous amino acids of the SEQ ID NOs above.

An anti-IL-23 antibody can further optionally comprise a polypeptide of at least one of 70-100% of 5, 17, 10, 11, 7, 9, 119, or 108 contiguous amino acids of the SEQ ID NOs above. In one embodiment, the amino acid sequence of an immunoglobulin chain, or portion thereof (e.g., variable region, CDR) has about 70-100% identity (e.g., 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or any range or value therein) to the amino acid sequence of the corresponding chain of at least one of the SEQ ID NOs above. For example, the amino acid sequence of a light chain variable region can be compared with the sequence of the SEQ ID NOs above, or the amino acid sequence of a heavy chain CDR3 can be compared with the SEQ ID NOs above. Preferably, 70-100% amino acid identity (i.e., 90, 91, 92, 93, 94, 95, 96, 97, 98, 99, 100 or any range or value therein) is determined using a suitable computer algorithm, as known in the art.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. "Identity" and "similarity" can be readily calculated by known methods, including, but not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., Siam J. Applied Math., 48:1073 (1988). In addition, values for percentage identity can be obtained from amino acid and nucleotide sequence alignments generated using the default settings for the AlignX component of Vector NTI Suite 8.0 (Informax, Frederick, Md.).

Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., Nucleic Acids Research 12(1): 387 (1984)), BLASTP, BLASTN, and FASTA (Atschul, S. F. et al., J. Molec. Biol. 215:403-410 (1990)). The BLAST X program is publicly available from NCBI and other sources (BLAST Manual, Altschul, S., et al., NCBINLM NIH Bethesda, Md. 20894: Altschul, S., et al., J. Mol. Biol. 215:403-410 (1990). The well-known Smith Waterman algorithm may also be used to determine identity.

Preferred parameters for polypeptide sequence comparison include the following:
(1) Algorithm: Needleman and Wunsch, J. Mol Biol. 48:443-453 (1970) Comparison matrix: BLOSSUM62 from Hentikoff and Hentikoff, Proc. Natl. Acad. Sci, USA. 89:10915-10919 (1992)
Gap Penalty: 12
Gap Length Penalty: 4
A program useful with these parameters is publicly available as the "gap" program from Genetics Computer Group, Madison Wis. The aforementioned parameters are the default parameters for peptide sequence comparisons (along with no penalty for end gaps).

Preferred parameters for polynucleotide comparison include the following:
(1) Algorithm: Needleman and Wunsch, J. Mol Biol. 48:443-453 (1970)
Comparison matrix: matches=+10, mismatch=0
Gap Penalty: 50
Gap Length Penalty: 3
Available as: The "gap" program from Genetics Computer Group, Madison Wis. These are the default parameters for nucleic acid sequence comparisons.

By way of example, a polynucleotide sequence may be identical to another sequence, that is 100% identical, or it may include up to a certain integer number of nucleotide alterations as compared to the reference sequence. Such alterations are selected from the group consisting of at least one nucleotide deletion, substitution, including transition and transversion, or insertion, and wherein the alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in the sequence by the numerical percent of the respective percent identity (divided by 100) and subtracting that product from the total number of nucleotides in the sequence, or:
$n_n \le x_n - (x_n \cdot y)$,
wherein $n_n$ is the number of nucleotide alterations, $x_n$ is the total number of nucleotides in sequence, and y is, for instance, 0.70 for 70%, 0.80 for 80%, 0.85 for 85%, 0.90 for 90%, 0.95 for 95%, etc., and wherein any non-integer product of $x_n$ and y is rounded down to the nearest integer prior to subtracting from $x_n$.

Alterations of a polynucleotide sequence encoding the SEQ ID NOs above may create nonsense, missense or frameshift mutations in this coding sequence and thereby alter the polypeptide encoded by the polynucleotide following such alterations. Similarly, a polypeptide sequence may be identical to the reference sequence of the SEQ ID NOs above, that is be 100% identical, or it may include up to a certain integer number of amino acid alterations as compared to the reference sequence such that the percentage identity is less than 100%. Such alterations are selected from the group consisting of at least one amino acid deletion, substitution, including conservative and non-conservative substitution, or insertion, and wherein the alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the SEQ ID NOs above by the numerical percent of the respective percent identity (divided by 100) and then subtracting that product from the total number of amino acids in the SEQ ID NOs above, or:
$n_a \le x_a - (x_a \cdot y)$,
wherein $n_a$ is the number of amino acid alterations, $x_a$ is the total number of amino acids in the SEQ ID NOs above, and y is, for instance 0.70 for 70%, 0.80 for 80%, 0.85 for 85% etc., and wherein any non-integer produce of $x_a$ and y is rounded down to the nearest integer prior to subtracting it from $x_a$.

Exemplary heavy chain and light chain variable regions sequences and portions thereof are provided in the SEQ ID NOs above. The antibodies of the present invention, or specified variants thereof, can comprise any number of contiguous amino acid residues from an antibody of the present invention, wherein that number is selected from the group of integers consisting of from 10-100% of the number of contiguous residues in an anti-IL-23 antibody. Optionally, this subsequence of contiguous amino acids is at least about 10, 20, 30, 40, 50, 60, 70, 80, 90, 100, 110, 120, 130, 140, 150, 160, 170, 180, 190, 200, 210, 220, 230, 240, 250 or more amino acids in length, or any range or value therein. Further, the number of such subsequences can be any integer selected from the group consisting of from 1 to 20, such as at least 2, 3, 4, or 5.

As those of skill will appreciate, the present invention includes at least one biologically active antibody of the present invention. Biologically active antibodies have a specific activity at least 20%, 30%, or 40%, and, preferably, at least 50%, 60%, or 70%, and, most preferably, at least 80%, 90%, or 95%-100% or more (including, without limitation, up to 10 times the specific activity) of that of the native (non-synthetic), endogenous or related and known antibody. Methods of assaying and quantifying measures of enzymatic activity and substrate specificity are well known to those of skill in the art.

In another aspect, the invention relates to human antibodies and antigen-binding fragments, as described herein, which are modified by the covalent attachment of an organic moiety. Such modification can produce an antibody or antigen-binding fragment with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified antibodies and antigen-binding fragments can comprise one or more organic moieties that are covalently bonded, directly or indirectly, to the antibody. Each organic moiety that is bonded to an antibody or antigen-binding fragment of the invention can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, an antibody modified by the covalent attachment of polylysine is encompassed by the invention. Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the antibody of the invention has a molecular weight of about 800 to about 150,000 Daltons as a separate molecular entity. For example, $PEG_{5000}$ and $PEG_{20,000}$, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N, N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Fatty acids that are suitable for modifying antibodies of the invention include, for example, n-dodecanoate (Cu, laurate), n-tetradecanoate ($C_{14}$, myristate), n-octadecanoate ($C_{18}$, stearate), n-eicosanoate ($C_{20}$, arachidate), n-docosanoate ($C_{22}$, behenate), n-triacontanoate ($C_{30}$), n-tetracontanoate ($C_{40}$), cis-Δ9-octadecanoate ($C_{18}$, oleate), all cis-Δ5,8,11,14-eicosatetraenoate ($C_{20}$, arachidonate), octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably, one to about six, carbon atoms.

The modified human antibodies and antigen-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups, such as tosylate, mesylate, halo (chloro, bromo, fluoro, iodo), N-hydroxysuccinimidyl esters (NETS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson, G. T., *Bioconjugate Techniques*, Academic Press: San Diego, Calif. (1996)). An activating group can be bonded directly to the organic group (e.g., hydrophilic polymer, fatty acid, fatty acid ester), or through a linker moiety, for example, a divalent $C_1$-$C_{12}$ group wherein one or more carbon atoms can be replaced by a heteroatom, such as oxygen, nitrogen or sulfur. Suitable linker moieties include, for example, tetraethylene glycol, —$(CH_2)_3$—, —NH—$(CH_2)_6$—NH—, —$(CH_2)_2$—NH— and —$CH_2$—O—$CH_2$—$CH_2$—O—$CH_2$—$CH_2$O—$CH$—NH—. Modifying agents that comprise a linker moiety can be produced, for example, by reacting a mono-Boc-alkyl-diamine (e.g., mono-Boc-ethylenediamine, mono-Boc-diaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate, as described, or can be reacted with maleic anhydride and the resulting product cyclized to produce an activated maleimido derivative of the fatty acid. (See, for example, Thompson, et al., WO 92/16221, the entire teachings of which are incorporated herein by reference.)

The modified antibodies can be produced by reacting a human antibody or antigen-binding fragment with a modifying agent. For example, the organic moieties can be bonded to the antibody in a non-site specific manner by employing an amine-reactive modifying agent, for example, an NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention. Modified human antibodies and antigen-binding fragments comprising an organic moiety that is bonded to specific sites of an antibody of the present invention can be prepared using suitable methods, such as reverse proteolysis (Fisch et al., *Bioconjugate Chem.*, 3:147-153 (1992); Werlen et al., *Bioconjugate Chem.*, 5:411-417 (1994); Kumaran et al., *Protein Sci.* 6(10):2233-2241 (1997); Itoh et al., *Bioorg. Chem.*, 24(1): 59-68 (1996); Capellas et al., *Biotechnol. Bioeng.*, 56(4):456-463 (1997)), and the methods described in Hermanson, G. T., *Bioconjugate Techniques*, Academic Press: San Diego, Calif. (1996).

The method of the present invention also uses an anti-IL-23 antibody composition comprising at least one, at least two, at least three, at least four, at least five, at least six or more anti-IL-23 antibodies thereof, as described herein and/or as known in the art that are provided in a non-naturally occurring composition, mixture or form. Such compositions comprise non-naturally occurring compositions comprising at least one or two full length, C- and/or N-terminally deleted variants, domains, fragments, or specified variants, of the anti-IL-23 antibody amino acid sequence selected from the group consisting of 70-100% of the contiguous amino acids of the SEQ ID NOs above, or specified fragments, domains or variants thereof. Preferred anti-IL-23 antibody compositions include at least one or two full length, fragments, domains or variants as at least one CDR or LBP containing portions of the anti-IL-23 antibody sequence described herein, for example, 70-100% of the SEQ ID NOs above, or specified fragments, domains or variants thereof. Further preferred compositions comprise, for example, 40-99% of at least one of 70-100% of the SEQ ID NOs above, etc., or specified fragments, domains or variants thereof. Such composition percentages are by weight, volume, concentration, molarity, or molality as liquid or dry solutions, mixtures, suspension, emulsions, particles, powder, or colloids, as known in the art or as described herein.

Antibody Compositions Comprising Further Therapeutically Active Ingredients

The antibody compositions used in the method of the invention can optionally further comprise an effective amount of at least one compound or protein selected from at least one of an anti-infective drug, a cardiovascular (CV) system drug, a central nervous system (CNS) drug, an autonomic nervous system (ANS) drug, a respiratory tract drug, a gastrointestinal (GI) tract drug, a hormonal drug, a drug for fluid or electrolyte balance, a hematologic drug, an antineoplastic, an immunomodulation drug, an ophthalmic, otic or nasal drug, a topical drug, a nutritional drug or the like. Such drugs are well known in the art, including formulations, indications, dosing and administration for each presented herein (see, e.g., Nursing 2001 Handbook of Drugs, 21$^{st}$ edition, Springhouse Corp., Springhouse, P A, 2001; Health Professional's Drug Guide 2001, ed., Shannon, Wilson, Stang, Prentice-Hall, Inc, Upper Saddle River, N.J.; Pharmcotherapy Handbook, Wells et al., ed., Appleton & Lange, Stamford, Conn., each entirely incorporated herein by reference).

By way of example of the drugs that can be combined with the antibodies for the method of the present invention, the anti-infective drug can be at least one selected from amebicides or at least one antiprotozoals, anthelmintics, antifungals, antimalarials, antituberculotics or at least one antileprotics, aminoglycosides, penicillins, cephalosporins, tetracyclines, sulfonamides, fluoroquinolones, antivirals, macrolide anti-infectives, and miscellaneous anti-infectives. The hormonal drug can be at least one selected from corticosteroids, androgens or at least one anabolic steroid, estrogen or at least one progestin, gonadotropin, antidiabetic drug or at least one glucagon, thyroid hormone, thyroid hormone antagonist, pituitary hormone, and parathyroid-like drug. The at least one cephalosporin can be at least one selected from cefaclor, cefadroxil, cefazolin sodium, cefdinir, cefepime hydrochloride, cefixime, cefmetazole sodium, cefonicid sodium, cefoperazone sodium, cefotaxime sodium, cefotetan disodium, cefoxitin sodium, cefpodoxime proxetil, cefprozil, ceftazidime, ceftibuten, ceftizoxime sodium, ceftriaxone sodium, cefuroxime axetil, cefuroxime sodium, cephalexin hydrochloride, cephalexin monohydrate, cephradine, and loracarbef.

The at least one coricosteroid can be at least one selected from betamethasone, betamethasone acetate or betamethasone sodium phosphate, betamethasone sodium phosphate, cortisone acetate, dexamethasone, dexamethasone acetate, dexamethasone sodium phosphate, fludrocortisone acetate, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, prednisolone, prednisolone acetate, prednisolone sodium phosphate, prednisolone tebutate, prednisone, triamcinolone, triamcinolone acetonide, and triamcinolone diacetate. The at least one androgen or anabolic steroid can be at least one selected from danazol, fluoxymesterone, methyltestosterone, nandrolone decanoate, nandrolone phenpropionate, testosterone, testosterone cypionate, testosterone enanthate, testosterone propionate, and testosterone transdermal system.

The at least one immunosuppressant can be at least one selected from azathioprine, basiliximab, cyclosporine, daclizumab, lymphocyte immune globulin, muromonab-CD3, mycophenolate mofetil, mycophenolate mofetil hydrochloride, sirolimus, and tacrolimus.

The at least one local anti-infective can be at least one selected from acyclovir, amphotericin B, azelaic acid cream, bacitracin, butoconazole nitrate, clindamycin phosphate, clotrimazole, econazole nitrate, erythromycin, gentamicin sulfate, ketoconazole, mafenide acetate, metronidazole (topical), miconazole nitrate, mupirocin, naftifine hydrochloride, neomycin sulfate, nitrofurazone, nystatin, silver sulfadiazine, terbinafine hydrochloride, terconazole, tetracycline hydrochloride, tioconazole, and tolnaftate. The at least one scabicide or pediculicide can be at least one selected from crotamiton, lindane, permethrin, and pyrethrins. The at least one topical corticosteroid can be at least one selected from betamethasone dipropionate, betamethasone valerate, clobetasol propionate, desonide, desoximetasone, dexamethasone, dexamethasone sodium phosphate, diflorasone diacetate, fluocinolone acetonide, fluocinonide, flurandrenolide, fluticasone propionate, halcionide, hydrocortisone, hydrocortisone acetate, hydrocortisone butyrate, hydrocorisone valerate, mometasone furoate, and triamcinolone acetonide. (See, e.g., pp. 1098-1136 of Nursing 2001 Drug Handbook.)

Anti-IL-23 antibody compositions can further comprise at least one of any suitable and effective amount of a composition or pharmaceutical composition comprising at least one anti-IL-23 antibody contacted or administered to a cell, tissue, organ, animal or patient in need of such modulation, treatment or therapy, optionally further comprising at least one selected from at least one TNF antagonist (e.g., but not limited to a TNF chemical or protein antagonist, TNF monoclonal or polyclonal antibody or fragment, a soluble TNF receptor (e.g., p55, p70 or p85) or fragment, fusion polypeptides thereof, or a small molecule TNF antagonist, e.g., TNF binding protein I or II (TBP-1 or TBP-II), nerelimonmab, infliximab, eternacept, CDP-571, CDP-870, afelimomab, lenercept, and the like), an antirheumatic (e.g., methotrexate, auranofin, aurothioglucose, azathioprine, etanercept, gold sodium thiomalate, hydroxychloroquine sulfate, leflunomide, sulfasalzine), an immunization, an immunoglobulin, an immunosuppressive (e.g., basiliximab, cyclosporine, daclizumab), a cytokine or a cytokine antagonist. Non-limiting examples of such cytokines include, but are not limited to, any of IL-1 to IL-23 et al. (e.g., IL-1, IL-2, etc.). Suitable dosages are well known in the art. See, e.g., Wells et al., eds., Pharmacotherapy Handbook, 2$^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

Anti-IL-23 antibody compounds, compositions or combinations used in the method of the present invention can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., *Remington's Pharmaceutical Sciences*, 18th Edition, Mack Publishing Co. (Easton, Pa.) 1990. Pharmaceutically acceptable carriers can be routinely selected that are suitable for the mode of administration, solubility and/or stability of the anti-IL-23 antibody, fragment or variant composition as well known in the art or as described herein.

Pharmaceutical excipients and additives useful in the present composition include, but are not limited to, proteins, peptides, amino acids, lipids, and carbohydrates (e.g., sugars, including monosaccharides, di-, tri-, tetra-, and oligo-saccharides; derivatized sugars, such as alditols, aldonic acids, esterified sugars and the like; and polysaccharides or sugar polymers), which can be present singly or in combination 1-99.99% by weight or volume. Exemplary protein excipients include serum albumin, such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients suitable for use in the invention include, for example, monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

Anti-IL-23 antibody compositions can also include a buffer or a pH adjusting agent; typically, the buffer is a salt prepared from an organic acid or base. Representative buffers include organic acid salts, such as salts of citric acid, ascorbic acid, gluconic acid, carbonic acid, tartaric acid, succinic acid, acetic acid, or phthalic acid; Tris, trometh-amine hydrochloride, or phosphate buffers. Preferred buffers for use in the present compositions are organic acid salts, such as citrate.

Additionally, anti-IL-23 antibody compositions can include polymeric excipients/additives, such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates, such as "TWEEN 20" and "TWEEN 80"), lipids (e.g., phospholipids, fatty acids), steroids (e.g., cholesterol), and chelating agents (e.g., EDTA).

These and additional known pharmaceutical excipients and/or additives suitable for use in the anti-IL-23 antibody, portion or variant compositions according to the invention are known in the art, e.g., as listed in "Remington: The Science & Practice of Pharmacy," 19th ed., Williams & Williams, (1995), and in the "Physician's Desk Reference," 52nd ed., Medical Economics, Montvale, N.J. (1998), the disclosures of which are entirely incorporated herein by reference. Preferred carrier or excipient materials are carbohydrates (e.g., saccharides and alditols) and buffers (e.g., citrate) or polymeric agents. An exemplary carrier molecule is the mucopolysaccharide, hyaluronic acid, which may be useful for intraarticular delivery.

Formulations

As noted above, the invention provides for stable formulations, which preferably comprise a phosphate buffer with saline or a chosen salt, as well as preserved solutions and formulations containing a preservative as well as multi-use preserved formulations suitable for pharmaceutical or veterinary use, comprising at least one anti-IL-23 antibody in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3, 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

As noted above, the method of the invention uses an article of manufacture, comprising packaging material and at least one vial comprising a solution of at least one anti-IL-23 specific antibody with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further uses an article of manufacture, comprising packaging material, a first vial comprising lyophilized anti-IL-23 specific antibody, and a second vial comprising an aqueous diluent of prescribed buffer or preservative, wherein said packaging material comprises a label that instructs a patient to reconstitute the anti-IL-23 specific antibody in the aqueous diluent to form a solution that can be held over a period of twenty-four hours or greater.

The anti-IL-23 specific antibody used in accordance with the present invention can be produced by recombinant means, including from mammalian cell or transgenic preparations, or can be purified from other biological sources, as described herein or as known in the art.

The range of the anti-IL-23 specific antibody includes amounts yielding upon reconstitution, if in a wet/dry system, concentrations from about 1.0 µg/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

Preferably, the aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an antimicrobial effect. Such concentrations are dependent on the preservative selected and are readily determined by the skilled artisan.

Other excipients, e.g., isotonicity agents, buffers, antioxidants, and preservative enhancers, can be optionally and preferably added to the diluent. An isotonicity agent, such as glycerin, is commonly used at known concentrations. A physiologically tolerated buffer is preferably added to provide improved pH control. The formulations can cover a wide range of pHs, such as from about pH 4 to about pH 10, and preferred ranges from about pH 5 to about pH 9, and a most preferred range of about 6.0 to about 8.0. Preferably, the formulations of the present invention have a pH between about 6.8 and about 7.8. Preferred buffers include phosphate buffers, most preferably, sodium phosphate, particularly, phosphate buffered saline (PBS).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or non-ionic surfactants, such as polysorbate 20 or 80 or poloxamer 184 or 188, Pluronic® polyls, other block co-polymers, and chelators, such as EDTA and EGTA, can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

The formulations can be prepared by a process which comprises mixing at least one anti-IL-23 specific antibody and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one anti-IL-23 specific antibody and preservative in an aqueous diluent is carried out using conventional dissolution and mixing procedures. To prepare a suitable formulation, for example, a measured amount of at least one anti-IL-23 specific antibody in buffered solution is combined with the desired preservative in a buffered solution in quantities sufficient to provide the protein and preservative at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The formulations can be provided to patients as clear solutions or as dual vials comprising a vial of lyophilized anti-IL-23 specific antibody that is reconstituted with a second vial containing water, a preservative and/or excipients, preferably, a phosphate buffer and/or saline and a chosen salt, in an aqueous diluent. Either a single solution vial or dual vial requiring reconstitution can be reused multiple times and can suffice for a single or multiple cycles of patient treatment and thus can provide a more convenient treatment regimen than currently available.

The present articles of manufacture are useful for administration over a period ranging from immediate to twenty-four hours or greater. Accordingly, the presently claimed articles of manufacture offer significant advantages to the patient. Formulations of the invention can optionally be safely stored at temperatures of from about 2° C. to about 40° C. and retain the biologically activity of the protein for extended periods of time, thus allowing a package label indicating that the solution can be held and/or used over a period of 6, 12, 18, 24, 36, 48, 72, or 96 hours or greater. If preserved diluent is used, such label can include use up to 1-12 months, one-half, one and a half, and/or two years.

The solutions of anti-IL-23 specific antibody can be prepared by a process that comprises mixing at least one antibody in an aqueous diluent. Mixing is carried out using conventional dissolution and mixing procedures. To prepare a suitable diluent, for example, a measured amount of at least one antibody in water or buffer is combined in quantities sufficient to provide the protein and, optionally, a preservative or buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed products can be provided to patients as clear solutions or as dual vials comprising a vial of lyophilized at least one anti-IL-23 specific antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available.

The claimed products can be provided indirectly to patients by providing to pharmacies, clinics, or other such institutions and facilities, clear solutions or dual vials comprising a vial of lyophilized at least one anti-IL-23 specific antibody that is reconstituted with a second vial containing the aqueous diluent. The clear solution in this case can be up to one liter or even larger in size, providing a large reservoir from which smaller portions of the at least one antibody solution can be retrieved one or multiple times for transfer into smaller vials and provided by the pharmacy or clinic to their customers and/or patients.

Recognized devices comprising single vial systems include pen-injector devices for delivery of a solution, such as BD Pens, BD Autojector®, Humaject®, NovoPen®, B-D® Pen, AutoPen®, and OptiPen®, GenotropinPen®, Genotronorm Pen®, Humatro Pen®, Reco-Pen®, Roferon Pen®, Biojector®, Iject®, J-tip Needle-Free Injector®, Intraject®, Medi-Ject®, Smartject® e.g., as made or developed by Becton Dickensen (Franklin Lakes, N.J., www.bectondickenson.com), Disetronic (Burgdorf, Switzerland, www.disetronic.com; Bioject, Portland, Oreg. (www.bioject.com); National Medical Products, Weston Medical (Peterborough, UK, www.weston-medical.com), Medi-Ject Corp (Minneapolis, Minn., www.mediject.com), and similary suitable devices. Recognized devices comprising a dual vial system include those pen-injector systems for reconstituting a lyophilized drug in a cartridge for delivery of the reconstituted solution, such as the HumatroPen®. Examples of other devices suitable include pre-filled syringes, auto-injectors, needle free injectors, and needle free IV infusion sets.

The products may include packaging material. The packaging material provides, in addition to the information required by the regulatory agencies, the conditions under which the product can be used. The packaging material of the present invention provides instructions to the patient, as applicable, to reconstitute the at least one anti-IL-23 antibody in the aqueous diluent to form a solution and to use the solution over a period of 2-24 hours or greater for the two vial, wet/dry, product. For the single vial, solution product, pre-filled syringe or auto-injector, the label indicates that such solution can be used over a period of 2-24 hours or greater. The products are useful for human pharmaceutical product use.

The formulations used in the method of the present invention can be prepared by a process that comprises mixing an anti-IL-23 antibody and a selected buffer, preferably, a phosphate buffer containing saline or a chosen salt. Mixing the anti-IL-23 antibody and buffer in an aqueous diluent is carried out using conventional dissolution and mixing procedures. To prepare a suitable formulation, for example, a measured amount of at least one antibody in water or buffer is combined with the desired buffering agent in water in quantities sufficient to provide the protein and buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The method of the invention provides pharmaceutical compositions comprising various formulations useful and acceptable for administration to a human or animal patient. Such pharmaceutical compositions are prepared using water at "standard state" as the diluent and routine methods well known to those of ordinary skill in the art. For example, buffering components such as histidine and histidine monohydrochloride hydrate, may be provided first followed by the addition of an appropriate, non-final volume of water diluent, sucrose and polysorbate 80 at "standard state." Isolated antibody may then be added. Last, the volume of the pharmaceutical composition is adjusted to the desired final volume under "standard state" conditions using water as the diluent. Those skilled in the art will recognize a number of other methods suitable for the preparation of the pharmaceutical compositions.

The pharmaceutical compositions may be aqueous solutions or suspensions comprising the indicated mass of each constituent per unit of water volume or having an indicated pH at "standard state." As used herein, the term "standard state" means a temperature of 25° C.+/−2° C. and a pressure of 1 atmosphere. The term "standard state" is not used in the art to refer to a single art recognized set of temperatures or pressure, but is instead a reference state that specifies temperatures and pressure to be used to describe a solution or suspension with a particular composition under the reference "standard state" conditions. This is because the volume of a solution is, in part, a function of temperature and pressure. Those skilled in the art will recognize that pharmaceutical compositions equivalent to those disclosed here can be produced at other temperatures and pressures. Whether such pharmaceutical compositions are equivalent to those disclosed here should be determined under the "standard state" conditions defined above (e.g. 25° C.+/−2° C. and a pressure of 1 atmosphere).

Importantly, such pharmaceutical compositions may contain component masses "about" a certain value (e.g. "about 0.53 mg L-histidine") per unit volume of the pharmaceutical composition or have pH values about a certain value. A component mass present in a pharmaceutical composition or pH value is "about" a given numerical value if the isolated antibody present in the pharmaceutical composition is able to bind a peptide chain while the isolated antibody is present in the pharmaceutical composition or after the isolated antibody has been removed from the pharmaceutical composition (e.g., by dilution). Stated differently, a value, such as a component mass value or pH value, is "about" a given numerical value when the binding activity of the isolated antibody is maintained and detectable after placing the isolated antibody in the pharmaceutical composition.

Competition binding analysis is performed to determine if the IL-23 specific mAbs bind to similar or different epitopes and/or compete with each other. Abs are individually coated on ELISA plates. Competing mAbs are added, followed by the addition of biotinylated hrIL-23. For positive control, the same mAb for coating may be used as the competing mAb ("self-competition"). IL-23 binding is detected using streptavidin. These results demonstrate whether the mAbs recognize similar or partially overlapping epitopes on IL-23.

One aspect of the method of the invention administers to a patient a pharmaceutical composition comprising In one embodiment of the pharmaceutical compositions, the isolated antibody concentration is from about 77 to about 104 mg per ml of the pharmaceutical composition. In another embodiment of the pharmaceutical compositions the pH is from about 5.5 to about 6.5.

The stable or preserved formulations can be provided to patients as clear solutions or as dual vials comprising a vial of lyophilized at least one anti-IL-23 antibody that is reconstituted with a second vial containing a preservative or buffer and excipients in an aqueous diluent. Either a single solution vial or dual vial requiring reconstitution can be reused multiple times and can suffice for a single or multiple cycles of patient treatment and thus provides a more convenient treatment regimen than currently available.

Other formulations or methods of stabilizing the anti-IL-23 antibody may result in other than a clear solution of lyophilized powder comprising the antibody. Among non-clear solutions are formulations comprising particulate suspensions, said particulates being a composition containing the anti-IL-23 antibody in a structure of variable dimension and known variously as a microsphere, microparticle, nanoparticle, nanosphere, or liposome. Such relatively homogenous, essentially spherical, particulate formulations containing an active agent can be formed by contacting an aqueous phase containing the active agent and a polymer and a nonaqueous phase followed by evaporation of the nonaqueous phase to cause the coalescence of particles from the aqueous phase as taught in U.S. Pat. No. 4,589,330. Porous microparticles can be prepared using a first phase containing active agent and a polymer dispersed in a continuous solvent and removing said solvent from the suspension by freeze-drying or dilution-extraction-precipitation as taught in U.S. Pat. No. 4,818,542. Preferred polymers for such preparations are natural or synthetic copolymers or polymers selected from the group consisting of gleatin agar, starch, arabinogalactan, albumin, collagen, polyglycolic acid, polylactic aced, glycolide-L(−) lactide poly(epsilon-caprolactone, poly(epsilon-caprolactone-CO-lactic acid), poly(epsilon-caprolactone-CO-glycolic acid), poly($\beta$-hydroxy butyric acid), polyethylene oxide, polyethylene, poly(alkyl-2-cyanoacrylate), poly(hydroxyethyl methacrylate), polyamides, poly(amino acids), poly(2-hydroxyethyl DL-aspartamide), poly(ester urea), poly(L-phenylalanine/ethylene glycol/1,6-diisocyanatohexane) and poly(methyl methacrylate). Particularly preferred polymers are polyesters, such as polyglycolic acid, polylactic aced, glycolide-L(-) lactide poly(episilon-caprolactone, poly(epsilon-caprolactone-CO-lactic acid), and poly(epsilon-caprolactone-CO-glycolic acid. Solvents useful for dissolving the polymer and/or the active include: water, hexafluoroisopropanol, methylenechloride, tetrahydrofuran, hexane, benzene, or hexafluoroacetone sesquihydrate. The process of dispersing the active containing phase with a second phase may include pressure forcing said first phase through an orifice in a nozzle to affect droplet formation.

Dry powder formulations may result from processes other than lyophilization, such as by spray drying or solvent extraction by evaporation or by precipitation of a crystalline composition followed by one or more steps to remove aqueous or nonaqueous solvent. Preparation of a spray-dried antibody preparation is taught in U.S. Pat. No. 6,019,968. The antibody-based dry powder compositions may be produced by spray drying solutions or slurries of the antibody and, optionally, excipients, in a solvent under conditions to provide a respirable dry powder. Solvents may include polar compounds, such as water and ethanol, which may be readily dried. Antibody stability may be enhanced by performing the spray drying procedures in the absence of oxygen, such as under a nitrogen blanket or by using nitrogen as the drying gas. Another relatively dry formulation is a dispersion of a plurality of perforated microstructures dispersed in a suspension medium that typically comprises a hydrofluoroalkane propellant as taught in WO 9916419. The stabilized dispersions may be administered to the lung of a patient using a metered dose inhaler. Equipment useful in the commercial manufacture of spray dried medicaments are manufactured by Buchi Ltd. or Niro Corp.

An anti-IL-23 antibody in either the stable or preserved formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

Therapeutic Applications

The present invention also provides a method for modulating or treating psoriasis, in a cell, tissue, organ, animal, or patient, as known in the art or as described herein, using at least one IL-23 antibody of the present invention, e.g., administering or contacting the cell, tissue, organ, animal, or patient with a therapeutic effective amount of IL-23 specific antibody.

Any method of the present invention can comprise administering an effective amount of a composition or pharmaceutical composition comprising an anti-IL-23 antibody to a cell, tissue, organ, animal or patient in need of such modulation, treatment or therapy. Such a method can optionally further comprise co-administration or combination therapy for treating such diseases or disorders, wherein the administering of said at least one anti-IL-23 antibody, specified portion or variant thereof, further comprises administering, before concurrently, and/or after, at least one selected from at least one TNF antagonist (e.g., but not limited to, a TNF chemical or protein antagonist, TNF monoclonal or polyclonal antibody or fragment, a soluble TNF receptor (e.g., p55, p70 or p85) or fragment, fusion polypeptides thereof, or a small molecule TNF antagonist, e.g., TNF binding protein I or II (TBP-1 or TBP-II), nerelimonmab, infliximab, eternacept (Enbrel™), adalimulab (Humira™), CDP-571, CDP-870, afelimomab, lenercept, and the like), an antirheumatic (e.g., methotrexate, auranofin, aurothioglucose, azathioprine, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropoietin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, dacliuzumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Suitable dosages are well known in the art. See, e.g., Wells et al., eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, C A (2000); Nursing 2001 Handbook of Drugs, $21^{st}$ edition, Springhouse Corp., Springhouse, P A, 2001; Health Professional's Drug Guide 2001, ed., Shannon, Wilson, Stang, Prentice-Hall, Inc, Upper Saddle River, N.J., each of which references are entirely incorporated herein by reference.

Therapeutic Treatments

Typically, treatment of psoriasis is affected by administering an effective amount or dosage of an anti-IL-23 antibody composition that total, on average, a range from at least about 0.01 to 500 milligrams of an anti-IL-23 antibody per kilogram of patient per dose, and, preferably, from at least about 0.1 to 100 milligrams antibody/kilogram of patient per single or multiple administration, depending upon the specific activity of the active agent contained in the composition. Alternatively, the effective serum concentration can comprise 0.1-5000 µg/ml serum concentration per single or multiple administrations. Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved.

Preferred doses can optionally include 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100-500 mg/kg/administration, or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 µg/ml serum concentration per single or multiple administration, or any range, value or fraction thereof.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually a dosage of active ingredient can be about 0.1 to 100 milligrams per kilogram of body weight. Ordinarily 0.1 to 50, and, preferably, 0.1 to 10 milligrams per kilogram per administration or in sustained release form is effective to obtain desired results.

As a non-limiting example, treatment of humans or animals can be provided as a one-time or periodic dosage of at least one antibody of the present invention 0.1 to 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or, alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or, alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Dosage forms (composition) suitable for internal administration generally contain from about 0.001 milligram to about 500 milligrams of active ingredient per unit or container. In these pharmaceutical compositions the active ingredient will ordinarily be present in an amount of about 0.5-99.999% by weight based on the total weight of the composition.

For parenteral administration, the antibody can be formulated as a solution, suspension, emulsion, particle, powder, or lyophilized powder in association, or separately provided, with a pharmaceutically acceptable parenteral vehicle. Examples of such vehicles are water, saline, Ringer's solution, dextrose solution, and 1-10% human serum albumin. Liposomes and nonaqueous vehicles, such as fixed oils, can also be used. The vehicle or lyophilized powder can contain additives that maintain isotonicity (e.g., sodium chloride, mannitol) and chemical stability (e.g., buffers and preservatives). The formulation is sterilized by known or suitable techniques.

Suitable pharmaceutical carriers are described in the most recent edition of Remington's Pharmaceutical Sciences, A. Osol, a standard reference text in this field.

Alternative Administration

Many known and developed modes can be used according to the present invention for administering pharmaceutically effective amounts of an anti-IL-23 antibody. While pulmonary administration is used in the following description, other modes of administration can be used according to the present invention with suitable results. IL-23 specific antibodies of the present invention can be delivered in a carrier, as a solution, emulsion, colloid, or suspension, or as a dry powder, using any of a variety of devices and methods suitable for administration by inhalation or other modes described here within or known in the art.

Parenteral Formulations and Administration

Formulations for parenteral administration can contain as common excipients sterile water or saline, polyalkylene glycols, such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent, such as aqueous solution, a sterile injectable solution or suspension in a solvent. As the usable vehicle or solvent, water, Ringer's solution, isotonic saline, etc. are allowed; as an ordinary solvent or suspending solvent, sterile involatile oil can be used. For these purposes, any kind of involatile oil and fatty acid can be used, including natural or synthetic or semisynthetic fatty oils or fatty acids; natural or synthetic or semi-synthtetic mono- or di- or tri-glycerides. Parental administration is known in the art and includes, but is not limited to, conventional means of injections, a gas pressured needleless injection device as described in U.S. Pat. No. 5,851,198, and a laser perforator device as described in U.S. Pat. No. 5,839,446 entirely incorporated herein by reference.

Alternative Delivery

The invention further relates to the administration of an anti-IL-23 antibody by parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, or transdermal means. An anti-IL-23 antibody composition can be prepared for use for parenteral (subcutaneous, intramuscular or intravenous) or any other administration particularly in the form of liquid solutions or suspensions; for use in vaginal or rectal administration particularly in semisolid forms, such as, but not limited to, creams and suppositories; for buccal, or sublingual administration, such as, but not limited to, in the form of tablets or capsules; or intranasally, such as, but not limited to, the form of powders, nasal drops or aerosols or certain agents; or transdermally, such as not limited to a gel, ointment, lotion, suspension or patch delivery system with chemical enhancers such as dimethyl sulfoxide to either modify the skin structure or to increase the drug concentration in the transdermal patch (Junginger, et al. In "Drug Permeation Enhancement;" Hsieh, D. S., Eds., pp. 59-90 (Marcel Dekker, Inc. New York 1994, entirely incorporated herein by reference), or with oxidizing agents that enable the application of formulations containing proteins and peptides onto the skin (WO 98/53847), or applications of electric fields to create transient transport pathways, such as elec troporation, or to increase the mobility of charged drugs through the skin, such as iontophoresis, or application of ultrasound, such as sonophoresis (U.S. Pat. Nos. 4,309,989 and 4,767,402) (the above publications and patents being entirely incorporated herein by reference).

Method of Selling and/or Promoting

The invention further relates to a method of selling and/or promoting an approved pharmaceutical product (by the US FDA or equivalent ex-US regulatory agency) comprising an antibody to IL-23, such as an antibody described herein, e.g., guselkumab, comprising advertising, promoting and/or otherwise highlighting in connection with sales of guselkumab (Tremfya®) the superiority of clinical endpoint results at week 44 and/or week 48 from initial treatment after continuous treatment with the antibody to IL-23 versus clinical endpoint results at week 44 and/or week 48 from initial treatment after continuous treatment with secukinumab in treated psoriasis patients.

Having generally described the invention, the same will be more readily understood by reference to the following Examples, which are provided by way of illustration and are not intended as limiting. Further details of the invention are illustrated by the following non-limiting Examples. The disclosures of all citations in the specification are expressly incorporated herein by reference.

Example 1: A Phase 3, Multicenter, Randomized, Double-Blind Study Evaluating the Comparative Efficacy of CNTO 1959 (Guselkumab) and Secukinumab for the Treatment of Moderate to Severe Plaque-Type Psorisis Study Design:
A Phase 3, randomized, double-blind, multicenter, active-comparator-controlled study in subjects with moderate to severe plaque-type psoriasis with 2 parallel treatment groups: guselkumab 100 mg and secukinumab 300 mg.
Randomization: At Week 0, approximately 1040 subjects who satisfy all inclusion and exclusion criteria were planned to be randomized in a 1:1 ratio to 1 of 2 arms based on permuted block randomization with stratification by study site:
Group I (n=520): guselkumab 100 mg SC at Weeks 0, 4, 12, 20, and q8w thereafter through Week 44.
Group II (n=520): secukinumab 300 mg SC at Weeks 0, 1, 2, 3, 4, and q4w thereafter through Week 44.
Treatment duration/Trial duration: Week 44 was the last dosing visit; subjects were followed for an additional 12 weeks after Week 44, with a final safety visit at Week 56. The end of the study was defined as the time when last subject completes the Week 56 visit. There was 1 database lock (DBL) in this study at Week 56.
A schematic of the study is shown below in Table 4.

TABLE 4

Overview of the Study

| Week | Guselkumab 100 mg SC (n = 520) | Secukinumab 300 mg SC (n = 520) |
|---|---|---|
| | Randomization | |
| 0 | Guselkumab (one 100 mg injection + Placebo (one injection) | Secukinumab (two 150 mg injections) |
| 1 | Placebo (two injections) | Secukinumab (two 150 mg injections) |
| 2 | Placebo (two injections) | Secukinumab (two 150 mg injections) |
| 3 | Placebo (two injections) | Secukinumab (two 150 mg injections) |
| 4 | Guselkumab (one 100 mg injection + Placebo (one injection) | Secukinumab (two 150 mg injections) |
| 8 | Placebo (two injections) | Secukinumab (two 150 mg injections) |
| 12 | Guselkiunab (one 100 mg injection + Placebo (one injection) | Secukinumab (two 150 mg injections) |
| 16 | Placebo (two injections) | Secukinumab (two 150 mg injections) |
| 20 | Guselkumab (one 100 mg injection + Placebo (one injection) | Secukinumab (two 150 mg injections) |
| 24 | Placebo (two injections) | Secukinumab (two 150 mg injections) |
| 28 | Guselkumab (one 100 mg injection + Placebo (one injection) | Secukinumab (two 150 mg injections) |
| 32 | Placebo (two injections) | Secukinumab (two 150 mg injections) |
| 36 | Guselkumab (one 100 mg injection + Placebo (one injection) | Secukinumab (two 150 mg injections) |
| 40 | Placebo (two injections) | Secukinumab (two 150 mg injections) |
| 44 | Guselkumab (one 100 mg injection + Placebo (one injection) | Secukinumab (two 150 mg injections) |
| 48 | Primary Endpoint | |
| 56 | Database Lock | |

Primary analysis set for efficacy: The primary efficacy analysis included all randomized subjects according to subjects' assigned treatment at Week 0, regardless of the treatment they actually received. This is also referred to as the full analysis set (FAS). The full analysis set was also used for all secondary efficacy analyses.
Primary endpoint: the proportion of subjects who achieved a PASI 90 response at Week 48 (non-inferiority test followed by superiority)
Major secondary efficacy variables: There were 6 major secondary endpoints in this study:
The proportion of subjects who achieved a PASI 75 response at both Week 12 and Week 48 (non-inferiority test followed by superiority)
The proportion of subjects who achieved a PASI 90 response at Week 12 (non-inferiority)
The proportion of subjects who achieved a PASI 75 response at Week 12 (non-inferiority)
The proportion of subjects who achieved a PASI 100 response at Week 48 (non-inferiority test followed by superiority)

The proportion of subjects who achieved an IGA score of cleared (0) at Week 48 (non-inferiority test followed by superiority)

The proportion of subjects who achieved an IGA score of cleared (0) or minimal (1) at Week 48 (non-inferiority test followed by superiority)

Non-inferiority margin was set to be 10% for all endpoints.

To control the overall Type 1 error rate, it was specified that the primary analyses and major secondary analyses would be tested in a fixed sequence as ordered above. That is, the first major secondary endpoint would be tested only if the primary endpoint was positive, and the subsequent endpoint(s) would be tested only if the preceding endpoint in the sequence was positive.

Planned sample size and power: A total of approximately 1,040 subjects randomized in a 1:1 ratio was expected to detect the differences between guselkumab group and secukinumab group with at least 92% power for PASI 90 response rate at Week 48 at a 2-sided significance level of 0.05. The assumptions for the sample size and power calculations, based on the data from the guselkumab CNTO1959PS03001 and CNTO1959PS03002 and the secukinumab Phase 3 studies (ERASURE and FIXTURE), were:

PASI 90 response rate at Week 48 was 70% to 80% for guselkumab group and 60% to 70% for secukinumab group.

Based on the above assumptions, the planned sample size, and a noninferiority margin of 10%, the power to demonstrate the non-inferiority for the primary endpoint of PASI 90 at Week 48 would be >99%.

Primary Objective(s):

The primary objective is to evaluate the efficacy of guselkumab compared with secukinumab for the treatment of subjects with moderate to severe plaque-type psoriasis systemic therapy or phototherapy. This database lock includes all data through Week 56 for all randomized subjects.

A total of 1200 subjects were screened of which 1048 subjects were randomized into guselkumab (n=534) or secukinumab (n=514) treatment groups. The study was conducted at 141 sites in 9 countries: Australia, Canada, Czech Republic, France, Germany, Hungary, Poland, Spain, and the US. The treatment groups were well balanced for baseline demographic and psoriasis characteristics. The majority of the subjects were white (93.4%) and male (67.5%). The median age was 46.0 years, and mean baseline weight was 89.2 kg (Appendix 1). Three subjects randomized to the secukinumab group did not receive any study agent due to violation of a study entry criterion. These 3 subjects were included in all efficacy analyses but excluded from the safety analyses.

Baseline disease characteristics were generally comparable between the treatment groups. The median duration of psoriasis was 16.1 years. The median percent of body surface area (BSA) involved was 20.0, with a median PASI score of 18.0. In addition, 76.1% subjects presented with an IGA=3, and 23.8% of subjects had severe disease as defined by their baseline IGA score of 4 (Appendix 2).

The proportions of subjects receiving previous therapies in each previous psoriasis medication category were comparable between the treatment groups. Overall, 51.8% previously received phototherapy, 53.7% previously received systemic therapy and 29.1% previously received biologic therapy. Overall, 37.1% of subjects were naïve to non-biologic systemic and biologic therapies (Appendix 3).

The key baseline demographics, psoriasis disease characteristics and previous psoriasis medications/therapies are summarized in Table 1.

TABLE 1

Summary of Important Baseline Demographic, PSO Characteristics, and Previous Psoriasis Medications and Therapies by Medication Category

|  | Guselkumab | Secukinumab | Total |
| --- | --- | --- | --- |
| Analysis set: Subjects in full analysis set | 534 | 514 | 1048 |
| Weight (kg) (Mean) | 89.3 | 89.1 | 89.2 |
| PSO Characteristics |  |  |  |
| BSA (Mean) | 23.7 | 24.5 | 24.1 |
| PASI Score (0-72) (Mean) | 20.0 | 20.1 | 20.0 |
| IGA score |  |  |  |
| Mild (2) | 0 | 0.2% | 0.1% |
| Moderate (3) | 76.2% | 76.1% | 76.1% |
| Severe (4) | 23.8% | 23.7% | 23.8% |
| Previous Psoriasis Medications and Therapies |  |  |  |
| Phototherapy (PUVA or UVB) | 52.6% | 50.9% | 51.8% |
| Non-biologic systemics | 51.7% | 55.8% | 53.7% |
| Biologics | 29.2% | 29.0% | 29.1% |
| Naïve to non-biologic systemics and biologics | 38.6% | 35.6% | 37.1% |

Topline Results Summary

CNTO1959PSO3009 is a Phase 3, randomized, double-blind, multicenter, active-comparator-controlled study in subjects with moderate to severe plaque psoriasis, defined by a IGA≥3, PASI≥12, and BSA involvement of at least 10%, who were candidates for or previously received either Through Week 44, 5.1% of subjects in the guselkumab group and 9.3% of subjects in the secukinumab group discontinued study agent. The most common reason for study agent discontinuation was adverse event (1.7%) and withdrawal by subject (1.3%) in the guselkumab group, and withdrawal by subject (3.7%) and adverse events (2.1%) in the secukinumab group (Appendix 4).

Primary Efficacy Endpoints:
Significantly greater proportions of subjects in the guselkumab group achieved a PASI 90 response at Week 48 (84.5%) than in the secukinumab group (70.0%) (p-value <0.001) (Table 2).

TABLE 2

Number of PASI 90 Responders at Week 48 (Superiority Analysis); Full Analysis Set (Study CNTO1959PSO3009)

|  | Guselkumab | Secukinumab |
| --- | --- | --- |
| Analysis set: Full analysis set | 534 | 514 |
| PASI 90 responders | 451 (84.5%) | 360 (70.0%) |
| Treatment differences (95% CI) |  | 14.2% (9.6%, 18.8%) |
| p-value |  | <0.001 |

Note 1:
Treatment difference and 95% CI were calculated adjusting for investigator site (pooled) using MH weights.
Note 2:
P-value was based on CMH chi-square test stratified by the investigator site (pooled)

Major Secondary Efficacy Endpoints:
  Guselkumab is non-inferior to secukinumab for the proportion of subjects who achieved a PASI 75 response at both Week 12 and Week 48 [84.6% (guselknumab) vs. 80.2% (secukinumab); 95% CI: (−0.2%, 8.9%); p<0.001] (Appendix 6); however, though the response rate of guselkumab group was numerically higher than that of the secukinumab group, the superiority test was not significant (p=0.062) (Appendix 7). Therefore, because of the stipulation that the primary analyses and major secondary analyses would be tested in a fixed sequence to control the overall Type 1 error rate, the p-values reported for the rest of the major secondary endpoints are considered nominal.
  Non-inferiority for the proportion of subjects who achieved a PASI 90 response at Week 12 was not demonstrated [69.1% (guselknumab) vs. 76.1% (secukinumab); 95% CI: (−12.2%, −1.7%); p=0.127] (Appendix 8).
  Guselkumab is non-inferior to secukinumab as assessed by the proportion of subjects who achieved a PASI 75 response at Week 12 [89.3% (guselkunumab) vs. 91.6% (secukinumab); 95% CI: (−6.0%, 1.2%); p<0.001] (Appendix 9).
  The proportion of subjects who achieved a PASI 100 response at Week 48 was significantly higher in the guselkumab group compared to the secukinumab group [58.2% (guselkunumab) vs. 48.4% (secukinumab); p=0.001)] (Appendix 10).
  The proportion of subjects who achieved an IGA score of cleared (0) at Week 48 was significantly higher in the guselkumab group compared to the secukinumab group [62.2% (guselkunumab) vs. 50.4% (secukinumab); p<0.001] (Appendix 11).
  The proportion of subjects who achieved an IGA score of cleared (0) or minimal (1) at Week 48 was significantly higher in the guselkumab group compared to the secukinumab group [85.0% (guselkunumab) vs. 74.9% (secukinumab); p<0.001] (Appendix 12).
Other Efficacy Endpoints:
  The proportion of subjects who achieved a PASI 90 response at all 7 visits from Week 24 through Week 48 was significantly higher in the guselkumab group compared to the secukinumab group [71.0% (guselkunumab) vs. 61.5% (secukinumab); p<0.001] (Appendix 13).

IGA and PASI responses over time
  The proportions of subjects achieving a PASI 90 response, a PASI 100 response, an IGA score of cleared (0), and an IGA score of cleared (0) or minimal (1) over time from Week 1 through Week 48 are summarized in FIG. 1A FIG. 1D (also see Appendix 14 and 15).
  These curves highlight differences in the rate and maintenance of response over time between guselkumab and secukinumab. The PASI 90 figure panel, for example, shows that responses start occurring for both treatments at Weeks 2 and 3. Between Weeks 3 and 12, secukinumab PASI 90 response rates are higher than those for guselkumab. At Weeks 16 and 20, both drugs show similar PASI 90 response rates, and PASI 90 response rates for guselkumab are higher than those for secukinumab at all visits from Week 24 through Week 48. The guselkumab PASI 90 response rate curve reaches a plateau at Week 28, and then the response rate remains stable through Week 48. In contrast, the PASI 90 response rate curve for secukinumab plateaus earlier, at Week 20, and the response rate then declines steadily from Week 20 through Week 48. For the other 3 endpoints, the patterns of response rates are similar to that of PASI 90, although there is variability in the timing of when response rates plateau, and the visits at which the switch from higher response rates for secukinumab to higher rates for guselkumab occur.

Safety:
Safety was assessed among all randomized and treated subjects who received at least 1 dose of study agent (partial or complete) according to the actual treatment received during the study, irrespective of the treatment assigned at randomization. This is also referred to as the safety analysis set. Key safety events are summarized in Table 3.

TABLE 3

Key safety events; treated subjects

|  | Guselkumab | Secukinumab |
| --- | --- | --- |
| Analysis set: Safety analysis set | 534 | 511 |
| Avg duration of follow-up (weeks) | 54.90 | 53.67 |
| Avg exposure (number of administrations)[a] | 14.65 | 14.41 |
| Avg number of active injections received | 6.8 | 28.8 |
| Subjects who discontinued study agent because of 1 or more adverse events | 10 (1.9%) | 12 (2.3%) |
| Subjects with 1 or more: |  |  |
| Adverse events | 416 (77.9%) | 417 (81.6%) |
| Serious adverse events | 33 (6.2%) | 37 (7.2%) |
| Overall infections | 313 (58.6%) | 331 (64.8%) |
| Infections requiring treatment | 118 (22.1%) | 147 (28.8%) |
| Serious infections | 6 (1.1%) | 5 (1.0%) |
| Malignancy | 7 (1.3%) | 4 (0.8%) |
| NMSC | 6 (1.1%) | 2 (0.4%) |
| Other malignancy | 1 (0.2%) | 2 (0.4%) |
| MACE[b] | 0 | 1 (0.2%) |
| Suicidal ideation or behavior[c] | 8 (1.5%) | 8 (1.6%) |
| Inflammatory bowel disease[d] | 0 | 3 (0.6%) |
| Anaphylactic reaction or serum sickness-like reaction to active study agent | 0 | 0 |

TABLE 3-continued

Key safety events; treated subjects

| | Guselkumab | Secukinumab |
|---|---|---|
| ISR to active study agent[e] | 13 (2.4%) | 20 (3.9%) |
| Total number of active injections | 3644 | 14722 |
| Active injections with ISR | 19 (0.5%) | 63 (0.4%) |

[a]All administrations were counted regardless of whether they are active or placebo injections. Each administration includes two injections.
[b]MACE: investigator reported nonfatal myocardial infarction (MI), nonfatal stroke or CV death. One stroke (PT: cerebrovascular accident) was reported in the secukinumab group.
[c]Suicidal ideation and behavior data was collected by electronic Columbia-Suicide Severity Rating Scale (eC-SSRS) at scheduled visits. When suicidal ideation or behavior-related adverse events occurred outside of a study visit, they were reported on the AE eCRF.
[d]Preferred terms of IBD: Crohn's disease and inflammatory bowel disease
[e]ISR: injection site reactions The proportion of subjects experiencing 1 or more adverse events categorized as infections by the investigator was lower in the guselkumab group compared with the secukinumab group (58.6% [313/534] in the guselkumab group, 64.8% [331/511] in the secukinumab group) (Appendix 19).

The most common infections were PTs of nasopharyngitis [21.9% (guselkumab) vs. 24.5% (secukinumab)] and upper respiratory tract infection [15.5% (guselkumab) vs. 18.0% (secukinumab)].

Individual PTs representing fungal infections reported in >2% of subjects included tinea pedis (1.1% vs. 3.1%), oral candidiasis (0.9% vs. 2.2%) and vulvovaginal candidiasis (0.9% vs 2.5%) for the guselkumab and secukinumab groups.

All serious infections were single events in both treatment groups and there was no pattern or trend for either treatment group. No cases of active tuberculosis or opportunistic infections were reported during the study (Appendix 21).

A total of 3 BCCs (0.6%) were reported in the guselkumab group versus 2 BCCs (0.4%) in the secukinumab group.

Two skin squamous cell carcinomas and 1 Bowen's disease were reported in the guselkumab group.

One subject in the guselkumab group was diagnosed with invasive ductal breast carcinoma. One subject in the secukinumab group was diagnosed with non-small cell lung cancer and another subject was diagnosed with mycosis fungoides.

A total of 3 subjects in the secukinumab group reported an event of Crohn's disease, IBD or colitis:

One subject, was diagnosed with a serious AE of Crohn's disease. This subject received 5 scheduled doses of study agent.

Two subjects reported a non-serious AE of IBD.

One subject, with a history of chronic IBD that was not identified in screening was randomized and received 5 doses of study agent before being discontinued upon confirmation of Crohn's colitis.

A second subject, approximately a month after completing the 44 weeks of treatment presented with symptoms that were suggestive of, and later confirmed to be Crohn's disease.

Analysis of Patients with PsA

Post hoc analyses examined the subgroup of patients with self-reported Psoriatic Arthritis (PsA). For the PsA subpopulation, treatment differences and 95% confidence intervals (CIs) were calculated. Missing data were imputed as non-response. Both efficacy and safety were assessed through Week 56. Overall, treatment groups [GUS (n=534), SEC (n=514)] were comparable at baseline: weight 89 kg, 24% body surface area PsO, and Investigator Global Assessment (IGA) moderate (76%) or severe (24%). These characteristics were similar to those of subgroups with self-reported PsA [GUS (n=97), SEC (n=79)]. In the overall population, the primary endpoint of PASI 90 response at Week 48 was reached by 84.5% GUS patients vs 70.0% SEC patients (P<0.001). Results of the first major secondary endpoint (proportion of patients with a PASI 75 response at both Week 12 and 48) showed non-inferiority of GUS vs SEC (GUS-84.6% vs SEC-80.2% of patients, p<0.001), but superiority was not demonstrated (p=0.062). Among patients with PsA, the primary endpoint of Week-48 PASI 90 response was reached by 82.5% GUS vs 63.3% SEC patients (treatment difference 19.2% [95% CI=5.0, 33.4]). In both the overall population and the subgroup of patients with PsA, peak PASI 90 response rates were achieved between Weeks 16 and 24 for both drugs. GUS-treated patients sustained this response through Week 48, whereas SEC patients demonstrated reduction in response rate from Weeks 24 to 48. Adverse events observed in the overall population were generally consistent with the established safety profiles for GUS and SEC. Safety results among patients with PsA were consistent with that of the overall population. In the subset of patients with self-reported PsA in the ECLIPSE study, GUS demonstrated higher long-term efficacy and maintenance of response compared with SEC in the treatment of moderate to severe plaque PsO, consistent with the overall trial population with plaque PsO.

Weight Quartile Analysis

Efficacy data were analyzed by baseline body weight quartiles (Q1, ≤74 kg; Q2, >74 to ≤87 kg; Q3, >87 to ≤100 kg; Q4, >100 kg) and BMI categories (normal, <25 kg/m$^2$; overweight, ≥25 to <30 kg/m$^2$; obese, ≥30 kg/m$^2$). This post-hoc analysis evaluated efficacy by baseline body weight quartiles and body mass index (BMI) categories. There were no body weight restrictions for enrollment in the study.

The data are shown in Tables 12-16 below. Missing data were imputed as non-response after applying treatment failure rules. The proportions of patients achieving a PASI90 response at Week48 in the guselkumab and secukinumab groups, respectively were as follows: by baseline body weight quartiles—Q1, 86.7% vs 75.6% (11.1% [0.9%-21.3%]); Q2, 89.1% vs 73.0% (16.0% [6.0%-26.0%]); Q3, 80.3% vs 71.0% (9.3% [−1.9%-20.6%]); Q4, 82.1% vs 61.3% (20.9% [9.4%-32.3%]); by BMI categories-normal, 88.1% vs 75.2% (12.8% [2.2%-23.5%]); overweight, 84.1% vs 73.4% (10.6% [1.6%-19.7%]); obese, 82.5% vs 65.3% (17.2% [8.8%-25.6%]) (percent difference [95% CI]). These results are consistent with the primary endpoint of PASI90 at Week 48 in the overall study population (guselkumab, 84.5% vs secukinumab, 70.0% [14.2% (9.2%-19.2%)]). Similar results were observed across all body weight quartiles and BMI categories for PASI100, IGA0, and IGA0/1 responses, with all between-treatment differences numerically favoring guselkumab. In conclusion, across baseline body weight quartiles and BMI categories, efficacy outcome response rates at Week48 were consistently numerically greater for guselkumab compared to secukinumab in the treatment of moderate to severe psoriasis.

Body Region Analysis

As shown in Table 17, guselkumab showed numerically greater levels of efficacy than secukinumab through 48 weeks in body region components of the PASI, including head and neck, trunk, and upper and lower extremities, compared with secukinumab in the treatment of moderate to severe psoriasis. Improvement in body region components of PASI, including the head and neck, trunk, and upper and lower extremities, was also evaluated. Missing data were imputed as nonresponse.

At Week 48, numerically greater proportions of patients achieved improvement (100% improvement and ≥90% improvement) with guselkumab than with secukinumab for the PASI components of head and neck, trunk, and upper and lower extremities (Table 17).

Patient Geographic Area Analysis

Patients from North America (United States, Canada; n=391), Eastern Europe (Czech Republic, Hungary, Poland; n=338), Western Europe (France, Germany, Spain; n=248), and Australia (n=71) were randomized to receive guselkumab 100 mg subcutaneous (SC) at Weeks 0, 4, 12, then every 8 weeks (n=534), or secukinumab 300 mg SC at Weeks 0, 1, 2, 3, 4, then every 4 weeks (n=514), both through Week 44. The primary endpoint was the proportion of patients achieving a PASI 90 response at Week 48. Missing data were imputed as nonresponse.

As shown in Table 18, regardless of geographic region, PASI 90 response rates with guselkumab treatment were higher at Week 48 compared with secukinumab in the treatment of moderate to severe psoriasis. Subgroup analyses by geographical region showed higher PASI 90 response rates among guselkumab-treated patients versus secukinumab-treated patients in all regions: North America (guselkumab 78.9% vs secukinumab 60.4%); Eastern Europe (guselkumab 90.6% vs secukinumab 76.0%); Western Europe (guselkumab 82.9% vs secukinumab 74.8%); and Australia (guselkumab 91.4% vs secukinumab 77.8%) (Table 18).

Example 2—Assessment of the Treatment Effect of Anti-IL-23 and Anti-IL-17A on Immune Cell Populations in Skin and Serum IL-17F and IL-22 Levels Skin biopsies were collected at wks 0, 4 and 24. Skin gene expression profiles were generated in whole biopsy via RNAseq. The composition of T cells was determined by immunophenotyping of cell suspensions from dissociated biopsies using flow cytometry combined with unbiased clustering analysis. Serum was collected at wks 0, 4, 24 and 48 and analyzed by ultrasensitive immunoassays for IL17A, IL17F, IL22, IL23 and beta defensin-2 (BD-2) levels. In addition, the numbers of $CD4^+$ and $CD8^+$ T cells were measured in skin lesions.

Results

Serum IL17A, IL17F and IL22 levels were reduced at wks 4, 24, and 48 after guselkumab treatment. In contrast, treatment with secukinumab reduced IL17F levels less efficiently than guselkumab ($p<0.0001$, all timepoints) and had no effect on IL22 levels (free IL17A levels in SEC cohort could not be measured with the assay used). Accordingly, there was a greater reduction in serum levels of IL-17F and IL-22 from guselkumab treatment versus secukinumab treatment at weeks 4, 24 and 48.

Reduction in levels of BD-2, a biomarker highly correlated with skin inflammation, was greater with secukinumab vs guselkumab treatment at wk 4 ($p<0.0001$), and was equivalent at wk 24; however, BD-2 increased in secukinumab arm but remained reduced in the guselkumab arm at wk 48 ($p<0.05$) such that there was a greater reduction in BD-2 levels by guselkumab versus secukinumab at wk 48. Normalization of skin transcriptional changes was more pronounced in the secukinumab vs guselkumab group at wk 4, but equivalent at wk 24. Normalization of increased skin gene expression of IL17A, IL22 and IL23 was comparable between both treatments at wk 4 and 24, while expression of IL23R was significantly reduced by guselkumab only ($p<0.01$). At wk 24 of treatment, the numbers of $CD4^+$ and $CD8^+$ T cells decreased in skin lesions in both cohorts. However, the frequency of $CD8^+$ TRMs ($CD3^+$, $CD8^+$, $CD103^+$ and/or $CD49a^+$) decreased relative to baseline with guselkumab ($p=0.036$) but not with secukinumab. The reduction in $IL17A^+/CD8^+$ TRMs in lesional skin did not differ between treatments. In contrast, the frequency of regulatory T cells (Tregs) ($FoxP3^+$, $CD25^+$, $IL17A^-$) was higher in the guselkumab arm at wk 24 ($p=0.042$).

Genes that are part of the psoriasis transcriptome that are better normalized by GUS vs SEC, including IL23R were identified Increased expression in PSO lesional skin of a group of genes associated with mucosal-associated invariant T cells (MAIT) (including IL23R) was better normalized by GUS vs SEC at Week 24

Frequency of CD8+ tissue resident memory cells (TRMs) (CD3+, CD8+, CD103+ and/or CD49a+) was decreased relative to lesional baseline with GUS treatment ($p<0.05$) but not with SEC at week 24 Frequency of regulatory T cells (Tregs) (CD3+, FoxP3+, CD25+, IL17A−) were higher in the GUS arm compared to SEC arm at week 24 ($p<0.05$)

Analysis of IL-23+APC indicated that CD14+CD64+DC were responsible for majority of IL-23 expression in PsO lesional skin. Expansion of CD4 T cells were associated with relative increase of non-TRM (CD103−CD49a−). Expansion of CD8 T cells were associated with relative increase in the frequency of TRMs (CD103+ and/or CD49a+). A large increase in CD8 TRMs and non-TRMs and CD4 non TRMs in PsO SkinCD4+non-TRM and CD8+TRMs are the major contributors of IL-17A in PsO (Baseline). The frequency of Treg population in T cells is significantly increased in PsO lesions. 2 distinct clusters of Tregs were identified, one IL17A+ and one IL17A-N. An increased frequency of IL17A expression within T cell subsets in lesional vs non-lesional skin. CD4+ T cells making IL-17A were mostly non-TRMs while CD8+ T cells making IL-17A were mostly TRMs. Tregs contribute to a low amount of IL17A expression in PsO skin. A more significant decrease in the frequency of TRMs in CD8+ T cells in response to guselkumab vs secukinumab in cohort at wk 24. No difference in frequency of TRMs in CD4+ T cell subsets in response to guselkumab vs secukinumab at wk 24. No difference in non-TRM CD4+ or non-TRM CD8+ T cell subsets between guselkumab or secukinumab treatments at wk 24. IL17A was reduced significantly in guselkumab group (measurement in SEC cohort complicated by inability of assay to differentiate SEC bound vs free IL17A resulting in increases in IL17A). An increased frequency of IL17A expression within CD8TRMs in lesional skin at baseline seems to be associated with not achieving PASI>90 at week 48 (regardless of treatment arm). No similar pattern observed in non lesional skin at baseline.

Figure 2:
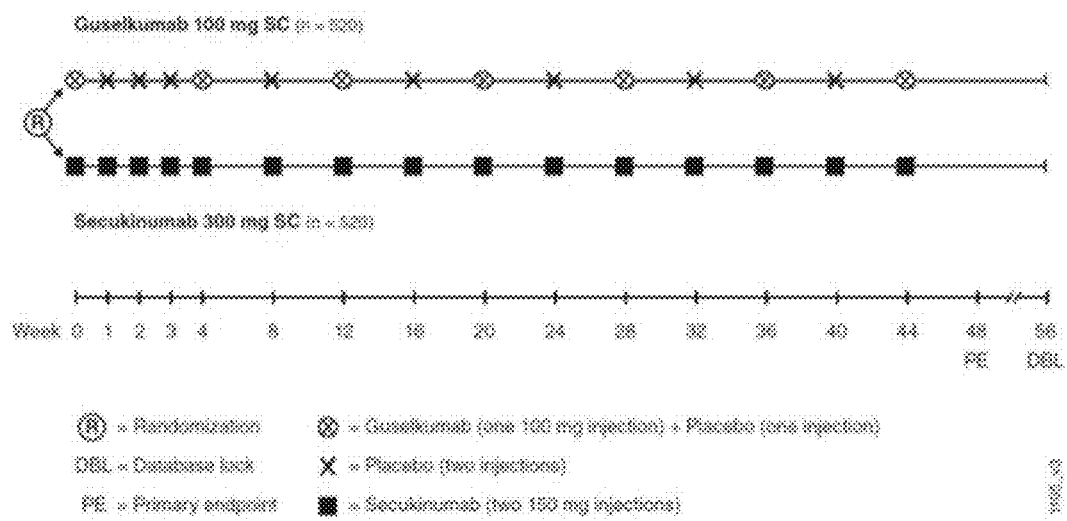
FIG. 2 is a diagram of the ECLIPSE study design.

FIG. 2 shows the ECLIPSE study design through Week 48 and samples collected for biomarker sub-studies. Blood samples for the serum protein biomarker sub-study were collected from all participated subjects at Weeks 0, 4, 24, and 48. Skin samples, including a pair of non-lesional skin and lesional skin at Week 0, and lesional skin after Weeks 4 and 24, were collected from a subset of subjects (19 GUS-treated and 16 SEC treated) for a skin transcriptome biomarker sub-study. Separately, skin samples, including a pair of non-lesional skin and lesional skin at Week 0, and lesional skin after Weeks 4 and 24, were collected from another subset of subjects (11 GUS-treated and 9 SEC treated) for immunophenotyping of skin immune cells sub-study.

Figure 3:
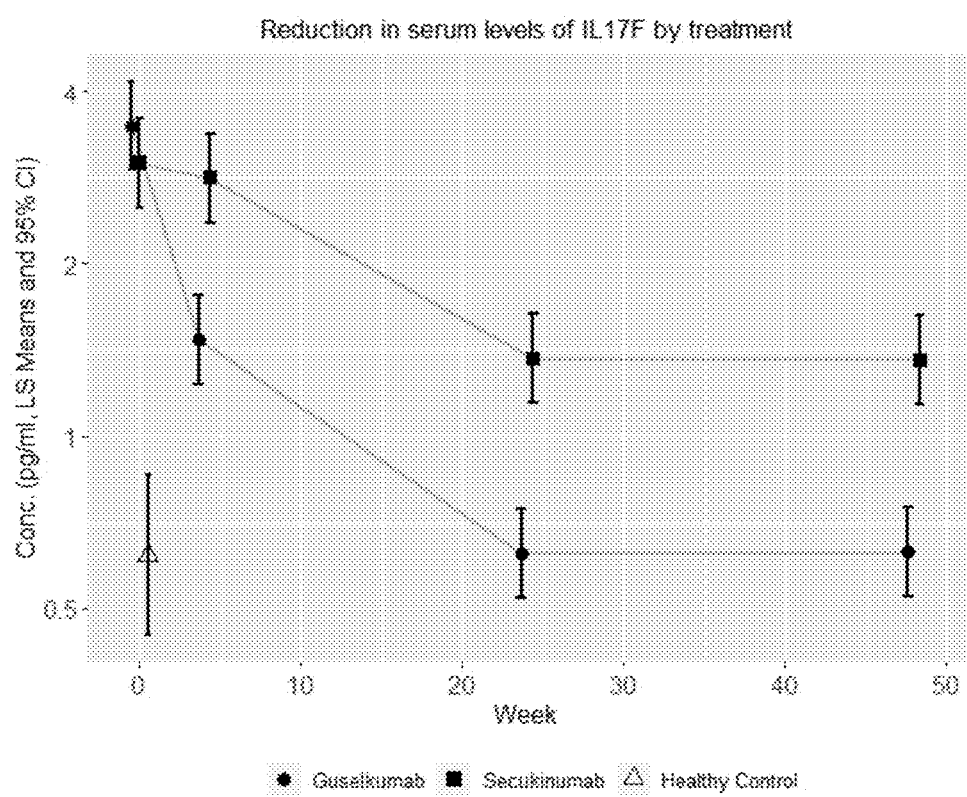
FIG. 3 shows serum levels of IL-17F in psoriasis patients treated with guselkumab and secukinumab.

As shown in FIG. 3, elevated serum levels of IL-17F in psoriasis patients were reduced by both treatments, with faster and greater reduction by guselkumab. Compared to healthy controls (n=25), serum levels of IL-17F were elevated in psoriasis patients (n=200), with 5.2 fold and p<0.0001. Reduction in elevated serum IL-17F was greater in guselkumab treated samples (n=100) vs secukinumab treated samples (n=100) at all visits after week 4: 2.26 fold vs 1.12 fold, p<0.0001 at Week 4; 5.32 fold vs 2.31 fold, p<0.0001 at Week 24; and 5.28 fold vs 2.33 fold, p<0.0001 at Week 48. Serum IL-17F was normalized to the level of healthy controls in guselkumab-treated patients at Weeks 24 and 48. LS Means: Least Squares Means; CI: confidence intervals. LS Means and 95% CI were computed based on log transformed concentration using a mixed-effects model with repeated-measures, where the treatment (guselkumab and secukinumab) and visits (Weeks 0, 4, 24, and 48) are fixed effects and subject is a random effect.

Figure 4:
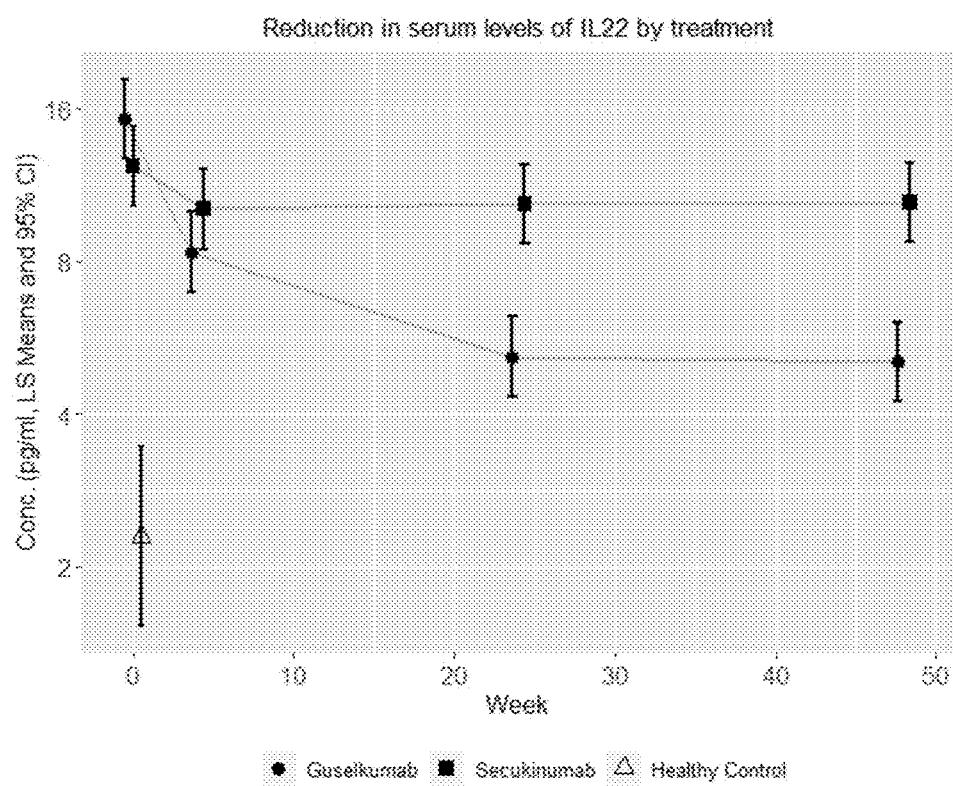
FIG. 4 shows serum levels of IL-22 in psoriasis patients treated with guselkumab and secukinumab.

As shown in FIG. 4, elevated serum levels of IL-22 in psoriasis were reduced by both treatments, with faster and greater reduction by guselkumab. Compared to healthy controls (n=25), serum levels of IL-22 were elevated in psoriasis patients (n=200), with 6.0 fold and p<0.0001. Reduction in elevated serum IL-22 was greater by guselkumab (n=100) vs secukinumab (n=100) at all visits after week 4: 1.74 fold vs 1.28 fold, p=0.057 at Week 4; 2.79 fold vs 1.25 fold, p<0.0001 at Week 24; and 2.85 fold vs 1.24 fold, p<0.0001 at Week 48.
LS Means: Least Squares Means; CI: confidence intervals. LS Means and 95% CI were computed based on log transformed concentration using a mixed-effects model with repeated-measures, where the treatment (guselkumab and secukinumab) and visits (Weeks 0, 4, 24, and 48) are fixed effects, and subject is a random effect.

Figure 5:
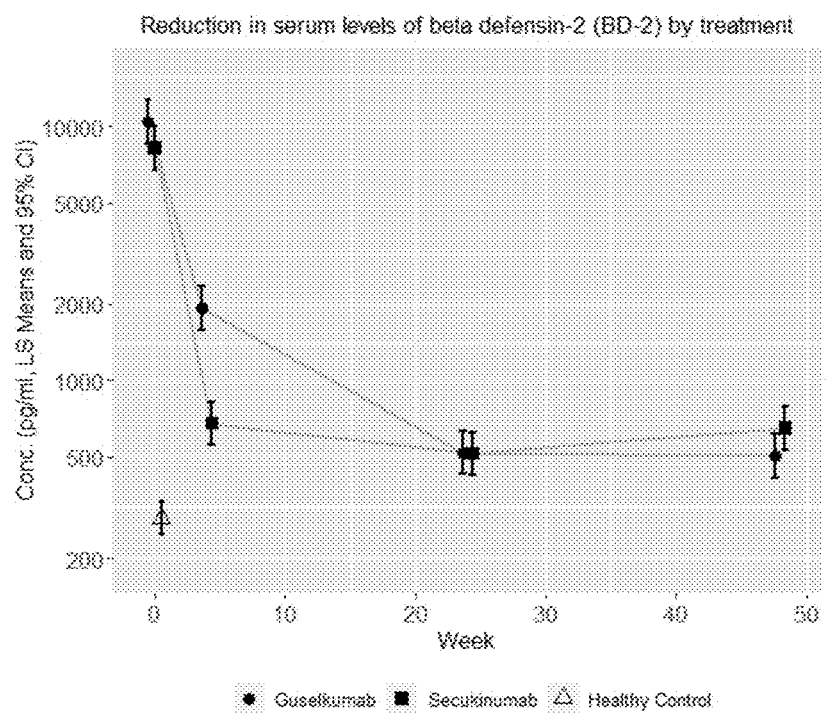
FIG. 5 shows serum levels of BD-2 in psoriasis patients treated with guselkumab and secukinumab.

As shown in FIG. 5, elevated serum levels of beta defensin-2 (BD-2) in psoriasis were reduced by both treatments, with faster reduction by secukinumab but more sustained reduction by guselkumab. Compared to healthy controls (n=25), serum levels of BD-2 were elevated in psoriasis patients (n=200), with >32 fold and p<0.0001. Reduction in elevated serum BD-2 was greater with secukinumab (n=100) vs guselkumab (n=100) (13.1 fold vs 5.0 fold, p<0.0001) at Week 4, and was equivalent (18.4 fold vs 17.3 fold, p=0.99) at Week 24, but was reversed (18.9 fold with guselkumab vs. 13.7 fold with secukinumab, p<0.05) at Week 48.
LS Means: Least Squares Means; CI: confidence intervals. LS Means and 95% CI were computed based on log transformed concentration using a mixed-effects model with repeated-measures, where the treatment (guselkumab and secukinumab) and visits (Weeks 0, 4, 24, and 48) are fixed effects, and subject is a random effect.

Figure 6:
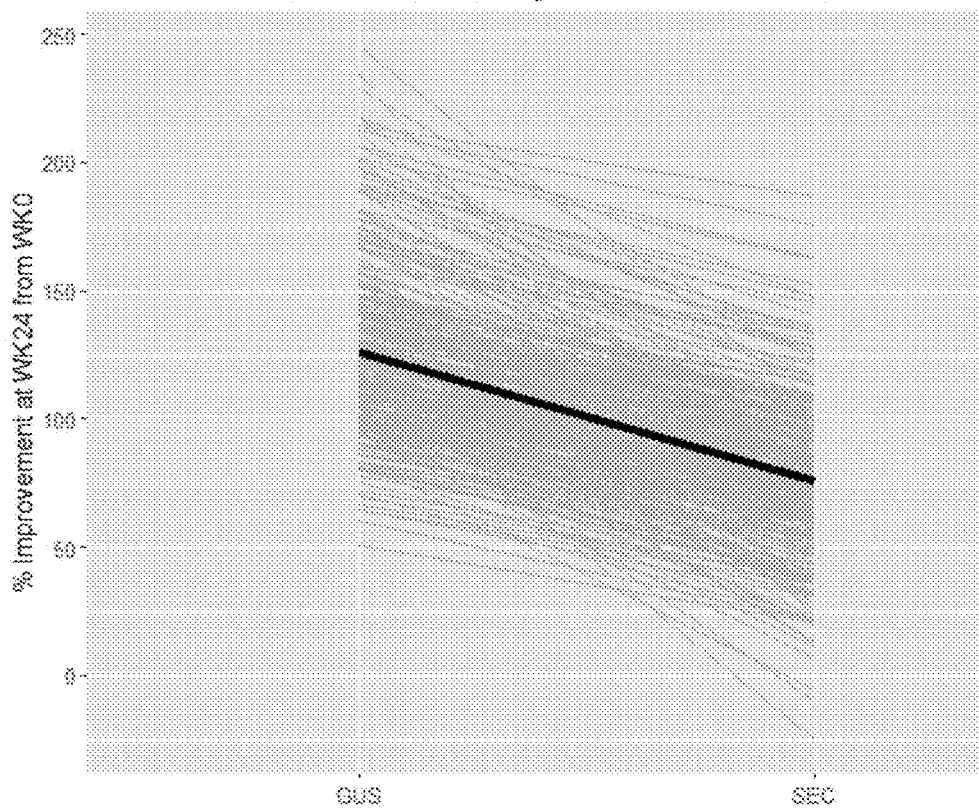
FIG. 6 shows the normalization of a subset of induced genes in psoriasis lesional skin.
Figure 7:
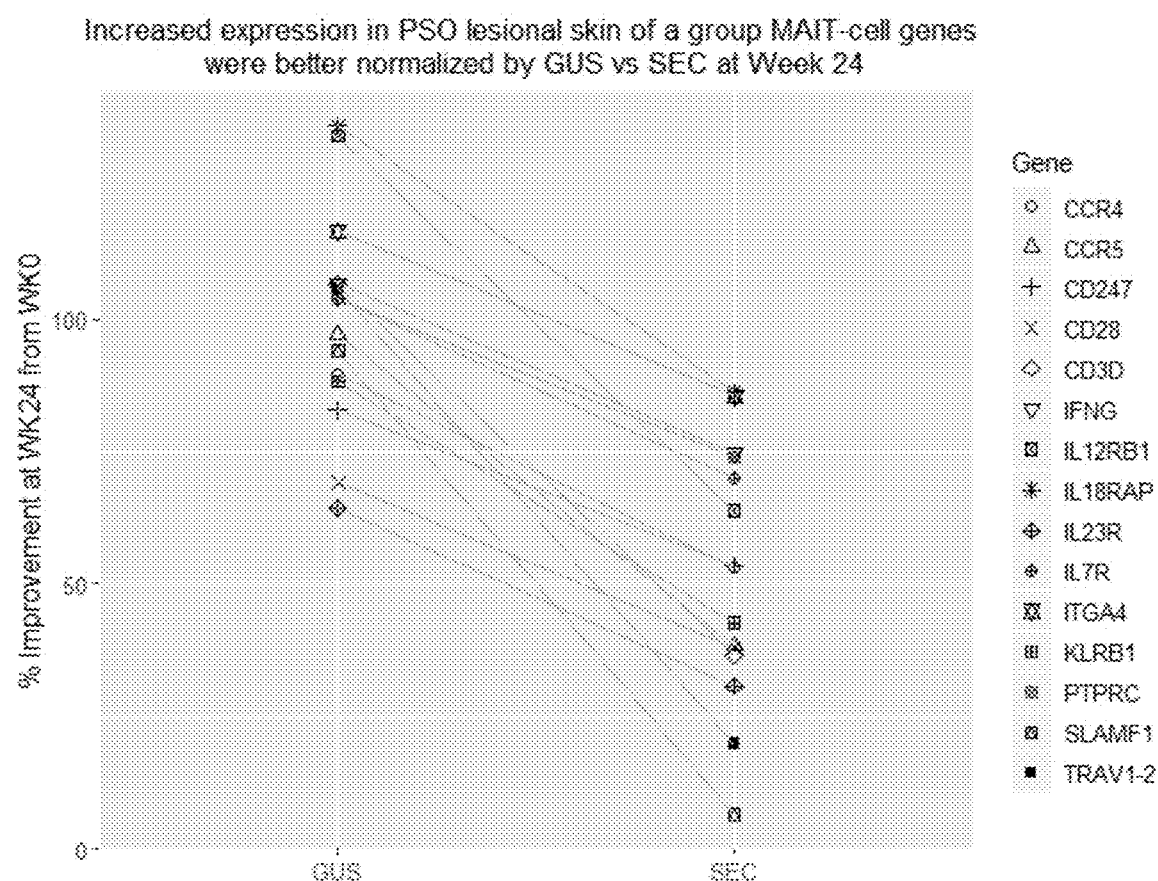
FIG. 7 shows the expression in psoriasis lesional skin of a group of genes associated with mucosal-associated invariant T (MAIT) cells

As shown in FIG. 6, a subset of induced genes in psoriasis lesional skin were better normalized by guselkumab than secukinumab at Week 24. Quantification of gene expression in individual skin biopsies were computed as log 2 transformed Transcripts per Million (TPM) from RNA-Seq Differential gene expression between lesional skin (LS) and non-lesional skin (NL) at baseline were calculated as the log 2 transformed ratios based on paired t test among 35 psoriasis patients. 1655 genes had increased expression in LS, with fold change >1.5 and false discovery rate (FDR) <0.05. Differential gene expression in LS in response to treatment at Week 4 and 24 were computed as log 2 transformed ratio using a mixed-effects model with repeated-measures, where the treatment (guselkumab and secukinumab) and visits (Weeks 4 and 24) are fixed effects, subject is a random effect, and the differential gene expression at baseline (between lesional skin and non-lesional skin) is a covariate. For a given gene, % of improvement in response to a treatment at a given visit is calculated as the negative ratio of the log 2 transformed ratio for the response in LS vs the log 2 transformed ratio of the difference between LS and NL at baseline. Among the 1655 genes had increased expression in LS at baseline, 328 (19.8%) had greater improvement in response to guselkumab than secukinumab at Week 24, as defined as >50% improvement in response to guselkumab, and >25% of difference in improvement between guselkumab vs secukinumab. Light grey lines represent individual genes, and the thick black line represents the average of % improvement among 328 genes in response to guselkumab (126%) vs secukinumab (76%). GUS: guselkumab, SEC: secukinumab As shown in FIG. 7, increased expression in psoriasis lesional skin of a group of genes associated with mucosal-associated invariant T (MAIT) cells was better normalized by guselkumab than secukinumab at Week 24. Light grey lines represent individual genes. GUS: guselkumab, SEC: secukinumab.

PsO is a T cell driven disease where skin resident T cells that produce multiple inflammatory cytokines are believed to play an important role in orchestrating the inflammatory immune response that leads to activation and proliferation of keratinocytes and culminates in hyperkeratosis, erythema and scaling, hallmarks of PsO inflamed skin. Inflammatory T cells in the skin and other tissues are believed to express IL23R and are dependent on IL-23 for becoming immunopathogenic. To better understand the mechanism of action of guselkumab, we sought to characterize PsO skin T cells by flow cytometry-based immunophenotyping of cell suspensions from dissociated biopsies. Using this approach, we showed that the frequency of CD8+ tissue resident memory T cells (TRMs) in lesional skin at week 24 was decreased relative to baseline levels in the GUS cohort (p=0.036) but not in the secukinumab. This leads to higher frequency of CD8 TRMs in the secukinumab cohort compared to guselkumab cohort at week 24 (p=0.0048).

TABLE 20

Summary of P values - Frequency of CD8 TRM within CD3 T cells

| Treatment | Week | P values |
| --- | --- | --- |
| Guselkumab | Week 0-NL vs Week 0-L | 0.021683 |
| Guselkumab | Week 0-NL vs Week 4 | 0.028696 |
| Guselkumab | Week 0-NL vs Week 24 | 0.83748 |
| Guselkumab | Week 0-L vs Week 4 | 0.909182 |
| Guselkumab | Week 0-L vs Week 24 | 0.035655 |
| Guselkumab | Week 4 vs Week 24 | 0.046409 |
| Secukinumab | Week 0-NL vs Week 0-L | 0.800505 |
| Secukinumab | Week 0-NL vs Week 4 | 0.18244 |
| Secukinumab | Week 0-NL vs Week 24 | 0.300364 |
| Secukinumab | Week 0-L vs Week 4 | 0.278196 |
| Secukinumab | Week 0-L vs Week 24 | 0.432394 |
| Secukinumab | Week 4 vs Week 24 | 0.762684 |
| Guselkumab vs Secukinumab | 0-NL | 0.048327 |
| Guselkumab vs Secukinumab | 0-L | 0.961635 |
| Guselkumab vs Secukinumab | 4 | 0.196808 |
| Guselkumab vs Secukinumab | 24 | 0.004842 |

Figure 8:
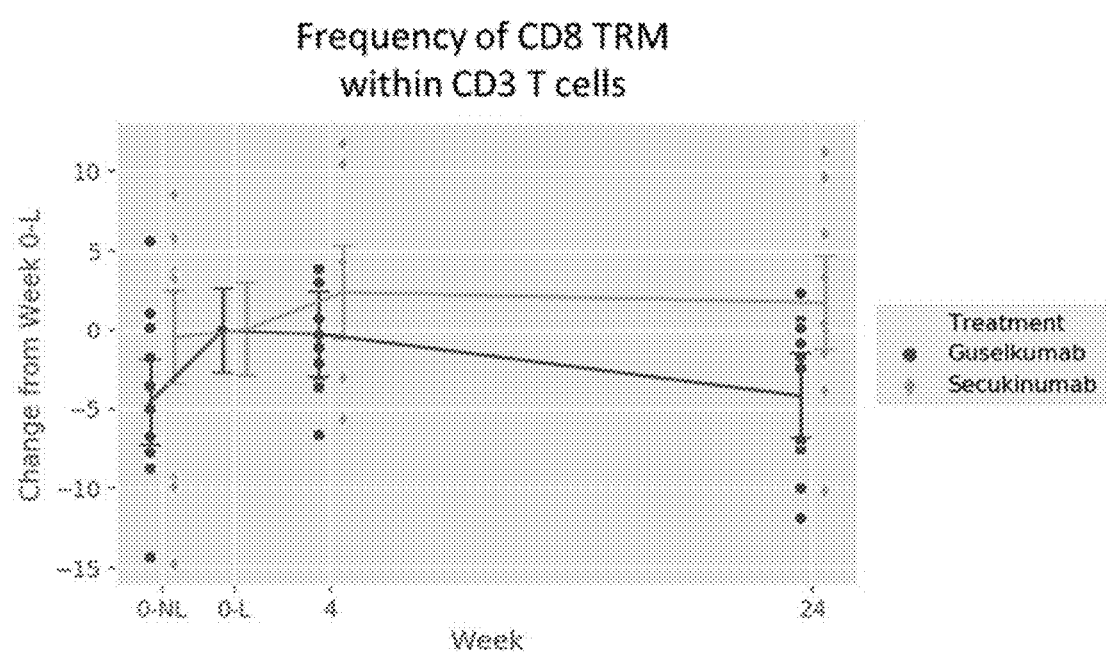
FIG. 8 shows the frequency of CD8 TRM in PSO skin treated with guselkumab and secukinumab.

As shown in FIG. 8, the frequency of CD8 TRM in PSO skin was reduced by guselkumab, but not by secukinumab at Week 24. Characterization of PSO skin T cells was done by immunophenotyping of cell suspension obtained from dissociated biopsy. Compared to baseline lesional skin, frequency of CD8 TRMs (CD3$^+$, CD8$^+$, CD103$^+$ and/or CD49a$^+$) was reduced at Week 24 in the guselkumab arm (n=11, p<0.05) but not in the secukinumab arm (n=9). Statistical analysis was performed using SAS 9.4 software using longitudinal regression model with difference from lesion at baseline as response, lesion at baseline as predictor, treatment and week as factor and interaction term between treatment and week, and AR1 as covariance structure. Data was plotted as change from baseline lesion using least square means and 95% confidence interval.

IL23 has also been reported to have an antagonistic effect on the function of regulatory T cells (Treg). Treg in PsO blood and skin have been reported to be increased but are defective in function. To better understand the mechanism of action of guselkumab, we sought to characterize PsO skin T cells by flow cytometry-based immunophenotyping of cell suspensions from dissociated biopsies. Using this novel approach, we showed that the frequency of Treg (CD3$^+$, FoxP3$^+$, CD25$^+$) in the GUS arm was maintained relative to baseline levels at week 24. In comparison, in the cohort treated with secukinumab, the levels of Tregs were reduced relative to baseline at week 24 (p=0.00013). Thus, GUS was able to maintain the relative frequency of Treg during the course of treatment.

TABLE 21

Summary of P values - Frequency of Tregs within CD3 T cells

| Treatment | Week | P values |
|---|---|---|
| Guselkumab | Week 0-NL vs Week 0-L | 0.00704 |
| Guselkumab | Week 0-NL vs Week 4 | 0.055978 |
| Guselkumab | Week 0-NL vs Week 24 | 0.065898 |
| Guselkumab | Week 0-L vs Week 4 | 0.408284 |
| Guselkumab | Week 0-L vs Week 24 | 0.36752 |
| Guselkumab | Week 4 vs Week 24 | 0.94038 |
| Secukinumab | Week 0-NL vs Week 0-L | 8.3E−06 |
| Secukinumab | Week 0-NL vs Week 4 | 0.029787 |
| Secukinumab | Week 0-NL vs Week 24 | 0.457042 |
| Secukinumab | Week 0-L vs Week 4 | 0.011765 |
| Secukinumab | Week 0-L vs Week 24 | 0.000126 |
| Secukinumab | Week 4 vs Week 24 | 0.146146 |
| Guselkumab vs Secukinumab | 0-NL | 0.346175 |
| Guselkumab vs Secukinumab | 0-L | 0.161581 |
| Guselkumab vs Secukinumab | 4 | 0.636662 |
| Guselkumab vs Secukinumab | 24 | 0.059004 |

Figure 9:
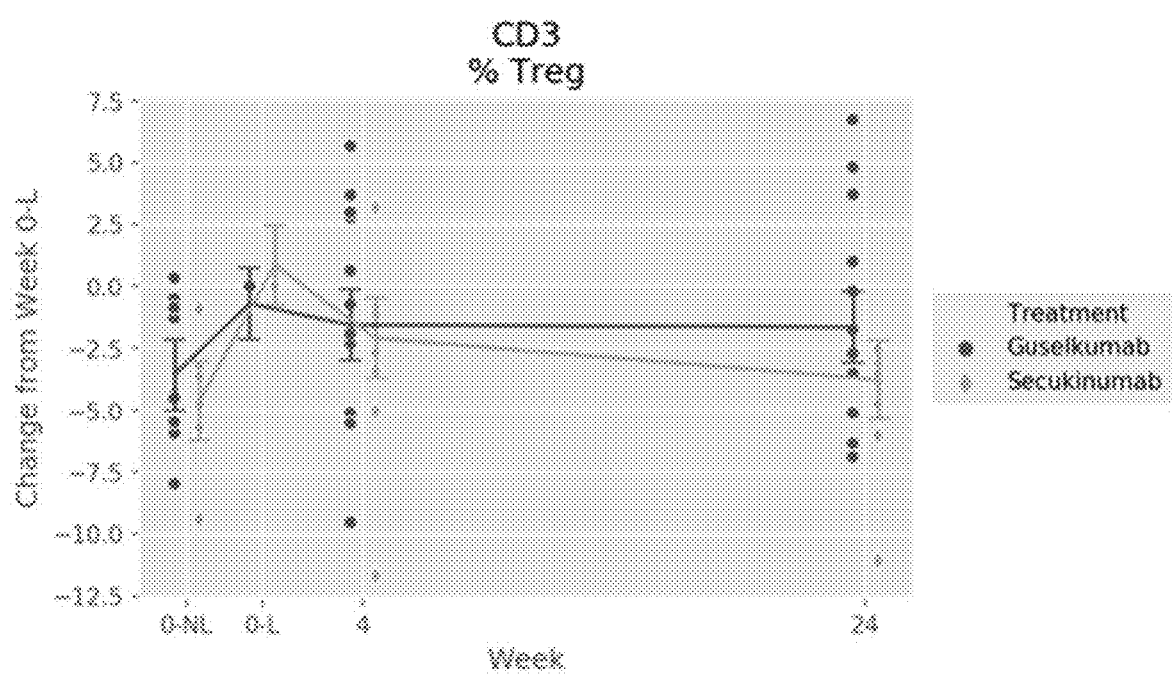
FIG. 9 shows the frequency of regulatory T cells (Tregs) in PSO skin treated with guselkumab and secukinumab.

As shown in FIG. 9, the frequency of regulatory T cells (Tregs) was reduced in the secukinumab arm but not in guselkumab arm at Week 24. Characterization of PSO skin T cells by immunophenotyping of skin cells showed that compared to baseline, the frequency of Treg population was maintained in the guselkumab arm (n=11), but was reduced in the secukinumab arm (n=9, p<0.001) at Week 24. Statistical analysis was performed using SAS 9.4 software using longitudinal regression model with difference from lesion at baseline as response, lesion at baseline as predictor, treatment and week as factor and interaction term between treatment and week, and AR1 as covariance structure. Data was plotted as change from baseline lesion using least square means and 95% confidence interval.

To better understand the mechanism of action of Guselkumab (GUS) (trademark name TREMFYA), we sought to characterize PsO skin T cells by flow cytometry-based immunophenotyping of cell suspensions from dissociated biopsies. Using this approach, we showed that the relative frequency of Treg to CD8+ tissue resident memory T cells (TRMs) in PsO skin was higher in the guselkumab cohort compared to the cohort treated with IL17A mAb blocker, secukinumab (COSENTYX), at week 24 (p=0.006).

TABLE 22

Summary of P values - Ratio of Tregs to CD8TRM

| Treatment | Week | P values |
|---|---|---|
| Guselkumab | Week 0-NL vs Week 0-L | 0.617381 |
| Guselkumab | Week 0-NL vs Week 4 | 0.770112 |
| Guselkumab | Week 0-NL vs Week 24 | 0.085235 |
| Guselkumab | Week 0-L vs Week 4 | 0.835498 |
| Guselkumab | Week 0-L vs Week 24 | 0.217772 |
| Guselkumab | Week 4 vs Week 24 | 0.150912 |
| Secukinumab | Week 0-NL vs Week 0-L | 0.061484 |
| Secukinumab | Week 0-NL vs Week 4 | 0.594812 |
| Secukinumab | Week 0-NL vs Week 24 | 0.993097 |
| Secukinumab | Week 0-L vs Week 4 | 0.176379 |
| Secukinumab | Week 0-L vs Week 24 | 0.060335 |
| Secukinumab | Week 4 vs Week 24 | 0.588851 |
| Guselkumab vs Secukinumab | 0-NL | 0.247194 |
| Guselkumab vs Secukinumab | 0-L | 0.729469 |
| Guselkumab vs Secukinumab | 4 | 0.379056 |
| Guselkumab vs Secukinumab | 24 | 0.006053 |

Figure 10:
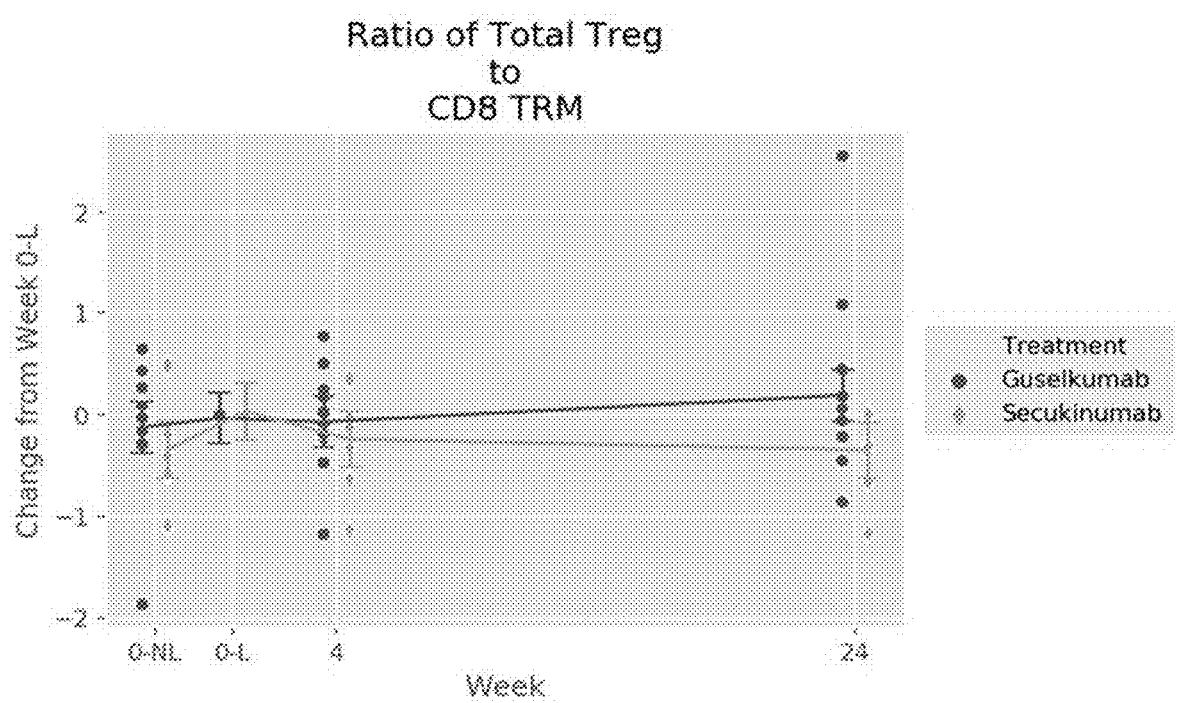
FIG. 10 shows the ratio of regulatory T cells (Tregs) to CD8 tissue resident memory T cells (TRMs) in PSO skin treated with guselkumab and secukinumab.

As shown in FIG. 10, there are a higher relative frequency of regulatory T cells (Tregs) to CD8 tissue resident memory T cells (TRMs) in guselkumab arm compared to secukinumab arm at Week 24. Characterization of PSO skin T cells by immunophenotyping of skin cells showed that the ratio of Treg population to CD8 TRM population was higher in the guselkumab arm (n=11) compared to secukinumab arm (n=9, p<0.01) at Week 24. Statistical analysis was performed using SAS 9.4 software using longitudinal regression model with difference from lesion at baseline as response, lesion at baseline as predictor, treatment and week as factor and interaction term between treatment and week, and AR1 as covariance structure. Data was plotted as change from baseline lesion using least square means and 95% confidence interval.

APPENDIX

APPENDIX 1

Summary of Demographics and Baseline Characteristics; Full Analysis Set (Study CNTO1959PSO3009)

| | Guselkumab 100 mg | Secukinumab 300 mg | Total |
|---|---|---|---|
| Analysis set: Full analysis set | 534 | 514 | 1048 |
| Age, years | | | |
| N | 534 | 514 | 1048 |
| Mean (SD) | 46.3 (13.67) | 45.3 (13.57) | 45.8 (13.63) |
| Median | 47.0 | 44.0 | 46.0 |
| Range | (18; 87) | (18; 76) | (18; 87) |

APPENDIX 1-continued

Summary of Demographics and Baseline Characteristics; Full Analysis Set (Study CNTO1959PSO3009)

| | Guselkumab 100 mg | Secukinumab 300 mg | Total |
|---|---|---|---|
| IQ range | (37.0; 56.0) | (35.0; 55.0) | (36.0; 55.0) |
| <45 years | 226 (42.3%) | 262 (51.0%) | 488 (46.6%) |
| ≥45 to <65 years | 254 (47.6%) | 207 (40.3%) | 461 (44.0%) |
| ≥65 years | 54 (10.1%) | 45 (8.8%) | 99 (9.4%) |
| Sex | | | |
| N | 534 | 514 | 1048 |
| Female | 169 (31.6%) | 172 (33.5%) | 341 (32.5%) |
| Male | 365 (68.4%) | 342 (66.5%) | 707 (67.5%) |
| Race | | | |
| N | 534 | 514 | 1048 |
| American Indian or Alaska Native | 2 (0.4%) | 2 (0.4%) | 4 (0.4%) |
| Asian | 18 (3.4%) | 12 (2.3%) | 30 (2.9%) |
| Black or African American | 5 (0.9%) | 11 (2.1%) | 16 (1.5%) |
| Native Hawaiian or Other Pacific Islander | 0 | 3 (0.6%) | 3 (0.3%) |
| White | 499 (93.4%) | 480 (93.4%) | 979 (93.4%) |
| Other | 6 (1.1%) | 6 (1.2%) | 12 (1.1%) |
| Multiple | 4 (0.7%) | 0 | 4 (0.4%) |
| Ethnicity | | | |
| N | 534 | 514 | 1048 |
| Hispanic or Latino | 27 (5.1%) | 36 (7.0%) | 63 (6.0%) |
| Not Hispanic or Latino | 502 (94.0%) | 472 (91.8%) | 974 (92.9%) |
| Not Reported | 5 (0.9%) | 4 (0.8%) | 9 (0.9%) |
| Unknown | 0 | 2 (0.4%) | 2 (0.2%) |
| Weight, kg | | | |
| N | 534 | 512 | 1046 |
| Mean (SD) | 89.31 (22.953) | 89.13 (20.212) | 89.23 (21.645) |
| Median | 87.60 | 87.00 | 87.00 |
| Range | (42.4; 201.1) | (42.8; 177.6) | (42.4; 201.1) |
| IQ range | (73.10; 101.30) | (75.00; 100.00) | (74.00; 100.60) |
| ≤90 kg | 297 (55.6%) | 292 (57.0%) | 589 (56.3%) |
| >90 kg | 237 (44.4%) | 220 (43.0%) | 457 (43.7%) |
| Height, cm | | | |
| N | 533 | 511 | 1044 |
| Mean (SD) | 172.9 (10.27) | 172.3 (9.63) | 172.6 (9.96) |
| Median | 173.0 | 172.5 | 172.8 |
| Range | (149; 198) | (143; 205) | (143; 205) |
| IQ range | (166.0; 180.0) | (165.1; 179.0) | (165.2; 180.0) |
| Body mass index, kg/m$^2$ | | | |
| N | 533 | 511 | 1044 |
| Mean (SD) | 29.8 (7.10) | 30.0 (6.33) | 29.9 (6.73) |
| Median | 28.4 | 29.2 | 28.8 |
| Range | (16; 70) | (16; 65) | (16; 70) |
| IQ range | (25.0; 33.4) | (25.5; 33.6) | (25.1; 33.6) |
| Normal < 25 kg/m$^2$ | 134 (25.1%) | 109 (21.3%) | 243 (23.3%) |
| Overweight > 25 to <30 kg/m$^2$ | 176 (33.0%) | 177 (34.6%) | 353 (33.8%) |
| Obese > 30 kg/m$^2$ | 223 (41.8%) | 225 (44.0%) | 448 (42.9%) |

Key: IQ = Interquartile
[TSIDEM01.RTF] [CNTO1959\PSO3009\DBR_WEEK_056\RE_WEEK_056_CSR\PROD\TSIDEM01.SAS] 23OCT2018, 12:56

APPENDIX 2

Summary of Psoriasis Baseline Clinical Disease Characteristics; Full Analysis Set (Study CNTO1959PSO3009)

| | Guselkumab 100 mg | Secukinumab 300 mg | Total |
|---|---|---|---|
| Analysis set: Full analysis set | 534 | 514 | 1048 |
| Psoriasis disease duration (years) | | | |
| N | 534 | 514 | 1048 |
| Mean (SD) | 18.5 (12.16) | 18.3 (12.67) | 18.4 (12.41) |
| Median | 17.0 | 15.7 | 16.1 |
| Range | (1; 60) | (1; 68) | (1; 68) |
| IQ range | (9.0; 27.0) | (9.0; 25.0) | (9.0; 26.0) |

APPENDIX 2-continued

Summary of Psoriasis Baseline Clinical Disease Characteristics;
Full Analysis Set (Study CNTO1959PSO3009)

| | Guselkumab 100 mg | Secukinumab 300 mg | Total |
|---|---|---|---|
| Psoriasis disease duration (years) | | | |
| N | 534 | 514 | 1048 |
| <15 years | 222 (41.6%) | 239 (46.5%) | 461 (44.0%) |
| ≥15 years | 312 (58.4%) | 275 (53.5%) | 587 (56.0%) |
| Age at diagnosis (years) | | | |
| N | 534 | 514 | 1048 |
| Mean (SD) | 27.9 (14.72) | 27.1 (15.05) | 27.5 (14.88) |
| Median | 26.0 | 25.0 | 25.0 |
| Range | (0; 84) | (0; 76) | (0; 84) |
| IQ range | (16.0; 38.0) | (16.0; 37.0) | (16.0; 37.0) |
| Age at diagnosis (years) | | | |
| N | 534 | 514 | 1048 |
| <25 years | 253 (47.4%) | 255 (49.6%) | 508 (48.5%) |
| ≥25 years | 281 (52.6%) | 259 (50.4%) | 540 (51.5%) |
| Psoriatic arthritis | | | |
| N | 534 | 514 | 1048 |
| Yes | 97 (18.2%) | 79 (15.4%) | 176 (16.8%) |
| No | 437 (81.8%) | 435 (84.6%) | 872 (83.2%) |
| BSA (%) | | | |
| N | 534 | 514 | 1048 |
| Mean (SD) | 23.7 (12.85) | 24.5 (14.59) | 24.1 (13.73) |
| Median | 20.0 | 20.0 | 20.0 |
| Range | (10; 86) | (10; 95) | (10; 95) |
| IQ range | (14.0; 29.0) | (15.0; 30.0) | (15.0; 29.0) |
| BSA | | | |
| N | 534 | 514 | 1048 |
| <20% | 249 (46.6%) | 240 (46.7%) | 489 (46.7%) |
| ≥20% | 285 (53.4%) | 274 (53.3%) | 559 (53.3%) |
| IGA score | | | |
| N | 534 | 514 | 1048 |
| Cleared (0) | 0 | 0 | 0 |
| Minimal (1) | 0 | 0 | 0 |
| Mild (2) | 0 | 1 (0.2%) | 1 (0.1%) |
| Moderate (3) | 407 (76.2%) | 391 (76.1%) | 798 (76.1%) |
| Severe (4) | 127 (23.8%) | 122 (23.7%) | 249 (23.8%) |
| IGA score | | | |
| N | 534 | 514 | 1048 |
| <4 | 407 (76.2%) | 392 (76.3%) | 799 (76.2%) |
| =4 | 127 (23.8%) | 122 (23.7%) | 249 (23.8%) |
| PASI score (0-72) | | | |
| N | 534 | 514 | 1048 |
| Mean (SD) | 20.0 (7.38) | 20.1 (7.63) | 20.0 (7.50) |
| Median | 18.0 | 17.8 | 18.0 |
| Range | (12; 59) | (5; 65) | (5; 65) |
| IQ range | (15.0; 22.4) | (15.2; 22.2) | (15.1; 22.3) |
| PASI score | | | |
| N | 534 | 514 | 1048 |
| <20 | 344 (64.4%) | 326 (63.4%) | 670 (63.9%) |
| ≥20 | 190 (35.6%) | 188 (36.6%) | 378 (36.1%) |

Key: IQ = Interquartile

[TSIDEM04.RTF] [CNTO1959\PSO3009\DBR_WEEK_056\RE_WEEK_056_CSR\PROD\TSIDEM04.SAS] 23OCT2018, 12:56

APPENDIX 3

Summary of Previous Psoriasis Medications and Therapies by Medication Category; Full Analysis Set (Study CNTO1959PSO3009)

|  | Guselkumab 100 mg | Secukinumab 300 mg | Total |
|---|---|---|---|
| Analysis set: Full analysis set | 534 | 514 | 1048 |
| Topical agents | | | |
| N | 531 | 514 | 1045 |
| Never Used | 22 (4.1%) | 34 (6.6%) | 56 (5.4%) |
| Ever Used | 509 (95.9%) | 480 (93.4%) | 989 (94.6%) |
| Phototherapy (PUVA or UVB) | | | |
| N | 534 | 513 | 1047 |
| Never Used | 253 (47.4%) | 252 (49.1%) | 505 (48.2%) |
| Ever Used | 281 (52.6%) | 261 (50.9%) | 542 (51.8%) |
| Non-biologic systemic (PUVA, methotrexate, cyclosporine, acitretin, apremilast, or tofacitinib) | | | |
| N | 534 | 514 | 1048 |
| Never Used | 258 (48.3%) | 227 (44.2%) | 485 (46.3%) |
| ≥1 therapy | 276 (51.7%) | 287 (55.8%) | 563 (53.7%) |
| ≥2 therapies | 126 (23.6%) | 132 (25.7%) | 258 (24.6%) |
| ≥3 therapies | 46 (8.6%) | 53 (10.3%) | 99 (9.4%) |
| ≥4 therapies | 10 (1.9%) | 4 (0.8%) | 14 (1.3%) |
| Biologics (etanercept, infliximab, alefacept, efalizumab, ustekinumab, briakinumab, ixekizumab, adalimumab, brodalumab, tildrakizuinab, or risankizuniab) | | | |
| N | 534 | 514 | 1048 |
| Never Used | 378 (70.8%) | 365 (71.0%) | 743 (70.9%) |
| Ever Used | 156 (29.2%) | 149 (29.0%) | 305 (29.1%) |
| Non-biologic systemic or biologics | | | |
| N | 534 | 514 | 1048 |
| Never Used | 206 (38.6%) | 183 (35.6%) | 389 (37.1%) |
| Ever Used | 328 (61.4%) | 331 (64.4%) | 659 (62.9%) |
| Anti-TNFα agent (etanercept, infliximab, adalimumab) | | | |
| N | 534 | 514 | 1048 |
| Never Used | 452 (84.6%) | 429 (83.5%) | 881 (84.1%) |
| Ever Used | 82 (15.4%) | 85 (16.5%) | 167 (15.9%) |
| IL-12/23 inhibitors (ustekinumab, briakinumab, tildrakizumab, risankizumab) | | | |
| N | 534 | 514 | 1048 |
| Never Used | 489 (91.6%) | 470 (91.4%) | 959 (91.5%) |
| Ever Used | 45 (8.4%) | 44 (8.6%) | 89 (8.5%) |
| IL-17 inhibitors (ixekizumab, brodalumab) | | | |
| N | 534 | 514 | 1048 |
| Never Used | 465 (87.1%) | 445 (86.6%) | 910 (86.8%) |
| Ever Used | 69 (12.9%) | 69 (13.4%) | 138 (13.2%) |

[TSICM01A.RTF]  [CNTO1959\PSO3009\DBR_WEEK_056\RE_WEEK_056_CSR\PROD\TSICM01A.SAS] 23OCT2018, 12:57

APPENDIX 4

Treatment Disposition Through Week 44; Full Analysis Set (Study CNTO1959PSO3009)

|  | Guselkumab 100 mg | Secukinumab 300 mg | Total |
|---|---|---|---|
| Analysis set: Full analysis set | 534 | 514 | 1048 |
| Discontinued study treatment | 27 (5.1%) | 48 (9.3%) | 75 (7.2%) |
| Reason for discontinuation | | | |
| Adverse event | 9 (1.7%) | 11 (2.1%) | 20 (1.9%) |
| Worsening of Psoriasis | 1 (0.2%) | 1 (0.2%) | 2 (0.2%) |

APPENDIX 4-continued

Treatment Disposition Through Week 44; Full Analysis Set (Study CNTO1959PSO3009)

|  | Guselkumab 100 mg | Secukinumab 300 mg | Total |
|---|---|---|---|
| Other Adverse event | 8 (1.5%) | 10 (1.9%) | 18 (1.7%) |
| Death | 0 | 0 | 0 |
| Lack of Efficacy | 2 (0.4%) | 7 (1.4%) | 9 (0.9%) |
| Lost to Follow-Up | 2 (0.4%) | 2 (0.4%) | 4 (0.4%) |
| Non-Compliance with Study Drug | 2 (0.4%) | 0 | 2 (0.2%) |
| Product Quality Complaint | 0 | 0 | 0 |
| Study Terminated by Sponsor | 0 | 0 | 0 |
| Trial Site Terminated by Sponsor | 0 | 0 | 0 |
| Withdrawal by Subject | 7 (1.3%) | 19 (3.7%) | 26 (2.5%) |
| Pregnancy | 1 (0.2%) | 1 (0.2%) | 2 (0.2%) |
| Protocol Violation | 2 (0.4%) | 6 (1.2%) | 8 (0.8%) |
| Other | 2 (0.4%) | 2 (0.4%) | 4 (0.4%) |

[TSIDS02.RTF]  [CNTO1959\PSO3009\DBR_WEEK_056\RE_WEEK_056_CSR\PROD\TSIDS02.SAS] 23OCT2018, 12:56

APPENDIX 5

Summary of Exposure to Study Agent Through Week 44; Safety Analysis Set (Study CNTO1959PSO3009)

|  | Guselkumab 100 mg | Secukinumab 300 mg |
|---|---|---|
| Analysis set: Safety analysis set | 534 | 511 |
| Total number of active injections received |  |  |
| N | 534 | 511 |
| Mean (SD) | 6.8 (0.86) | 28.8 (4.18) |
| Median | 7.0 | 30.0 |
| Range | (1; 9) | (2; 30) |
| Total number of active injections received |  |  |
| 1 | 4 (0.7%) | 0 |
| 2 | 6 (1.1%) | 2 (0.4%) |
| 3 | 3 (0.6%) | 0 |
| 4 | 3 (0.6%) | 0 |
| 5 | 7 (1.3%) | 0 |
| 6 | 9 (1.7%) | 2 (0.4%) |
| 7 | 499 (93.4%) | 0 |
| 8 | 2 (0.4%) | 1 (0.2%) |
| 9 | 1 (0.2%) | 0 |
| 10 | 0 | 4 (0.8%) |
| 11 | 0 | 0 |
| 12 | 0 | 4 (0.8%) |
| 13 | 0 | 0 |
| 14 | 0 | 4 (0.8%) |
| 15 | 0 | 0 |
| 16 | 0 | 5 (1.0%) |
| 17 | 0 | 0 |
| 18 | 0 | 6 (1.2%) |
| 19 | 0 | 0 |
| 20 | 0 | 3 (0.6%) |
| 21 | 0 | 0 |
| 22 | 0 | 3 (0.6%) |
| 23 | 0 | 0 |
| 24 | 0 | 1 (0.2%) |
| 25 | 0 | 0 |
| 26 | 0 | 3 (0.6%) |
| 27 | 0 | 0 |
| 28 | 0 | 26 (5.1%) |
| 29 | 0 | 0 |

APPENDIX 5-continued

Summary of Exposure to Study Agent Through Week 44; Safety Analysis Set (Study CNTO1959PSO3009)

|  | Guselkumab 100 mg | Secukinumab 300 mg |
|---|---|---|
| 30 | 0 | 447 (87.5%) |
| Total dose of study agent, mg |  |  |
| N | 534 | 511 |
| Mean (SD) | 682.4 (86.14) | 4321.5 (627.48) |
| Median | 700.0 | 4500.0 |
| Range | (100; 900) | (300; 4500) |

[TSIEX01.RTF]  [CNTO1959\PSO3009\DBR_WEEK_056\RE_WEEK_056_CSR\PROD\TSIEX01.SAS] 23OCT2018, 12:58

Efficacy

APPENDIX 6

Number of PASI 75 Responders at Both Week 12 and Week 48 (Non-Inferiority Analysis); Full Analysis Set (Study CNTO1959PSO3009)

|  | Guselkumab 100 mg | Secukinumab 300 mg |
|---|---|---|
| Analysis set: Full analysis set | 534 | 514 |
| PASI 75 responders | 452 (84.6%) | 412 (80.2%) |
| Treatment difference (95% CI) |  | 4.3% (−0.2%, 8.9%) |
| p-value |  | <0.001 |

Note 1:
Treatment difference was calculated adjusting for investigator site (pooled) using MH weights and 95% CI was calculated adjusting for investigator site (pooled) with MH weights using Miettinen-Nurminen method.
Note 2:
P-value was based on 1-sided MH Z-test adjusted for investigator site (pooled).
[TEFPASI03A.RTF]  [CNTO1959\PSO3009\DBR_WEEK_056\RE_WEEK_056_CSR\PROD\TEFPASI03A.SAS] 23OCT2018, 13:06

APPENDIX 7

Number of PASI 75 Responders at Both Week 12 and Week 48 (Superiority Analysis); Full Analysis Set (Study CNTO1959PSO3009)

|  | Guselkumab 100 mg | Secukinumab 300 mg |
|---|---|---|
| Analysis set: Full analysis set | 534 | 514 |
| PASI 75 responders | 452 (84.6%) | 412 (80.2%) |
| Treatment differences (95% CI) |  | 4.3% (0.1%, 8.5%) |
| p-value |  | 0.062 |

Note 1:
Treatment difference and 95% CI were calculated adjusting for investigator site (pooled) using MH weights.
Note 2:
P-value was based on 1-sided CMH chi-square test stratified by the investigator site (pooled).
[TEFPASI03B.RTF]  [CNTO1959\PSO3009\DBR_WEEK_056\RE_WEEK_056_CSR\PROD\TEFPASI03B.SAS] 23OCT2018, 13:06

APPENDIX 8

Number of PASI 90 Responders at Week 12 (Non-Inferiority Analysis); Full Analysis Set (Study CNTO1959PSO3009)

|  | Guselkumab 100 mg | Secukinumab 300 mg |
|---|---|---|
| Analysis set: Full analysis set | 534 | 514 |

APPENDIX 8-continued

Number of PASI 90 Responders at Week 12 (Non-Inferiority Analysis); Full Analysis Set (Study CNTO1959PSO3009)

|  | Guselkumab 100 mg | Secukinumab 300 mg |
|---|---|---|
| PASI 90 responders | 369 (69.1%) | 391 (76.1%) |
| Treatment difference (95% CI) |  | −7.0% (−12.2%, −1.7%) |
| p-value |  | 0.127 |

Note 1:
Treatment difference was calculated adjusting for investigator site (pooled) using MH weights and 95% CI was calculated adjusting for investigator site (pooled) with MH weights using Miettinen-Nurminen method.
Note 2:
P-value was based on 1-sided MH Z-test adjusted for investigator site (pooled).
[TEFPASI04A.RTF] [CNTO1959\PSO3009\DBR_WEEK_056\RE_WEEK_056_CSR\PROD\TEFPASI04A.SAS] 23OCT2018, 13:10

APPENDIX 9

Number of PASI 75 Responders at Week 12 (Non-Inferiority Analysis); Full Analysis Set (Study CNTO1959PSO3009)

|  | Guselkumab 100 mg | Secukinumab 300 mg |
|---|---|---|
| Analysis set: Full analysis set | 534 | 514 |
| PASI 75 responders | 477 (89.3%) | 471 (91.6%) |
| Treatment difference (95% CI) |  | −2.3% (−6.0%, 1.2%) |
| p-value |  | <0.001 |

Note 1:
Treatment difference was calculated adjusting for investigator site (pooled) using MH weights and 95% CI was calculated adjusting for investigator site (pooled) with MH weights using Miettinen-Nurminen method.
Note 2:
P-value was based on 1-sided MH Z-test adjusted for investigator site (pooled).
[TEFPASI05A.RTF] [CNTO1959\PSO3009\DBR_WEEK_056\RE_WEEK_056_CSR\PROD\TEFPASI05A.SAS] 23OCT2018, 13:13

APPENDIX 10

Number of PASI 100 Responders at Week 48 (Superiority Analysis); Full Analysis Set (Study CNTO1959PSO3009)

|  | Guselkumab 100 mg | Secukinumab 300 mg |
|---|---|---|
| Analysis set: Full analysis set | 534 | 514 |
| PASI 100 responders | 311 (58.2%) | 249 (48.4%) |
| Treatment differences (95% CI) |  | 9.7% (4.2%, 15.1%) |
| p-value |  | 0.001 |

Note 1:
Treatment difference and 95% CI were calculated adjusting for investigator site (pooled) using MH weights.
Note 2:
P-value was based on CMH chi-square test stratified by the investigator site (pooled).
[TEFPASI06B.RTF] [CNTO1959\PSO3009\DBR_WEEK_056\RE_WEEK_056_CSR\PROD\TEFPASI06B.SAS] 23OCT2018, 13:17

APPENDIX 11

Number of Subjects With IGA Score of Cleared (0) at Week 48 (Superiority Analysis); Full Analysis Set (Study CNTO1959PSO3009)

|  | Guselkumab 100 mg | Secukinumab 300 mg |
|---|---|---|
| Analysis set: Full analysis set | 534 | 514 |
| Subjects with IGA score of cleared (0) | 332 (62.2%) | 259 (50.4%) |
| Treatment difference (95% CI) |  | 11.6% (6.2%, 17.1%) |
| p-value |  | <0.001 |

Note 1:
Treatment difference and 95% CI were calculated adjusting for investigator site (pooled) using MH weights.
Note 2:
P-value was based on CMH chi-square test stratified by the investigator site (pooled).
[TEFIGA01B.RTF] [CNTO1959\PSO3009\DBR_WEEK_056\RE_WEEK_056_CSR\PROD\TEFIGA01B.SAS] 23OCT2018, 13:20

APPENDIX 12

Number of Subjects With IGA Score of Cleared (0) or Minimal (1) at Week 48 (Superiority Analysis); Full Analysis Set (Study CNTO1959PSO3009)

|  | Guselkumab 100 mg | Secukinumab 300 mg |
|---|---|---|
| Analysis set: Full analysis set | 534 | 514 |
| Subjects with IGA score of cleared (0) or minimal (1) | 454 (85.0%) | 385 (74.9%) |
| Treatment difference (95% CI) |  | 9.7% (5.3%, 14.0%) |
| p-value |  | <0.001 |

Note 1:
Treatment difference and 95% CI were calculated adjusting for investigator site (pooled) using MH weights.
Note 2:
P-value was based on CMH chi-square test stratified by the investigator site (pooled).
[TEFIGA02B.RTF] [CNTO1959\PSO3009\DBR_WEEK_056\RE_WEEK_056_CSR\PROD\TEFIGA02B.SAS] 23OCT2018, 13:24

APPENDIX 13

Number of Subjects Achieving a PASI 90 Response at All 7 Visits From Week 24 Through Week 48 (Superiority Analysis); Full Analysis Set (Study CNTO1959PSO3009)

|  | Guselkumab 100 mg | Secukinumab 300 mg |
|---|---|---|
| Analysis set: Full analysis set | 534 | 514 |
| PASI 90 responders | 379 (71.0%) | 316 (61.5%) |
| Treatment difference (95% CI) |  | 9.8% (4.6%, 14.9%) |
| p-value |  | <0.001 |

Note 1:
Treatment difference and 95% CI were calculated adjusting for investigator site (pooled) using MH weights.
Note 2:
P-value was based on CMH chi-square test stratified by the investigator site (pooled).
[TEFPASI10B.RTF] [CNTO1959\PSO3009\DBR_WEEK_056\RE_WEEK_056_CSR\PROD\TEFPASI10B.SAS] 23OCT2018, 13:28

APPENDIX 14

Summary of PASI Responses Through Week 56 by Visit;
Full Analysis Set (Study CNTO1959PSO3009)

| | Guselkumab 100 mg | Secukinumab 300 mg |
|---|---|---|
| Analysis set: Full analysis set | 534 | 514 |
| Week 1 | | |
| N | 534 | 514 |
| 100% improvement | 0 | 0 |
| ≥90% improvement | 0 | 0 |
| ≥75% improvement | 11 (2.1%) | 9 (1.8%) |
| ≥50% improvement | 57 (10.7%) | 66 (12.8%) |
| Week 2 | | |
| N | 534 | 514 |
| 100% improvement | 1 (0.2%) | 3 (0.6%) |
| ≥90% improvement | 6 (1.1%) | 14 (2.7%) |
| ≥75% improvement | 34 (6.4%) | 59 (11.5%) |
| ≥50% improvement | 165 (30.9%) | 216 (42.0%) |
| Week 3 | | |
| N | 534 | 514 |
| 100% improvement | 9 (1.7%) | 8 (1.6%) |
| ≥90% improvement | 30 (5.6%) | 44 (8.6%) |
| ≥75% improvement | 104 (19.5%) | 146 (28.4%) |
| ≥50% improvement | 301 (56.4%) | 344 (66.9%) |
| Week 4 | | |
| N | 534 | 514 |
| 100% improvement | 22 (4.1%) | 26 (5.1%) |
| ≥90% improvement | 70 (13.1%) | 112 (21.8%) |
| ≥75% improvement | 210 (39.3%) | 258 (50.2%) |
| ≥50% improvement | 392 (73.4%) | 439 (85.4%) |
| Week 8 | | |
| N | 534 | 514 |
| 100% improvement | 107 (20.0%) | 140 (27.2%) |
| ≥90% improvement | 260 (48.7%) | 319 (62.1%) |
| ≥75% improvement | 408 (76.4%) | 443 (86.2%) |
| ≥50% improvement | 509 (95.3%) | 498 (96.9%) |
| Week 12 | | |
| N | 534 | 514 |
| 100% improvement | 202 (37.8%) | 216 (42.0%) |
| ≥90% improvement | 369 (69.1%) | 391 (76.1%) |
| ≥75% improvement | 477 (89.3%) | 471 (91.6%) |
| ≥50% improvement | 517 (96.8%) | 494 (96.1%) |
| Week 16 | | |
| N | 534 | 514 |
| 100% improvement | 255 (47.8%) | 237 (46.1%) |
| ≥90% improvement | 419 (78.5%) | 409 (79.6%) |
| ≥75% improvement | 495 (92.7%) | 477 (92.8%) |
| ≥50% improvement | 521 (97.6%) | 495 (96.3%) |
| Week 20 | | |
| N | 534 | 514 |
| 100% improvement | 274 (51.3%) | 250 (48.6%) |
| ≥90% improvement | 428 (80.1%) | 417 (81.1%) |
| ≥75% improvement | 500 (93.6%) | 475 (92.4%) |
| ≥50% improvement | 521 (97.6%) | 489 (95.1%) |
| Week 24 | | |
| N | 534 | 514 |
| 100% improvement | 292 (54.7%) | 259 (50.4%) |
| ≥90% improvement | 444 (83.1%) | 402 (78.2%) |
| ≥75% improvement | 503 (94.2%) | 464 (90.3%) |
| ≥50% improvement | 522 (97.8%) | 478 (93.0%) |
| Week 28 | | |
| N | 534 | 514 |
| 100% improvement | 305 (57.1%) | 262 (51.0%) |
| ≥90% improvement | 456 (85.4%) | 397 (77.2%) |
| ≥75% improvement | 502 (94.0%) | 464 (90.3%) |
| ≥50% improvement | 519 (97.2%) | 478 (93.0%) |
| Week 32 | | |
| N | 534 | 514 |
| 100% improvement | 307 (57.5%) | 258 (50.2%) |
| ≥90% improvement | 453 (84.8%) | 398 (77.4%) |
| ≥75% improvement | 502 (94.0%) | 459 (89.3%) |
| ≥50% improvement | 518 (97.0%) | 478 (93.0%) |
| Week 36 | | |
| N | 534 | 514 |
| 100% improvement | 313 (58.6%) | 257 (50.0%) |
| ≥90% improvement | 451 (84.5%) | 389 (75.7%) |
| ≥75% improvement | 500 (93.6%) | 447 (87.0%) |
| ≥50% improvement | 519 (97.2%) | 474 (92.2%) |
| Week 40 | | |
| N | 534 | 514 |
| 100% improvement | 311 (58.2%) | 250 (48.6%) |
| ≥90% improvement | 452 (84.6%) | 379 (73.7%) |
| ≥75% improvement | 496 (92.9%) | 441 (85.8%) |
| ≥50% improvement | 512 (95.9%) | 467 (90.9%) |
| Week 44 | | |
| N | 534 | 514 |
| 100% improvement | 313 (58.6%) | 254 (49.4%) |
| ≥90% improvement | 449 (84.1%) | 373 (72.6%) |
| ≥75% improvement | 493 (92.3%) | 438 (85.2%) |
| ≥50% improvement | 503 (94.2%) | 470 (91.4%) |
| Week 48 | | |
| N | 534 | 514 |
| 100% improvement | 311 (58.2%) | 249 (48.4%) |
| ≥90% improvement | 451 (84.5%) | 360 (70.0%) |
| ≥75% improvement | 492 (92.1%) | 429 (83.5%) |
| ≥50% improvement | 502 (94.0%) | 459 (89.3%) |
| Week 56 | | |
| N | 534 | 514 |
| 100% improvement | 269 (50.4%) | 139 (27.0%) |
| ≥90% improvement | 413 (77.3%) | 264 (51.4%) |
| ≥75% improvement | 470 (88.0%) | 362 (70.4%) |
| ≥50% improvement | 486 (91.0%) | 422 (82.1%) |

[TEFPASI13A.RTF]   [CNTO1959\PSO3009\DBR_WEEK_056\RE_WEEK_056_CSR\PROD\TEFPASI13A.SAS] 23OCT2018, 13:29

APPENDIX 15

Summary of IGA Responses Through Week 56 by Visit;
Full Analysis Set (Study CNTO1959PSO3009)

| | Guselkumab 100 mg | Secukinumab 300 mg |
|---|---|---|
| Analysis set: Full analysis set | 534 | 514 |
| Week 1 | | |
| N | 534 | 514 |
| IGA of cleared (0) | 0 | 0 |
| IGA of cleared (0) or minimal (1) | 18 (3.4%) | 13 (2.5%) |
| IGA of mild or better (≤2) | 145 (27.2%) | 176 (34.2%) |
| Week 2 | | |
| N | 534 | 514 |
| IGA of cleared (0) | 1 (0.2%) | 4 (0.8%) |
| IGA of cleared (0) or minimal (1) | 66 (12.4%) | 104 (20.2%) |
| IGA of mild or better (≤2) | 289 (54.1%) | 328 (63.8%) |
| Week 3 | | |
| N | 534 | 514 |
| IGA of cleared (0) | 14 (2.6%) | 17 (3.3%) |
| IGA of cleared (0) or minimal (1) | 145 (27.2%) | 205 (39.9%) |
| IGA of mild or better (≤2) | 402 (75.3%) | 424 (82.5%) |

APPENDIX 15-continued

Summary of IGA Responses Through Week 56 by Visit;
Full Analysis Set (Study CNTO1959PSO3009)

|  | Guselkumab 100 mg | Secukinumab 300 mg |
|---|---|---|
| Week 4 | | |
| N | 534 | 514 |
| IGA of cleared (0) | 36 (6.7%) | 50 (9.7%) |
| IGA of cleared (0) or minimal (1) | 236 (44.2%) | 305 (59.3%) |
| IGA of mild or better (≤2) | 457 (85.6%) | 474 (92.2%) |
| Week 8 | | |
| N | 534 | 514 |
| IGA of cleared (0) | 156 (29.2%) | 184 (35.8%) |
| IGA of cleared (0) or minimal (1) | 409 (76.6%) | 429 (83.5%) |
| IGA of mild or better (≤2) | 514 (96.3%) | 495 (96.3%) |
| Week 12 | | |
| N | 534 | 514 |
| IGA of cleared (0) | 247 (46.3%) | 258 (50.2%) |
| IGA of cleared (0) or minimal (1) | 457 (85.6%) | 444 (86.4%) |
| IGA of mild or better (≤2) | 517 (96.8%) | 490 (95.3%) |
| Week 16 | | |
| N | 534 | 514 |
| IGA of cleared (0) | 296 (55.4%) | 275 (53.5%) |
| IGA of cleared (0) or minimal (1) | 463 (86.7%) | 445 (86.6%) |
| IGA of mild or better (≤2) | 517 (96.8%) | 487 (94.7%) |
| Week 20 | | |
| N | 534 | 514 |
| IGA of cleared (0) | 304 (56.9%) | 277 (53.9%) |
| IGA of cleared (0) or minimal (1) | 469 (87.8%) | 440 (85.6%) |
| IGA of mild or better (≤2) | 509 (95.3%) | 479 (93.2%) |
| Week 24 | | |
| N | 534 | 514 |
| IGA of cleared (0) | 326 (61.0%) | 288 (56.0%) |
| IGA of cleared (0) or minimal (1) | 473 (88.6%) | 425 (82.7%) |
| IGA of mild or better (≤2) | 514 (96.3%) | 471 (91.6%) |
| Week 28 | | |
| N | 534 | 514 |
| IGA of cleared (0) | 332 (62.2%) | 289 (56.2%) |
| IGA of cleared (0) or minimal (1) | 469 (87.8%) | 426 (82.9%) |
| IGA of mild or better (≤2) | 510 (95.5%) | 467 (90.9%) |
| Week 32 | | |
| N | 534 | 514 |
| IGA of cleared (0) | 337 (63.1%) | 280 (54.5%) |
| IGA of cleared (0) or minimal (1) | 473 (88.6%) | 419 (81.5%) |
| IGA of mild or better (≤2) | 510 (95.5%) | 465 (90.5%) |
| Week 36 | | |
| N | 534 | 514 |
| IGA of cleared (0) | 324 (60.7%) | 276 (53.7%) |
| IGA of cleared (0) or minimal (1) | 462 (86.5%) | 409 (79.6%) |
| IGA of mild or better (≤2) | 510 (95.5%) | 457 (88.9%) |
| Week 40 | | |
| N | 534 | 514 |
| IGA of cleared (0) | 337 (63.1%) | 269 (52.3%) |
| IGA of cleared (0) or minimal (1) | 461 (86.3%) | 401 (78.0%) |
| IGA of mild or better (≤2) | 500 (93.6%) | 452 (87.9%) |
| Week 44 | | |
| N | 534 | 514 |
| IGA of cleared (0) | 332 (62.2%) | 267 (51.9%) |
| IGA of cleared (0) or minimal (1) | 459 (86.0%) | 393 (76.5%) |
| IGA of mild or better (≤2) | 493 (92.3%) | 450 (87.5%) |
| Week 48 | | |
| N | 534 | 514 |
| IGA of cleared (0) | 332 (62.2%) | 259 (50.4%) |
| IGA of cleared (0) or minimal (1) | 454 (85.0%) | 385 (74.9%) |
| IGA of mild or better (≤2) | 495 (92.7%) | 446 (86.8%) |
| Week 56 | | |
| N | 534 | 514 |
| IGA of cleared (0) | 290 (54.3%) | 151 (29.4%) |
| IGA of cleared (0) or minimal (1) | 421 (78.8%) | 299 (58.2%) |
| IGA of mild or better (≤2) | 467 (87.5%) | 392 (76.3%) |

[TEFIGA05A.RTF] [CNTO1959\PSO3009\DBR_WEEK_056\RE_WEEK_056_CSR\PROD\TEFIGA05A.SAS] 23OCT2018,13:28

Safety

APPENDIX 16

Number of Subjects With Treatment-Emergent Adverse Events Through Week 56 by System Organ Class and Preferred Term; Safety Analysis Set (Study CNTO1959PSO3009)

|  | Guselkumab 100 mg | Secukinumab 300 mg |
|---|---|---|
| Analysis set: Safety analysis set | 534 | 511 |
| Avg duration of follow-up (weeks) | 54.90 | 53.67 |
| Avg exposure (number of administrations) | 14.65 | 14.41 |
| Subjects with 1 or more AEs | 416 (77.9%) | 417 (81.6%) |
| System organ class Preferred term | | |
| Infections and infestations | 310 (58.1%) | 324 (63.4%) |
| Nasopharyngitis | 118 (22.1%) | 125 (24.5%) |
| Upper respiratory tract infection | 83 (15.5%) | 92 (18.0%) |
| Pharyngitis | 24 (4.5%) | 22 (4.3%) |
| Influenza | 20 (3.7%) | 13 (2.5%) |
| Bronchitis | 17 (3.2%) | 15 (2.9%) |
| Oral herpes | 11 (2.1%) | 14 (2.7%) |
| Urinary tract infection | 11 (2.1%) | 11 (2.2%) |
| Gastroenteritis | 10 (1.9%) | 9 (1.8%) |
| Sinusitis | 10 (1.9%) | 12 (2.3%) |
| Gastroenteritis viral | 9 (1.7%) | 8 (1.6%) |
| Rhinitis | 9 (1.7%) | 13 (2.5%) |
| Viral upper respiratory tract infection | 9 (1.7%) | 8 (1.6%) |
| Folliculitis | 8 (1.5%) | 10 (2.0%) |
| Tonsillitis | 7 (1.3%) | 15 (2.9%) |
| Tinea pedis | 6 (1.1%) | 16 (3.1%) |
| Gastrointestinal infection | 5 (0.9%) | 0 |
| Oral candidiasis | 5 (0.9%) | 11 (2.2%) |
| Tooth abscess | 5 (0.9%) | 3 (0.6%) |
| Tooth infection | 5 (0.9%) | 2 (0.4%) |
| Vulvovaginal candidiasis | 5 (0.9%) | 13 (2.5%) |
| Acute sinusitis | 4 (0.7%) | 0 |
| Cellulitis | 4 (0.7%) | 3 (0.6%) |
| Conjunctivitis | 4 (0.7%) | 17 (3.3%) |
| Respiratory tract infection | 4 (0.7%) | 2 (0.4%) |
| Tinea versicolour | 4 (0.7%) | 5 (1.0%) |
| Gastrointestinal viral infection | 3 (0.6%) | 1 (0.2%) |
| Periodontitis | 3 (0.6%) | 5 (1.0%) |
| Pneumonia | 3 (0.6%) | 6 (1.2%) |
| Cystitis | 2 (0.4%) | 2 (0.4%) |
| Ear infection | 2 (0.4%) | 5 (1.0%) |
| *Helicobacter* gastritis | 2 (0.4%) | 0 |
| Hordeolum | 2 (0.4%) | 8 (1.6%) |
| Laryngitis | 2 (0.4%) | 2 (0.4%) |
| Localised infection | 2 (0.4%) | 1 (0.2%) |
| Otitis media | 2 (0.4%) | 6 (1.2%) |
| Postoperative wound infection | 2 (0.4%) | 0 |
| Skin *Candida* | 2 (0.4%) | 3 (0.6%) |
| Tinea cruris | 2 (0.4%) | 4 (0.8%) |
| Wound infection | 2 (0.4%) | 1 (0.2%) |
| Acarodermatitis | 1 (0.2%) | 2 (0.4%) |
| Anal abscess | 1 (0.2%) | 0 |
| Anal fistula infection | 1 (0.2%) | 0 |

APPENDIX 16-continued

Number of Subjects With Treatment-Emergent Adverse Events Through Week 56 by System Organ Class and Preferred Term; Safety Analysis Set (Study CNTO1959PSO3009)

| | Guselkumab 100 mg | Secukinumab 300 mg |
|---|---|---|
| Appendicitis | 1 (0.2%) | 0 |
| Arthritis infective | 1 (0.2%) | 0 |
| Bacterial rhinitis | 1 (0.2%) | 0 |
| Bacterial vulvovaginitis | 1 (0.2%) | 0 |
| *Candida* infection | 1 (0.2%) | 0 |
| Conjunctivitis bacterial | 1 (0.2%) | 0 |
| Dermatitis infected | 1 (0.2%) | 2 (0.4%) |
| Dermo-hypodermitis | 1 (0.2%) | 0 |
| Diverticulitis | 1 (0.2%) | 3 (0.6%) |
| Enterobiasis | 1 (0.2%) | 0 |
| Erysipelas | 1 (0.2%) | 0 |
| Fungal skin infection | 1 (0.2%) | 0 |
| Furuncle | 1 (0.2%) | 2 (0.4%) |
| Gangrene | 1 (0.2%) | 0 |
| Gastroenteritis *yersinia* | 1 (0.2%) | 0 |
| Genital herpes | 1 (0.2%) | 3 (0.6%) |
| Gingivitis | 1 (0.2%) | 2 (0.4%) |
| Impetigo | 1 (0.2%) | 4 (0.8%) |
| Labyrinthitis | 1 (0.2%) | 0 |
| Mastitis | 1 (0.2%) | 0 |
| Nasal herpes | 1 (0.2%) | 1 (0.2%) |
| Ophthalmic herpes zoster | 1 (0.2%) | 0 |
| Paronychia | 1 (0.2%) | 2 (0.4%) |
| Peritonsillar abscess | 1 (0.2%) | 0 |
| Pilonidal cyst | 1 (0.2%) | 0 |
| Pyoderma | 1 (0.2%) | 0 |
| Salmonellosis | 1 (0.2%) | 0 |
| Sepsis | 1 (0.2%) | 0 |
| Skin bacterial infection | 1 (0.2%) | 0 |
| Upper respiratory tract infection bacterial | 1 (0.2%) | 0 |
| Urinary tract infection bacterial | 1 (0.2%) | 0 |
| Viral pharyngitis | 1 (0.2%) | 0 |
| Abscess | 0 | 1 (0.2%) |
| Abscess limb | 0 | 1 (0.2%) |
| Angular cheilitis | 0 | 3 (0.6%) |
| Application site cellulitis | 0 | 1 (0.2%) |
| Bacterial vaginosis | 0 | 1 (0.2%) |
| Balanitis *Candida* | 0 | 2 (0.4%) |
| Blister infected | 0 | 1 (0.2%) |
| Body tinea | 0 | 2 (0.4%) |
| Bullous impetigo | 0 | 1 (0.2%) |
| Dermatophytosis | 0 | 1 (0.2%) |
| Eczema impetiginous | 0 | 1 (0.2%) |
| Eczema infected | 0 | 2 (0.4%) |
| Groin abscess | 0 | 1 (0.2%) |
| *Helicobacter* infection | 0 | 1 (0.2%) |
| Herpes simplex | 0 | 1 (0.2%) |
| Herpes zoster | 0 | 4 (0.8%) |
| Neuroborreliosis | 0 | 1 (0.2%) |
| Onychomycosis | 0 | 1 (0.2%) |
| Otitis externa | 0 | 3 (0.6%) |
| Otitis media acute | 0 | 1 (0.2%) |
| Perianal streptococcal infection | 0 | 1 (0.2%) |
| Peritonsillitis | 0 | 1 (0.2%) |
| Pharyngitis streptococcal | 0 | 4 (0.8%) |
| Pharyngotonsillitis | 0 | 1 (0.2%) |
| Pulpitis dental | 0 | 2 (0.4%) |
| Pyelonephritis | 0 | 1 (0.2%) |
| Respiratory syncytial virus infection | 0 | 1 (0.2%) |
| Respiratory tract infection viral | 0 | 1 (0.2%) |
| Sialoadenitis | 0 | 1 (0.2%) |
| Soft tissue infection | 0 | 1 (0.2%) |
| Staphylococcal skin infection | 0 | 3 (0.6%) |
| Subcutaneous abscess | 0 | 2 (0.4%) |
| Tracheobronchitis | 0 | 1 (0.2%) |
| Vaginal infection | 0 | 2 (0.4%) |
| Vulvovaginal mycotic infection | 0 | 2 (0.4%) |
| Musculoskeletal and connective tissue disorders | 98 (18.4%) | 93 (18.2%) |
| Arthralgia | 30 (5.6%) | 25 (4.9%) |
| Back pain | 29 (5.4%) | 18 (3.5%) |
| Myalgia | 11 (2.1%) | 7 (1.4%) |
| Musculoskeletal pain | 7 (1.3%) | 7 (1.4%) |
| Psoriatic arthropathy | 7 (1.3%) | 3 (0.6%) |
| Osteoarthritis | 6 (1.1%) | 4 (0.8%) |
| Joint swelling | 5 (0.9%) | 3 (0.6%) |
| Tendonitis | 5 (0.9%) | 2 (0.4%) |
| Muscle spasms | 4 (0.7%) | 5 (1.0%) |
| Neck pain | 4 (0.7%) | 5 (1.0%) |
| Joint effusion | 3 (0.6%) | 1 (0.2%) |
| Pain in extremity | 3 (0.6%) | 6 (1.2%) |
| Musculoskeletal chest pain | 2 (0.4%) | 2 (0.4%) |
| Plantar fasciitis | 2 (0.4%) | 0 |
| Spinal pain | 2 (0.4%) | 3 (0.6%) |
| Arthritis | 1 (0.2%) | 1 (0.2%) |
| Chondropathy | 1 (0.2%) | 0 |
| Enthesopathy | 1 (0.2%) | 0 |
| Exostosis | 1 (0.2%) | 0 |
| Fibromyalgia | 1 (0.2%) | 0 |
| Groin pain | 1 (0.2%) | 1 (0.2%) |
| Intervertebral disc degeneration | 1 (0.2%) | 0 |
| Joint stiffness | 1 (0.2%) | 1 (0.2%) |
| Muscle tightness | 1 (0.2%) | 0 |
| Myofascial pain syndrome | 1 (0.2%) | 0 |
| Rotator cuff syndrome | 1 (0.2%) | 2 (0.4%) |
| Spinal osteoarthritis | 1 (0.2%) | 3 (0.6%) |
| Synovial cyst | 1 (0.2%) | 0 |
| Synovitis | 1 (0.2%) | 1 (0.2%) |
| Trigger finger | 1 (0.2%) | 0 |
| Bursitis | 0 | 3 (0.6%) |
| Costochondritis | 0 | 1 (0.2%) |
| Flank pain | 0 | 1 (0.2%) |
| Intervertebral disc disorder | 0 | 3 (0.6%) |
| Intervertebral disc protrusion | 0 | 2 (0.4%) |
| Musculoskeletal stiffness | 0 | 1 (0.2%) |
| Osteopenia | 0 | 1 (0.2%) |
| Periarthritis | 0 | 1 (0.2%) |
| Sacroiliitis | 0 | 1 (0.2%) |
| Spinal column stenosis | 0 | 1 (0.2%) |
| Spondylolisthesis | 0 | 1 (0.2%) |
| Temporomandibular joint syndrome | 0 | 1 (0.2%) |
| Tenosynovitis stenosans | 0 | 1 (0.2%) |
| Nervous system disorders | 79 (14.8%) | 71 (13.9%) |
| Headache | 49 (9.2%) | 48 (9.4%) |
| Sciatica | 8 (1.5%) | 6 (1.2%) |
| Migraine | 6 (1.1%) | 4 (0.8%) |
| Hypoaesthesia | 3 (0.6%) | 2 (0.4%) |
| Paraesthesia | 3 (0.6%) | 0 |
| Presyncope | 2 (0.4%) | 1 (0.2%) |
| Aphonia | 1 (0.2%) | 0 |
| Burning sensation | 1 (0.2%) | 0 |
| Carpal tunnel syndrome | 1 (0.2%) | 2 (0.4%) |
| Cervicobrachial syndrome | 1 (0.2%) | 0 |
| Cluster headache | 1 (0.2%) | 0 |
| Disturbance in attention | 1 (0.2%) | 0 |
| Dizziness postural | 1 (0.2%) | 0 |
| Dysaesthesia | 1 (0.2%) | 1 (0.2%) |
| Facial neuralgia | 1 (0.2%) | 0 |
| Hyperaesthesia | 1 (0.2%) | 0 |
| Memory impairment | 1 (0.2%) | 0 |
| Nerve compression | 1 (0.2%) | 0 |
| Piriformis syndrome | 1 (0.2%) | 0 |
| Spinal cord infarction | 1 (0.2%) | 0 |
| Spinal meningeal cyst | 1 (0.2%) | 0 |
| Syncope | 1 (0.2%) | 4 (0.8%) |
| Tension headache | 1 (0.2%) | 0 |
| Tremor | 1 (0.2%) | 0 |
| Vertebral artery stenosis | 1 (0.2%) | 0 |
| White matter lesion | 1 (0.2%) | 0 |
| Cerebral cyst | 0 | 1 (0.2%) |
| Cerebrovascular accident | 0 | 1 (0.2%) |
| Dizziness | 0 | 5 (1.0%) |
| Dysgeusia | 0 | 1 (0.2%) |
| Facial paralysis | 0 | 1 (0.2%) |

APPENDIX 16-continued

Number of Subjects With Treatment-Emergent Adverse Events Through Week 56 by System Organ Class and Preferred Term; Safety Analysis Set (Study CNTO1959PSO3009)

| | Guselkumab 100 mg | Secukinumab 300 mg |
|---|---|---|
| Head discomfort | 0 | 1 (0.2%) |
| Lethargy | 0 | 1 (0.2%) |
| Neuralgia | 0 | 3 (0.6%) |
| Neuropathy peripheral | 0 | 1 (0.2%) |
| Post herpetic neuralgia | 0 | 1 (0.2%) |
| Post-traumatic headache | 0 | 1 (0.2%) |
| Gastrointestinal disorders | 78 (14.6%) | 77 (15.1%) |
| Diarrhoea | 27 (5.1%) | 20 (3.9%) |
| Abdominal pain upper | 10 (1.9%) | 7 (1.4%) |
| Gastrooesophageal reflux disease | 7 (1.3%) | 8 (1.6%) |
| Abdominal pain | 6 (1.1%) | 7 (1.4%) |
| Nausea | 6 (1.1%) | 8 (1.6%) |
| Vomiting | 6 (1.1%) | 2 (0.4%) |
| Toothache | 5 (0.9%) | 4 (0.8%) |
| Constipation | 3 (0.6%) | 4 (0.8%) |
| Enteritis | 3 (0.6%) | 0 |
| Flatulence | 3 (0.6%) | 1 (0.2%) |
| Gastritis | 3 (0.6%) | 2 (0.4%) |
| Dental caries | 2 (0.4%) | 0 |
| Frequent bowel movements | 2 (0.4%) | 1 (0.2%) |
| Umbilical hernia | 2 (0.4%) | 1 (0.2%) |
| Abdominal discomfort | 1 (0.2%) | 1 (0.2%) |
| Abdominal distension | 1 (0.2%) | 0 |
| Abdominal pain lower | 1 (0.2%) | 0 |
| Anal fissure | 1 (0.2%) | 0 |
| Anal fistula | 1 (0.2%) | 0 |
| Colitis microscopic | 1 (0.2%) | 0 |
| Diverticulum intestinal | 1 (0.2%) | 0 |
| Dry mouth | 1 (0.2%) | 0 |
| Dyspepsia | 1 (0.2%) | 2 (0.4%) |
| Glossitis | 1 (0.2%) | 0 |
| Haematochezia | 1 (0.2%) | 1 (0.2%) |
| Haemorrhoidal haemorrhage | 1 (0.2%) | 0 |
| Haemorrhoids | 1 (0.2%) | 2 (0.4%) |
| Hyperchlorhydria | 1 (0.2%) | 0 |
| Inguinal hernia | 1 (0.2%) | 0 |
| Irritable bowel syndrome | 1 (0.2%) | 1 (0.2%) |
| Large intestine polyp | 1 (0.2%) | 1 (0.2%) |
| Leukoplakia oral | 1 (0.2%) | 0 |
| Mucous stools | 1 (0.2%) | 0 |
| Palatal oedema | 1 (0.2%) | 0 |
| Rectal polyp | 1 (0.2%) | 0 |
| Abdominal hernia | 0 | 1 (0.2%) |
| Anal pruritus | 0 | 1 (0.2%) |
| Aphthous ulcer | 0 | 8 (1.6%) |
| Apical granuloma | 0 | 1 (0.2%) |
| Burning mouth syndrome | 0 | 1 (0.2%) |
| Chronic gastritis | 0 | 1 (0.2%) |
| Colitis | 0 | 1 (0.2%) |
| Crohn's disease | 0 | 1 (0.2%) |
| Dysphagia | 0 | 3 (0.6%) |
| Food poisoning | 0 | 2 (0.4%) |
| Functional gastrointestinal disorder | 0 | 1 (0.2%) |
| Gingival bleeding | 0 | 1 (0.2%) |
| Gingival recession | 0 | 1 (0.2%) |
| Hiatus hernia | 0 | 1 (0.2%) |
| Inflammatory bowel disease | 0 | 2 (0.4%) |
| Odynophagia | 0 | 2 (0.4%) |
| Tooth impacted | 0 | 1 (0.2%) |
| Skin and subcutaneous tissue disorders | 76 (14.2%) | 92 (18.0%) |
| Pruritus | 17 (3.2%) | 12 (2.3%) |
| Acne | 4 (0.7%) | 3 (0.6%) |
| Dermatitis | 4 (0.7%) | 7 (1.4%) |
| Dermatitis contact | 4 (0.7%) | 8 (1.6%) |
| Eczema | 4 (0.7%) | 7 (1.4%) |
| Psoriasis | 4 (0.7%) | 11 (2.2%) |
| Skin lesion | 3 (0.6%) | 2 (0.4%) |
| Urticaria | 3 (0.6%) | 9 (1.8%) |
| Actinic keratosis | 2 (0.4%) | 2 (0.4%) |
| Alopecia | 2 (0.4%) | 4 (0.8%) |
| Blister | 2 (0.4%) | 0 |
| Chronic cutaneous lupus erythematosus | 2 (0.4%) | 0 |
| Drug eruption | 2 (0.4%) | 1 (0.2%) |
| Dry skin | 2 (0.4%) | 3 (0.6%) |
| Eczema asteatotic | 2 (0.4%) | 2 (0.4%) |
| Hyperkeratosis | 2 (0.4%) | 0 |
| Papule | 2 (0.4%) | 1 (0.2%) |
| Photosensitivity reaction | 2 (0.4%) | 0 |
| Polymorphic light eruption | 2 (0.4%) | 0 |
| Pruritus generalised | 2 (0.4%) | 2 (0.4%) |
| Rash | 2 (0.4%) | 1 (0.2%) |
| Angioedema | 1 (0.2%) | 0 |
| Cafe au lait spots | 1 (0.2%) | 2 (0.4%) |
| Dermal cyst | 1 (0.2%) | 3 (0.6%) |
| Dermatitis atopic | 1 (0.2%) | 1 (0.2%) |
| Erythema | 1 (0.2%) | 2 (0.4%) |
| Ingrowing nail | 1 (0.2%) | 0 |
| Ingrown hair | 1 (0.2%) | 0 |
| Intertrigo | 1 (0.2%) | 8 (1.6%) |
| Lentigo | 1 (0.2%) | 0 |
| Milia | 1 (0.2%) | 0 |
| Miliaria | 1 (0.2%) | 1 (0.2%) |
| Night sweats | 1 (0.2%) | 1 (0.2%) |
| Onycholysis | 1 (0.2%) | 1 (0.2%) |
| Perioral dermatitis | 1 (0.2%) | 0 |
| Pityriasis | 1 (0.2%) | 0 |
| Pityriasis rosea | 1 (0.2%) | 0 |
| Rash morbilliform | 1 (0.2%) | 0 |
| Rash papular | 1 (0.2%) | 2 (0.4%) |
| Rosacea | 1 (0.2%) | 0 |
| Seborrhoeic dermatitis | 1 (0.2%) | 8 (1.6%) |
| Skin burning sensation | 1 (0.2%) | 0 |
| Skin exfoliation | 1 (0.2%) | 0 |
| Skin ulcer | 1 (0.2%) | 1 (0.2%) |
| Solar dermatitis | 1 (0.2%) | 0 |
| Alopecia scarring | 0 | 1 (0.2%) |
| Dermatitis allergic | 0 | 1 (0.2%) |
| Diffuse alopecia | 0 | 1 (0.2%) |
| Dyshidrotic eczema | 0 | 2 (0.4%) |
| Eczema nummular | 0 | 1 (0.2%) |
| Ephelides | 0 | 1 (0.2%) |
| Hair growth rate abnormal | 0 | 1 (0.2%) |
| Hand dermatitis | 0 | 1 (0.2%) |
| Hyperhidrosis | 0 | 1 (0.2%) |
| Idiopathic urticaria | 0 | 1 (0.2%) |
| Keratolysis exfoliativa acquired | 0 | 1 (0.2%) |
| Keratosis pilaris | 0 | 1 (0.2%) |
| Myxoid cyst | 0 | 1 (0.2%) |
| Neurodermatitis | 0 | 3 (0.6%) |
| Photodermatosis | 0 | 1 (0.2%) |
| Pruritus allergic | 0 | 1 (0.2%) |
| Rash maculo-papular | 0 | 1 (0.2%) |
| Skin fissures | 0 | 3 (0.6%) |
| Skin texture abnormal | 0 | 1 (0.2%) |
| Stasis dermatitis | 0 | 1 (0.2%) |
| Urticaria pressure | 0 | 1 (0.2%) |
| Respiratory, thoracic and mediastinal disorders | 59 (11.0%) | 59 (11.5%) |
| Cough | 20 (3.7%) | 21 (4.1%) |
| Oropharyngeal pain | 12 (2.2%) | 11 (2.2%) |
| Nasal congestion | 7 (1.3%) | 6 (1.2%) |
| Rhinorrhoea | 6 (1.1%) | 9 (1.8%) |
| Rhinitis allergic | 4 (0.7%) | 0 |
| Sinus congestion | 4 (0.7%) | 3 (0.6%) |
| Dysphonia | 2 (0.4%) | 0 |
| Dyspnoea | 2 (0.4%) | 2 (0.4%) |
| Productive cough | 2 (0.4%) | 1 (0.2%) |
| Asthma | 1 (0.2%) | 3 (0.6%) |
| Catarrh | 1 (0.2%) | 0 |
| Dry throat | 1 (0.2%) | 0 |
| Dyspnoea exertional | 1 (0.2%) | 0 |
| Epistaxis | 1 (0.2%) | 0 |
| Interstitial lung disease | 1 (0.2%) | 0 |

APPENDIX 16-continued

Number of Subjects With Treatment-Emergent Adverse Events Through Week 56 by System Organ Class and Preferred Term; Safety Analysis Set (Study CNTO1959PSO3009)

| | Guselkumab 100 mg | Secukinumab 300 mg |
|---|---|---|
| Nasal cyst | 1 (0.2%) | 0 |
| Nasal polyps | 1 (0.2%) | 0 |
| Oropharyngeal discomfort | 1 (0.2%) | 0 |
| Pneumonia aspiration | 1 (0.2%) | 0 |
| Respiratory disorder | 1 (0.2%) | 0 |
| Sneezing | 1 (0.2%) | 0 |
| Upper respiratory tract congestion | 1 (0.2%) | 0 |
| Adenoidal hypertrophy | 0 | 1 (0.2%) |
| Asthmatic crisis | 0 | 1 (0.2%) |
| Bronchial hyperreactivity | 0 | 1 (0.2%) |
| Chronic obstructive pulmonary disease | 0 | 1 (0.2%) |
| Lower respiratory tract congestion | 0 | 1 (0.2%) |
| Nasal ulcer | 0 | 1 (0.2%) |
| Pulmonary embolism | 0 | 1 (0.2%) |
| Sleep apnoea syndrome | 0 | 1 (0.2%) |
| Throat irritation | 0 | 2 (0.4%) |
| General disorders and administration site conditions | 56 (10.5%) | 58 (11.4%) |
| Fatigue | 10 (1.9%) | 7 (1.4%) |
| Injection site erythema | 10 (1.9%) | 7 (1.4%) |
| Injection site haematoma | 6 (1.1%) | 5 (1.0%) |
| Injection site pain | 6 (1.1%) | 7 (1.4%) |
| Injection site pruritus | 5 (0.9%) | 0 |
| Non-cardiac chest pain | 5 (0.9%) | 6 (1.2%) |
| Pyrexia | 5 (0.9%) | 6 (1.2%) |
| Oedema peripheral | 4 (0.7%) | 4 (0.8%) |
| Influenza like illness | 3 (0.6%) | 5 (1.0%) |
| Injection site bruising | 3 (0.6%) | 2 (0.4%) |
| Injection site swelling | 3 (0.6%) | 1 (0.2%) |
| Adverse drug reaction | 2 (0.4%) | 0 |
| Asthenia | 2 (0.4%) | 2 (0.4%) |
| Cyst | 2 (0.4%) | 1 (0.2%) |
| Injection site induration | 2 (0.4%) | 0 |
| Calcinosis | 1 (0.2%) | 0 |
| Chest pain | 1 (0.2%) | 1 (0.2%) |
| Face oedema | 1 (0.2%) | 0 |
| General physical health deterioration | 1 (0.2%) | 0 |
| Generalised oedema | 1 (0.2%) | 0 |
| Hernia pain | 1 (0.2%) | 0 |
| Injection site extravasation | 1 (0.2%) | 0 |
| Injection site haemorrhage | 1 (0.2%) | 2 (0.4%) |
| Injection site oedema | 1 (0.2%) | 2 (0.4%) |
| Injection site rash | 1 (0.2%) | 0 |
| Malaise | 1 (0.2%) | 0 |
| Pain | 1 (0.2%) | 0 |
| Tenderness | 1 (0.2%) | 0 |
| Xerosis | 1 (0.2%) | 2 (0.4%) |
| Axillary pain | 0 | 1 (0.2%) |
| Chest discomfort | 0 | 1 (0.2%) |
| Discomfort | 0 | 2 (0.4%) |
| Exercise tolerance decreased | 0 | 1 (0.2%) |
| Feeling cold | 0 | 2 (0.4%) |
| Injection site inflammation | 0 | 1 (0.2%) |
| Injury associated with device | 0 | 1 (0.2%) |
| Nodule | 0 | 1 (0.2%) |
| Swelling | 0 | 1 (0.2%) |
| Vessel puncture site haemorrhage | 0 | 1 (0.2%) |
| Injury, poisoning and procedural complications | 56 (10.5%) | 54 (10.6%) |
| Laceration | 7 (1.3%) | 6 (1.2%) |
| Ligament sprain | 5 (0.9%) | 4 (0.8%) |
| Procedural pain | 4 (0.7%) | 1 (0.2%) |
| Arthropod sting | 3 (0.6%) | 0 |
| Contusion | 3 (0.6%) | 8 (1.6%) |
| Limb injury | 3 (0.6%) | 1 (0.2%) |
| Arthropod bite | 2 (0.4%) | 1 (0.2%) |
| Hand fracture | 2 (0.4%) | 1 (0.2%) |
| Joint dislocation | 2 (0.4%) | 0 |
| Ligament rupture | 2 (0.4%) | 1 (0.2%) |
| Meniscus injury | 2 (0.4%) | 1 (0.2%) |
| Muscle strain | 2 (0.4%) | 6 (1.2%) |
| Rib fracture | 2 (0.4%) | 2 (0.4%) |
| Tooth fracture | 2 (0.4%) | 1 (0.2%) |
| Tooth injury | 2 (0.4%) | 0 |
| Wound | 2 (0.4%) | 0 |
| Animal scratch | 1 (0.2%) | 0 |
| Arterial injury | 1 (0.2%) | 0 |
| Chest injury | 1 (0.2%) | 0 |
| Clavicle fracture | 1 (0.2%) | 0 |
| Concussion | 1 (0.2%) | 0 |
| Craniocerebral injury | 1 (0.2%) | 1 (0.2%) |
| Electrical burn | 1 (0.2%) | 0 |
| Foot fracture | 1 (0.2%) | 1 (0.2%) |
| Foreign body in eye | 1 (0.2%) | 0 |
| Joint injury | 1 (0.2%) | 1 (0.2%) |
| Overdose | 1 (0.2%) | 0 |
| Procedural hypertension | 1 (0.2%) | 0 |
| Radius fracture | 1 (0.2%) | 1 (0.2%) |
| Skin abrasion | 1 (0.2%) | 5 (1.0%) |
| Skull fracture | 1 (0.2%) | 0 |
| Spinal column injury | 1 (0.2%) | 0 |
| Thermal burn | 1 (0.2%) | 4 (0.8%) |
| Venomous sting | 1 (0.2%) | 0 |
| Bone contusion | 0 | 2 (0.4%) |
| Dental restoration failure | 0 | 1 (0.2%) |
| Ear abrasion | 0 | 1 (0.2%) |
| Epicondylitis | 0 | 3 (0.6%) |
| Eye contusion | 0 | 1 (0.2%) |
| Femoral neck fracture | 0 | 1 (0.2%) |
| Palate injury | 0 | 1 (0.2%) |
| Post procedural diarrhoea | 0 | 1 (0.2%) |
| Post-traumatic neck syndrome | 0 | 1 (0.2%) |
| Soft tissue injury | 0 | 2 (0.4%) |
| Tendon rupture | 0 | 2 (0.4%) |
| Upper limb fracture | 0 | 1 (0.2%) |
| Wrist fracture | 0 | 1 (0.2%) |
| Investigations | 37 (6.9%) | 32 (6.3%) |
| Alanine aminotransferase increased | 15 (2.8%) | 10 (2.0%) |
| Aspartate aminotransferase increased | 10 (1.9%) | 6 (1.2%) |
| Blood pressure increased | 6 (1.1%) | 4 (0.8%) |
| Blood bilirubin increased | 3 (0.6%) | 0 |
| Blood glucose increased | 2 (0.4%) | 1 (0.2%) |
| Electrocardiogram T wave amplitude decreased | 2 (0.4%) | 0 |
| Faecal calprotectin increased | 2 (0.4%) | 0 |
| Hepatic enzyme increased | 2 (0.4%) | 3 (0.6%) |
| Transaminases increased | 2 (0.4%) | 2 (0.4%) |
| Blood iron decreased | 1 (0.2%) | 0 |
| C-reactive protein increased | 1 (0.2%) | 0 |
| Electrocardiogram T wave inversion | 1 (0.2%) | 0 |
| Electrocardiogram repolarisation abnormality | 1 (0.2%) | 0 |
| Liver function test increased | 1 (0.2%) | 0 |
| Serum ferritin decreased | 1 (0.2%) | 0 |
| Weight increased | 1 (0.2%) | 1 (0.2%) |
| Blood alkaline phosphatase increased | 0 | 2 (0.4%) |
| Blood creatine phosphokinase increased | 0 | 1 (0.2%) |
| Blood creatinine increased | 0 | 1 (0.2%) |
| Blood pressure systolic increased | 0 | 1 (0.2%) |
| Blood triglycerides increased | 0 | 1 (0.2%) |
| Computerised tomogram coronary artery abnormal | 0 | 1 (0.2%) |
| Ejection fraction abnormal | 0 | 1 (0.2%) |
| Neutrophil count decreased | 0 | 2 (0.4%) |
| Occult blood | 0 | 1 (0.2%) |
| Platelet count decreased | 0 | 1 (0.2%) |
| Ultrasound liver abnormal | 0 | 1 (0.2%) |
| Weight decreased | 0 | 2 (0.4%) |
| White blood cell count decreased | 0 | 1 (0.2%) |
| Vascular disorders | 33 (6.2%) | 33 (6.5%) |

APPENDIX 16-continued

Number of Subjects With Treatment-Emergent Adverse Events Through Week 56 by System Organ Class and Preferred Term; Safety Analysis Set (Study CNTO1959PSO3009)

| | Guselkumab 100 mg | Secukinumab 300 mg |
|---|---|---|
| Hypertension | 22 (4.1%) | 22 (4.3%) |
| Hypertensive crisis | 2 (0.4%) | 0 |
| Peripheral arterial occlusive disease | 2 (0.4%) | 0 |
| Aortic aneurysm | 1 (0.2%) | 0 |
| Arteriosclerosis | 1 (0.2%) | 0 |
| Haematoma | 1 (0.2%) | 1 (0.2%) |
| Hot flush | 1 (0.2%) | 2 (0.4%) |
| Hypotension | 1 (0.2%) | 2 (0.4%) |
| Varicose vein | 1 (0.2%) | 0 |
| Vein rupture | 1 (0.2%) | 0 |
| Deep vein thrombosis | 0 | 1 (0.2%) |
| Diastolic hypertension | 0 | 1 (0.2%) |
| Flushing | 0 | 1 (0.2%) |
| Lymphoedema | 0 | 1 (0.2%) |
| Orthostatic hypotension | 0 | 1 (0.2%) |
| Peripheral vascular disorder | 0 | 1 (0.2%) |
| Phlebitis superficial | 0 | 1 (0.2%) |
| Neoplasms benign, malignant and unspecified (incl cysts and polyps) | 24 (4.5%) | 19 (3.7%) |
| Skin papilloma | 6 (1.1%) | 3 (0.6%) |
| Melanocytic naevus | 5 (0.9%) | 4 (0.8%) |
| Basal cell carcinoma | 3 (0.6%) | 2 (0.4%) |
| Squamous cell carcinoma of skin | 2 (0.4%) | 0 |
| Acrochordon | 1 (0.2%) | 0 |
| Anogenital warts | 1 (0.2%) | 0 |
| Bowen's disease | 1 (0.2%) | 0 |
| Colon adenoma | 1 (0.2%) | 1 (0.2%) |
| Dysplastic naevus | 1 (0.2%) | 2 (0.4%) |
| Fibroma | 1 (0.2%) | 0 |
| Invasive ductal breast carcinoma | 1 (0.2%) | 0 |
| Lipoma | 1 (0.2%) | 1 (0.2%) |
| Ductal adenocarcinoma of pancreas | 0 | 1 (0.2%) |
| Haemangioma | 0 | 1 (0.2%) |
| Kidney angiomyolipoma | 0 | 1 (0.2%) |
| Mycosis fungoides | 0 | 1 (0.2%) |
| Non-small cell lung cancer | 0 | 1 (0.2%) |
| Seborrhoeic keratosis | 0 | 2 (0.4%) |
| Uterine leiomyoma | 0 | 2 (0.4%) |
| Psychiatric disorders | 24 (4.5%) | 27 (5.3%) |
| Anxiety | 8 (1.5%) | 9 (1.8%) |
| Depression | 5 (0.9%) | 4 (0.8%) |
| Insomnia | 4 (0.7%) | 7 (1.4%) |
| Suicidal ideation | 3 (0.6%) | 3 (0.6%) |
| Alcoholism | 1 (0.2%) | 0 |
| Borderline personality disorder | 1 (0.2%) | 0 |
| Depressed mood | 1 (0.2%) | 1 (0.2%) |
| Grief reaction | 1 (0.2%) | 0 |
| Psychotic disorder | 1 (0.2%) | 0 |
| Restlessness | 1 (0.2%) | 0 |
| Sleep disorder | 1 (0.2%) | 0 |
| Stress | 1 (0.2%) | 2 (0.4%) |
| Adjustment disorder with depressed mood | 0 | 1 (0.2%) |
| Intentional self-injury | 0 | 1 (0.2%) |
| Irritability | 0 | 1 (0.2%) |
| Mental disorder | 0 | 1 (0.2%) |
| Mixed anxiety and depressive disorder | 0 | 1 (0.2%) |
| Panic attack | 0 | 1 (0.2%) |
| Seasonal affective disorder | 0 | 1 (0.2%) |
| Suicide attempt | 0 | 1 (0.2%) |
| Metabolism and nutrition disorders | 22 (4.1%) | 16 (3.1%) |
| Hyperglycaemia | 9 (1.7%) | 1 (0.2%) |
| Hyperlipidaemia | 3 (0.6%) | 0 |
| Abnormal loss of weight | 1 (0.2%) | 0 |
| Decreased appetite | 1 (0.2%) | 2 (0.4%) |
| Diabetes mellitus | 1 (0.2%) | 3 (0.6%) |
| Gout | 1 (0.2%) | 2 (0.4%) |
| Haemochromatosis | 1 (0.2%) | 0 |
| Hypercholesterolaemia | 1 (0.2%) | 0 |
| Hyperkalaemia | 1 (0.2%) | 1 (0.2%) |
| Hypertriglyceridaemia | 1 (0.2%) | 0 |
| Hyperuricaemia | 1 (0.2%) | 0 |
| Hypokalaemia | 1 (0.2%) | 2 (0.4%) |
| Increased appetite | 1 (0.2%) | 1 (0.2%) |
| Overweight | 1 (0.2%) | 0 |
| Type 2 diabetes mellitus | 1 (0.2%) | 2 (0.4%) |
| Dehydration | 0 | 1 (0.2%) |
| Diabetes mellitus inadequate control | 0 | 1 (0.2%) |
| Glucose tolerance impaired | 0 | 1 (0.2%) |
| Hyperhomocysteinaemia | 0 | 1 (0.2%) |
| Hypoglycaemia | 0 | 1 (0.2%) |
| Hyponatraemia | 0 | 1 (0.2%) |
| Polydipsia | 0 | 1 (0.2%) |
| Type 1 diabetes mellitus | 0 | 1 (0.2%) |
| Vitamin D deficiency | 0 | 1 (0.2%) |
| Cardiac disorders | 20 (3.7%) | 11 (2.2%) |
| Tachycardia | 5 (0.9%) | 1 (0.2%) |
| Atrial fibrillation | 4 (0.7%) | 2 (0.4%) |
| Bundle branch block left | 3 (0.6%) | 0 |
| Palpitations | 2 (0.4%) | 0 |
| Aortic valve stenosis | 1 (0.2%) | 0 |
| Bundle branch block right | 1 (0.2%) | 0 |
| Coronary artery occlusion | 1 (0.2%) | 0 |
| Defect conduction intraventricular | 1 (0.2%) | 0 |
| Sinus bradycardia | 1 (0.2%) | 0 |
| Supraventricular tachycardia | 1 (0.2%) | 0 |
| Ventricular extrasystoles | 1 (0.2%) | 0 |
| Wolff-Parkinson-White syndrome | 1 (0.2%) | 0 |
| Atrial thrombosis | 0 | 1 (0.2%) |
| Atrioventricular block complete | 0 | 1 (0.2%) |
| Atrioventricular block first degree | 0 | 2 (0.4%) |
| Cardiac disorder | 0 | 1 (0.2%) |
| Cardiac failure congestive | 0 | 1 (0.2%) |
| Coronary artery disease | 0 | 1 (0.2%) |
| Extrasystoles | 0 | 1 (0.2%) |
| Left ventricular dilatation | 0 | 1 (0.2%) |
| Sinus tachycardia | 0 | 2 (0.4%) |
| Eye disorders | 18 (3.4%) | 17 (3.3%) |
| Cataract | 5 (0.9%) | 2 (0.4%) |
| Conjunctivitis allergic | 3 (0.6%) | 3 (0.6%) |
| Dry eye | 2 (0.4%) | 2 (0.4%) |
| Blepharitis | 1 (0.2%) | 4 (0.8%) |
| Cataract subcapsular | 1 (0.2%) | 0 |
| Chalazion | 1 (0.2%) | 0 |
| Conjunctival haemorrhage | 1 (0.2%) | 1 (0.2%) |
| Conjunctival hyperaemia | 1 (0.2%) | 0 |
| Diabetic retinopathy | 1 (0.2%) | 0 |
| Episcleritis | 1 (0.2%) | 0 |
| Eye oedema | 1 (0.2%) | 0 |
| Eye swelling | 1 (0.2%) | 0 |
| Glaucoma | 1 (0.2%) | 0 |
| Macular fibrosis | 1 (0.2%) | 0 |
| Ocular hyperaemia | 1 (0.2%) | 0 |
| Ocular hypertension | 1 (0.2%) | 0 |
| Retinal degeneration | 1 (0.2%) | 0 |
| Vitreous detachment | 1 (0.2%) | 0 |
| Blepharospasm | 0 | 1 (0.2%) |
| Eczema eyelids | 0 | 1 (0.2%) |
| Eye discharge | 0 | 1 (0.2%) |
| Myopia | 0 | 1 (0.2%) |
| Pupils unequal | 0 | 1 (0.2%) |
| Visual acuity reduced | 0 | 2 (0.4%) |
| Ear and labyrinth disorders | 13 (2.4%) | 13 (2.5%) |
| Vertigo | 7 (1.3%) | 6 (1.2%) |
| Ear pain | 3 (0.6%) | 3 (0.6%) |
| Cerumen impaction | 1 (0.2%) | 0 |
| Ear canal erythema | 1 (0.2%) | 0 |
| Ear discomfort | 1 (0.2%) | 0 |
| Ear pruritus | 1 (0.2%) | 0 |
| Tinnitus | 1 (0.2%) | 1 (0.2%) |
| Deafness unilateral | 0 | 1 (0.2%) |
| Ear canal stenosis | 0 | 1 (0.2%) |

APPENDIX 16-continued

Number of Subjects With Treatment-Emergent Adverse Events Through Week 56 by System Organ Class and Preferred Term; Safety Analysis Set (Study CNTO1959PSO3009)

|  | Guselkumab 100 mg | Secukinumab 300 mg |
|---|---|---|
| Hypoacusis | 0 | 1 (0.2%) |
| Middle ear effusion | 0 | 1 (0.2%) |
| Blood and lymphatic system disorders | 10 (1.9%) | 9 (1.8%) |
| Lymphadenopathy | 3 (0.6%) | 2 (0.4%) |
| Anaemia | 2 (0.4%) | 0 |
| Leukocytosis | 2 (0.4%) | 0 |
| Thrombocytopenia | 2 (0.4%) | 0 |
| Neutrophilia | 1 (0.2%) | 0 |
| Pancytopenia | 1 (0.2%) | 0 |
| Erythropenia | 0 | 1 (0.2%) |
| Leukopenia | 0 | 1 (0.2%) |
| Lymphopenia | 0 | 2 (0.4%) |
| Neutropenia | 0 | 4 (0.8%) |
| Reproductive system and breast disorders | 9 (1.7%) | 12 (2.3%) |
| Dysmenorrhoea | 2 (0.4%) | 1 (0.2%) |
| Bartholin's cyst | 1 (0.2%) | 0 |
| Benign prostatic hyperplasia | 1 (0.2%) | 2 (0.4%) |
| Breast cyst | 1 (0.2%) | 0 |
| Breast mass | 1 (0.2%) | 1 (0.2%) |
| Endometriosis | 1 (0.2%) | 0 |
| Erectile dysfunction | 1 (0.2%) | 0 |
| Varicocele | 1 (0.2%) | 0 |
| Acquired phimosis | 0 | 1 (0.2%) |
| Endometrial disorder | 0 | 2 (0.4%) |
| Prostatomegaly | 0 | 1 (0.2%) |
| Vulvovaginal dryness | 0 | 1 (0.2%) |
| Vulvovaginal inflammation | 0 | 1 (0.2%) |
| Vulvovaginal pruritus | 0 | 2 (0.4%) |
| Hepatobiliary disorders | 7 (1.3%) | 10 (2.0%) |
| Hepatic steatosis | 3 (0.6%) | 5 (1.0%) |
| Biliary colic | 2 (0.4%) | 0 |
| Cholelithiasis | 2 (0.4%) | 3 (0.6%) |
| Cholecystitis acute | 1 (0.2%) | 0 |
| Cholangitis | 0 | 1 (0.2%) |
| Cholecystitis | 0 | 1 (0.2%) |
| Drug-induced liver injury | 0 | 1 (0.2%) |
| Gallbladder polyp | 0 | 1 (0.2%) |
| Hepatomegaly | 0 | 1 (0.2%) |
| Jaundice | 0 | 1 (0.2%) |
| Immune system disorders | 6 (1.1%) | 9 (1.8%) |
| Seasonal allergy | 4 (0.7%) | 6 (1.2%) |
| Allergy to arthropod bite | 1 (0.2%) | 2 (0.4%) |
| Drug hypersensitivity | 1 (0.2%) | 0 |
| Anaphylactoid reaction | 0 | 1 (0.2%) |
| Renal and urinary disorders | 6 (1.1%) | 8 (1.6%) |
| Nephrolithiasis | 4 (0.7%) | 2 (0.4%) |
| Acute kidney injury | 1 (0.2%) | 1 (0.2%) |
| Haematuria | 1 (0.2%) | 0 |
| Cystitis noninfective | 0 | 1 (0.2%) |
| Glycosuria | 0 | 1 (0.2%) |
| Incontinence | 0 | 1 (0.2%) |
| Ketonuria | 0 | 1 (0.2%) |
| Leukocyturia | 0 | 1 (0.2%) |
| Micturition urgency | 0 | 1 (0.2%) |
| Pollakiuria | 0 | 2 (0.4%) |
| Congenital, familial and genetic disorders | 2 (0.4%) | 0 |
| Dermoid cyst | 1 (0.2%) | 0 |
| Hydrocele | 1 (0.2%) | 0 |
| Endocrine disorders | 2 (0.4%) | 3 (0.6%) |
| Hyperthyroidism | 1 (0.2%) | 1 (0.2%) |
| Hypothyroidism | 1 (0.2%) | 0 |
| Androgen deficiency | 0 | 1 (0.2%) |
| Autoimmune thyroiditis | 0 | 1 (0.2%) |
| Pregnancy, puerperium and perinatal conditions | 1 (0.2%) | 3 (0.6%) |
| Pregnancy | 1 (0.2%) | 2 (0.4%) |
| Unintended pregnancy | 0 | 1 (0.2%) |
| Social circumstances | 1 (0.2%) | 2 (0.4%) |
| Pregnancy of partner | 1 (0.2%) | 2 (0.4%) |
| Product issues | 0 | 3 (0.6%) |
| Device dislocation | 0 | 1 (0.2%) |
| Device loosening | 0 | 1 (0.2%) |
| Device material opacification | 0 | 1 (0.2%) |
| Surgical and medical procedures | 0 | 1 (0.2%) |
| Finger amputation | 0 | 1 (0.2%) |

Key: AE = adverse event, Avg = average.

Note:
Subjects are counted only once for any given event, regardless of the number of times they actually experienced the event.
Adverse events are coded using MedDRA Version 21.0.
[TSFAE01.RTF] [CNTO1959\PSO3009\DBR_WEEK_056\RE_WEEK_056_CSR\PROD\TSFAE01A.SAS] 23OCT2018, 12:58

APPENDIX 17

Number of Subjects With Treatment-Emergent Serious Adverse Events Through Week 56 by System Organ Class and Preferred Term; Safety Analysis Set (Study CNTO1959PSO3009)

|  | Guselkumab 100 mg | Secukinumab 300 mg |
|---|---|---|
| Analysis set: Safety analysis set | 534 | 511 |
| Avg duration of follow-up (weeks) | 54.90 | 53.67 |
| Avg exposure (number of administrations) | 14.65 | 14.41 |
| Subjects with 1 or more SAEs | 33 (6.2%) | 37 (7.2%) |
| System organ class Preferred term | | |
| Infections and infestations | 4 (0.7%) | 5 (1.0%) |
| Appendicitis | 1 (0.2%) | 0 |
| Cellulitis | 1 (0.2%) | 1 (0.2%) |
| Labyrinthitis | 1 (0.2%) | 0 |
| Pneumonia | 1 (0.2%) | 1 (0.2%) |
| Abscess limb | 0 | 1 (0.2%) |
| Neuroborreliosis | 0 | 1 (0.2%) |
| Pyelonephritis | 0 | 1 (0.2%) |
| Injury, poisoning and procedural complications | 4 (0.7%) | 4 (0.8%) |
| Clavicle fracture | 1 (0.2%) | 0 |
| Ligament rupture | 1 (0.2%) | 0 |
| Meniscus injury | 1 (0.2%) | 0 |
| Skull fracture | 1 (0.2%) | 0 |

APPENDIX 17-continued

Number of Subjects With Treatment-Emergent Serious Adverse Events Through Week 56 by System Organ Class and Preferred Term; Safety Analysis Set (Study CNTO1959PSO3009)

|  | Guselkumab 100 mg | Secukinumab 300 mg |
|---|---|---|
| Femoral neck fracture | 0 | 1 (0.2%) |
| Foot fracture | 0 | 1 (0.2%) |
| Tendon rupture | 0 | 1 (0.2%) |
| Upper limb fracture | 0 | 1 (0.2%) |
| Respiratory, thoracic and mediastinal disorders | 4 (0.7%) | 1 (0.2%) |
| Interstitial lung disease | 1 (0.2%) | 0 |
| Nasal cyst | 1 (0.2%) | 0 |
| Nasal polyps | 1 (0.2%) | 0 |
| Pneumonia aspiration | 1 (0.2%) | 0 |
| Pulmonary embolism | 0 | 1 (0.2%) |
| Cardiac disorders | 3 (0.6%) | 3 (0.6%) |
| Atrial fibrillation | 1 (0.2%) | 1 (0.2%) |
| Coronary artery occlusion | 1 (0.2%) | 0 |
| Wolff-Parkinson-White syndrome | 1 (0.2%) | 0 |
| Atrioventricular block complete | 0 | 1 (0.2%) |
| Cardiac failure congestive | 0 | 1 (0.2%) |
| Gastrointestinal disorders | 3 (0.6%) | 2 (0.4%) |
| Constipation | 1 (0.2%) | 0 |
| Leukoplakia oral | 1 (0.2%) | 0 |
| Umbilical hernia | 1 (0.2%) | 0 |
| Crohn's disease | 0 | 1 (0.2%) |
| Haemorrhoids | 0 | 1 (0.2%) |
| Skin and subcutaneous tissue disorders | 3 (0.6%) | 1 (0.2%) |
| Chronic cutaneous lupus erythematosus | 1 (0.2%) | 0 |
| Drug eruption | 1 (0.2%) | 0 |
| Rash morbilliform | 1 (0.2%) | 0 |
| Psoriasis | 0 | 1 (0.2%) |
| General disorders and administration site conditions | 2 (0.4%) | 3 (0.6%) |
| General physical health deterioration | 1 (0.2%) | 0 |
| Non-cardiac chest pain | 1 (0.2%) | 1 (0.2%) |
| Chest pain | 0 | 1 (0.2%) |
| Exercise tolerance decreased | 0 | 1 (0.2%) |
| Hepatobiliary disorders | 2 (0.4%) | 3 (0.6%) |
| Cholecystitis acute | 1 (0.2%) | 0 |
| Cholelithiasis | 1 (0.2%) | 1 (0.2%) |
| Cholecystitis | 0 | 1 (0.2%) |
| Drug-induced liver injury | 0 | 1 (0.2%) |
| Musculoskeletal and connective tissue disorders | 2 (0.4%) | 5 (1.0%) |
| Osteoarthritis | 1 (0.2%) | 1 (0.2%) |
| Rotator cuff syndrome | 1 (0.2%) | 0 |
| Intervertebral disc protrusion | 0 | 2 (0.4%) |
| Spinal column stenosis | 0 | 1 (0.2%) |
| Spinal osteoarthritis | 0 | 1 (0.2%) |
| Reproductive system and breast disorders | 2 (0.4%) | 2 (0.4%) |
| Bartholin's cyst | 1 (0.2%) | 0 |
| Endometriosis | 1 (0.2%) | 0 |
| Benign prostatic hyperplasia | 0 | 1 (0.2%) |
| Prostatomegaly | 0 | 1 (0.2%) |
| Vascular disorders | 2 (0.4%) | 1 (0.2%) |
| Arteriosclerosis | 1 (0.2%) | 0 |
| Hypotension | 1 (0.2%) | 0 |
| Deep vein thrombosis | 0 | 1 (0.2%) |
| Eye disorders | 1 (0.2%) | 0 |
| Macular fibrosis | 1 (0.2%) | 0 |
| Investigations | 1 (0.2%) | 0 |
| Electrocardiogram repolarisation abnormality | 1 (0.2%) | 0 |
| Neoplasms benign, malignant and unspecified (incl cysts and polyps) | 1 (0.2%) | 1 (0.2%) |
| Invasive ductal breast carcinoma | 1 (0.2%) | 0 |
| Non-small cell lung cancer | 0 | 1 (0.2%) |
| Nervous system disorders | 1 (0.2%) | 1 (0.2%) |
| Headache | 1 (0.2%) | 0 |
| Cerebrovascular accident | 0 | 1 (0.2%) |
| Syncope | 0 | 1 (0.2%) |
| Psychiatric disorders | 1 (0.2%) | 2 (0.4%) |
| Anxiety | 1 (0.2%) | 1 (0.2%) |
| Depression | 0 | 1 (0.2%) |
| Mixed anxiety and depressive disorder | 0 | 1 (0.2%) |
| Renal and urinary disorders | 1 (0.2%) | 2 (0.4%) |
| Acute kidney injury | 1 (0.2%) | 1 (0.2%) |
| Nephrolithiasis | 0 | 1 (0.2%) |

APPENDIX 17-continued

Number of Subjects With Treatment-Emergent Serious Adverse Events Through Week 56 by System Organ Class and Preferred Term; Safety Analysis Set (Study CNTO1959PSO3009)

|  | Guselkumab 100 mg | Secukinumab 300 mg |
|---|---|---|
| Immune system disorders | 0 | 1 (0.2%) |
| Anaphylactoid reaction | 0 | 1 (0.2%) |
| Surgical and medical procedures | 0 | 1 (0.2%) |
| Finger amputation | 0 | 1 (0.2%) |

Key: AE = adverse event, Avg = average.

Note:

Subjects are counted only once for any given event, regardless of the number of times they actually experienced the event. Adverse events are coded using MedDRA Version 21.0.

[TSFAE04.RTF]  [CNTO1959\PSO3009\DBR_WEEK_056\RE_WEEK_056_CSR\PROD\TSFAE04.SAS] 23OCT2018, 12:58

APPENDIX 18

Number of Subjects With Treatment-Emergent Adverse Events Leading to Discontinuation of Study Agent Through Week 44 by System Organ Class and Preferred Term; Safety Analysis Set (Study CNTO1959PSO3009)

|  | Guselkumab 100 mg | Secukinumab 300 mg |
|---|---|---|
| Analysis set: Safety analysis set | 534 | 511 |
| Avg duration of follow-up (weeks) | 54.90 | 53.67 |
| Avg exposure (number of administrations) | 14.65 | 14.41 |
| Subjects with 1 or more AEs leading to discontinuation of study agent | 10 (1.9%) | 12 (2.3%) |
| System organ class |  |  |
| Preferred term |  |  |
| Neoplasms benign, malignant and unspecified (incl cysts and polyps) | 4 (0.7%) | 2 (0.4%) |
| Squamous cell carcinoma of skin | 2 (0.4%) | 0 |
| Bowen's disease | 1 (0.2%) | 0 |
| Invasive ductal breast carcinoma | 1 (0.2%) | 0 |
| Mycosis fungoides | 0 | 1 (0.2%) |
| Non-small cell lung cancer | 0 | 1 (0.2%) |
| Skin and subcutaneous tissue disorders | 3 (0.6%) | 2 (0.4%) |
| Drug eruption | 1 (0.2%) | 0 |
| Psoriasis | 1 (0.2%) | 1 (0.2%) |
| Rash morbilliform | 1 (0.2%) | 0 |
| Rash maculo-papular | 0 | 1 (0.2%) |
| Gastrointestinal disorders | 1 (0.2%) | 2 (0.4%) |
| Colitis microscopic | 1 (0.2%) | 0 |
| Crohn's disease | 0 | 1 (0.2%) |
| Inflammatory bowel disease | 0 | 1 (0.2%) |
| Investigations | 1 (0.2%) | 1 (0.2%) |
| Transaminases increased | 1 (0.2%) | 0 |
| Platelet count decreased | 0 | 1 (0.2%) |
| Pregnancy, puerperium and perinatal conditions | 1 (0.2%) | 1 (0.2%) |
| Pregnancy | 1 (0.2%) | 1 (0.2%) |
| Hepatobiliary disorders | 0 | 1 (0.2%) |
| Drug-induced liver injury | 0 | 1 (0.2%) |
| Infections and infestations | 0 | 1 (0.2%) |
| Abscess limb | 0 | 1 (0.2%) |
| Nervous system disorders | 0 | 1 (0.2%) |
| Cerebrovascular accident | 0 | 1 (0.2%) |
| Vascular disorders | 0 | 1 (0.2%) |
| Deep vein thrombosis | 0 | 1 (0.2%) |

Key: AE = adverse event, Avg = average.

Note:

Subjects are counted only once for any given event, regardless of the number of times they actually experienced the event. Adverse events are coded using MedDRA Version 21.0.

[TSFAE05.RTF]  [CNTO1959\PSO3009\DBR_WEEK_056\RE_WEEK_056_CSR\PROD\TSFAE05.SAS] 23OCT2018, 12:58

APPENDIX 19

Number of Subjects With Treatment-Emergent Infections Through Week 56 by System Organ Class and Preferred Term; Safety Analysis Set (Study CNTO1959PSO3009)

| | Guselkumab 100 mg | Secukinumab 300 mg |
|---|---|---|
| Analysis set: Safety analysis set | 534 | 511 |
| Avg duration of follow-up (weeks) | 54.90 | 53.67 |
| Avg exposure (number of administrations) | 14.65 | 14.41 |
| Subjects with 1 or more infections | 313 (58.6%) | 331 (64.8%) |
| System organ class | | |
| Preferred term | | |
| Infections and infestations | 308 (57.7%) | 323 (63.2%) |
| Nasopharyngitis | 117 (21.9%) | 125 (24.5%) |
| Upper respiratory tract infection | 83 (15.5%) | 92 (18.0%) |
| Pharyngitis | 24 (4.5%) | 22 (4.3%) |
| Influenza | 20 (3.7%) | 13 (2.5%) |
| Bronchitis | 17 (3.2%) | 15 (2.9%) |
| Oral herpes | 11 (2.1%) | 14 (2.7%) |
| Urinary tract infection | 11 (2.1%) | 11 (2.2%) |
| Gastroenteritis | 10 (1.9%) | 9 (1.8%) |
| Sinusitis | 10 (1.9%) | 12 (2.3%) |
| Gastroenteritis viral | 9 (1.7%) | 8 (1.6%) |
| Viral upper respiratory tract infection | 9 (1.7%) | 8 (1.6%) |
| Folliculitis | 8 (1.5%) | 9 (1.8%) |
| Rhinitis | 8 (1.5%) | 13 (2.5%) |
| Tonsillitis | 7 (1.3%) | 15 (2.9%) |
| Tinea pedis | 6 (1.1%) | 16 (3.1%) |
| Gastrointestinal infection | 5 (0.9%) | 0 |
| Oral candidiasis | 5 (0.9%) | 11 (2.2%) |
| Tooth abscess | 5 (0.9%) | 3 (0.6%) |
| Tooth infection | 5 (0.9%) | 2 (0.4%) |
| Vulvovaginal candidiasis | 5 (0.9%) | 13 (2.5%) |
| Acute sinusitis | 4 (0.7%) | 0 |
| Cellulitis | 4 (0.7%) | 3 (0.6%) |
| Conjunctivitis | 4 (0.7%) | 16 (3.1%) |
| Respiratory tract infection | 4 (0.7%) | 2 (0.4%) |
| Tinea versicolour | 4 (0.7%) | 5 (1.0%) |
| Gastrointestinal viral infection | 3 (0.6%) | 1 (0.2%) |
| Periodontitis | 3 (0.6%) | 4 (0.8%) |
| Pneumonia | 3 (0.6%) | 6 (1.2%) |
| Cystitis | 2 (0.4%) | 2 (0.4%) |
| Ear infection | 2 (0.4%) | 5 (1.0%) |
| Helicobacter gastritis | 2 (0.4%) | 0 |
| Laryngitis | 2 (0.4%) | 2 (0.4%) |
| Localised infection | 2 (0.4%) | 1 (0.2%) |
| Otitis media | 2 (0.4%) | 6 (1.2%) |
| Postoperative wound infection | 2 (0.4%) | 0 |
| Skin candida | 2 (0.4%) | 3 (0.6%) |
| Tinea cruris | 2 (0.4%) | 4 (0.8%) |
| Wound infection | 2 (0.4%) | 1 (0.2%) |
| Anal abscess | 1 (0.2%) | 0 |
| Anal fistula infection | 1 (0.2%) | 0 |
| Appendicitis | 1 (0.2%) | 0 |
| Arthritis infective | 1 (0.2%) | 0 |
| Bacterial rhinitis | 1 (0.2%) | 0 |
| Bacterial vulvovaginitis | 1 (0.2%) | 0 |
| Candida infection | 1 (0.2%) | 0 |
| Conjunctivitis bacterial | 1 (0.2%) | 0 |
| Dermatitis infected | 1 (0.2%) | 2 (0.4%) |
| Dermo-hypodermitis | 1 (0.2%) | 0 |
| Diverticulitis | 1 (0.2%) | 2 (0.4%) |
| Enterobiasis | 1 (0.2%) | 0 |
| Erysipelas | 1 (0.2%) | 0 |
| Furuncle | 1 (0.2%) | 2 (0.4%) |
| Gangrene | 1 (0.2%) | 0 |
| Gastroenteritis yersinia | 1 (0.2%) | 0 |
| Genital herpes | 1 (0.2%) | 3 (0.6%) |
| Gingivitis | 1 (0.2%) | 2 (0.4%) |
| Hordeolum | 1 (0.2%) | 8 (1.6%) |
| Impetigo | 1 (0.2%) | 4 (0.8%) |
| Labyrinthitis | 1 (0.2%) | 0 |
| Mastitis | 1 (0.2%) | 0 |
| Nasal herpes | 1 (0.2%) | 1 (0.2%) |
| Ophthalmic herpes zoster | 1 (0.2%) | 0 |
| Paronychia | 1 (0.2%) | 2 (0.4%) |
| Peritonsillar abscess | 1 (0.2%) | 0 |
| Pyoderma | 1 (0.2%) | 0 |
| Salmonellosis | 1 (0.2%) | 0 |
| Sepsis | 1 (0.2%) | 0 |

APPENDIX 19-continued

Number of Subjects With Treatment-Emergent Infections Through Week 56 by System Organ Class and Preferred Term; Safety Analysis Set (Study CNTO1959PSO3009)

|  | Guselkumab 100 mg | Secukinumab 300 mg |
|---|---|---|
| Skin bacterial infection | 1 (0.2%) | 0 |
| Upper respiratory tract infection bacterial | 1 (0.2%) | 0 |
| Urinary tract infection bacterial | 1 (0.2%) | 0 |
| Viral pharyngitis | 1 (0.2%) | 0 |
| Abscess | 0 | 1 (0.2%) |
| Abscess limb | 0 | 1 (0.2%) |
| Acarodermatitis | 0 | 2 (0.4%) |
| Angular cheilitis | 0 | 2 (0.4%) |
| Application site cellulitis | 0 | 1 (0.2%) |
| Bacterial vaginosis | 0 | 1 (0.2%) |
| Balanitis candida | 0 | 1 (0.2%) |
| Blister infected | 0 | 1 (0.2%) |
| Body tinea | 0 | 2 (0.4%) |
| Bullous impetigo | 0 | 1 (0.2%) |
| Eczema impetiginous | 0 | 1 (0.2%) |
| Eczema infected | 0 | 2 (0.4%) |
| Groin abscess | 0 | 1 (0.2%) |
| Helicobacter infection | 0 | 1 (0.2%) |
| Herpes simplex | 0 | 1 (0.2%) |
| Herpes zoster | 0 | 4 (0.8%) |
| Neuroborreliosis | 0 | 1 (0.2%) |
| Onychomycosis | 0 | 1 (0.2%) |
| Otitis externa | 0 | 3 (0.6%) |
| Otitis media acute | 0 | 1 (0.2%) |
| Perianal streptococcal infection | 0 | 1 (0.2%) |
| Peritonsillitis | 0 | 1 (0.2%) |
| Pharyngitis streptococcal | 0 | 4 (0.8%) |
| Pharyngotonsillitis | 0 | 1 (0.2%) |
| Pulpitis dental | 0 | 1 (0.2%) |
| Pyelonephritis | 0 | 1 (0.2%) |
| Respiratory syncytial virus infection | 0 | 1 (0.2%) |
| Respiratory tract infection viral | 0 | 1 (0.2%) |
| Soft tissue infection | 0 | 1 (0.2%) |
| Staphylococcal skin infection | 0 | 3 (0.6%) |
| Subcutaneous abscess | 0 | 2 (0.4%) |
| Tracheobronchitis | 0 | 1 (0.2%) |
| Vaginal infection | 0 | 2 (0.4%) |
| Vulvovaginal mycotic infection | 0 | 2 (0.4%) |
| Respiratory, thoracic and mediastinal disorders | 12 (2.2%) | 11 (2.2%) |
| Cough | 5 (0.9%) | 1 (0.2%) |
| Oropharyngeal pain | 3 (0.6%) | 3 (0.6%) |
| Rhinorrhoea | 2 (0.4%) | 5 (1.0%) |
| Nasal congestion | 1 (0.2%) | 0 |
| Pneumonia aspiration | 1 (0.2%) | 0 |
| Respiratory disorder | 1 (0.2%) | 0 |
| Nasal ulcer | 0 | 1 (0.2%) |
| Sinus congestion | 0 | 1 (0.2%) |
| Gastrointestinal disorders | 7 (1.3%) | 3 (0.6%) |
| Diarrhoea | 3 (0.6%) | 0 |
| Enteritis | 3 (0.6%) | 0 |
| Dental caries | 1 (0.2%) | 0 |
| Aphthous ulcer | 0 | 2 (0.4%) |
| Apical granuloma | 0 | 1 (0.2%) |
| General disorders and administration site conditions | 5 (0.9%) | 8 (1.6%) |
| Influenza like illness | 3 (0.6%) | 5 (1.0%) |
| Pyrexia | 2 (0.4%) | 2 (0.4%) |
| Nodule | 0 | 1 (0.2%) |
| Neoplasms benign, malignant and unspecified (incl cysts and polyps) | 4 (0.7%) | 2 (0.4%) |
| Skin papilloma | 3 (0.6%) | 2 (0.4%) |
| Anogenital warts | 1 (0.2%) | 0 |
| Skin and subcutaneous tissue disorders | 4 (0.7%) | 10 (2.0%) |
| Acne | 1 (0.2%) | 0 |
| Intertrigo | 1 (0.2%) | 7 (1.4%) |
| Onycholysis | 1 (0.2%) | 0 |
| Skin ulcer | 1 (0.2%) | 1 (0.2%) |
| Dermal cyst | 0 | 1 (0.2%) |
| Psoriasis | 0 | 1 (0.2%) |
| Congenital, familial and genetic disorders | 1 (0.2%) | 0 |
| Dermoid cyst | 1 (0.2%) | 0 |
| Reproductive system and breast disorders | 1 (0.2%) | 0 |
| Bartholin's cyst | 1 (0.2%) | 0 |
| Eye disorders | 0 | 2 (0.4%) |
| Blepharitis | 0 | 2 (0.4%) |

APPENDIX 19-continued

Number of Subjects With Treatment-Emergent Infections Through Week 56 by System Organ Class and Preferred Term; Safety Analysis Set (Study CNTO1959PSO3009)

|  | Guselkumab 100 mg | Secukinumab 300 mg |
|---|---|---|
| Nervous system disorders | 0 | 1 (0.2%) |
| Post herpetic neuralgia | 0 | 1 (0.2%) |
| Renal and urinary disorders | 0 | 1 (0.2%) |
| Cystitis noninfective | 0 | 1 (0.2%) |
| Vascular disorders | 0 | 1 (0.2%) |
| Phlebitis superficial | 0 | 1 (0.2%) |

Key: Avg = average.
Note:
Subjects are counted only once for any given event, regardless of the number of times they actually experienced the event. Adverse events are coded using MedDRA Version 21.0.
[TSFINFE01.RTF]　　　　　　　　　[CNTO1959\PSO3009\DBR_WEEK_056\RE_WEEK_056_CSR\PROD\TSFINFE01.SAS] 23OCT2018, 12:59

APPENDIX 20

Number of Subjects With Treatment-Emergent Infections Requiring Oral or Parenteral Antimicrobial Treatment Through Week 56 by System Organ Class and Preferred Term; Safety Analysis Set (Study CNTO1959PSO3009)

|  | Guselkumab 100 mg | Secukinumab 300 mg |
|---|---|---|
| Analysis set: Safety analysis set | 534 | 511 |
| Avg duration of follow-up (weeks) | 54.90 | 53.67 |
| Avg exposure (number of administrations) | 14.65 | 14.41 |
| Subjects with 1 or more infections requiring treatment | 118 (22.1%) | 147 (28.8%) |
| System organ class Preferred term |  |  |
| Infections and infestations | 116 (21.7%) | 139 (27.2%) |
| Upper respiratory tract infection | 19 (3.6%) | 28 (5.5%) |
| Bronchitis | 14 (2.6%) | 12 (2.3%) |
| Pharyngitis | 13 (2.4%) | 10 (2.0%) |
| Nasopharyngitis | 11 (2.1%) | 12 (2.3%) |
| Urinary tract infection | 9 (1.7%) | 9 (1.8%) |
| Tonsillitis | 5 (0.9%) | 13 (2.5%) |
| Cellulitis | 4 (0.7%) | 3 (0.6%) |
| Sinusitis | 4 (0.7%) | 4 (0.8%) |
| Tooth abscess | 4 (0.7%) | 3 (0.6%) |
| Tooth infection | 4 (0.7%) | 1 (0.2%) |
| Acute sinusitis | 3 (0.6%) | 0 |
| Influenza | 3 (0.6%) | 2 (0.4%) |
| Pneumonia | 3 (0.6%) | 6 (1.2%) |
| Respiratory tract infection | 3 (0.6%) | 0 |
| Viral upper respiratory tract infection | 3 (0.6%) | 1 (0.2%) |
| Folliculitis | 2 (0.4%) | 3 (0.6%) |
| Gastroenteritis | 2 (0.4%) | 0 |
| Localised infection | 2 (0.4%) | 1 (0.2%) |
| Periodontitis | 2 (0.4%) | 2 (0.4%) |
| Postoperative wound infection | 2 (0.4%) | 0 |
| Wound infection | 2 (0.4%) | 0 |
| Arthritis infective | 1 (0.2%) | 0 |
| Bacterial rhinitis | 1 (0.2%) | 0 |
| Bacterial vulvovaginitis | 1 (0.2%) | 0 |
| Conjunctivitis bacterial | 1 (0.2%) | 0 |
| Cystitis | 1 (0.2%) | 2 (0.4%) |
| Dermo-hypodermitis | 1 (0.2%) | 0 |
| Diverticulitis | 1 (0.2%) | 2 (0.4%) |
| Ear infection | 1 (0.2%) | 4 (0.8%) |
| Erysipelas | 1 (0.2%) | 0 |
| Gastroenteritis yersinia | 1 (0.2%) | 0 |
| Gingivitis | 1 (0.2%) | 2 (0.4%) |
| Helicobacter gastritis | 1 (0.2%) | 0 |
| Hordeolum | 1 (0.2%) | 2 (0.4%) |
| Impetigo | 1 (0.2%) | 2 (0.4%) |
| Laryngitis | 1 (0.2%) | 1 (0.2%) |
| Mastitis | 1 (0.2%) | 0 |
| Ophthalmic herpes zoster | 1 (0.2%) | 0 |
| Oral candidiasis | 1 (0.2%) | 1 (0.2%) |
| Otitis media | 1 (0.2%) | 6 (1.2%) |
| Paronychia | 1 (0.2%) | 1 (0.2%) |
| Peritonsillar abscess | 1 (0.2%) | 0 |
| Pyoderma | 1 (0.2%) | 0 |

APPENDIX 20-continued

Number of Subjects With Treatment-Emergent Infections Requiring Oral or Parenteral Antimicrobial Treatment Through Week 56 by System Organ Class and Preferred Term; Safety Analysis Set (Study CNTO1959PSO3009)

| | Guselkumab 100 mg | Secukinumab 300 mg |
|---|---|---|
| Salmonellosis | 1 (0.2%) | 0 |
| Sepsis | 1 (0.2%) | 0 |
| Skin bacterial infection | 1 (0.2%) | 0 |
| Upper respiratory tract infection bacterial | 1 (0.2%) | 0 |
| Urinary tract infection bacterial | 1 (0.2%) | 0 |
| Viral pharyngitis | 1 (0.2%) | 0 |
| Abscess | 0 | 1 (0.2%) |
| Abscess limb | 0 | 1 (0.2%) |
| Application site cellulitis | 0 | 1 (0.2%) |
| Blister infected | 0 | 1 (0.2%) |
| Bullous impetigo | 0 | 1 (0.2%) |
| Conjunctivitis | 0 | 5 (1.0%) |
| Dermatitis infected | 0 | 1 (0.2%) |
| Furuncle | 0 | 1 (0.2%) |
| Gastroenteritis viral | 0 | 1 (0.2%) |
| Gastrointestinal viral infection | 0 | 1 (0.2%) |
| Groin abscess | 0 | 1 (0.2%) |
| Helicobacter infection | 0 | 1 (0.2%) |
| Herpes zoster | 0 | 1 (0.2%) |
| Neuroborreliosis | 0 | 1 (0.2%) |
| Otitis media acute | 0 | 1 (0.2%) |
| Perianal streptococcal infection | 0 | 1 (0.2%) |
| Peritonsillitis | 0 | 1 (0.2%) |
| Pharyngitis streptococcal | 0 | 3 (0.6%) |
| Pharyngotonsillitis | 0 | 1 (0.2%) |
| Pulpitis dental | 0 | 1 (0.2%) |
| Pyelonephritis | 0 | 1 (0.2%) |
| Respiratory syncytial virus infection | 0 | 1 (0.2%) |
| Rhinitis | 0 | 1 (0.2%) |
| Soft tissue infection | 0 | 1 (0.2%) |
| Staphylococcal skin infection | 0 | 1 (0.2%) |
| Subcutaneous abscess | 0 | 2 (0.4%) |
| Tracheobronchitis | 0 | 1 (0.2%) |
| Vaginal infection | 0 | 1 (0.2%) |
| Vulvovaginal candidiasis | 0 | 1 (0.2%) |
| Skin and subcutaneous tissue disorders | 3 (0.6%) | 4 (0.8%) |
| Acne | 1 (0.2%) | 0 |
| Intertrigo | 1 (0.2%) | 1 (0.2%) |
| Skin ulcer | 1 (0.2%) | 1 (0.2%) |
| Dermal cyst | 0 | 1 (0.2%) |
| Psoriasis | 0 | 1 (0.2%) |
| Gastrointestinal disorders | 1 (0.2%) | 1 (0.2%) |
| Diarrhoea | 1 (0.2%) | 0 |
| Apical granuloma | 0 | 1 (0.2%) |
| General disorders and administration site conditions | 1 (0.2%) | 1 (0.2%) |
| Influenza like illness | 1 (0.2%) | 0 |
| Pyrexia | 0 | 1 (0.2%) |
| Reproductive system and breast disorders | 1 (0.2%) | 0 |
| Bartholin's cyst | 1 (0.2%) | 0 |
| Respiratory, thoracic and mediastinal disorders | 1 (0.2%) | 4 (0.8%) |
| Pneumonia aspiration | 1 (0.2%) | 0 |
| Nasal ulcer | 0 | 1 (0.2%) |
| Oropharyngeal pain | 0 | 3 (0.6%) |
| Renal and urinary disorders | 0 | 1 (0.2%) |
| Cystitis noninfective | 0 | 1 (0.2%) |
| Vascular disorders | 0 | 1 (0.2%) |
| Phlebitis superficial | 0 | 1 (0.2%) |

Key: Avg = average.

Note:

Subjects are counted only once for any given event, regardless of the number of times they actually experienced the event. Adverse events are coded using MedDRA Version 21.0.
[TSFINFE03.RTF]　　　　　　　　[CNTO1959\PSO3009\DBR_WEEK_056\RE_WEEK_056_CSR\PROD\TSFINFE03.SAS] 23OCT2018, 12:59

APPENDIX 21

Number of Subjects With Treatment-Emergent Serious Infections Through Week 56 by System Organ Class and Preferred Term; Safety Analysis Set (Study CNTO1959PSO3009)

|  | Guselkumab 100 mg | Secukinumab 300 mg |
|---|---|---|
| Analysis set: Safety analysis set | 534 | 511 |
| Avg duration of follow-up (weeks) | 54.90 | 53.67 |
| Avg exposure (number of administrations) | 14.65 | 14.41 |
| Subjects with 1 or more serious infections | 6 (1.1%) | 5 (1.0%) |
| System organ class | | |
| Preferred term | | |
| Infections and infestations | 4 (0.7%) | 5 (1.0%) |
| Appendicitis | 1 (0.2%) | 0 |
| Cellulitis | 1 (0.2%) | 1 (0.2%) |
| Labyrinthitis | 1 (0.2%) | 0 |
| Pneumonia | 1 (0.2%) | 1 (0.2%) |
| Abscess limb | 0 | 1 (0.2%) |
| Neuroborreliosis | 0 | 1 (0.2%) |
| Pyelonephritis | 0 | 1 (0.2%) |
| Reproductive system and breast disorders | 1 (0.2%) | 0 |
| Bartholin's cyst | 1 (0.2%) | 0 |
| Respiratory, thoracic and mediastinal disorders | 1 (0.2%) | 0 |
| Pneumonia aspiration | 1 (0.2%) | 0 |

Key: Avg = average.
Note:
Subjects are counted only once for any given event, regardless of the number of times they actually experienced the event. Adverse events are coded using MedDRA Version 21.0.
[TSFINFE02.RTF]   [CNTO1959\PSO3009\DBR_WEEK_056\RE_WEEK_056_CSR\PROD\TSFINFE02.SAS] 23OCT2018, 12:59

APPENDIX 22

Number of Subjects With Treatment-Emergent Adverse Events of Psoriasis Through Week 56 by MedDRA Lower Level Term Category; Safety Analysis Set (Study CNTO1959PSO3009)

|  | Guselkumab 100 mg | Secukinumab 300 mg |
|---|---|---|
| Analysis set: Safety analysis set | 534 | 511 |
| Avg duration of follow-up (weeks) | 54.90 | 53.67 |
| Avg exposure (number of administrations) | 14.65 | 14.41 |
| Subjects with 1 or more AEs of psoriasis | 4 (0.7%) | 11 (2.2%) |
| Lower level term category | | |
| Worsening or exacerbation of psoriasis | 4 (0.7%) | 11 (2.2%) |

Key: AE = adverse event, Avg = average.
Note:
Subjects are counted only once for any given event, regardless of the number of times they actually experienced the event. Adverse events are coded using MedDRA Version 21.0.
[TSFAE08.RTF]   [CNTO1959\PSO3009\DBR_WEEK_056\RE_WEEK_056_CSR\PROD\TSFAE08.SAS] 23OCT2018, 12:59

APPENDIX 23

Summary of Injection-Site Reactions Through Week 56 by Intensity; Treated Subjects by Study Agent Injection Received (Study CNTO1959PSO3009)

|  | Placebo Injections | Guselkumab Injections | Secukinumab Injections |
|---|---|---|---|
| Analysis set: Treated subjects by study agent injection received | 534 | 534 | 511 |
| Avg number of injections | 22.5 | 6.8 | 28.8 |
| Subjects with 1 or more injection-site reactions | 20 (3.7%) | 13 (2.4%) | 20 (3.9%) |
| Total number of injections | 11998 | 3644 | 14722 |
| Injections with injection-site reactions | 32 (0.3%) | 19 (0.5%) | 63 (0.4%) |
| Mild | 30 (0.3%) | 19 (0.5%) | 55 (0.4%) |
| Moderate | 2 (<0.1%) | 0 | 8 (0.1%) |
| Severe | 0 | 0 | 0 |

[TSFIR01.RTF]   [CNTO1959\PSO3009\DBR_WEEK_056\RE_WEEK_056_CSR\PROD\TSFIR01.SAS] 23OCT2018, 12:59

APPENDIX 24

Summary of Injection-Site Reactions Through Week 56 by System Organ Class and Preferred Term; Treated Subjects by Study Agent Injection Received (Study CNTO1959PSO3009)

|  | Placebo Injections | Guselkumab Injections | Secukinumab Injections |
|---|---|---|---|
| Analysis set: Treated subjects by study agent injection received | 534 | 534 | 511 |
| Avg number of injections | 22.5 | 6.8 | 28.8 |
| Total number of injections | 11998 | 3644 | 14722 |
| Injections with injection-site reactions | 32 (0.3%) | 19 (0.5%) | 63 (0.4%) |
| Subjects with 1 or more injection-site reactions | 20 (3.7%) | 13 (2.4%) | 20 (3.9%) |
| System organ class Preferred term |  |  |  |
| General disorders and administration site conditions | 20 (3.7%) | 13 (2.4%) | 20 (3.9%) |
| Injection site erythema | 8 (1.5%) | 6 (1.1%) | 7 (1.4%) |
| Injection site pruritus | 3 (0.6%) | 4 (0.7%) | 0 |
| Injection site haematoma | 3 (0.6%) | 3 (0.6%) | 5 (1.0%) |
| Injection site swelling | 3 (0.6%) | 3 (0.6%) | 1 (0.2%) |
| Injection site pain | 5 (0.9%) | 2 (0.4%) | 6 (1.2%) |
| Injection site extravasation | 0 | 1 (0.2%) | 0 |
| Injection site induration | 2 (0.4%) | 1 (0.2%) | 0 |
| Injection site rash | 0 | 1 (0.2%) | 0 |
| Injection site bruising | 3 (0.6%) | 0 | 2 (0.4%) |
| Injection site haemorrhage | 1 (0.2%) | 0 | 2 (0.4%) |
| Injection site inflammation | 0 | 0 | 1 (0.2%) |
| Injection site oedema | 1 (0.2%) | 0 | 2 (0.4%) |

[TSFIR02.RTF]
[CNTO1959\PSO3009\DBR_Week_056\RE_WEEK_056_CSR\PROD\TSFIR02.SAS] 23OCT2018, 12:59

APPENDIX 25

Number of Subjects with 1 or More Post-Baseline Suicidal Ideation or Suicidal Behavior Through Week 56; Safety Analysis Set (Study CNTO1959PSO3009)

|  | Guselkumab 100 mg | Secukinumab 300 mg |
|---|---|---|
| Analysis set: Safety analysis set | 534 | 511 |
| Suicidal ideation or behavior | 8 (1.5%) | 8 (1.6%) |
| Suicidal ideation | 5 (0.9%) | 4 (0.8%) |
| 1 - Wish to be dead | 2 (0.4%) | 3 (0.6%) |
| 2 - Non-specific active suicidal thoughts | 1 (0.2%) | 1 (0.2%) |
| 3 - Active suicidal ideation with any methods (not plan) without intent to act | 1 (0.2%) | 0 |
| 4 - Active suicidal ideation with some intent to act, without specific plan | 0 | 0 |
| 5 - Active suicidal ideation with specific plan and intent | 0 | 0 |
| Suicidal behavior | 3 (0.6%) | 4 (0.8%) |
| 6 - Preparatory acts or behavior | 1 (0.2%) | 1 (0.2%) |
| 7 - Aborted attempt | 1 (0.2%) | 0 |
| 8 - Interrupted attempt | 1 (0.2%) | 0 |
| 9 - Non-fatal suicide attempt | 0 | 2 (0.4%) |
| 10 - Completed suicide | 0 | 0 |

Note 1:
Each subject is counted only once in the above table, based on the most severe postbaseline eC-SSRS score.
Note 2:
The categories of suicidal ideation or behavior, suicidal ideation, and suicidal behavior are based on the eC-SSRS and AE.
Note 3:
Score 1 to 9 are only based the eC-SSRS, not including AE. Completed suicide is from AE.
[TSFECSSRS01.RTF]
[CNTO1959\PSO3009\DBR_WEEK_056\RE_WEEK_056_CSR\PROD\TSFECSSRS01. SAS] 23OCT2018, 13:02

Data Summary of Patients with Psoriatic Arthritis (PsA) in Addition to PsO:

TABLE 5

Table 5 -TEFPASI13A_PSA: Summary of PASI Responses Through Week 56 by Visit; Full Analysis Set (Study CNTO01959PSO3009)

|  | Guselkumab 100 mg | Secukinumab 300 mg |
|---|---|---|
| Full analysis set with PSA | 97 | 79 |
| Week 1 |  |  |
| N | 97 | 79 |
| 100% improvement | 0 | 0 |
| ≥90% improvement | 0 | 0 |
| ≥75% improvement | 0 | 0 |
| ≥50% improvement | 6 (6.2%) | 5 (6.3%) |
| Week 2 |  |  |
| N | 97 | 79 |
| 100% improvement | 1 (1.0%) | 1 (1.3%) |
| ≥90% improvement | 1 (1.0%) | 1 (1.3%) |
| ≥75% improvement | 2 (2.1%) | 5 (6.3%) |
| ≥50% improvement | 28 (28.9%) | 28 (35.4%) |
| Week 3 |  |  |
| N | 97 | 79 |
| 100% improvement | 3 (3.1%) | 1 (1.3%) |
| ≥90% improvement | 8 (8.2%) | 5 (6.3%) |
| ≥75% improvement | 20 (20.6%) | 13 (16.5%) |
| ≥50% improvement | 46 (47.4%) | 47 (59.5%) |
| Week 4 |  |  |
| N | 97 | 79 |
| 100% improvement | 6 (6.2%) | 3 (3.8%) |
| ≥90% improvement | 14 (14.4%) | 7 (8.9%) |
| ≥75% improvement | 33 (34.0%) | 30 (38.0%) |
| ≥50% improvement | 68 (70.1%) | 60 (75.9%) |
| Week 8 |  |  |
| N | 97 | 79 |
| 100% improvement | 17 (17.5%) | 19 (24.1%) |
| ≥90% improvement | 41 (42.3%) | 44 (55.7%) |
| ≥75% improvement | 71 (73.2%) | 64 (81.0%) |
| ≥50% improvement | 92 (94.8%) | 77 (97.5%) |
| Week 12 |  |  |
| N | 97 | 79 |
| 100% improvement | 37 (38.1%) | 31 (39.2%) |
| ≥90% improvement | 69 (71.1%) | 57 (72.2%) |
| ≥75% improvement | 89 (91.8%) | 72 (91.1%) |
| ≥50% improvement | 96 (99.0%) | 76 (96.2%) |
| Week 16 |  |  |
| N | 97 | 79 |
| 100% improvement | 42 (43.3%) | 37 (46.8%) |
| ≥90% improvement | 70 (72.2%) | 59 (74.7%) |
| ≥75% improvement | 91 (93.8%) | 74 (93.7%) |
| ≥50% improvement | 95 (97.9%) | 76 (96.2%) |
| Week 20 |  |  |
| N | 97 | 79 |
| 100% improvement | 47 (48.5%) | 43 (54.4%) |
| ≥90% improvement | 74 (76.3%) | 60 (75.9%) |
| ≥75% improvement | 89 (91.8%) | 71 (89.9%) |
| ≥50% improvement | 95 (97.9%) | 74 (93.7%) |
| Week 24 |  |  |
| N | 97 | 79 |
| 100% improvement | 56 (57.7%) | 36 (45.6%) |
| ≥90% improvement | 76 (78.4%) | 59 (74.7%) |
| ≥75% improvement | 92 (94.8%) | 70 (88.6%) |
| ≥50% improvement | 95 (97.9%) | 71 (89.9%) |
| Week 28 |  |  |
| N | 97 | 79 |
| 100% improvement | 53 (54.6%) | 38 (48.1%) |
| ≥90% improvement | 80 (82.5%) | 61 (77.2%) |

TABLE 5-continued

Table 5 -TEFPASI13A_PSA: Summary of PASI Responses Through Week 56 by Visit; Full Analysis Set (Study CNTO01959PSO3009)

|  | Guselkumab 100 mg | Secukinumab 300 mg |
|---|---|---|
| ≥75% improvement | 89 (91.8%) | 72 (91.1%) |
| ≥50% improvement | 94 (96.9%) | 72 (91.1%) |
| Week 32 | | |
| N | 97 | 79 |
| 100% improvement | 53 (54.6%) | 38 (48.1%) |
| ≥90% improvement | 80 (82.5%) | 58 (73.4%) |
| ≥75% improvement | 92 (94.8%) | 68 (86.1%) |
| ≥50% improvement | 95 (97.9%) | 72 (91.1%) |
| Week 36 | | |
| N | 97 | 79 |
| 100% improvement | 54 (55.7%) | 36 (45.6%) |
| ≥90% improvement | 78 (80.4%) | 59 (74.7%) |
| ≥75% improvement | 92 (94.8%) | 68 (86.1%) |
| ≥50% improvement | 94 (96.9%) | 71 (89.9%) |
| Week 40 | | |
| N | 97 | 79 |
| 100% improvement | 53 (54.6%) | 36 (45.6%) |
| ≥90% improvement | 79 (81.4%) | 56 (70.9%) |
| ≥75% improvement | 90 (92.8%) | 67 (84.8%) |
| ≥50% improvement | 95 (97.9%) | 69 (87.3%) |
| Week 44 | | |
| N | 97 | 79 |
| 100% improvement | 55 (56.7%) | 34 (43.0%) |
| ≥90% improvement | 79 (81.4%) | 55 (69.6%) |
| ≥75% improvement | 91 (93.8%) | 68 (86.1%) |
| ≥50% improvement | 95 (97.9%) | 70 (88.6%) |
| Week 48 | | |
| N | 97 | 79 |
| 100% improvement | 55 (56.7%) | 35 (44.3%) |
| ≥90% improvement | 80 (82.5%) | 50 (63.3%) |
| ≥75% improvement | 93 (95.9%) | 65 (82.3%) |
| ≥50% improvement | 95 (97.9%) | 68 (86.1%) |
| Week 56 | | |
| N | 97 | 79 |
| 100% improvement | 39 (40.2%) | 24 (30.4%) |
| ≥90% improvement | 66 (68.0%) | 33 (41.8%) |
| ≥75% improvement | 81 (83.5%) | 50 (63.3%) |
| ≥50% improvement | 87 (89.7%) | 61 (77.2%) |

[TEFPASI13A.RTF]
[CNTO1959\PSO3009\DBR_WEEK_056\RE_WEEK_056_CSR\PDEV\TEFPASI13A_PSA.SAS]07DEC2018, 18:12

TABLE 6

Table 6 - TSICM01A_PSA: Summary of Previous Psoriasis Medications and Therapies by Medication Category; Full Analysis Set (Study CNTO1959PSO3009)

|  | Guselkumab 100 mg | Secukinumab 300 mg | Total |
|---|---|---|---|
| Full analysis set with PSA | 97 | 79 | 176 |
| Topical agents | | | |
| N | 97 | 79 | 176 |
| Never Used | 3 (3.1%) | 6 (7.6%) | 9 (5.1%) |
| Ever Used | 94 (96.9%) | 73 (92.4%) | 167 (94.9%) |
| Phototherapy (PUVA or UVB) | | | |
| N | 97 | 78 | 175 |
| Never Used | 40 (41.2%) | 42 (53.8%) | 82 (46.9%) |
| Ever Used | 57 (58.8%) | 36 (46.2%) | 93 (53.1%) |
| Non-biologic systemic (PUVA, methotrexate, cyclosporine, acitretin, apremilast, or tofacitinib) | | | |
| N | 97 | 79 | 176 |
| Never Used | 26 (26.8%) | 18 (22.8%) | 44 (25.0%) |
| ≥1 therapy | 71 (73.2%) | 61 (77.2%) | 132 (75.0%) |
| ≥2 therapies | 41 (42.3%) | 33 (41.8%) | 74 (42.0%) |
| ≥3 therapies | 18 (18.6%) | 17 (21.5%) | 35 (19.9%) |
| ≥4 therapies | 3 (3.1%) | 1 (1.3%) | 4 (2.3%) |
| Biologics (etanercept, infliximab, alefacept, efalizumab, ustekinumab, briakinumab, ixekizumab, adalimumab, brodalumab, tildrakizumab, or risankizumab) | | | |
| N | 97 | 79 | 176 |
| Never Used | 56 (57.7%) | 45 (57.0%) | 101 (57.4%) |
| Ever Used | 41 (42.3%) | 34 (43.0%) | 75 (42.6%) |
| Non-biologic systemic or biologics | | | |
| N | 97 | 79 | 176 |
| Never Used | 19 (19.6%) | 11 (13.9%) | 30 (17.0%) |
| Ever Used | 78 (80.4%) | 68 (86.1%) | 146 (83.0%) |
| Anti-TNFα agent (etanercept, infliximab, adalimumab) | | | |
| N | 97 | 79 | 176 |
| Never Used | 67 (69.1%) | 54 (68.4%) | 121 (68.8%) |
| Ever Used | 30 (30.9%) | 25 (31.6%) | 55 (31.3%) |

TABLE 6-continued

Table 6 - TSICM01A_PSA: Summary of Previous Psoriasis Medications and Therapies by Medication Category; Full Analysis Set (Study CNTO1959PSO3009)

|  | Guselkumab 100 mg | Secukinumab 300 mg | Total |
|---|---|---|---|
| IL-12/23 inhibitors (ustekinumab, briakinumab, tildrakizumab, risankizumab) | | | |
| N | 97 | 79 | 176 |
| Never Used | 85 (87.6%) | 66 (83.5%) | 151 (85.8%) |
| Ever Used | 12 (12.4%) | 13 (16.5%) | 25 (14.2%) |
| IL-17 inhibitors (ixekizumab, brodalumab) | | | |
| N | 97 | 79 | 176 |
| Never Used | 81 (83.5%) | 64 (81.0%) | 145 (82.4%) |
| Ever Used | 16 (16.5%) | 15 (19.0%) | 31 (17.6%) |

[TSICM01A.RTF][CNTO1959\PSO3009\DBR_WEEK_056\RE_WEEK_056_CSR\PDEV\TSICM01A_PSA.SAS] 07DEC2018, 18:00

TABLE 7

Table 7 - TSIDEM01_PSA: Summary of Demographics and Baseline Characteristics; Full Analysis Set (Study CNTO1959PSO3009)

|  | Guselkumab 100 mg | Secukinumab 300 mg | Total |
|---|---|---|---|
| Full analysis set with PSA | 97 | 79 | 176 |
| Age, years | | | |
| N | 97 | 79 | 176 |
| Mean (SD) | 50.7 (12.01) | 46.9 (14.04) | 49.0 (13.06) |
| Median | 52.0 | 47.0 | 48.5 |
| Range | (20; 77) | (20; 74) | (20; 77) |
| IQ range | (41.0; 59.0) | (35.0; 59.0) | (40.0; 59.0) |
| <45 years | 29 (29.9%) | 38 (48.1%) | 67 (38.1%) |
| ≥45 to <65 years | 53 (54.6%) | 33 (41.8%) | 86 (48.9%) |
| ≥65 years | 15 (15.5%) | 8 (10.1%) | 23 (13.1%) |
| Sex | | | |
| N | 97 | 79 | 176 |
| Female | 30 (30.9%) | 33 (41.8%) | 63 (35.8%) |
| Male | 67 (69.1%) | 46 (58.2%) | 113 (64.2%) |
| Race | | | |
| N | 97 | 79 | 176 |
| American Indian or Alaska Native | 0 | 1 (1.3%) | 1 (0.6%) |
| Asian | 2 (2.1%) | 3 (3.8%) | 5 (2.8%) |
| Black or African American | 2 (2.1%) | 0 | 2 (1.1%) |
| White | 91 (93.8%) | 75 (94.9%) | 166 (94.3%) |
| Other | 2 (2.1%) | 0 | 2 (1.1%) |
| Ethnicity | | | |
| N | 97 | 79 | 176 |
| Hispanic or Latino | 4 (4.1%) | 4 (5.1%) | 8 (4.5%) |
| Not Hispanic or Latino | 93 (95.9%) | 75 (94.9%) | 168 (95.5%) |
| Weight, kg | | | |
| N | 97 | 79 | 176 |
| Mean (SD) | 89.20 (21.231) | 87.96 (21.376) | 88.64 (21.244) |
| Median | 89.00 | 85.10 | 86.75 |
| Range | (50.0; 158.9) | (53.8; 177.6) | (50.0; 177.6) |
| IQ range | (73.50; 100.00) | (73.00; 98.30) | (73.25; 100.00) |
| ≤90 kg | 52 (53.6%) | 47 (59.5%) | 99 (56.3%) |
| >90 kg | 45 (46.4%) | 32 (40.5%) | 77 (43.8%) |
| Height, cm | | | |
| N | 97 | 79 | 176 |
| Mean (SD) | 174.1 (10.05) | 171.5 (8.79) | 172.9 (9.57) |
| Median | 174.4 | 172.0 | 173.0 |
| Range | (152; 192) | (148; 196) | (148; 196) |
| IQ range | (168.0; 182.8) | (165.1; 177.0) | (167.0; 179.0) |
| Body mass index, kg/m² | | | |
| N | 97 | 79 | 176 |
| Mean (SD) | 29.3 (6.04) | 29.8 (6.81) | 29.6 (6.38) |
| Median | 28.4 | 28.8 | 28.7 |
| Range | (17; 48) | (20; 65) | (17; 65) |
| IQ range | (25.4; 32.3) | (25.1; 33.2) | (25.2; 32.8) |
| Normal <25 kg/m² | 20 (20.6%) | 18 (22.8%) | 38 (21.6%) |
| Overweight ≥25 to <30 kg/m² | 41 (42.3%) | 24 (30.4%) | 65 (36.9%) |
| Obese ≥30 kg/m² | 36 (37.1%) | 37 (46.8%) | 73 (41.5%) |

Key: IQ = Interquartile
[TSIDEM01.RTF][CNTO1959\PSO3009\DBR_WEEK_056\RE_WEEK_056_CSR\PDEV\TSIDEM01_PSA.SAS] 07DEC2018, 17:53

TABLE 8

Table 8 - TEFPASI13A _PSA: Summary of PASI Responses Through Week 56 by Visit; Full Analysis Set (Study CNT01959PSO3009)

|  | Guselkumab 100 mg | Secukinumab 300 mg |
|---|---|---|
| Full analysis set with PSA | 97 | 79 |
| Week 1 | | |
| N | 97 | 79 |
| 100% improvement | 0 | 0 |
| ≥90% improvement | 0 | 0 |
| ≥75% improvement | 0 | 0 |
| ≥50% improvement | 6 (6.2%) | 5 (6.3%) |
| Week 2 | | |
| N | 97 | 79 |
| 100% improvement | 1 (1.0%) | 1 (1.3%) |
| ≥90% improvement | 1 (1.0%) | 1 (1.3%) |
| ≥75% improvement | 2 (2.1%) | 5 (6.3%) |
| ≥50% improvement | 28 (28.9%) | 28 (35.4%) |

TABLE 8-continued

Table 8 - TEFPASI13A_PSA: Summary of PASI Responses Through Week 56 by Visit; Full Analysis Set (Study CNT01959PSO3009)

| | Guselkumab 100 mg | Secukinumab 300 mg |
|---|---|---|
| Week 3 | | |
| N | 97 | 79 |
| 100% improvement | 3 (3.1%) | 1 (1.3%) |
| ≥90% improvement | 8 (8.2%) | 5 (6.3%) |
| ≥75% improvement | 20 (20.6%) | 13 (16.5%) |
| ≥50% improvement | 46 (47.4%) | 47 (59.5%) |
| Week 4 | | |
| N | 97 | 79 |
| 100% improvement | 6 (6.2%) | 3 (3.8%) |
| ≥90% improvement | 14 (14.4%) | 7 (8.9%) |
| ≥75% improvement | 33 (34.0%) | 30 (38.0%) |
| ≥50% improvement | 68 (70.1%) | 60 (75.9%) |
| Week 8 | | |
| N | 97 | 79 |
| 100% improvement | 17 (17.5%) | 19 (24.1%) |
| ≥90% improvement | 41 (42.3%) | 44 (55.7%) |
| ≥75% improvement | 71 (73.2%) | 64 (81.0%) |
| ≥50% improvement | 92 (94.8%) | 77 (97.5%) |
| Week 12 | | |
| N | 97 | 79 |
| 100% improvement | 37 (38.1%) | 31 (39.2%) |
| ≥90% improvement | 69 (71.1%) | 57 (72.2%) |
| ≥75% improvement | 89 (91.8%) | 72 (91.1%) |
| ≥50% improvement | 96 (99.0%) | 76 (96.2%) |
| Week 16 | | |
| N | 97 | 79 |
| 100% improvement | 42 (43.3%) | 37 (46.8%) |
| ≥90% improvement | 70 (72.2%) | 59 (74.7%) |
| ≥75% improvement | 91 (93.8%) | 74 (93.7%) |
| ≥50% improvement | 95 (97.9%) | 76 (96.2%) |
| Week 20 | | |
| N | 97 | 79 |
| 100% improvement | 47 (48.5%) | 43 (54.4%) |
| ≥90% improvement | 74 (76.3%) | 60 (75.9%) |
| ≥75% improvement | 89 (91.8%) | 71 (89.9%) |
| ≥50% improvement | 95 (97.9%) | 74 (93.7%) |
| Week 24 | | |
| N | 97 | 79 |
| 100% improvement | 56 (57.7%) | 36 (45.6%) |
| ≥90% improvement | 76 (78.4%) | 59 (74.7%) |
| ≥75% improvement | 92 (94.8%) | 70 (88.6%) |
| ≥50% improvement | 95 (97.9%) | 71 (89.9%) |
| Week 28 | | |
| N | 97 | 79 |
| 100% improvement | 53 (54.6%) | 38 (48.1%) |
| ≥90% improvement | 80 (82.5%) | 61 (77.2%) |
| ≥75% improvement | 89 (91.8%) | 72 (91.1%) |
| ≥50% improvement | 94 (96.9%) | 72 (91.1%) |
| Week 32 | | |
| N | 97 | 79 |
| 100% improvement | 53 (54.6%) | 38 (48.1%) |
| ≥90% improvement | 80 (82.5%) | 58 (73.4%) |
| ≥75% improvement | 92 (94.8%) | 68 (86.1%) |
| ≥50% improvement | 95 (97.9%) | 72 (91.1%) |
| Week 36 | | |
| N | 97 | 79 |
| 100% improvement | 54 (55.7%) | 36 (45.6%) |
| ≥90% improvement | 78 (80.4%) | 59 (74.7%) |
| ≥75% improvement | 92 (94.8%) | 68 (86.1%) |
| ≥50% improvement | 94 (96.9%) | 71 (89.9%) |
| Week 40 | | |
| N | 97 | 79 |
| 100% improvement | 53 (54.6%) | 36 (45.6%) |
| ≥90% improvement | 79 (81.4%) | 56 (70.9%) |
| ≥75% improvement | 90 (92.8%) | 67 (84.8%) |
| ≥50% improvement | 95 (97.9%) | 69 (87.3%) |
| Week 44 | | |
| N | 97 | 79 |
| 100% improvement | 55 (56.7%) | 34 (43.0%) |
| ≥90% improvement | 79 (81.4%) | 55 (69.6%) |
| ≥75% improvement | 91 (93.8%) | 68 (86.1%) |
| ≥50% improvement | 95 (97.9%) | 70 (88.6%) |
| Week 48 | | |
| N | 97 | 79 |
| 100% improvement | 55 (56.7%) | 35 (44.3%) |
| ≥90% improvement | 80 (82.5%) | 50 (63.3%) |
| ≥75% improvement | 93 (95.9%) | 65 (82.3%) |
| ≥50% improvement | 95 (97.9%) | 68 (86.1%) |
| Week 56 | | |
| N | 97 | 79 |
| 100% improvement | 39 (40.2%) | 24 (30.4%) |
| ≥90% improvement | 66 (68.0%) | 33 (41.8%) |
| ≥75% improvement | 81 (83.5%) | 50 (63.3%) |
| ≥50% improvement | 87 (89.7%) | 61 (77.2%) |

[TEFPASI13A.RTF]
[CNTO1959\PSO3009\DBR_WEEK_056\RE_WEEK_056_CSR\PDEV\TEFPASI13A_PSA.SAS] 07DEC2018, 18:12

TABLE 9

Table 9 - TSFAE_PSA: Number of Subjects with Treatment-Emergent Adverse Events Through Week 56; PSA Subjects in Safety Analysis Set (Study CNTO1959PSO3009)

| | Guselkumab 100 mg | Secukinumab 300 mg |
|---|---|---|
| Safety analysis set, with PSA | 97 | 79 |
| Avg duration of follow-up (weeks) | 55.36 | 52.68 |
| Avg exposure (number of administrations) | 14.76 | 14.13 |
| Subjects with 1 or more AEs | 73 (75.3%) | 67 (84.8%) |
| Subjects with 1 or more SAEs | 3 (3.1%) | 11 (13.9%) |
| Subjects with 1 or more AEs leading to discontinuation of study agent | 1 (1.0%) | 3 (3.8%) |
| Subjects with 1 or more infections | 54 (55.7%) | 54 (68.4%) |
| Subjects with 1 or more serious infections | 0 | 2 (2.5%) |

Key: AE = adverse event, Avg = average.
Note:
Subjects are counted only once for any given event, regardless of the number of times they actually experienced the event. Adverse events are coded using MedDRA Version 21.0.
[TSFAE01.RTF]
[CNTO1959\PSO3009\DBR_WEEK_056\RE_WEEK_056_CSR\PDEV\TSFAE_PSA.SAS] 07DEC2018, 12:37

TABLE 10

Table 10 - TSIDEM04_PSA: Summary of Psoriasis Baseline Clinical Disease Characteristics; Full Analysis Set (Study CNTO1959PSO3009)

| | Guselkumab 100 mg | Secukinumab 300 mg | Total |
|---|---|---|---|
| Full analysis set with PSA | 97 | 79 | 176 |
| Psoriasis disease duration (years) | | | |
| N | 97 | 79 | 176 |
| Mean (SD) | 21.9 (11.25) | 20.0 (13.46) | 21.1 (12.29) |
| Median | 21.0 | 17.0 | 20.0 |
| Range | (1; 48) | (1; 57) | (1; 57) |
| IQ range | (14.7; 27.0) | (10.0; 28.0) | (12.0; 27.5) |
| Psoriasis disease duration (years) | | | |
| N | 97 | 79 | 176 |
| <15 years | 25 (25.8%) | 31 (39.2%) | 56 (31.8%) |
| ≥15 years | 72 (74.2%) | 48 (60.8%) | 120 (68.2%) |
| Age at diagnosis (years) | | | |
| N | 97 | 79 | 176 |
| Mean (SD) | 28.9 (13.37) | 26.9 (13.28) | 28.0 (13.33) |
| Median | 27.0 | 25.0 | 27.0 |
| Range | (5; 67) | (6; 61) | (5; 67) |
| IQ range | (18.0; 37.0) | (16.0; 34.0) | (17.5; 36.0) |
| Age at diagnosis (years) | | | |
| N | 97 | 79 | 176 |
| <25 years | 40 (41.2%) | 36 (45.6%) | 76 (43.2%) |
| ≥25 years | 57 (58.8%) | 43 (54.4%) | 100 (56.8%) |
| Psoriatic arthritis | | | |
| N | 97 | 79 | 176 |
| Yes | 97 (100.0%) | 79 (100.0%) | 176 (100.0%) |
| No | 0 | 0 | 0 |
| BSA (%) | | | |
| N | 97 | 79 | 176 |
| Mean (SD) | 27.3 (13.16) | 25.0 (13.29) | 26.3 (13.24) |
| Median | 23.0 | 21.0 | 23.0 |
| Range | (10; 74) | (10; 68) | (10; 74) |
| IQ range | (17.0; 36.0) | (15.0; 32.0) | (16.5; 34.5) |
| BSA | | | |
| N | 97 | 79 | 176 |
| <20% | 26 (26.8%) | 36 (45.6%) | 62 (35.2%) |
| ≥20% | 71 (73.2%) | 43 (54.4%) | 114 (64.8%) |
| IGA score | | | |
| N | 97 | 79 | 176 |
| Cleared (0) | 0 | 0 | 0 |
| Minimal (1) | 0 | 0 | 0 |
| Mild (2) | 0 | 0 | 0 |
| Moderate (3) | 69 (71.1%) | 57 (72.2%) | 126 (71.6%) |
| Severe (4) | 28 (28.9%) | 22 (27.8%) | 50 (28.4%) |
| IGA score | | | |
| N | 97 | 79 | 176 |
| <4 | 69 (71.1%) | 57 (72.2%) | 126 (71.6%) |
| =4 | 28 (28.9%) | 22 (27.8%) | 50 (28.4%) |
| PASI score (0-72) | | | |
| N | 97 | 79 | 176 |
| Mean (SD) | 21.6 (8.29) | 20.2 (7.03) | 21.0 (7.76) |
| Median | 18.8 | 18.0 | 18.6 |
| Range | (12; 59) | (12; 50) | (12; 59) |
| IQ range | (15.7; 25.5) | (16.0; 22.0) | (15.9; 24.3) |
| PASI score | | | |
| N | 97 | 79 | 176 |
| <20 | 53 (54.6%) | 51 (64.6%) | 104 (59.1%) |
| ≥20 | 44 (45.4%) | 28 (35.4%) | 72 (40.9%) |

Key: IQ = Interquartile
[TSIDEM04.RTF]
[CNTO1959\PSO3009\DBR_WEEK_056\RE_WEEK_056_CSR\PDEV\TSIDEM04_PSA.SAS] 07DEC2018, 17:53

TABLE 11

Table 11 - TEFFECACY PSA:

| Efficacy Endpoint | Guselkumab 100 mg | Secukinumab 300 mg | Difference | 95% CI |
|---|---|---|---|---|
| PASI 90 at WEEK 48 | 84.5% (451/534) | 70.0% (360/514) | 14.4 | (9.2, 19.6) |
| Psoriatic arthritis | 82.5% (80/97) | 63.3% (50/79) | 19.2 | (5.0, 33.4) |
| PASI 75 at WEEK 12 AND WEEK 48 | 84.6% (452/534) | 80.2% (412/514) | 4.5 | (−0.3, 9.3) |
| Psoriatic arthritis | 90.7% (88/97) | 78.5% (62/79) | 12.2 | (0.3, 24.1) |
| PASI 90 at WEEK 12 | 69.1% (369/534) | 76.1% (391/514) | −7 | (−12.5, −1.4) |
| Psoriatic arthritis | 71.1% (69/97) | 72.2% (57/79) | −1 | (−15.5, 13.5) |
| PASI 75 at WEEK 12 | 89.3% (477/534) | 91.6% (471/514) | −2.3 | (−6.0, 1.4) |
| Psoriatic arthritis | 91.8% (89/97) | 91.1% (72/79) | 0.6 | (−8.9, 10.1) |
| PASI 100 at WEEK 48 | 58.2% (311/534) | 48.4% (249/514) | 9.8 | (3.6, 16.0) |
| Psoriatic arthritis | 56.7% (55/97) | 44.3% (35/79) | 12.4 | (−3.5, 28.3) |
| IGA 0 at WEEK 48 | 62.2% (332/534) | 50.4% (259/514) | 11.8 | (5.6, 17.9) |
| Psoriatic arthritis | 58.8% (57/97) | 45.6% (36/79) | 13.2 | (−2.7, 29.1) |
| IGA 0/1 at WEEK 48 | 85.0% (454/534) | 74.9% (385/514) | 10.1 | (5.1, 15.1) |
| Psoriatic arthritis | 88.7% (86/97) | 73.4% (58/79) | 15.2 | (2.5, 28.0) |

[TEFFECACY_PSA.RTF]
[CNTO1959\PSO3009\DBR_WEEK_056\RE_WEEK_056_CSR\PDEV\TEFFECACY_PSA.SAS] 08DEC2018, 10:03

PASI 90/PASI 100 and IGA 0/1 Organized by Weight Quartiles

TABLE 12

PASI 90 at Week 48 by weight quartiles

| Weight Category (kg) | Guselkumab 100 mg | Secukinumab 300 mg | Treatment Difference | Lower Limit | Upper Limit |
| --- | --- | --- | --- | --- | --- |
| <=74 | 86.7% (124/143) | 75.6% (93/123) | 11.1% | 0.9% | 21.3% |
| >74-<=87 | 89.1% (106/119) | 73.0% (103/141) | 16.0% | 6.0% | 26.0% |
| >87-<=100 | 80.3% (106/132) | 71.0% (88/124) | 9.3% | -1.9% | 20.6% |
| >100 | 82.1% (115/140) | 61.3% (76/124) | 20.9% | 9.4% | 32.3% |

TABLE 13

PASI 100 at Week 48 by weight quartiles

| Weight Category (kg) | Guselkumab 100 mg | Secukinumab 300 mg | Treatment Difference | Lower Limit | Upper Limit |
| --- | --- | --- | --- | --- | --- |
| <=74 | 58.7% (84/143) | 56.1% (69/123) | 2.6% | -10.0% | 15.3% |
| >74-<=87 | 66.4% (79/119) | 51.8% (73/141) | 14.6% | 2.0% | 27.2% |
| >87-<=100 | 59.1% (78/132) | 47.6% (59/124) | 11.5% | -1.4% | 24.4% |
| >100 | 50.0% (70/140) | 38.7% (48/124) | 11.3% | -1.4% | 24.0% |

TABLE 14

IGA 0/1 at Week 48 by weight quartiles

| Weight Category (kg) | Guselkumab 100 mg | Secukinumab 300 mg | Treatment Difference | Lower Limit | Upper Limit |
| --- | --- | --- | --- | --- | --- |
| <=74 | 84.6% (121/143) | 78.0% (96/123) | 6.6% | -3.6% | 16.7% |
| >74-<=87 | 89.9% (107/119) | 78.7% (111/141) | 11.2% | 1.8% | 20.6% |
| >87-<=100 | 83.3% (110/132) | 80.6% (100/124) | 2.7% | -7.5% | 12.9% |
| >100 | 82.9% (116/140) | 62.9% (78/124) | 20.0% | 8.6% | 31.3% |

TABLE 15

IGA 0 at Week 48 by weight quartiles

| Weight Category (kg) | Guselkumab 100 mg | Secukinumab 300 mg | Treatment Difference | Lower Limit | Upper Limit |
| --- | --- | --- | --- | --- | --- |
| <=74 | 61.5% (88/143) | 58.5% (72/123) | 3.0% | -9.6% | 15.6% |
| >74-<=87 | 71.4% (85/119) | 53.9% (76/141) | 17.5% | 5.2% | 29.9% |
| >87-<=100 | 61.4% (81/132) | 50.0% (62/124) | 11.4% | -1.5% | 24.2% |
| >100 | 55.7% (78/140) | 39.5% (49/124) | 16.2% | 3.5% | 28.9% |

Note:
There were two patients in Secukinumab 300 mg group without baseline weight such that Secukinumab group only has 512 patients listed, instead of 514 patients.

TABLE 16

IGA0/1 by BMI category

| Baseline BMI Group 1 | Guselkumab 100 mg | Secukinumab 300 mg | Treatment Difference | Lower Limit | Upper Limit |
| --- | --- | --- | --- | --- | --- |
| Normal (<25) | 85.8% (115/134) | 77.1% (84/109) | 8.8% | -1.9% | 19.4% |
| Overweight (>=25 to <30) | 86.9% (153/176) | 81.9% (145/177) | 5.0% | -3.1% | 13.1% |
| Obese (>=30) | 83.0% (185/223) | 69.3% (156/225) | 13.6% | 5.4% | 21.9% |

TABLE 17

Summary of PASI component responses at Week 48

|  | Guselkumab 100 mg | Secukinumab 300 mg |
|---|---|---|
| Full analysis set, n | 534 | 514 |
| Head and neck, n | 499 | 481 |
| 100% improvement, n (%) | 399 (80.0) | 360 (74.8) |
| ≥90% improvement, n (%) | 424 (85.0) | 371 (77.1) |
| Trunk, n | 512 | 494 |
| 100% improvement, n (%) | 432 (84.4) | 384 (77.7) |
| ≥90% improvement, n (%) | 444 (86.7) | 395 (80.0) |
| Upper extremities, n | 532 | 510 |
| 100% improvement, n (%) | 422 (79.3) | 322 (63.1) |
| ≥90% improvement, n (%) | 435 (81.8) | 341 (66.9) |
| Lower extremities, n | 534 | 513 |
| 100% improvement, n (%) | 400 (74.9) | 315 (61.4) |
| ≥90% improvement, n (%) | 433 (81.1) | 343 (66.9) |

TABLE 18

Proportion of patients achieving PASI 90 response at Week 48 with guselkumab (GUS) or secukinumab (SEC) by geographic region

|  | North America | | Eastern Europe | | Western Europe | | Australia | | Overall | |
|---|---|---|---|---|---|---|---|---|---|---|
|  | GUS 100 mg | SEC 300 mg | GUS 100 mg | SEC 300 mg | GUS 100 mg | SEC 300 mg | GUS 100 mg | SEC 300 mg | GUS 100 mg | SEC 300 mg |
| Randomized patients, n | 199 | 192 | 171 | 167 | 129 | 119 | 35 | 36 | 534 | 514 |
| PASI 90 responders, n (%) | 157 (78.9) | 116 (60.4) | 155 (90.6) | 127 (76.0) | 107 (82.9) | 89 (74.8) | 32 (91.4) | 28 (77.8) | 451 (84.5) | 360 (70.0) |

What is claimed is:

1. A method of treating psoriasis in a patient previously treated with at least one dose of secukinumab, comprising discontinuing secukinumab treatment to the patient; and administering an antibody to IL-23 to the patient in a clinically proven safe and clinically proven effective amount, wherein the antibody to IL-23 comprises a light chain variable region and a heavy chain variable region, said light chain variable region comprising:
   a complementarity determining region light chain 1 (CDRL1) amino acid sequence of SEQ ID NO:50;
   a CDRL2 amino acid sequence of SEQ ID NO:56; and
   a CDRL3 amino acid sequence of SEQ ID NO:73,
   said heavy chain variable region comprising:
   a complementarity determining region heavy chain 1 (CDRH1) amino acid sequence of SEQ ID NO:5;
   a CDRH2 amino acid sequence of SEQ ID NO:20; and
   a CDRH3 amino acid sequence of SEQ ID NO:44.

2. The method of claim 1, wherein the patient is treated with the antibody to IL-23 for at least 44 weeks to demonstrate efficacy in a psoriasis clinical endpoint selected from the group consisting of PASI90, PASI100, IGA 0 and IGA 1.

3. The method of claim 2, wherein the psoriasis clinical endpoint is measured 44 and/or 48 weeks after initial treatment with the antibody to IL-23.

4. The method of claim 3, wherein the psoriasis clinical endpoint is measured 48 weeks after initial treatment with the antibody to IL-23.

5. The method of claim 1, wherein the antibody to IL-23 is administered in an initial dose, 4 weeks after the initial dose and every 8 weeks after the dose at 4 weeks.

6. The method of claim 1, wherein the secukinumab antibody was administered in an initial dose, 1 week after the initial dose, 2 weeks after the initial dose, 3 weeks after the initial dose, 4 weeks after the initial dose and every 4 weeks after the dose at 4 weeks.

7. The method of claim 1, wherein the antibody to IL-23 is administered at a dose of 100 mg.

8. The method of claim 7, wherein the antibody to IL-23 is in a composition comprising 100 mg/mL of antibody; 7.9% (w/v) sucrose, 4.0 mM Histidine, 6.9 mM L-Histidine monohydrochloride monohydrate; 0.053% (w/v) Polysorbate 80 of the pharmaceutical composition; wherein the diluent is water at standard state.

9. The method of claim 1, wherein the antibody to IL-23 is safe and effective treating psoriasis at an area of a patient selected from the group consisting of scalp, nails, hands and feet.

10. The method of claim 1, further comprising administering to the patient one or more additional drugs used to treat psoriasis.

11. The method of claim 10, wherein the additional drug is selected from the group consisting of: immunosuppressive agents, non-steroidal anti-inflammatory drugs (NSAIDs), methotrexate (MTX), anti-B-cell surface marker antibodies, anti-CD20 antibodies, rituximab, TNF-inhibitors, corticosteroids, and co-stimulatory modifiers.

12. The method of claim 1, wherein the antibody to IL-23 is effective to reduce a symptom of psoriasis in the patient, induce clinical response, induce or maintain clinical remission, inhibit disease progression, or inhibit a disease complication in the patient.

13. The method of claim 1, wherein the patient is treated for moderate to severe psoriasis.

14. The method of claim 1, further comprising the step of measuring the psoriasis clinical endpoint PASI90, PASI100, IGA 0 and/or IGA 1 at 44 and/or 48 weeks after initial treatment and discontinuing treatment of a patient previously treated with at least one dose of secukinumab and treating the patient with guselkumab.

15. The method of claim 1, wherein the patient has psoriatic arthritis.

16. A method of treating psoriasis in a patient previously treated with at least one dose of secukinumab, comprising discontinuing secukinumab treatment to the patient; and administering an antibody to IL-23 to the patient in a clinically proven safe and clinically proven effective amount, the antibody to IL-23 comprising a light chain variable region of the amino acid sequence of SEQ ID NO: 116 and a heavy chain variable region of the amino acid sequence of SEQ ID NO: 106.

17. The method of claim 16, wherein the patient is treated with the antibody to IL-23 for at least 44 weeks to demonstrate efficacy in a psoriasis clinical endpoint selected from the group consisting of PASI90, PASI100, IGA 0 and IGA 1.

18. The method of claim 17, wherein the psoriasis clinical endpoint is measured 44 and/or 48 weeks after initial treatment with the antibody to IL-23.

19. The method of claim 18, wherein the psoriasis clinical endpoint is measured 48 weeks after initial treatment with the antibody to IL-23.

20. The method of claim 16, wherein the antibody to IL-23 is administered in an initial dose, 4 weeks after the initial dose and every 8 weeks after the dose at 4 weeks.

21. The method of claim 16, wherein the secukinumab antibody was administered in an initial dose, 1 week after the initial dose, 2 weeks after the initial dose, 3 weeks after the initial dose, 4 weeks after the initial dose and every 4 weeks after the dose at 4 weeks.

22. The method of claim 16, wherein the antibody to IL-23 is administered at a dose of 100 mg.

23. The method of claim 22, wherein the antibody to IL-23 is in a composition comprising 100 mg/mL of antibody; 7.9% (w/v) sucrose, 4.0 mM Histidine, 6.9 mM L-Histidine monohydrochloride monohydrate; 0.053% (w/v) Polysorbate 80 of the pharmaceutical composition; wherein the diluent is water at standard state.

24. The method of claim 16, wherein the antibody to IL-23 is safe and effective treating psoriasis at an area of a patient selected from the group consisting of scalp, nails, hands and feet.

25. The method of claim 16, further comprising administering to the patient one or more additional drugs used to treat psoriasis.

26. The method of claim 25, wherein the additional drug is selected from the group consisting of: immunosuppressive agents, non-steroidal anti-inflammatory drugs (NSAIDs), methotrexate (MTX), anti-B-cell surface marker antibodies, anti-CD20 antibodies, rituximab, TNF-inhibitors, corticosteroids, and co-stimulatory modifiers.

27. The method of claim 16, wherein the antibody to IL-23 is effective to reduce a symptom of psoriasis in the patient, induce clinical response, induce or maintain clinical remission, inhibit disease progression, or inhibit a disease complication in the patient.

28. The method of claim 16, wherein the patient is treated for moderate to severe psoriasis.

29. The method of claim 16, further comprising the step of measuring the psoriasis clinical endpoint PASI90, PASI100, IGA 0 and/or IGA 1 at 44 and/or 48 weeks after initial treatment and discontinuing treatment of a patient previously treated with at least one dose of secukinumab and treating the patient with guselkumab.

30. The method of claim 16, wherein the patient has psoriatic arthritis.

31. A method of treating moderate-to-severe plaque psoriasis in an adult patient who is a candidate for systemic therapy or phototherapy and who has previously been treated with at least one dose of secukinumab, comprising discontinuing secukinumab treatment to the patient; and administering an antibody to IL-23 to the patient in a clinically proven safe and clinically proven effective amount, wherein the antibody comprises a light chain variable region of the amino acid sequence of SEQ ID NO: 116 and a heavy chain variable region of the amino acid sequence of SEQ ID NO: 106, the dosage is 100 mg administered by subcutaneous injection at Week 0, Week 4 and every 8 weeks thereafter and the antibody is at a concentration of 100 mg/mL in a single-dose prefilled syringe comprising 7.9% (w/v) sucrose, 4.0 mM Histidine, 6.9 mM L-Histidine monohydrochloride monohydrate; 0.053% (w/v) Polysorbate 80 and the diluent is water at standard state.

\* \* \* \* \*